United States Patent
Reichert et al.

(10) Patent No.: US 6,524,589 B1
(45) Date of Patent: Feb. 25, 2003

(54) COMPOSITIONS OF HEPATITIS C VIRUS NS3/NS4A COMPLEX AND METHODS FOR CRYSTALLIZING SAME

(75) Inventors: Paul Reichert, Montville, NJ (US); Winifred W. Prosise, Ramsey, NJ (US); Shahriar Shane Taremi, Upper Montclair, NJ (US); Nanhua Yao, Edison, NJ (US); Patricia C. Weber, Yardley, PA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/543,376

(22) Filed: Apr. 5, 2000

Related U.S. Application Data
(60) Provisional application No. 60/128,253, filed on Apr. 8, 1999.

(51) Int. Cl.[7] .............................................. A61K 39/29
(52) U.S. Cl. ................... 424/228.1; 702/19; 424/184.1; 424/225.1; 514/2; 514/12; 514/13
(58) Field of Search ............................ 435/69.1, 195; 514/2, 12, 13; 530/324, 350, 402, 412–421; 424/184.1, 225.1, 228.1; 702/19

(56) References Cited

U.S. PATENT DOCUMENTS
6,153,579 A * 11/2000 Kim et al. ....................... 514/2
6,211,338 B1 * 4/2001 Malcolm et al. ............ 530/350

FOREIGN PATENT DOCUMENTS
WO    WO 98/11134    3/1998

OTHER PUBLICATIONS

Alter et al., "Detection of antibody to hepatitis C virus in prospectively followed transfusion recipients with acute and chronic non–A, non–B hepatitis", *N Engl J Med*, 321:1494–1500 (1989).

Brunger, "Patterson correlation searches and refinement", *Meth Enzy*, 276:558–580 (1997).

Choo et al., "Isolation of a cDNA clone derived from a blood–borne non–A, non–B viral hepatitis genome", *Science*, 244:359–362 (1989).

Failla et al., "An amino–terminal domain of the hepatitis C virus NS3 protease if essential for interaction with NS4A", *J Virol*, 69:1769–1777 (1995).

Fernandez et al., "The motif V of plum pox potyvirus CI RNA helicase is involved in NTP hydrolysis and is essential for virus RNA replication", *Nucleic Acids Res*, 25:4474–4480 (1997).

Gorbalenya et al., "A novel superfamily of nucleoside triphosphate–binding motif containing proteins which are probably involved in duplex unwinding in DNA and RNA replication and recombination", *FEBS Lett*, 235:16–24 (1988).

Grakoui et al., "Expression and identification of hepatitis C virus polyprotein cleavage products", *J Virol*, 67:1385–1395 (1993).

Gross and Shuman, "Vaccinia virions lacking the RNA helicase nucleoside triphosphate phosphohydrolase II are defective in early transciption", *J Virol*, 70:8549–8557 (1996).

Gross and Shuman, "The nucleoside triphosphatase and helicase activities of vaccinia virus NPH–11 are essential for virus replication", *J Virol*, 72:4729–4736 (1998).

Heinz, "Comparative molecular biology of flaviviruses and hepatitis C virus", *Arch Virol* Suppl. 4:163–171 (1992).

Howe et al., "A novel recombinant single–chain hepatitis C virus NS3–NS4A protein with improved helicase activity", *Protein Sci*, 8:1332–1341 (1999).

Kim et al., "Crystal structure of the hepatitis C virus NS3 protease domain complexed with a synthetic NS4A cofactor peptide", *Cell*, 87:343–355 (1996).

Kim et al., "Towards defining a minimal functional domain for NTPase and RNA helicase activities of the hepatitis C virus NS3 protein", *Virus Res*, 49:17–25 (1997).

Koonin and Dolja, "Evolution and taxonomy of positive–strand RNA viruses: implications of comparative analysis of amino acid sequences", *Crit Rev Biochem Mol Biol*, 28:375–430 (1993).

Korolev et al., "Comparisons between the structures of HCV and Rep helicases reveal structural similarities between SF1 and SF2 super–families of helicases", *Protein Sci*, 7:605–610 (1998).

Kuo et al., "An assay for circulating antibodies to a major etiologic virus of human non–A, non–B hepatitis", *Science*, 244:362–364 (1989).

Lohmann et al., "Processing pathways of the hepatitis C virus proteins", *J Hepatol*, 24(Suppl. 2):11–19 (1996).

Mizokami and Ohba, "Molecular classification of hepatitis C virus", *Gastroenterol Jpn*, 28(Suppl. 5):42–44 (1993).

Morgenstern et al., "Polynucleotide modulation of the protease, nucleoside triphophatase, and helicase activities of a hepatitis C virus NS3–NS4A complex isolated from transfected COS cells", *J Virol*, 71:3767–3775 (1997).

Ohba et al., "Evolutionary relationship of hepatitis C, pesti–, flavi–, plantviruses, and newly discovered GB hepatitis agents", *FEBS Lett*, 378:232–234 (1996).

(List continued on next page.)

Primary Examiner—Marianne P. Allen
(74) Attorney, Agent, or Firm—J. Darrell Fontenot

(57) ABSTRACT

The invention relates to the purification and crystallization of hepatitis C virus (HCV) NS3/NS4A polypeptide complex. Also, crystallization conditions for NS3/NS4A are provided. Further, the atomic coordinates for the NS3/NS4A protein are disclosed. Examples of its use for the determination of the three–dimensional atomic structures of HCV NS3/NS4A with substrate(s) or substrate analog(s) or inhibitor complexes are also provided.

10 Claims, 1 Drawing Sheet

OTHER PUBLICATIONS

Reichard et al., "Randomised, double–blind, placebo–controlled trial of interferon alpha–2b with and without ribavirin for chronic hepatitis C", *Lancet*, 351:83–87 (1998).

Sali et al., "Serine protease of hepatitis C virus expressed in insect cells as the NS3/4A complex", *Biochemistry*, 37:3392–3401 (1998).

Shimotohno et al., "Processing of the hepatitis C virus precursor protein", *J Hepatol*, 22(Suppl. 1):87–92 (1995).

Simmonds, "Virology of hepatitis C virus", *Clin Ther*, 18(Suppl. B):9–36 (1996).

Suzich et al., "Hepatitis C virus NS3 protein polynucleotide–stimulated nucleoside triphosphatase and comparison with the related pestivirus and flavivirus enzymes", *J Virol*, 67:6152–6158 (1993).

Takamizawa et al., "Structure and organization of the hepatitis C virus genome isolated from human carriers", *J Virol*, 65:1105–1113 (1991).

Taremi et al., "Construction, expression, and characterization of a novel fully activated recombinant single–chain hepatitis C virus protease", *Protein Sci*, 7:2143–2149 (1998).

Weber, "Physical principles of protein crystallization", *Advances in Protein Chemistry*, 41:1–36 (1991).

Yao et al., "Structure of the hepatitis C virus helicase domain", *Nat Struct Biol*, 4:463–467 (1997).

* cited by examiner

COMPOSITIONS OF HEPATITIS C VIRUS NS3/NS4A COMPLEX AND METHODS FOR CRYSTALLIZING SAME

This application claims priority under 35 U.S.C. §119(e) to U.S. Provisional Patent Application No. 60/128,253 filed Apr. 8, 1999.

FIELD OF THE INVENTION

The present invention relates to crystalline HCV NS3/NS4A complex, the structure of HCV NS3/NS4A complex as determined by X-ray crystallography, the use of that structure to solve the structure of HCV NS3, NS3/NS4A complex homologues and other crystal forms of the HCV NS3/NS4A complex, mutants and co-complexes thereof and the use of HCV NS3/NS4A complex, mutants and co-complexes thereof to design inhibitors of HCV NS3/NS4A complex.

BACKGROUND OF THE INVENTION

The hepatitis C virus causes one of the world's most pandemic and insidious diseases. According to the World Health Organization, there are approximately 170 million HCV carriers worldwide with prevalence up to 0.5–10% (Release:, 1998), and in the United States, four million individuals are hepatitis C virus carriers (Alter and Mast, 1994). The hepatitis C virus (HCV) was identified in 1989 and accounted for 50–60% of the non-A, non-B transfusion associated hepatitis (Alter et al *N Engl J Med* 321:1494–1500 (1989); Choo, et al., *Science* 244:359–362 (1989); Kuo, et al., *Science* 244:362–364 (1989)). To date, interferon-alpha monotherapy and interferon-alpha-2b and ribavirin combination therapy (Rebetron, Schering-Plough, Kenilworth, N.J.) are the only approved treatments. Twenty percent of the patients responded to interferon-α monotherapy and 42% of the patients responded to Rebetron combination therapy (Reichard, et al., *Lancet* 351:83–87 (1998)). It is important to develop more effective antiviral agents against the various viral targets in order to effectively combat the disease.

HCV, a member of the Flaviviridae family, is a positive-sense, single-stranded RNA virus with genome size of approximately 9.4 kb (Heinz, *Arch Virol Suppl* 4:163–171 (1992); Mizokami & Ohba, *Gastroenterol Jpn* 28 *Suppl* 5:42–44 (1993); Ohba, et al., *FEBS Lett* 378:232–234 (1996); Takamizawa, et al., *J Virol* 65:1105–1113 (1991)). The genomic RNA encodes a polyprotein of approximately 3000 amino acid residues in the order of NH2-C-E1-E2-p7-NS2-NS3-NS4A-NS4B-NS5A-NS5B-COOH (Lohmann, et al., *J Hepatol* 24:11–19 (1996); Simmonds, *Clin Ther* 18 *Suppl* B:9–36 (1996)). This polyprotein is processed by host and viral proteases (Grakoui, et al., *J Virol* 67:1385–1395 (1993); Shimotohno, et al., *J Hepatol* 22:87–92 (1995)). NS3 has been the target of interest for antiviral discovery because of its important roles in HCV maturation and replication. NS3 has two major functional domains: the amino terminal one third of the protein is a serine protease responsible for some key aspects of polyprotein processing (Shimotohno, et al., *J Hepatol* 22:87–92 (1995)), and the carboxyl terminal two thirds of NS3 share sequence similarity with those of the DEAD box family of RNA helicases (Gorbalenya, et al., *FEBS Lett* 235:16–24 (1988); Koonin & Dolja, *Crit Rev Biochem Mol Biol* 28:375–430 (1993); Korolev, et al., *Protein Sci* 7:605–610 (1998)). Virus encoded helicases such as vaccinia NPH-II and plum pox potyvirus CI have been demonstrated to be important for viral replication and production of infectious virions (Fernandez, et al., *Nucleic Acids Res* 25:4474–4480 (1997); Gross & Shuman *J Virol* 72:4729–4736 (1998); Gross & Shuman, *J Virol* 70:8549–8557 (1996)). There are two enzymatic activities associated with the HCV helicase-NTPase and nucleic acid unwinding; the former is believed to provide an energy source for the unwinding reaction through NTP hydrolysis (Kim, et al., *Virus Res* 49:17–25 (1997); Suzich, et al., *J Virol* 67:6152–6158 (1993)). Studies of the crystal structure of HCV helicase reveal that this molecule consists of three domains—domain I contains the NTP and $Mg^{++}$ binding sites, domain II is speculated to be an nucleic acid binding site and domain III is characterized as having extensive helical structure. Between domain I and II lies a coupling region speculated to be involved in the RNA unwinding function of the holoenzyme (Kim et al., *Cell* 87:343–355 (1996); Yao, et al., *Nat Struct Biol* 4:463–467 (1997)).

In spite of these different functions during the HCV life cycle, there is no evidence that the NS3 protease and helicase are ever separated from one another in HCV infected cells. Likewise, only the 70 kDa NS3 protein containing both the protease and helicase domains has ever been detected in cells transfected with recombinant vaccinia expressing HCV nonstructural proteins (Grakoui, et al., *J Virol* 67:1385–1395 (1993)). In addition, NS3 has been found to spontaneously associate with NS4A to form a stable noncovalent NS3/NS4A complex in vivo (Failla, et al., *J Virol* 69:1769–1777 (1995); Grakoui, et al., *J Virol* 67:1385–1395 (1993)). The covalent fusion of the protease and helicase domains in NS3 as well as the spontaneous formation of a complex with NS4A suggests that there may be functional dependence between these polypeptides to achieve additional activities other than the fundamental enzymatic properties.

In order to study the enzymatic properties of HCV helicase with as much biological relevance as possible, it is desirable to generate a full length NS3/NS4A complex. Previous attempts to express a full length NS3/NS4A protein complex in recombinant baculovirus resulted in a material with a propensity to aggregate which limited its application (Sali, et al., *Biochemistry* 37:3392–3401 (1998)).

The NS3 protein and the NS3/NS4A complex are considered a valuable target for antiviral agents. However, drug discovery efforts directed towards the NS3 protein have been hampered by a lack of structural information about the holoenzyme NS3. Such structural information would provide valuable information in discovery of HCV NS3 protein inhibitors. There have been no crystals reported of a NS3 holoenzyme or NS3 holoenzyme complex. Thus, x-ray crystallographic analysis of such proteins has not previously been available.

SUMMARY OF THE INVENTION

The present invention addresses this need by providing, for the first time, compositions comprising a crystallized hepatitis C virus (HCV) NS3/NS4A polypeptide complex. The present invention relates to crystalline HCV NS3/NS4A complex, the structure of HCV NS3/NS4A complex as determined by x-ray crystallography, the use of the structure to solve the structure of HCV NS3/NS4A complex homologues and other crystal forms of a HCV NS3/NS4A complex and mutants and co-complexes thereof, and the use of the HCV NS3/NS4A complex structure and that of its homologues, mutants, and co-complexes thereof to design inhibitors of HCV NS3/NS4A complex.

One aspect of the present invention is directed to the three-dimensional structure of an isolated and purified protein designated HCV NS3 and its structure coordinates. Another aspect of the invention is to use the structure coordinates of the HCV NS3/NS4A complex crystal to reveal the atomic details of the active sites and one or more of the accessory binding sites of HCV NS3/NS4A complex.

A further aspect of the invention is to provide HCV NS3/NS4A complex mutants characterized by one or more different properties compared to wild-type HCV NS3/NS4A complex.

The invention also provides a machine-readable data storage medium encoded with the structural coordinates of a NS3/NS4A polypeptide complex or a homologue thereof. Such a homologue contains alpha carbon (Cα) atoms having a root mean square deviation of equivalent Cα atoms of less than 3.0 Å when compared to the NS3/NS4A polypeptide complex.

The invention also provides a method for determining at least a portion of the three-dimensional structure of molecules or molecular complexes which contain at least some structurally similar features to a HCV NS3/NS4A polypeptide complex.

Another aspect of this invention is to use the structure coordinates and atomic details of HCV NS3/NS4A complex or mutants or homologues or co-complexes thereof to design, evaluate computationally, synthesize and use inhibitors of HCV NS3/NS4A complex that prevent or treat the undesirable physical and pharmacological properties of HCV. These inhibitors may be used as therapies that are beneficial in the treatment of HCV infection.

Still another aspect of the present invention comprises a method of selecting a potential ligand or inhibitor by performing structure-based drug design with a three-dimensional structure determined for the crystal, preferably in conjunction with computer modeling. The potential ligand or inhibitor is then contacted with the NS3 polypeptide or NS3/NS4A complex and the binding thereof is detected. If the ligand is a potential inhibitor of NS3 or NS3/NS4A complex activity, the candidate drug may then be contacted with a cell that expresses NS3 and the inhibition of its activity can be measured.

In another embodiment of the invention, a method of obtaining structural information concerning a molecular complex of unknown structure by using the structure coordinates set forth in Tables 2 and 3 is provided. Such a method comprises the steps of: generating x-ray diffraction data from said crystallized molecule, and applying crystallographic phases derived from at least a portion of the structure coordinates set forth in Tables 2 and 3 to said x-ray diffraction pattern to generate a three-dimensional electron density map of at least a portion of the molecule.

DETAILED DESCRIPTION OF THE INVENTION

Figure 1:
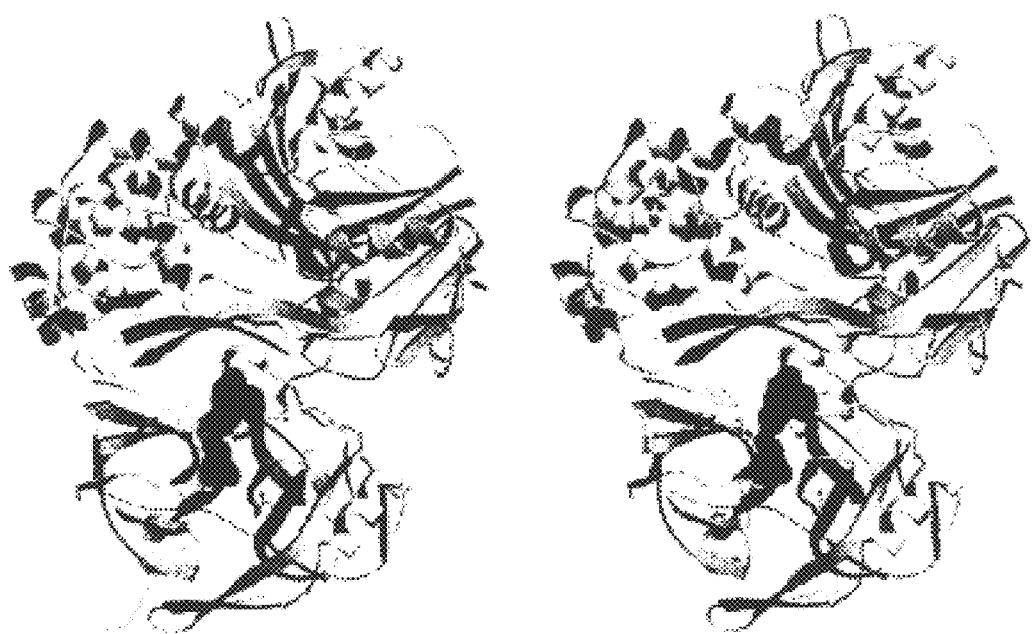
FIG. 1 depicts a stereo ribbon diagram of the HCV NS3/NS4A complex.

In order that the invention described herein may be more fully understood, the following detailed description is set forth. All references cited herein are incorporated in their entirety by reference.

The present invention provides, for the first time, crystallizable compositions comprising a HCV NS3/NS4A polypeptide complex having both helicase and protease activity. Thus, one embodiment of this invention provides a composition comprising a crystalline hepatitis C virus NS3/NS4A polypeptide containing the NS3 holoenzyme. Such a composition may be used for various purposes, including for example pharmaceutical purposes.

One aspect of the invention resides in obtaining crystals of HCV NS3/NS4A complex of sufficient quality to determine the three dimensional structure of the protein by x-ray diffraction methods. Accordingly, one object of the present invention is to provide crystals of sufficient quality to obtain a determination of the three dimensional of the HCV NS3/NS4A complex to high resolution. The value of the crystals of HCV NS3/NS4A complex extends beyond merely being able to obtain the structure for HCV NS3/NS4A complex alone but rather may be used to model the tertiary structure of related proteins and/or protein complexes.

Another aspect of the present invention is to provide a starting material for the structure determination of other members of the HCV NS3/NS4A protein family of proteins. The knowledge of the structure of the HCV NS3 family of proteins provides a tool for investigating the mechanism of action of HCV NS3 protein. Knowledge of the protein structure allows for the design and synthesis of small molecules which inhibit the functional activities of the HCV NS3 protein. One preferred method is structure-based drug design. Accordingly, another aspect of the invention is to provide material which is the starting material in the structural design of drugs which inhibit the action of HCV NS3 protein.

There have been no reports of the crystallization of natural or recombinant HCV NS3 protein or HCV NS3/NS4A complex, where the NS3 has both helicase and protease activities. This is the first report of the crystallization of HCV NS3 protein and the crystallographic solution of the structure of the multi-domain bi-functional enzyme.

Preferably, a crystal of the present invention effectively diffracts x-rays for the determination of the atomic coordinates of the protein to a resolution of greater than 4.0 Ångströms. More preferably, the crystal effectively diffracts x-rays for the determination of the atomic coordinates of the protein to a resolution of greater than 2.8 Ångströms. In a most preferred embodiment, the crystal effectively diffracts x-rays for the determination of the atomic coordinates of the protein to a resolution of greater than 2.5 Ångströms.

HCV "NS3/NS4A polypeptide complexes" are polypeptides which have both helicase and protease domains of the NS3 similar to naturally-occurring HCV NS3. The term also includes HCV NS3/NS4A complexes containing NS3 or polypeptide fragments of NS3 having helicase and protease functionalities. These polypeptides also include polypeptides that differ from the NS3 protein by having amino acid deletions, substitutions, and additions. NS3 and NS4A polypeptides may be derived from various HCV genotypes or subtypes known in the art.

The NS3 and NS4A polypeptides may be produced by any well-known method, including synthetic methods, such as solid phase, liquid phase and combination solid/liquid phase syntheses; recombinant DNA methods, including cDNA cloning, optionally combined with site-directed mutagenesis; and/or purification of the natural products, optionally combined with enzymatic or chemical cleavage methods to produce fragments of naturally-occurring NS3 and/or NS4A. NS3/NS4A polypeptides may be produced as a single fusion protein or as separate polypeptide chains. If a single fusion protein is prepared, it may optionally be desirable to cleave the protein parts prior to crystallization. Cleavage may be carried out by standards methods known in the art, including but not limited to chemical or enzymatic cleavage.

Optionally, it may also be desirable to add amino acids onto the NS3 and/or NS4A polypeptides. One preferred addition is a polyhistidine tag, 5–20 amino acids in length. Most preferred is a 6 amino acid histidine tag added to the amino-terminus of the NS3 protein or a truncated form of NS3. Preferably, the NS3 protein has a histidine tag at its amino-terminus for use in purifying the protein.

Another embodiment of the present invention provides a single chain recombinant NS3-N4A protein. See co-pending U.S. application Ser. No. 09/198,723, now U.S. Pat. No. 6,211,338 incorporated herein by reference. This purified recombinant His-NS4A$_{21-32}$-GSGS-NS-3$_{3-631}$ has properties similar to those described for the NS3/NS4A protein complex generated in eukaryotes (Morgenstern, et al., *J Virol* 71:3767–3775 (1997)), and also appears to be stable, more soluble and more active at unwinding RNA as compared with the His-NS3/NS4A complex previously reported (Sali, et al., *Biochemistry* 37:3392–3401 (1998)). In addition, comparison of the unwinding activity of the recombinant His-NS4A$_{21-32}$-GSGS-NS3$_{3-631}$ with that of the helicase domain and that of the full length NS3 (without NS4A) indicated that the presence of the protease domain and the core peptide of NS4A are important for optimal HCV helicase activity [Howe et al., "A Novel Recombinant Single Chain Hepatitis C Virus NS3-NS4A Protein with Improved Helicase Activity," *Protein Sci.* In Press, 1999].

In other embodiments of the invention, the NS4A hydrophobic domain and the NS3 polypeptide are covalently tethered using different amino acid linkers. The preferred amino acid linkers of the invention comprise at least about four amino acid residues. More preferably, the linkers consist of from four to six amino acid residues. More preferably, four-residue linkers are used.

Routine procedures in the art allow one to construct covalent NS4A-NS3 complexes of the invention having linkers of various sizes. It will be understood by one skilled in the art, for example, that if smaller or larger portions of the NS3 or NS4A domains are used to construct the covalent complexes of the invention, longer or shorter amino acid linkers can be used.

Other embodiments of the present invention contain smaller or larger portions of the NS4A cofactor peptide. In preferred embodiments, the complexes contain an NS4A hydrophobic domain comprising at least amino acid residues 22–32 of the full length NS4A cofactor peptide. More preferably, the complexes contain from 12–19 amino acid residues spanning the central hydrophobic domain of the full length NS4A peptide. Most preferably, the complexes contain amino acid residues 21–32 of full length NS4A peptide.

One aspect of the present invention relates to a method of purifying the NS3/NS4A polypeptides and obtaining NS3/NS4A crystals. Preferably, the NS3/NS4A polypeptide complex may be produced recombinantly in *E. coli* and initial purification may be accomplished by nickel chelate chromatography, as previously described (Petty (1996) "Metal chelate affinity chromatography" in: Ausubel, et al., eds. *Current Protocols in Molecular Biol.*, Vol.2 New York, John Wiley and Sons). This NS3/NS4A preparation may be subjected to anion exchange chromatography for further purification. Preferably, it may also be desirable to subject the NS3/NS4A preparation to standard size exclusion gel filtration. The protein preparation may be further concentrated using standard techniques. Finally, the preparation is preferably subjected to ultracentrifugation, which produces a monodisperse preparation of NS3/NS4A complex. The resulting supernatant is useful for crystallization purposes. The NS3/NS4A solution preferably contains a protein stabilizing agent, a salt, a buffering agent and optionally a reducing agent or an oxygen scavenger. Examples of suitable reducing agents are dithiothreitol (DTT), dithioerythritol (DET) and β-mercaptoethanol (BME). If necessary, the reducing agent is present in the buffered solution at a concentration of about 10 mM and is preferably BME. The pH of the buffering agent may range from 4.5 to 8, preferably between pH 7 and 8.

Although other solution components can be substituted for the above described components, the protein stabilizing agent and salt appear to be important for the solubility of the NS3/NS4A protein complex preparation. Protein stabilizing agents include polyols, sugars as well as amino acids and amino acid analogs. Some examples include erythritol, sorbitol, glycerol, fructose, trehalose, proline, β-alanine, taurine and glycine betaine. These agents are sometimes referred to as cosmotropic agents and are well known in the art. See Jeruzalmi & Steitz, *J. Mol. Biol.* 274: 748–756 (1997). The concentration of such agents will vary depending upon the type of agent employed. For example, if glycerol is chosen, it is preferably provided in a concentration range from about 2 (w/v) to about 20% (w/v), preferably about 10% (w/v), while a salt may be provided in a concentration of above about 300 mM. Many salts are routinely used in the art and may be variously used in the method of the present invention.

Compounds known as "precipitants" are often used to decrease the solubility of the polypeptide in a concentrated solution. Alternatively, "precipitants" can be changes in physical or chemical parameters which decrease polypeptide solubility, including temperature, pH and salt concentrations. Precipitants induce crystallization by forming an energetically unfavorable precipitant-depleted layer around the polypeptide molecules. To minimize the relative amount of this depletion layer, the polypeptides form associations and ultimately crystals as explained in Weber, *Advances in Protein Chemistry* 41:1–36 (1991) which is incorporated by reference. In addition to precipitants, other materials are sometimes added to the polypeptide crystallization solution. These include buffers to adjust the pH of the solution (and hence surface charge on the peptide) and salts to reduce the solubility of the polypeptide. Various precipitants are known in the art and include the following: ammonium sulfate, ethanol, 3-ethyl-2,4 pentanediol; and many of the polyglycols, such as polyethylene glycol. A suitable precipitant for crystallization of NS3/NS4A polypeptide complex is polyethylene glycol (PEG), which combines some of the characteristics of the salts and other organic precipitants.

Crystallization may be accomplished by using any of the known methods in the art. (Giegé, et al., *Acta Crystallogr.* D50: 339–350 (1994); McPherson, *Eur. J. Biochem.* 189: 1–23 (1990)). Such techniques include microbatch, hanging drop, seeding and dialysis. Preferably, hanging-drop vapor diffusion (McPherson, *J. Biol. Chem.* 251: 6300–6303 (1976)) or microbatch methods (Chayen *Structure* 5: 1269–1274 (1997)) are used. In each of these methods, it is important to promote continued crystal growth after nucleation by maintaining a supersaturated solution. In the microbatch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels.

It is desirable to use a NS3/NS4A protein preparation having a concentration of at least 1 mg/mL and preferably less than 65 mg/mL. Crystallization may be best achieved in a precipitant solution containing polyethylene glycol 1000–20,000 (PEG; average molecular weight ranging from 1000–20,000 Da), preferably 5000–7000 with concentrations ranging from 15–25% (w/v). It is further desirable to avoid the use of extremely high and low molecular weight PEGs. It may also be desirable to include a protein stabilizing agent. If glycerol is chosen as the protein stabilizing agent, it is preferably provided at concentration ranging from 0.5 to 20%. A suitable salt, such as sodium chloride, may also be desirable in the precipitant solution, preferably in concentration ranging from 1 to 1000 mM. The precipitant is preferably buffered to a pH of about 4.5 to 8.0. Most preferred is a buffer solution at a pH of about 6 to 7. Specific buffers useful in the precipitant solution may vary and are well-known in the art (Scopes, *Protein Purification: Principles and Practice*, Third ed., (1994) Springer-Verlag, N.Y.). Examples of useful buffers include but are not limited to Tris, MES and acetate. Crystals routinely grow in a wide range of temperature. It is however preferred that crystals form at temperatures between 2° C. and 26° C., and more preferably at 2° C. to 8° C., most preferably at 4° C.

The crystals of the present invention have a wide range of uses. For example, high quality crystals are suitable for x-ray or neutron diffraction analysis to determine the three dimensional structure of NS3/NS4A polypeptide complex and in particular to assist in the identification of the protein's active and effector sites. Knowledge of these sites and solvent accessible residues allow structure-based design and construction of agonists and antagonists for NS3 and/or NS3/NS4A polypeptide complex.

In addition, crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing the high-quality crystals necessary for diffraction analysis.

Once a crystal of the present invention is grown, x-ray diffraction data can be collected. One method for determining structure uses synchrotron radiation, under standard cryogenic condition for such x-ray diffraction data collection. However alternative methods may also be used. For example, crystals can be characterized by using x-rays produced in a conventional source (such as a sealed tube or a rotating anode). Methods of characterization include, but are not limited to, precession photography, oscillation photography and diffractometer data collection.

Advantageously, the crystallizable compositions provided by this invention are amenable to x-ray crystallography. Thus, this invention also provides the three-dimensional structure of a HCV NS3/NS4A polypeptide complex at 2.5 Å resolution. Importantly, this has provided for the first time, information about the shape and structure of the NS3/NS4A holoenzyme complex.

The three-dimensional structure of the HCV NS3/NS4A holoenzyme complexes of this invention are defined by a set of structure coordinates as set forth in Table 2 and 3. The term "structure coordinates" refers to Cartesian coordinates derived from mathematical equations related to the patterns obtained on diffraction of a beam of x-rays by the atoms (scattering centers) of NS3/NS4A polypeptide complexes in crystal form. The diffraction data are used to calculate electron density maps and to establish the positions of the individual atoms of the NS3/NS4A holoenzyme complexes.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above may be generated because of mathematical manipulations of the structure coordinates. For example, the structure coordinates set forth in Tables 2 and 3 can be manipulated by crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the original coordinates, the resulting three-dimensional shape is considered to be the same.

Various computational analyses are therefore necessary to determine whether a molecular complex or a portion thereof is sufficiently similar to all or part(s) of the NS3 polypeptide or NS3/NS4A polypeptide complex structure described above as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) input the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA (Molecular Simulations Inc., San Diego, Calif.) is defined by user input, for the purpose of this invention, equivalent atoms are defined as protein alpha carbon atoms (Cα) of less than 3 Å when superimposed on the relevant backbone atoms described by structure coordinates listed in Tables 2 and 3 are considered identical. More preferably, the root mean square deviation is less than 2.0 Å.

The term "root mean square deviation" means the square root of the arithmetic mean of the squares of the deviations from the mean. It is a way to express the deviation or variation from a trend or object. For purposes of this invention, the "root mean square deviation" defines the variation in the alpha carbon of a protein or protein complex from the relevant portion of the alpha carbon of the NS3/NS4A polypeptide complexes as defined by the structure coordinates described herein.

Thus, in accordance with the present invention, the structure coordinates of the NS3/NS4A polypeptide complex and portions thereof is stored in a machine-readable storage medium. Such data may be used for a variety of purposes, such as drug discovery and x-ray crystallographic analysis of a protein crystal.

Accordingly, one aspect of this invention provides a machine-readable data storage medium comprising a data storage material encoded with the structure coordinates set forth in Tables 2 and 3.

A computer system useful in reading the machine readable data storage medium includes a computer comprising a central processing unit ("CPU") and a memory storage device. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages will be known to those skilled in the art.

Input hardware coupled to the computer system by input line, may be implemented in a variety of ways. Machine-readable data of this invention may be inputted via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal for displaying a graphical representation of a binding pocket of this invention using a program such as INSIGHT (Molecular Simulations Inc., San Diego, Calif.) as described herein. Output hardware might also include a printer, so that hard copy output may be produced, or a disk drive, to store system output for later use.

In operation, the CPU coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In the case of CD-ROM, as is well known, a coating is reflective and is impressed with a plurality of pits to encode the machine-readable data. The arrangement of pits is read by reflecting laser light off the surface of the coating. A protective coating, which preferably is substantially transparent, is provided on top of the coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

The present invention permits the use of structure-based drug design techniques to design, select, and synthesize chemical entities, including inhibitory compounds that are capable of binding to HCV NS3/NS4A polypeptide complex or any portion thereof. Also, de novo and iterative drug design methods can be used to develop drugs from the crystal structure of the present invention.

One particularly useful drug design technique enabled by this invention is structure-based drug design. Structure-based drug design is a method for optimizing associations between a protein and a compound by determining and evaluating the three-dimensional structures of successive sets of protein/compound complexes.

Those skilled in the art will realize that association of natural ligands or substrates with the binding pockets of their corresponding receptors or enzymes is the basis of many biological mechanisms of action. The term "binding pocket", as used herein, refers to any region of a molecule or molecular complex, that, as a result of its shape, favorably associates with another chemical entity or compound. Similarly, drugs may exert their biological effects through association with the binding pockets of receptors and enzymes. Such association may occur with all or any part of the binding pockets. An understanding of such associations will help lead to the design of drugs having more favorable associations with the target enzyme, and thus, improved biological effects. Therefore, this information is valuable in designing potential enzyme inhibitors, such as inhibitors of HCV NS3/NS4A polypeptide complexes.

In iterative structure-based drug design, crystals of a series of protein/compound complexes are obtained and then the three-dimensional structure of each complex is solved. Such an approach provides insight into the association between the proteins and compounds of each complex. This is accomplished by selecting compounds with inhibitory activity, obtaining crystals of this new polypeptide, solving the three-dimensional structure of the polypeptide, and comparing the associations between the new protein and previously solved protein. By observing how changes in the compound affected the protein/compound associations, these associations may be optimized.

In some cases, iterative structure-based drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, the HCV NS3/NS4A polypeptide complex crystals, provided by this invention may be soaked in the presence of a compound or compounds, such as NS3 and/or NS4A inhibitors, substrates or other ligands to provide NS3 and/or NS4A polypeptide compound crystal complexes. As used herein, the term "soaked" refers to a process in which the crystal is transferred to a solution containing the compound of interest.

The structure coordinates set forth in Tables 2 and 3 can also be used to aid in obtaining structural information about another crystallized molecule or molecular complex. This may be achieved by any of a number of well-known techniques, including molecular replacement.

The structure coordinates set forth in Tables 2 and 3 can also be used for determining at least a portion of the three-dimensional structure of molecules or molecular complexes which contain at least some structurally similar features to HCV NS3 and/or NS4A or complexes thereof. In particular, structural information about another crystallized molecule or molecular complex may be well-known techniques, including molecular replacement.

Therefore, another aspect of this invention provides a method of utilizing molecular replacement to obtain structural information about a crystallized molecule or molecular complex whose structure is unknown comprising the steps of:

a) generating an x-ray diffraction pattern from said crystallized molecule or molecular complex; and b) applying crystallographic phases derived from at least a portion of the structure coordinates set forth in Tables 2 or 3 to the x-ray diffraction pattern to generate a three-dimensional electron density map of the molecule or molecular complex whose structure is unknown.

Once the structure coordinates of a protein crystal have been determined, they are useful in solving the structures of other crystals. In addition, the structures of NS3/NS4A complexes can be determined from the structure coordinates of the present invention. For example, complexes may be crystallized and their structure elucidated using such methods as difference Fourier or molecular replacement. NS3/NS4A complexes suitable for such analysis include, for example, NS3/NS4A further in complex with a peptide, nucleotide, polynucleic acid (i.e. substrate). Another example complex is NS3/NS4A complexed with a peptidomimetic nucleotide analog or an inhibitor unrelated in structure to substrate. Yet another NS3/NS4A complex suitable for structure determination using the structure coordinates of NS3/NS4A is NS3 in complex with other members of the putative replicase complex, such as HCV NS5B, an RNA dependent RNA polymerase, NS2 or additional HCV proteins. A further NS3/NS4A complex suitable for structure determination is NS3 in complex with one or more cellular host factors. Suitable complexes of NS3 and/or NS3/NS4A may contain several other molecules or combinations of the above described complexes.

Preferably, the crystallized molecule or molecular complex comprises a NS3\NS4A polypeptide complex. More preferably, the crystallized molecule or molecular complex is obtained by soaking a crystal of this invention in a solution. By using molecular replacement, all or part of the structure coordinates of the NS3/NS4A provided by this invention (and set forth in Tables 2 and 3) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be measured experimentally. Obtaining accurate values for the phases, by methods other than molecular replacement, is a time-consuming process. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the NS3/NS4A protein complex according to Table 2 or 3 within the unit cell of the crystal of the unknown molecule or molecular complex so as best to account for the observed x-ray diffraction pattern amplitudes to generate an election density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in *Meth. Enzymol.*, 115: 55–77 (1985); Rossman, ed., "The Molecular Replacement Method", *Int. Sci. Rev. Ser.*, No. 13, Gordon & Breach, New York (1972)).

Phase information from the structure coordinates of the present invention may be used to elucidate the structure of other crystals. For example, NS3/NS4A molecules in complex with other atoms or molecules, as described above, including complexes containing a heavy atom substructure from which useful phasing information may be extracted. Such complexes include, for example, those containing atoms soaked into or cocrystallized within the crystal lattice. Other structures which can be elucidated using the phase information of the present invention include for example other protease-helicase bifunctional proteins or homologues or mutants thereof having sufficient three-dimensional structure similarity to HCV NS3 and/or NS3/NS4A complex as to be solved using molecular replacement. Examples of such proteins include but are not limited to NS3 from Dengue, tick-borne encephalitis, Bovine viral diarrhea, Yellow Fever and other Flaviviruses. Also, these protein molecules in a complex with a small molecule substrate(s), inhibitor(s), transition state analog(s), product(s) or analog(s) of any of these may also be solved using the phase information of the present invention. Other complexes whose structure can be elucidated from the phase information of the present invention include an NS3/NS4A inhibitor or multiple inhibitors. Complexes containing a combination of the above molecules may also be solved using the phase information of the present invention.

The structure of any portion of any crystallized molecule or molecular complex that is sufficiently homologous to any portion of the NS3/NS4A protein complex can be solved by this method. The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

In a preferred embodiment, the method of molecular replacement is utilized to obtain structural information about a molecule wherein the molecule comprises a NS3/NS4A polypeptide complex. Preferably, NS3/NS4A polypeptide complexes comprise NS3/NS4A, NS3/NS4A(S139A), NS3/NS4A(R180A), NS3/NS4A(S139A/R180A) or homologues thereof. S139A relates to a mutation at amino acid position 139 from a serine to an alanine. R180A relates to a mutation at amino acid position 180 from an arginine to an alanine.

The structure coordinates of NS3/NS4A polypeptide complexes provided by this invention are particularly useful in solving the structure of other crystal forms of NS3/NS4A polypeptide complexes.

The structure coordinates are also particularly useful to solve the structure of crystals of NS3/NS4A polypeptide complexes, particularly NS3/NS4A(S139A), NS3/NS4A(R180A) and polypeptides related in structure to such complexes. This approach enables the determination of the optimal sites for interaction between chemical entities, including interaction of candidate NS3 inhibitors with NS3 or NS4A.

All of the complexes referred to above may be studied using well-known x-ray diffraction techniques may be refined versus x-ray data to 3 Å resolution or better to an $R_{free}$ value of about 0.40 or less using computer software, such as X-PLOR (Yale University, ©1992, distributed by Molecular Simulations, Inc.; see e.g., Blundell & Johnson, supra; *Meth, Enzymol.*, vol. 114 & 115, H. W. Wyckoff et al., eds., Academic Press (1985)). This information may thus be used to optimize known NS3 inhibitors, and to design new NS3 inhibitors.

In order that this invention be more fully understood, the following examples are set forth. These examples are for the illustrative purposes only and are not to be construed as limiting the scope of this invention in any way.

EXAMPLE 1

Construction Expression and Purification HIS-NS4A$_{21-32}$-CSGS-NS3$_{3-631}$ pNS4A$_{21-32}$-GSGS-NS3$_{3-631}$ was derived from plasmid BK138-1 which encoded the entire NS3 region of 1 b/BK strain of HCV (Takamizawa, et al., *J Virol* 65:1105–1113 (1991)). The recombinant pNS4A$_{21-32}$-GSGS-NS3$_{3-631}$ was constructed in two steps by first generating the pHis-NS4A$_{21-32}$-GSGS-NS3$_{3-181}$ which encoded the HCV NS3 protease domain (residues 3–181) (Taremi, et al., *Protein Sci* 7:2143–9. (1998)), followed by subcloning into an expression vector containing the NS3 (residues 49–631) via a cut and paste strategy. For the construction of pNS4A$_{21-32}$-GSGS-NS3$_{3-631}$, a 270 bp fragment was generated by restricting pHis-NS4A$_{21-32}$-GSGS-NS3$_{3-181}$ with XbaI/BspMI. This fragment contained the sequence encoding the histidine tag, the thrombin site, the NS4A peptide, GSV-VIVGRIILS (NS4A a.a. 21–32), the linker, glycine-serine-glycine-serine (GSGS) and the NS3 a.a. 3–48. A second fragment (7111 bp) was generated by treatment with restriction enzymes a pET-22b+ plasmid containing the full length NS3 (encoding a.a. 1–631 derived from BK138-1 plasmid) with XbaI/BspMI. This fragment encompassed the pET 22b+ expression vector in addition to the sequence encoding NS3 a.a. 49–631. These two fragments were ligated together to form pHis-NS4A$_{21-32}$-GSGS-NS3$_{3-631}$. The resulting plasmid was used to transform competent *E. coli* DH5a which were selected on LB agar plates with ampicillin (100 μg/ml). Recombinant clones were identified by restriction enzyme mapping and sequencing.

A single colony from *E. coli* BL21(DE3) transformed with the recombinant plasmids was used to initiate growth in Terrific Broth (Gibco, BRL, MD) supplemented with 100 μg/ml ampicillin. When the cell density reached an OD$_{600}$ of 2–3, the temperature was lowered rapidly to 23° C. and recombinant protein expression was induced with IPTG (0.2 mM final concentration). Cells were harvested 3 hours after induction and frozen at −20° C. prior to purification.

The cell pellet was resuspended in 600 ml of lysis buffer containing 50 mM HEPES [pH 7.4], 10% glycerol, 0.3 M NaCl, 0.1% n-octyl-b-D-octyl glucoside (bOG), 2 mM b-mercaptoethanol (bME) (buffer A) using a cell homogenizer (Omni Mixer ES) for 2 min and subsequently disrupted by two passes through a Microfluidizer, Model #M-100F (Microfluidics, MA) at 10,000 p.s.i. The lysate was cleared by centrifugation at 85,000×g for 45 min. The supernatant was applied at 25 ml/min to an 11-ml Ni-imidodiacetate (POROS 20 MC resin) column in the presence of 20 mM imidazole using a FPLC system (Pharmacia, NJ). The column was washed with 10 column volumes of buffer A, followed by 15 column volumes of buffer A containing 1.0 M NaCl and 20 mM imidazole (buffer B). The bound recombinant protein was eluted using buffer A supplemented with 1 M NaCl and 250 mM imidazole.

The pooled fractions were further purified by size exclusion chromatography using three sephacryl-200 sizing columns (26×60 cm, Pharmacia, NJ) in series (flow rate 0.5 ml/min.). All columns were pre-equilibrated in buffer containing 50 mM N-[2-hydroxyethyl]piperazine-N'-[2-ethanesulfonic acid] (HEPES) [pH 7.4], 10% glycerol, 0.3M NaCl and 10 mM bME. Fractions containing greater than 95% pure recombinant His-NS4A$_{21-32}$-GSGS-NS3$_{3-631}$ (SEQ ID NO: 1), as judged by sodium dodecyl sulfate-polyacrylamide gel electrophoresis (SDS-PAGE), were pooled. The pooled fractions was applied to a Q-sepharose column equilibrated in 25 mM N-[2-hydroxyethyl]piperazine-N'-[2-ethanesulfonic acid] (HEPES) [pH 7.6], 10% glycerol, 0.15M NaCl and 10 mM bME. The flowthrough containing the full-length NS3 protein was collected and final NaCl concentration was adjusted to 1.0M. The purified protein was flash frozen and stored at −80° C.

A HIS-NS4A$_{21-32}$-GSGS-NS3$_{3-631}$ (SEQ ID NO: 1) complex solution was monodisperse at 2 mgml$^{-1}$ as determined by dynamic light scattering analysis (Molecular Size Detector, Protein Solutions). The purified HCV His-NS4A$_{21-32}$-GSGS-NS3$_{3-631}$ (SEQ ID NO: 1) complex was concentrated by centrifugal filtration to 7 mgml$^{-1}$ in a buffer containing 1 M sodium chloride, 10% glycerol, 10 mM β-mercaptoethanol, 25 mM HEPES, pH 7.6. The purified protein was screened for conditions for crystallization under a wide range of pH, ionic strengh, protein concentration, precipitant concentration and incubation temperatures in hanging drop vapor diffusion experiments using an automated crystallization system (Cyberlab C2000, Cyberlab, Inc: Brookfield, Conn.).

EXAMPLE 2

Construction, Expression and Purification of HIS-NS4A$_{21-32}$-GSGS-NS3$_{3-631}$/139A An NS4A-tethered form of NS3 full-length domain, HIS-NS4A$_{21-32}$-GSGS-NS3$_{3-631}$/S139A, (SEQ ID NO: 2) was constructed via a cut and paste strategy as described above. Briefly, a 290 bp fragment was generated by restricting HIS-NS4A$_{21-32}$-GSGS-NS3$_{3-181}$ with XbaI/BspMI; this fragment encompass sequence encoding a histidine tag, a thrombin site, amino acids 21–32 of the NS4A peptide, the linker GSGS and NS3 amino acids 3–48. A second 7111 fragment (7111 bp) was generated by treatment with a restriction enzyme HIS-NS3$_{1-631}$/S139A construct with XbaI/BspmI resulting in a fragment encompassing the pET 22b+ vector backbone in addition to amino acids 49–631. These two fragments were then ligated together with T4 DNA ligase to form HIS-NS4A$_{21-32}$-GSGS-NS3$_{3-631}$/S139A (SEQ ID NO: 2).

A single colony from *E. coli* BL21(DE3) transformed with the recombinant plasmids was used to initiate growth in Terrific Broth (Gibco BRL, MD) supplemented with 100 μg/ml ampicillin. When the cell density reached an OD$_{600}$ of 2–3, the temperature was lowered rapidly to 23° C. and recombinant protein expression was induced with IPTG (0.2 mM final concentration). Cells were harvested 3 hours after induction and frozen at −20° C. prior to purification.

The cell pellet was resuspended in 600 ml of lysis buffer containing 50 mM HEPES [pH 7.4], 10% glycerol, 0.3 M NaCl, 0.1% n-octyl-b-D-octyl glucoside (bOG), 2 mM b-mercaptoethanol (bME) (buffer A) using a cell homogenizer (Omni Mixer ES) for 2 min and subsequently disrupted by two passes through a Microfluidizer, Model #M-110F (Microfluidics, MA) at 10,000 p.s.i. The lysate was cleared by centrifugation at 85,000×g for 45 min. The supernatant was applied at 25 ml/min to an 11-ml Ni-imidodiacetate (POROS 20 MC resin) column in the presence of 20 mM imidazole using a FPLC system (Pharmacia, NJ). The column was washed with 10 column volumes of buffer A, followed by 15 column volumes of buffer A containing 1.0 M NaCl and 20 mM imidazole (buffer B). The bound recombinant protein was eluted using buffer A supplemented with 1 M NaCl and 250 mM imidazole.

The pooled fractions were further purified by size exclusion chromatography using 3 sephacryl-200 sizing columns (26×60 cm, Pharmacia, NJ) in series (flow rate 0.5 ml/min.). All columns were pre-equilibrated in buffer containing 50 mM N-[2-hydroxyethyl]piperazine-N'-[2-ethanesulfonic acid] (HEPES) [pH 7.4], 10% glycerol, 0.3M NaCl and 10 mM bME. Fractions containing greater than 95% pure recombinant His-NS4A$_{21-32}$-GSGS-NS3$_{3-631}$/S139A (SEQ ID NO: 2) as judged by sodium dodecyl sulfate-polyacrylamide gel electrophoresis (SDS-PAGE), were pooled. The pooled fractions were applied to a Q-sepharose column equilibrated in 25 mM N-[2-hydroxyethyl] piperazine-N'-[2-ethanesulfonic acid] (HEPES) [pH 7.6], 10% glycerol, 0.15M NaCl and 10 mM bME. The flowthrough containing the full-length NS3 protein was collected and final NaCl concentration was adjusted to 1.0M. The purified protein was flash frozen and stored at −80° C.

EXAMPLE 3

Construction of Expression and Purification HIS-NS4A$_{21-32}$-GSGS-NS3$_{3-631}$/S139A,R180A A single amino acid mutant of HIS-NS4A$_{21-32}$-GSGS-NS3$_{3-631}$/S139A (SEQ ID NO: 2) was constructed by creating a point mutation at position 180 of the NS3 domain of HIS-NS4A$_{21-32}$-GSGS-NS3$_{3-631}$/S139A (SEQ ID NO: 2) construct using the quikchange site-directed mutagenesis kit (Stratagene) according to the manufacturer's protocol. Two oligonucleotide primers, each complementary to opposite strands of the template were generated which contain the point mutation which alters amino acid number 180 (arginine) to an alanine. The top strand primer was as follows:

5'GGAAACTACTATGGCGTCTCCGGTCTTCACG 3' (SEQ ID NO: 4) and the bottom strand read as follows: 5'CGTGAAGACCGGAGACGCCATAGTAGTTTCC 3' (SEQ ID NO: 5). 10 picomoles of each primer was used to amplify the entire plasmid encompassing the NS4A-tethered NS3 protease gene (50 or 100 ng/reaction) using pfu DNA polymerase (2.5 units/reaction) in a final reaction volume of 50 ml. The PCR conditions were as follows: 95° C. for 45 seconds (1 cycle); 95° C. for 30 seconds, 55° C. for 1 minute, 68° C. for 15 minutes (16 cycles). After amplification, the reaction mixture was treated with 1 ul of DpnI (1 Unit) for 1 hour at 37° C. in order to digest the parental DNA. One microliter of this digest was used to transform 50 ml of XLI Blue cells to repair nicks and propagate the mutated plasmid. Plasmid-DNA were purified and transformed into BL21 (DE3) cells for expression studies.

A single colony from E. coli BL21(DE3) transformed with the recombinant plasmids was used to initiate growth in Terrific Broth supplemented with 100 µg/ml ampicillin. When the cell density reached an OD$_{600}$ of 2–3, the temperature was lowered rapidly to 23° C. and recombinant protein expression was induced with IPTG (0.2 mM final concentration). Cells were harvested 3 hours after induction and frozen at −20° C. prior to purification.

The cell pellet was resuspended in 600 ml of lysis buffer containing 50 mM HEPES [pH 7.4], 10% glycerol, 0.3 M NaCl, 0.1% n-octyl-b-D-octyl glucoside (bOG), 2 mM b-mercaptoethanol (bME) (buffer A) using a cell homogenizer (Omni Mixer ES) for 2 min and subsequently disrupted by two passes through a Microfluidizer, Model #M-110F (Microfluidics, MA) at 10,000 p.s.i. The lysate was cleared by centrifugation at 85,000×g for 45 min. The supernatant was applied at 25 ml/min to an 11-ml Ni-imidodiacetate (POROS 20 MC resin) column in the presence of 20 mM imidazole using a FPLC system (Pharmacia, NJ). The column was washed with 10 column volumes of buffer A, followed by 15 column volumes of buffer A containing 1.0 M NaCl and 20 mM imidazole (buffer B). The bound recombinant protein was eluted using buffer A supplemented with 1 M NaCl and 250 mM imidazole.

The pooled fractions were further purified by size exclusion chromatography using 3 sephacryl-200 sizing columns (26×60 cm, Pharmacia, NJ) in series (flow rate 0.5 ml/min.). All columns were pre-equilibrated in buffer containing 50 mM N-[2-hydroxyethyl]piperazine-N'-[2-ethanesulfonic acid] (HEPES) [pH 7.4], 10% glycerol, 0.3M NaCl and 10 mM bME. Fractions containing greater than 95% pure recombinant His-NS4A$_{21-32}$-GSGS-NS3$_{3-631}$/S139A, R180A (SEQ ID NO: 3), as judged by sodium dodecyl sulfate-polyacrylamide gel electrophoresis (SDS-PAGE), were pooled. The pooled fractions were applied to a Q-sepharose column equilibrated in 25 mM N-[2-hydroxyethyl]piperazine-N'-[2-ethanesulfonic acid] (HEPES) [pH 7.6], 10% glycerol, 0.15M NaCl and 10 mM bME. The flowthrough containing the full-length NS3 protein was collected and final NaCl concentration was adjusted to 1.0M. The purified protein was flash frozen and stored at −80° C.

EXAMPLE 4

A. Crystallization of HCV-1b-His-NS4A$_{21-32}$-GSGS-NS3$_{3-631}$ Complex

E. coli derived His-NS4A$_{21-32}$-GSGS-NS3$_{3-631}$ complex was expressed and purified using conventional chromatographic methods. Purified HCV His-NS4A$_{21-32}$-GSGS-NS3$_{3-631}$ (SEQ ID NO: 1) complex was dialyzed against a 25 mM HEPES, pH 7.6, 1.0 M sodium chloride, 10% glycerol, 10 mM β-mercaptoethanol solution and concentrated by centrifugal filtration to 0.07 mM (5 mg/ml) followed by ultracentrifugation prior to crystallization. Vapor diffusion crystallization experiments were conducted using the hanging drop method with micro-seeding. Crystals suitable for structure determination were grown from a droplet containing 3 ul of protein: 3 ul of the reservoir solution (0.08 M sodium phosphate, pH 6.4, 16% PEG 6000, 32 mM di-potassium hydrogen phosphate, 8% methyl pentanediol (MPD), 5 mM HEPES, 0.2 M sodium chloride, 20% w/v glycerol, 2 mM β-mercaptoethanol). The droplet was microseeded with a HCV-1b-His-NS4A$_{21-32}$-GSGS-NS3$_{3-631}$ (SEQ ID NO: 1) complex at 4° C. Crystallization plates were incubated at 4° C., rectangular rods (0.04×0.3 mm) grew over 4–72 hours.

B. Crystallization of HCV-1b-His-NS4A$_{21-32}$-GSGS-NS3$_{3-361}$/S39A Complex E. coli derived HCV-1b-His-NS4A$_{21-32}$-GSGS-NS3$_{3-631}$/S139A complex was expressed and purified using conventional chromatographic methods. Purified HCV-1b-His-NS4A$_{21-32}$-GSGS-NS3$_{3-631}$/S139A (SEQ ID NO: 2) protein was dialyzed against a 25 mM HEPES, pH 7.6, 1.0 M sodium chloride, 10% glycerol, 10 mM β-mercaptoethanol solution and concentrated by centrifugal filtration to 0.07 mM (5 mg /ml) followed by ultracentrifugation prior to crystallization. Vapor diffusion crystallization experiments were conducted using the hanging drop method with micro-seeding. Crystals suitable for structure determination were grown from a droplet containing 3 ul of protein: 3 ul of the reservoir solution (0.08 M sodium phosphate, pH 6.4, 16% PEG 6000, 32 mM di-potassium hydrogen phosphate, 8% methyl-pentanediol, 5 mM HEPES, 0.2 M sodium chloride, 2% (w/v) glycerol, 2 mM β-mercaptoethanol). The droplet was subsequently micro-seeded with a HCV-1b-His-NS4A$_{21-32}$-GSGS-NS3$_{3-631}$/S139A (SEQ ID NO: 2) complex crystal at 4° C. Crystallization plates were incubated at 4° C., rectangular rods (0.04×0.3 mm) grew over 24–72 hours.

Alternatively, E. coli derived His-Ns4A21-32-GSGS-NS33-631 complex was expressed and purified using conventional chromatographic methods. Purified HCV His-NS4A21-32-GSGS-NS33-631 complex in 0.08 M sodium phosphate, pH 6.4, 16% PEG 600, 32 mM di-potassium hydrogen phosphate, 8% methyl pentenediol (MPD), 5 mM HEPES, 0.2 M sodium chloride, 2% glycerol, 2 mM β-mercaptoethanol solution was concentrated by centrifugal filtration to 0.07 mM (5 mg/ml) followed by ultracentrifugation prior to crystallization. Crystallization experiments were conducted using a batch method with micro-seeding. Crystals suitable for structure determination were grown from a droplet containing 4 ul of protein placed on a microbridge (Hampton Research) in a 0.08 M sodium phosphate, pH 6.4, 16% PEG 6y000, 32 mM di-potassium hydrogen phosphate, 8% methyl pentanediol (MPD), 5 mM HEPES, 0.2 M sodium chloride, 2% glycerol, 2 mM β-mercaptoethanol solution. The droplet was micro-seeded with a HCV-1b-His-NS4A21-32-GSGS-NS33-631 complex crystal below a layer of 20 ul of paraffin oil (Hampton Research) at 4° C. Sealed wells of crystallization plates (VDX; Hampton Research) were incubated at 4° C., rectangular rods (0.08×0.48 mm) grew over 4–72 hours.

C. Crystallization of HCV-1b-His-NS4A$_{21-32}$-GSGS-NS3$_{3-631}$/S139A,R180A Complex E. coli derived HCV-1b-His-NS4A$_{21-32}$-GSGS-NS3$_{3-631}$/S139A,R180A (SEQ ID NO: 3) complex was expressed and purified using conventional chromatographic methods. Purified HCV-1b-His-NS4A$_{21-32}$-GSGS-NS3$_{3-631}$/S139A, R180A complex was dialyzed against a 25 mM HEPES, pH 7.6, 1.0 M sodium chloride, 10% glycerol, 10 mM β-mercaptoethanol solution and concentrated by centrifugal filtration to 0.07 mM (5 mg/ml) followed by ultracentrifugation prior to crystallization. Vapor diffusion crystallization experiments were conducted using the hanging drop method with micro-seeding. Crystals suitable for structure determination were grown from a droplet containing 3 ul of protein: 3 ul of the reservoir solution (0.08 M sodium phosphate, pH 6.4, 16% PEG 6000, 32 mM di-potassium hydrogen phosphate, 8% methyl-pentanediol, 5 mM HEPES, 0.2 M sodium chloride, 2% (w/v) glycerol, 2 mM β-mercaptoethanol). The droplet was subsequently micro-seeded with a HCV-1b-His-NS4A$_{21-32}$-GSGS-NS3$_{3-631}$/S139A,R180A (SEQ ID NO: 3) complex crystal at 4° C. Crystallization plates were incubated at 4° C., rectangular rods (0.04×0.3 mm) grew over 24–72 hours.

EXAMPLE 6

A. Crystallographic Analysis of HCV-1b-His-NS4A$_{21-32}$-GSGS-NS3$_{3-631}$ Complex Prior to data collection, crystals were either taken directly from the crystallization droplet and by either addition of 20% glycerol or increasing MPD concentration to 25% were flash frozen using either nitrogen gas stream or liquid propane. A complete diffraction data of HCV-1b-His-NS4A21-32-GSGS-NS33-631 complex crystals was achieved from a Rigaku R-Axis IV image plate area detector mounted on a Rigaku RU-HR rotating Cu anode generator operating at 100 mA and 50 kV. Crystals belong to the orthorhombic space group P2$_1$2$_1$2$_1$. The unit cell dimensions are a=91 Å, b=111 Å, c=141 Å, α=β=γ=90° with two molecules in the asymmetric unit. Most crystals diffract beyond 2.5 Å. The data were obtained from a Bruker 2×2 Mosaic CCD area detector on beamline 17-ID at the Advanced Photon Source at Argonne National Laboratory. Data Collection Statistics:

| | |
|---|---|
| Resolution | 40–2.9 Å |
| No. of collected reflections | 168211 |
| No. of unique reflections (F >= 0) | 32167 |
| R-sym | 0.133 |
| Percent of theoretical (I/s >= 1) | 99.7% |
| Unit Cell | a = 91 Å, b = 111 Å, c = 141 Å |
| Space Group | P2$_1$2$_1$2$_1$ |
| Asymmetric unit | 2 molecules |

B. Crystallographic Analysis of HCV-1b-His-NS4A$_{21-32}$-GSGS-NS3$_{3-631}$/S139A Complex Prior to data collection, crystals were either taken directly from the crystallization droplet and by either addition of 20% glycerol or increasing MPD concentration to 25% gave reasonable freezing results under both cold nitrogen stream and liquid propane. A complete diffraction data of HCV-1b-His-NS4A$_{21-32}$-GSGS-NS3$_{3-631}$/S139A complex crystal was achieved from a synchrotron radiation facility in IMCA beamline, APS, Chicago, or a beamline 17-ID at the Advanced Photon Source at Argonne National Laboratory. Data Collection Statistics:

| | |
|---|---|
| Resolution | 40–2.5 Å |
| No. of collected reflections | 278808 |
| No. of unique reflections (F >= 0) | 50404 |
| R-sym | 0.082 |
| Percent of theoretical (I/s >= 1) | 99% |
| Unit Cell | a = 91 Å, b = 111 Å, c = 141 Å |
| Space Group | P2$_1$2$_1$2$_1$ |
| Asymmetric unit | 2 molecules |

EXAMPLE 7

Model Building and Refinement

HCV single chain (SCNS3/NS4A) scNS3/4A (SEQ ID NO: 1) structure was determined by molecular replacement methods as coded in XPLOR. The 2Fo-Fc map showed the C-termini of helicase in the active site of protease. The structure was further refined using simulated-annealing, and positional and B-factor refinement (XPLOR 3.1), while gradually extending the resolution. Both search models were derived from the HCV strain 1a, and the appropriate changes corresponding to the 1B strain of the scNS3/4A were made after the resolution or refinement was beyond 2.8 Å. The $R_{free}$ [Brunger, *Meth. Enzy.*, 276:558–580 (1997)] was closely monitored throughout the refinement.

TABLE 1

Refinement data of the HCV scNS3/NS4A

| Data | Parameter | Value |
|---|---|---|
| Refinement: | | |
| | $R_{free}$12345 unique reflections (40.0 to 2.5 Å resolution) | 0.29 |
| | R-factor | 0.22 |
| | Rms deviation from ideal bond distances (Å) | 0.008 |
| | Rms deviation from ideal angle (°) | 1.6 |
| | Protein heavy atoms | 9616 |
| | Phosphate ions | 2 |
| | Ordered water molecules | 372 |

EXAMPLE 8

Model Building and Refinement

HCV single chain (SCNS3/NS4A) scNS3/4A(S139A) (SEQ ID NO: 2) structure was determined by molecular replacement methods as coded in XPLOR. The 2Fo-Fc map showed the C-termini of helicase in the active site of protease. The structure was further refined using simulated-annealing, and positional and B-factor refinement (XPLOR 3.1), while gradually extending the resolution. Both search models were derived from the HCV strain 1a, and the appropriate changes corresponding to the 1B strain of the scNS3/4A(S139A) (SEQ ID NO: 2) were made after the resolution or refinement was beyond 2.8 Å. The $R_{free}$ [Brunger, *Meth. Enzy.*, 276:558–580 (1997)] was closely monitored throughout the refinement.

TABLE 4

Refinement data of the HCV scNS3/NS4A (S139A)

| Data | Parameter | Value |
|---|---|---|
| Refinement: | | |
| | $R_{free}$1500 unique reflections (40.0 to 2.5 Å resolution) | 0.29 |
| | R-factor | 0.20 |
| | Rms deviation from ideal bond distances (Å) | 0.006 |
| | Rms deviation from ideal angle (°) | 1.59 |
| | Protein heavy atoms | 9614 |
| | Phosphate ions | 2 |
| | Ordered water molecules | 362 |

Tables 2 and 3 list the atomic structure coordinates for hepatitis C virus recombinant scNS3/NS4A (SEQ ID NO: 1) and scNS3/NS4A (S139A) (SEQ ID NO: 2) respectively, as derived by x-ray diffraction from crystals. The specific columns in these Tables are defined as follows:

| Column | Description |
|---|---|
| 1 | Residue number (using numbering scheme of the Tables) |
| 2 | Residue name, using one-letter code (X = solvent) |
| 3 | Atom name, conventional PDB nomenclature (OW = solvent) |
| 4 | X-coordinate in orthogonal Ångstroms, multiplied by 10 |
| 5 | Y-coordinate in orthogonal Ångstroms, multiplied by 10 |
| 6 | Z-coordinate in orthogonal Ångstroms, multiplied by 10 |
| 7 | B-factor, in Å² |

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to utilize the invention in various embodiments and with various modifications as are suited to the particular use contemplated. It is intended that the scope of the invention be defined by the claims appended hereto.

TABLE 2

The following table contains one line for each atom in one HCV scNS3/NS4A monomer as well as solvent molecules. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor. The coordinates of the second monomer $(x_2, y_2, z_2)$ are related to the coordinates of the first monomer $(x_1, y_1, z_1)$ listed below according to the following operation:

$$x_2 = x_1 \cdot a_{11} + y_1 \cdot a_{12} + z_1 \cdot a_{13} + t_1$$
$$y_2 = x_1 \cdot a_{21} + y_1 \cdot a_{22} + z_1 \cdot a_{23} + t_2$$
$$z_2 = x_1 \cdot a_{31} + y_1 \cdot a_{32} + z_1 \cdot a_{33} + t_3 \quad 1 \text{ where}$$

| | | | |
|---|---|---|---|
| $a_{11}\ a_{12}\ a_{13} =$ | −0.9101 | −0.4141 | −0.0164 |
| $a_{21}\ a_{22}\ a_{23} =$ | −0.4141 | 0.9102 | −0.0043 |
| $a_{31}\ a_{32}\ a_{33} =$ | 0.0167 | 0.0029 | −0.9999 and |
| $t_1\ t_2\ t_3 =$ | 70.64 | 15.30 | 220.37 |

The noncrystallographic operation described above should only be applied to the HCV scNS3/NS4A protein atoms (residues 705 through 720 and residues 3 through 631). Following the protein atoms are listed all discrete solvent molecules (residue X, atom OH2), zinc ions (residue Z, atom ZN) and phosphate ions (residue P, atoms P, O1, O2, O3 and O4) which were modeled into the asymmetric unit.

| 705 | G | C | 303 | 871 | 1090 | 33 |
|---|---|---|---|---|---|---|
| 705 | G | O | 313 | 864 | 1089 | 33 |
| 705 | G | N | 299 | 870 | 1065 | 36 |
| 705 | G | CA | 293 | 873 | 1078 | 34 |
| 706 | S | N | 301 | 879 | 1101 | 29 |
| 706 | S | CA | 309 | 878 | 1112 | 27 |
| 706 | S | CB | 308 | 891 | 1120 | 25 |
| 706 | S | OG | 314 | 902 | 1113 | 24 |
| 706 | S | C | 304 | 867 | 1121 | 27 |
| 706 | S | O | 295 | 860 | 1117 | 33 |
| 707 | V | N | 311 | 864 | 1132 | 25 |
| 707 | V | CA | 308 | 854 | 1141 | 20 |
| 707 | V | CB | 321 | 848 | 1147 | 13 |
| 707 | V | CG1 | 318 | 841 | 1160 | 12 |
| 707 | V | CG2 | 326 | 838 | 1138 | 13 |
| 707 | V | C | 302 | 863 | 1152 | 22 |
| 707 | V | O | 307 | 874 | 1155 | 25 |
| 708 | V | N | 291 | 859 | 1158 | 24 |
| 708 | V | CA | 285 | 868 | 1168 | 23 |
| 708 | V | CB | 271 | 874 | 1163 | 26 |
| 708 | V | CG1 | 268 | 871 | 1148 | 19 |
| 708 | V | CG2 | 259 | 868 | 1172 | 26 |
| 708 | V | C | 283 | 860 | 1180 | 24 |
| 708 | V | O | 282 | 848 | 1181 | 27 |
| 709 | I | N | 284 | 868 | 1191 | 22 |
| 709 | I | CA | 282 | 862 | 1204 | 21 |
| 709 | I | CB | 290 | 870 | 1215 | 19 |

TABLE 2-continued

| | | | | | | |
|---|---|---|---|---|---|---|
| 709 | I | CG2 | 287 | 865 | 1229 | 17 |
| 709 | I | CG1 | 305 | 869 | 1212 | 13 |
| 709 | I | CD1 | 314 | 878 | 1220 | 8 |
| 709 | I | C | 267 | 862 | 1207 | 24 |
| 709 | I | O | 261 | 873 | 1207 | 28 |
| 710 | V | N | 262 | 851 | 1210 | 24 |
| 710 | V | CA | 248 | 849 | 1213 | 26 |
| 710 | V | CB | 242 | 838 | 1202 | 27 |
| 710 | V | CG1 | 243 | 844 | 1188 | 31 |
| 710 | V | CG2 | 250 | 825 | 1203 | 22 |
| 710 | V | C | 245 | 843 | 1227 | 23 |
| 710 | V | O | 233 | 841 | 1230 | 25 |
| 711 | G | N | 255 | 842 | 1235 | 24 |
| 711 | G | CA | 253 | 838 | 1249 | 24 |
| 711 | G | C | 266 | 835 | 1255 | 26 |
| 711 | G | O | 277 | 838 | 1249 | 23 |
| 712 | R | N | 266 | 830 | 1268 | 28 |
| 712 | R | CA | 279 | 828 | 1275 | 26 |
| 712 | R | CB | 284 | 841 | 1281 | 29 |
| 712 | R | CG | 275 | 849 | 1289 | 40 |
| 712 | R | CD | 281 | 861 | 1296 | 38 |
| 712 | R | NE | 278 | 873 | 1288 | 43 |
| 712 | R | CZ | 267 | 880 | 1289 | 47 |
| 712 | R | NH1 | 257 | 875 | 1296 | 42 |
| 712 | R | NH2 | 265 | 891 | 1282 | 45 |
| 712 | R | C | 277 | 818 | 1286 | 28 |
| 712 | R | O | 266 | 816 | 1291 | 27 |
| 713 | I | N | 288 | 812 | 1290 | 26 |
| 713 | I | CA | 288 | 802 | 1301 | 25 |
| 713 | I | CB | 296 | 789 | 1297 | 26 |
| 713 | I | CG2 | 293 | 778 | 1308 | 21 |
| 713 | I | CG1 | 291 | 784 | 1283 | 26 |
| 713 | I | CD1 | 277 | 779 | 1283 | 27 |
| 713 | I | C | 295 | 809 | 1312 | 31 |
| 713 | I | O | 307 | 813 | 1311 | 35 |
| 714 | I | N | 288 | 811 | 1323 | 29 |
| 714 | I | CA | 294 | 818 | 1335 | 30 |
| 714 | I | CB | 283 | 826 | 1342 | 34 |
| 714 | I | CG2 | 288 | 829 | 1357 | 27 |
| 714 | I | CG1 | 282 | 840 | 1335 | 37 |
| 714 | I | CD1 | 274 | 840 | 1323 | 44 |
| 714 | I | C | 299 | 807 | 1344 | 30 |
| 714 | I | O | 292 | 797 | 1347 | 32 |
| 715 | L | N | 311 | 808 | 1349 | 29 |
| 715 | L | CA | 317 | 798 | 1358 | 29 |
| 715 | L | CB | 331 | 795 | 1353 | 29 |
| 715 | L | CG | 331 | 789 | 1339 | 33 |
| 715 | L | CD1 | 343 | 794 | 1331 | 31 |
| 715 | L | CD2 | 331 | 774 | 1340 | 33 |
| 715 | L | C | 318 | 803 | 1372 | 30 |
| 715 | L | O | 318 | 814 | 1375 | 33 |
| 716 | S | N | 319 | 793 | 1381 | 28 |
| 716 | S | CA | 319 | 796 | 1395 | 31 |
| 716 | S | CB | 318 | 782 | 1403 | 27 |
| 716 | S | OG | 329 | 773 | 1401 | 34 |
| 716 | S | C | 333 | 803 | 1399 | 32 |
| 716 | S | O | 343 | 800 | 1393 | 34 |
| 717 | G | N | 332 | 811 | 1409 | 34 |
| 717 | G | CA | 344 | 819 | 1413 | 34 |
| 717 | G | C | 351 | 812 | 1425 | 37 |
| 717 | G | O | 362 | 816 | 1429 | 35 |
| 718 | S | N | 344 | 802 | 1431 | 39 |
| 718 | S | CA | 350 | 795 | 1442 | 42 |
| 718 | S | CB | 349 | 803 | 1455 | 50 |
| 718 | S | OG | 361 | 803 | 1463 | 59 |
| 718 | S | C | 344 | 781 | 1444 | 42 |
| 718 | S | O | 333 | 778 | 1439 | 42 |
| 719 | G | N | 350 | 773 | 1453 | 44 |
| 719 | G | CA | 344 | 760 | 1455 | 42 |
| 719 | G | C | 348 | 751 | 1443 | 46 |
| 719 | G | O | 357 | 754 | 1436 | 47 |
| 720 | S | N | 340 | 741 | 1441 | 43 |
| 720 | S | CA | 342 | 732 | 1430 | 44 |
| 720 | S | CB | 333 | 720 | 1431 | 42 |
| 720 | S | OG | 320 | 722 | 1426 | 47 |
| 720 | S | C | 338 | 740 | 1417 | 42 |
| 720 | S | O | 330 | 749 | 1418 | 42 |
| 3 | I | N | 343 | 736 | 1406 | 40 |
| 3 | I | CA | 340 | 743 | 1393 | 37 |
| 3 | I | CB | 350 | 740 | 1382 | 38 |
| 3 | I | CG2 | 345 | 745 | 1369 | 35 |
| 3 | I | CG1 | 364 | 746 | 1386 | 39 |
| 3 | I | CD1 | 376 | 738 | 1383 | 44 |
| 3 | I | C | 326 | 738 | 1388 | 34 |
| 3 | I | O | 324 | 727 | 1386 | 36 |
| 4 | T | N | 317 | 748 | 1388 | 31 |
| 4 | T | CA | 303 | 746 | 1383 | 28 |
| 4 | T | CB | 293 | 747 | 1394 | 30 |
| 4 | T | OG1 | 292 | 761 | 1399 | 26 |
| 4 | T | CG2 | 297 | 738 | 1406 | 34 |
| 4 | T | C | 301 | 757 | 1373 | 30 |
| 4 | T | O | 308 | 767 | 1372 | 30 |
| 5 | A | N | 290 | 756 | 1365 | 28 |
| 5 | A | CA | 287 | 766 | 1355 | 27 |
| 5 | A | CB | 296 | 763 | 1343 | 22 |
| 5 | A | C | 273 | 767 | 1350 | 25 |
| 5 | A | O | 265 | 757 | 1352 | 26 |
| 6 | Y | N | 269 | 778 | 1345 | 21 |
| 6 | Y | CA | 256 | 780 | 1340 | 21 |
| 6 | Y | CB | 246 | 786 | 1351 | 18 |
| 6 | Y | CG | 250 | 800 | 1355 | 19 |
| 6 | Y | CD1 | 245 | 811 | 1348 | 18 |
| 6 | Y | CE1 | 247 | 824 | 1352 | 19 |
| 6 | Y | CD2 | 258 | 803 | 1366 | 17 |
| 6 | Y | CE2 | 260 | 816 | 1370 | 13 |
| 6 | Y | CZ | 255 | 826 | 1363 | 18 |
| 6 | Y | OH | 257 | 839 | 1368 | 28 |
| 6 | Y | C | 256 | 789 | 1327 | 25 |
| 6 | Y | O | 265 | 797 | 1325 | 23 |
| 7 | S | N | 246 | 788 | 1319 | 27 |
| 7 | S | CA | 245 | 795 | 1307 | 26 |
| 7 | S | CB | 241 | 786 | 1295 | 30 |
| 7 | S | OG | 227 | 783 | 1296 | 40 |
| 7 | S | C | 236 | 808 | 1307 | 26 |
| 7 | S | O | 227 | 808 | 1315 | 26 |
| 8 | Q | N | 239 | 817 | 1298 | 27 |
| 8 | Q | CA | 231 | 829 | 1297 | 26 |
| 8 | Q | CB | 238 | 841 | 1303 | 26 |
| 8 | Q | CG | 239 | 840 | 1318 | 31 |
| 8 | Q | CD | 243 | 854 | 1324 | 41 |
| 8 | Q | OE1 | 248 | 862 | 1317 | 40 |
| 8 | Q | NE2 | 239 | 855 | 1337 | 45 |
| 8 | Q | C | 228 | 831 | 1282 | 26 |
| 8 | Q | O | 238 | 832 | 1275 | 29 |
| 9 | Q | N | 216 | 831 | 1278 | 25 |
| 9 | Q | CA | 213 | 833 | 1264 | 26 |
| 9 | Q | CB | 201 | 824 | 1260 | 26 |
| 9 | Q | CG | 203 | 818 | 1246 | 37 |
| 9 | Q | CD | 191 | 821 | 1237 | 39 |
| 9 | Q | OE1 | 186 | 812 | 1230 | 47 |
| 9 | Q | NE2 | 186 | 833 | 1238 | 45 |
| 9 | Q | C | 209 | 848 | 1261 | 28 |
| 9 | Q | O | 199 | 853 | 1265 | 34 |
| 10 | T | N | 219 | 855 | 1255 | 27 |
| 10 | T | CA | 218 | 869 | 1252 | 29 |
| 10 | T | CB | 231 | 876 | 1254 | 28 |
| 10 | T | OG1 | 240 | 872 | 1243 | 31 |
| 10 | T | CG2 | 237 | 872 | 1267 | 34 |
| 10 | T | C | 213 | 873 | 1238 | 30 |
| 10 | T | O | 210 | 885 | 1235 | 25 |
| 11 | R | N | 211 | 863 | 1230 | 30 |
| 11 | R | CA | 207 | 866 | 1216 | 34 |
| 11 | R | CB | 219 | 869 | 1207 | 35 |
| 11 | R | CG | 218 | 879 | 1197 | 29 |
| 11 | R | CD | 231 | 887 | 1194 | 32 |
| 11 | R | NE | 228 | 901 | 1192 | 38 |
| 11 | R | CZ | 237 | 910 | 1195 | 38 |
| 11 | R | NH1 | 248 | 907 | 1201 | 47 |
| 11 | R | NH2 | 234 | 923 | 1192 | 38 |
| 11 | R | C | 199 | 855 | 1210 | 36 |
| 11 | R | O | 201 | 844 | 1212 | 38 |
| 12 | G | N | 189 | 860 | 1202 | 36 |
| 12 | G | CA | 180 | 850 | 1195 | 34 |
| 12 | G | C | 184 | 849 | 1181 | 37 |
| 12 | G | O | 193 | 857 | 1176 | 40 |
| 13 | L | N | 178 | 841 | 1173 | 40 |
| 13 | L | CA | 181 | 839 | 1159 | 40 |
| 13 | L | CB | 172 | 828 | 1153 | 38 |

TABLE 2-continued

| | | | | | | |
|---|---|---|---|---|---|---|
| 13 | L | CG | 175 | 825 | 1138 | 40 |
| 13 | L | CD1 | 188 | 817 | 1136 | 39 |
| 13 | L | CD2 | 163 | 817 | 1132 | 35 |
| 13 | L | C | 181 | 851 | 1150 | 40 |
| 13 | L | O | 191 | 854 | 1144 | 39 |
| 14 | L | N | 171 | 859 | 1150 | 40 |
| 14 | L | CA | 170 | 871 | 1142 | 39 |
| 14 | L | CB | 156 | 877 | 1142 | 36 |
| 14 | L | CG | 156 | 891 | 1136 | 40 |
| 14 | L | CD1 | 156 | 891 | 1120 | 39 |
| 14 | L | CD2 | 144 | 898 | 1141 | 40 |
| 14 | L | C | 181 | 881 | 1146 | 39 |
| 14 | L | O | 186 | 888 | 1137 | 41 |
| 15 | G | N | 184 | 881 | 1159 | 38 |
| 15 | G | CA | 194 | 891 | 1163 | 36 |
| 15 | G | C | 208 | 886 | 1159 | 34 |
| 15 | G | O | 217 | 894 | 1156 | 33 |
| 16 | C | N | 210 | 873 | 1158 | 31 |
| 16 | C | CA | 223 | 868 | 1154 | 32 |
| 16 | C | CB | 224 | 853 | 1158 | 35 |
| 16 | C | SG | 237 | 844 | 1150 | 36 |
| 16 | C | C | 225 | 869 | 1139 | 34 |
| 16 | C | O | 236 | 873 | 1135 | 34 |
| 17 | I | N | 215 | 867 | 1130 | 35 |
| 17 | I | CA | 217 | 868 | 1116 | 36 |
| 17 | I | CB | 204 | 864 | 1108 | 39 |
| 17 | I | CG2 | 206 | 864 | 1093 | 29 |
| 17 | I | CG1 | 199 | 850 | 1113 | 38 |
| 17 | I | CD1 | 208 | 839 | 1110 | 39 |
| 17 | I | C | 220 | 883 | 1112 | 39 |
| 17 | I | O | 228 | 885 | 1103 | 40 |
| 18 | I | N | 213 | 892 | 1119 | 38 |
| 18 | I | CA | 215 | 906 | 1117 | 36 |
| 18 | I | CB | 205 | 914 | 1124 | 35 |
| 18 | I | CG2 | 210 | 929 | 1125 | 36 |
| 18 | I | CG1 | 192 | 915 | 1115 | 38 |
| 18 | I | CD1 | 179 | 915 | 1124 | 37 |
| 18 | I | C | 229 | 911 | 1121 | 36 |
| 18 | I | O | 236 | 917 | 1114 | 37 |
| 19 | T | N | 233 | 907 | 1133 | 36 |
| 19 | T | CA | 246 | 911 | 1139 | 36 |
| 19 | T | CB | 247 | 907 | 1153 | 35 |
| 19 | T | OG1 | 238 | 914 | 1162 | 29 |
| 19 | T | CG2 | 261 | 910 | 1158 | 32 |
| 19 | T | C | 257 | 905 | 1130 | 37 |
| 19 | T | O | 268 | 911 | 1129 | 36 |
| 20 | S | N | 254 | 893 | 1124 | 38 |
| 20 | S | CA | 264 | 886 | 1116 | 38 |
| 20 | S | CB | 259 | 872 | 1114 | 40 |
| 20 | S | OG | 266 | 866 | 1103 | 41 |
| 20 | S | C | 266 | 893 | 1103 | 38 |
| 20 | S | O | 277 | 893 | 1097 | 36 |
| 21 | L | N | 255 | 900 | 1098 | 42 |
| 21 | L | CA | 256 | 907 | 1086 | 40 |
| 21 | L | CB | 241 | 908 | 1081 | 44 |
| 21 | L | CG | 237 | 902 | 1067 | 48 |
| 21 | L | CD1 | 245 | 889 | 1065 | 48 |
| 21 | L | CD2 | 223 | 900 | 1068 | 44 |
| 21 | L | C | 262 | 921 | 1087 | 39 |
| 21 | L | O | 267 | 926 | 1077 | 39 |
| 22 | T | N | 261 | 927 | 1099 | 37 |
| 22 | T | CA | 267 | 940 | 1100 | 38 |
| 22 | T | CB | 257 | 949 | 1108 | 35 |
| 22 | T | OG1 | 255 | 944 | 1121 | 32 |
| 22 | T | CG2 | 244 | 950 | 1101 | 31 |
| 22 | T | C | 280 | 940 | 1108 | 41 |
| 22 | T | O | 287 | 950 | 1108 | 43 |
| 23 | G | N | 284 | 929 | 1114 | 41 |
| 23 | G | CA | 296 | 928 | 1121 | 41 |
| 23 | G | C | 296 | 938 | 1133 | 40 |
| 23 | G | O | 306 | 939 | 1140 | 38 |
| 24 | R | N | 285 | 945 | 1135 | 39 |
| 24 | R | CA | 284 | 955 | 1146 | 43 |
| 24 | R | CB | 279 | 969 | 1141 | 45 |
| 24 | R | CG | 283 | 980 | 1150 | 52 |
| 24 | R | CD | 277 | 993 | 1146 | 60 |
| 24 | R | NE | 282 | 1004 | 1154 | 67 |
| 24 | R | CZ | 293 | 1011 | 1151 | 69 |
| 24 | R | NH1 | 300 | 1008 | 1141 | 71 |
| 24 | R | NH2 | 297 | 1021 | 1159 | 72 |
| 24 | R | C | 276 | 950 | 1157 | 41 |
| 24 | R | O | 264 | 950 | 1157 | 47 |
| 25 | D | N | 282 | 946 | 1168 | 43 |
| 25 | D | CA | 275 | 941 | 1180 | 43 |
| 25 | D | CB | 278 | 927 | 1182 | 43 |
| 25 | D | CG | 273 | 922 | 1196 | 48 |
| 25 | D | OD1 | 278 | 911 | 1201 | 50 |
| 25 | D | OD2 | 265 | 929 | 1202 | 49 |
| 25 | D | C | 278 | 950 | 1192 | 47 |
| 25 | D | O | 289 | 949 | 1197 | 43 |
| 26 | K | N | 268 | 958 | 1196 | 49 |
| 26 | K | CA | 270 | 966 | 1208 | 52 |
| 26 | K | CB | 260 | 978 | 1206 | 54 |
| 26 | K | CG | 267 | 992 | 1204 | 54 |
| 26 | K | CD | 272 | 993 | 1190 | 58 |
| 26 | K | CE | 278 | 1007 | 1187 | 59 |
| 26 | K | NZ | 269 | 1015 | 1179 | 59 |
| 26 | K | C | 267 | 960 | 1221 | 54 |
| 26 | K | O | 274 | 964 | 1231 | 59 |
| 27 | N | N | 259 | 949 | 1222 | 52 |
| 27 | N | CA | 257 | 943 | 1235 | 53 |
| 27 | N | CB | 251 | 929 | 1234 | 47 |
| 27 | N | CG | 238 | 928 | 1228 | 48 |
| 27 | N | OD1 | 232 | 918 | 1225 | 50 |
| 27 | N | ND2 | 232 | 940 | 1225 | 48 |
| 27 | N | C | 270 | 942 | 1242 | 55 |
| 27 | N | O | 280 | 939 | 1236 | 57 |
| 28 | Q | N | 271 | 945 | 1255 | 56 |
| 28 | Q | CA | 283 | 945 | 1262 | 58 |
| 28 | Q | CB | 282 | 953 | 1275 | 63 |
| 28 | Q | CG | 270 | 950 | 1284 | 66 |
| 28 | Q | CD | 274 | 948 | 1298 | 68 |
| 28 | Q | OE1 | 286 | 950 | 1302 | 67 |
| 28 | Q | NE2 | 265 | 943 | 1306 | 68 |
| 28 | Q | C | 287 | 931 | 1266 | 55 |
| 28 | Q | O | 278 | 923 | 1270 | 54 |
| 29 | V | N | 299 | 927 | 1264 | 50 |
| 29 | V | CA | 303 | 913 | 1266 | 46 |
| 29 | V | CB | 316 | 908 | 1258 | 46 |
| 29 | V | CG1 | 318 | 918 | 1247 | 44 |
| 29 | V | CG2 | 328 | 907 | 1267 | 40 |
| 29 | V | C | 306 | 911 | 1281 | 45 |
| 29 | V | O | 309 | 920 | 1288 | 45 |
| 30 | E | N | 305 | 898 | 1286 | 44 |
| 30 | E | CA | 308 | 895 | 1299 | 41 |
| 30 | E | CB | 295 | 897 | 1308 | 47 |
| 30 | E | CG | 297 | 906 | 1320 | 56 |
| 30 | E | CD | 288 | 918 | 1319 | 58 |
| 30 | E | OE1 | 276 | 916 | 1317 | 61 |
| 30 | E | OE2 | 293 | 929 | 1320 | 60 |
| 30 | E | C | 313 | 881 | 1300 | 37 |
| 30 | E | O | 310 | 873 | 1292 | 33 |
| 31 | G | N | 320 | 878 | 1311 | 37 |
| 31 | G | CA | 325 | 864 | 1313 | 36 |
| 31 | G | C | 337 | 861 | 1304 | 38 |
| 31 | G | O | 342 | 870 | 1296 | 34 |
| 32 | E | N | 342 | 849 | 1304 | 36 |
| 32 | E | CA | 353 | 844 | 1296 | 38 |
| 32 | E | CB | 363 | 837 | 1305 | 41 |
| 32 | E | CG | 358 | 830 | 1317 | 51 |
| 32 | E | CD | 357 | 840 | 1329 | 55 |
| 32 | E | OE1 | 350 | 836 | 1339 | 56 |
| 32 | E | OE2 | 364 | 850 | 1329 | 57 |
| 32 | E | C | 348 | 835 | 1285 | 33 |
| 32 | E | O | 353 | 836 | 1273 | 32 |
| 33 | V | N | 340 | 825 | 1287 | 29 |
| 33 | V | CA | 335 | 816 | 1277 | 24 |
| 33 | V | CB | 331 | 803 | 1284 | 23 |
| 33 | V | CG1 | 329 | 792 | 1274 | 23 |
| 33 | V | CG2 | 342 | 799 | 1293 | 20 |
| 33 | V | C | 322 | 821 | 1270 | 24 |
| 33 | V | O | 312 | 822 | 1276 | 25 |
| 34 | Q | N | 324 | 825 | 1257 | 25 |
| 34 | Q | CA | 312 | 830 | 1250 | 20 |
| 34 | Q | CB | 317 | 841 | 1241 | 22 |
| 34 | Q | CG | 326 | 852 | 1247 | 26 |
| 34 | Q | CD | 319 | 859 | 1259 | 26 |
| 34 | Q | OE1 | 307 | 864 | 1257 | 26 |

TABLE 2-continued

| | | | | | | |
|---|---|---|---|---|---|---|
| 34 | Q | NE2 | 325 | 859 | 1271 | 26 |
| 34 | Q | C | 306 | 819 | 1241 | 24 |
| 34 | Q | O | 314 | 811 | 1236 | 25 |
| 35 | V | N | 293 | 820 | 1239 | 20 |
| 35 | V | CA | 287 | 810 | 1230 | 20 |
| 35 | V | CB | 273 | 806 | 1235 | 20 |
| 35 | V | CG1 | 268 | 795 | 1225 | 19 |
| 35 | V | CG2 | 274 | 801 | 1249 | 14 |
| 35 | V | C | 287 | 818 | 1217 | 24 |
| 35 | V | O | 282 | 830 | 1217 | 25 |
| 36 | V | N | 292 | 813 | 1206 | 25 |
| 36 | V | CA | 292 | 820 | 1194 | 20 |
| 36 | V | CB | 307 | 824 | 1190 | 23 |
| 36 | V | CG1 | 313 | 833 | 1200 | 18 |
| 36 | V | CG2 | 315 | 811 | 1188 | 19 |
| 36 | V | C | 286 | 812 | 1183 | 21 |
| 36 | V | O | 284 | 800 | 1184 | 22 |
| 37 | S | N | 282 | 819 | 1172 | 22 |
| 37 | S | CA | 276 | 812 | 1161 | 29 |
| 37 | S | CB | 261 | 809 | 1164 | 36 |
| 37 | S | OG | 253 | 815 | 1155 | 40 |
| 37 | S | C | 277 | 819 | 1148 | 26 |
| 37 | S | O | 279 | 832 | 1147 | 22 |
| 38 | T | N | 278 | 811 | 1137 | 29 |
| 38 | T | CA | 278 | 816 | 1123 | 33 |
| 38 | T | CB | 287 | 808 | 1114 | 33 |
| 38 | T | OG1 | 283 | 794 | 1116 | 37 |
| 38 | T | CG2 | 302 | 809 | 1117 | 29 |
| 38 | T | C | 264 | 815 | 1119 | 39 |
| 38 | T | O | 255 | 814 | 1128 | 42 |
| 39 | A | N | 261 | 815 | 1106 | 45 |
| 39 | A | CA | 247 | 813 | 1102 | 48 |
| 39 | A | CB | 245 | 821 | 1089 | 47 |
| 39 | A | C | 244 | 798 | 1099 | 49 |
| 39 | A | O | 234 | 795 | 1095 | 52 |
| 40 | T | N | 254 | 790 | 1102 | 46 |
| 40 | T | CA | 252 | 776 | 1101 | 45 |
| 40 | T | CB | 259 | 770 | 1088 | 51 |
| 40 | T | OG1 | 273 | 776 | 1087 | 54 |
| 40 | T | CG2 | 252 | 774 | 1076 | 50 |
| 40 | T | C | 257 | 768 | 1113 | 44 |
| 40 | T | O | 252 | 756 | 1115 | 47 |
| 41 | Q | N | 266 | 773 | 1120 | 38 |
| 41 | Q | CA | 270 | 765 | 1132 | 34 |
| 41 | Q | CB | 283 | 757 | 1129 | 38 |
| 41 | Q | CG | 295 | 765 | 1123 | 48 |
| 41 | Q | CD | 307 | 757 | 1121 | 52 |
| 41 | Q | OE1 | 308 | 745 | 1126 | 52 |
| 41 | Q | NE2 | 317 | 762 | 1113 | 49 |
| 41 | Q | C | 272 | 774 | 1145 | 27 |
| 41 | Q | O | 272 | 786 | 1145 | 23 |
| 42 | S | N | 272 | 766 | 1156 | 21 |
| 42 | S | CA | 274 | 773 | 1169 | 24 |
| 42 | S | CB | 261 | 773 | 1176 | 18 |
| 42 | S | OG | 262 | 780 | 1188 | 22 |
| 42 | S | C | 284 | 765 | 1176 | 23 |
| 42 | S | O | 285 | 752 | 1176 | 20 |
| 43 | F | N | 293 | 772 | 1183 | 18 |
| 43 | F | CA | 303 | 766 | 1191 | 18 |
| 43 | F | CB | 315 | 762 | 1182 | 13 |
| 43 | F | CG | 319 | 773 | 1172 | 15 |
| 43 | F | CD1 | 311 | 775 | 1161 | 14 |
| 43 | F | CD2 | 330 | 781 | 1174 | 12 |
| 43 | F | CE1 | 315 | 785 | 1151 | 15 |
| 43 | F | CE2 | 334 | 791 | 1165 | 12 |
| 43 | F | CZ | 327 | 793 | 1153 | 13 |
| 43 | F | C | 308 | 775 | 1202 | 22 |
| 43 | F | O | 301 | 785 | 1205 | 20 |
| 44 | L | N | 319 | 772 | 1208 | 19 |
| 44 | L | CA | 324 | 781 | 1219 | 21 |
| 44 | L | CB | 326 | 773 | 1232 | 14 |
| 44 | L | CG | 314 | 766 | 1238 | 21 |
| 44 | L | CD1 | 319 | 758 | 1250 | 7 |
| 44 | L | CD2 | 303 | 776 | 1242 | 12 |
| 44 | L | C | 336 | 789 | 1216 | 21 |
| 44 | L | O | 343 | 786 | 1206 | 25 |
| 45 | A | N | 339 | 800 | 1223 | 20 |
| 45 | A | CA | 350 | 808 | 1222 | 20 |
| 45 | A | CB | 347 | 821 | 1214 | 18 |
| 45 | A | C | 355 | 812 | 1236 | 23 |
| 45 | A | O | 346 | 816 | 1245 | 23 |
| 46 | T | N | 368 | 812 | 1238 | 17 |
| 46 | T | CA | 373 | 815 | 1252 | 22 |
| 46 | T | CB | 379 | 802 | 1258 | 20 |
| 46 | T | OG1 | 370 | 791 | 1258 | 20 |
| 46 | T | CG2 | 384 | 805 | 1272 | 25 |
| 46 | T | C | 383 | 826 | 1252 | 22 |
| 46 | T | O | 393 | 826 | 1245 | 26 |
| 47 | C | N | 381 | 836 | 1261 | 21 |
| 47 | C | CA | 390 | 847 | 1263 | 22 |
| 47 | C | CB | 383 | 859 | 1267 | 20 |
| 47 | C | SG | 370 | 864 | 1256 | 36 |
| 47 | C | C | 401 | 843 | 1272 | 26 |
| 47 | C | O | 399 | 842 | 1284 | 30 |
| 48 | V | N | 414 | 842 | 1267 | 25 |
| 48 | V | CA | 425 | 840 | 1276 | 25 |
| 48 | V | CB | 432 | 826 | 1273 | 22 |
| 48 | V | CG1 | 443 | 823 | 1283 | 26 |
| 48 | V | CG2 | 421 | 815 | 1274 | 25 |
| 48 | V | C | 436 | 850 | 1273 | 24 |
| 48 | V | O | 440 | 852 | 1261 | 19 |
| 49 | N | N | 440 | 857 | 1283 | 21 |
| 49 | N | CA | 450 | 868 | 1283 | 22 |
| 49 | N | CB | 464 | 862 | 1279 | 17 |
| 49 | N | CG | 470 | 854 | 1291 | 27 |
| 49 | N | OD1 | 464 | 853 | 1302 | 31 |
| 49 | N | ND2 | 482 | 848 | 1289 | 13 |
| 49 | N | C | 447 | 879 | 1273 | 21 |
| 49 | N | O | 456 | 884 | 1266 | 26 |
| 50 | G | N | 434 | 884 | 1273 | 24 |
| 50 | G | CA | 430 | 895 | 1264 | 25 |
| 50 | G | C | 426 | 891 | 1250 | 28 |
| 50 | G | O | 423 | 900 | 1242 | 25 |
| 51 | V | N | 427 | 879 | 1247 | 25 |
| 51 | V | CA | 424 | 874 | 1233 | 23 |
| 51 | V | CB | 436 | 868 | 1226 | 25 |
| 51 | V | CG1 | 432 | 863 | 1212 | 22 |
| 51 | V | CG2 | 447 | 878 | 1225 | 18 |
| 51 | V | C | 412 | 864 | 1234 | 23 |
| 51 | V | O | 412 | 856 | 1243 | 21 |
| 52 | C | N | 403 | 865 | 1225 | 23 |
| 52 | C | CA | 391 | 856 | 1224 | 23 |
| 52 | C | CB | 379 | 864 | 1219 | 26 |
| 52 | C | SG | 364 | 855 | 1220 | 38 |
| 52 | C | C | 395 | 845 | 1215 | 19 |
| 52 | C | O | 396 | 848 | 1203 | 18 |
| 53 | W | N | 397 | 833 | 1220 | 16 |
| 53 | W | CA | 401 | 822 | 1210 | 22 |
| 53 | W | CB | 413 | 814 | 1216 | 24 |
| 53 | W | CG | 424 | 822 | 1222 | 24 |
| 53 | W | CD2 | 437 | 825 | 1215 | 18 |
| 53 | W | CE2 | 445 | 831 | 1225 | 24 |
| 53 | W | CE3 | 442 | 822 | 1202 | 13 |
| 53 | W | CD1 | 426 | 827 | 1235 | 16 |
| 53 | W | NE1 | 438 | 832 | 1236 | 21 |
| 53 | W | CZ2 | 458 | 835 | 1221 | 22 |
| 53 | W | CZ3 | 454 | 826 | 1199 | 14 |
| 53 | W | CH2 | 463 | 833 | 1209 | 14 |
| 53 | W | C | 390 | 812 | 1207 | 22 |
| 53 | W | O | 380 | 812 | 1214 | 22 |
| 54 | T | N | 392 | 805 | 1196 | 25 |
| 54 | T | CA | 383 | 795 | 1192 | 24 |
| 54 | T | CB | 369 | 801 | 1187 | 21 |
| 54 | T | OG1 | 359 | 790 | 1186 | 21 |
| 54 | T | CG2 | 370 | 807 | 1174 | 20 |
| 54 | T | C | 389 | 787 | 1180 | 24 |
| 54 | T | O | 400 | 790 | 1175 | 21 |
| 55 | V | N | 382 | 776 | 1176 | 23 |
| 55 | V | CA | 387 | 767 | 1165 | 20 |
| 55 | V | CB | 379 | 754 | 1165 | 18 |
| 55 | V | CG1 | 385 | 744 | 1175 | 17 |
| 55 | V | CG2 | 364 | 756 | 1166 | 18 |
| 55 | V | C | 386 | 773 | 1151 | 22 |
| 55 | V | O | 376 | 780 | 1148 | 23 |
| 56 | Y | N | 395 | 769 | 1142 | 21 |
| 56 | Y | CA | 395 | 774 | 1128 | 16 |
| 56 | Y | CB | 408 | 772 | 1122 | 13 |
| 56 | Y | CG | 408 | 775 | 1107 | 11 |

TABLE 2-continued

| | | | | | | |
|---|---|---|---|---|---|---|
| 56 | Y | CD1 | 408 | 789 | 1103 | 16 |
| 56 | Y | CE1 | 408 | 792 | 1089 | 14 |
| 56 | Y | CD2 | 408 | 766 | 1097 | 15 |
| 56 | Y | CE2 | 407 | 769 | 1083 | 17 |
| 56 | Y | CZ | 407 | 782 | 1080 | 18 |
| 56 | Y | OH | 406 | 786 | 1066 | 15 |
| 56 | Y | C | 384 | 766 | 1121 | 20 |
| 56 | Y | O | 378 | 771 | 1112 | 20 |
| 57 | H | N | 382 | 753 | 1125 | 19 |
| 57 | H | CA | 372 | 745 | 1118 | 25 |
| 57 | H | CB | 374 | 730 | 1121 | 25 |
| 57 | H | CG | 369 | 726 | 1135 | 21 |
| 57 | H | CD2 | 376 | 723 | 1146 | 24 |
| 57 | H | ND1 | 356 | 725 | 1138 | 26 |
| 57 | H | CE1 | 355 | 721 | 1151 | 21 |
| 57 | H | NE2 | 367 | 720 | 1156 | 24 |
| 57 | H | C | 358 | 750 | 1122 | 27 |
| 57 | H | O | 348 | 745 | 1117 | 28 |
| 58 | G | N | 357 | 760 | 1130 | 29 |
| 58 | G | CA | 345 | 766 | 1134 | 24 |
| 58 | G | C | 343 | 780 | 1128 | 25 |
| 58 | G | O | 334 | 784 | 1121 | 25 |
| 59 | A | N | 353 | 789 | 1131 | 24 |
| 59 | A | CA | 353 | 803 | 1127 | 22 |
| 59 | A | CB | 360 | 811 | 1138 | 20 |
| 59 | A | C | 360 | 806 | 1113 | 25 |
| 59 | A | O | 357 | 817 | 1108 | 19 |
| 60 | G | N | 367 | 797 | 1108 | 22 |
| 60 | G | CA | 374 | 800 | 1095 | 19 |
| 60 | G | C | 382 | 813 | 1098 | 22 |
| 60 | G | O | 387 | 815 | 1109 | 17 |
| 61 | S | N | 383 | 822 | 1088 | 20 |
| 61 | S | CA | 389 | 834 | 1091 | 24 |
| 61 | S | CB | 399 | 838 | 1079 | 23 |
| 61 | S | OG | 408 | 827 | 1077 | 32 |
| 61 | S | C | 379 | 846 | 1092 | 20 |
| 61 | S | O | 382 | 857 | 1089 | 23 |
| 62 | K | N | 367 | 843 | 1098 | 20 |
| 62 | K | CA | 357 | 853 | 1100 | 20 |
| 62 | K | CB | 344 | 846 | 1103 | 19 |
| 62 | K | CG | 338 | 838 | 1092 | 19 |
| 62 | K | CD | 323 | 837 | 1093 | 28 |
| 62 | K | CE | 319 | 823 | 1091 | 25 |
| 62 | K | NZ | 320 | 819 | 1077 | 33 |
| 62 | K | C | 360 | 864 | 1110 | 18 |
| 62 | K | O | 367 | 861 | 1120 | 17 |
| 63 | T | N | 354 | 876 | 1108 | 18 |
| 63 | T | CA | 356 | 886 | 1118 | 17 |
| 63 | T | CB | 352 | 900 | 1112 | 15 |
| 63 | T | OG1 | 339 | 900 | 1107 | 14 |
| 63 | T | CG2 | 362 | 904 | 1100 | 14 |
| 63 | T | C | 346 | 883 | 1129 | 19 |
| 63 | T | O | 337 | 875 | 1127 | 21 |
| 64 | L | N | 348 | 890 | 1140 | 22 |
| 64 | L | CA | 340 | 889 | 1152 | 19 |
| 64 | L | CB | 349 | 887 | 1165 | 17 |
| 64 | L | CG | 344 | 881 | 1178 | 17 |
| 64 | L | CD1 | 350 | 888 | 1189 | 16 |
| 64 | L | CD2 | 329 | 880 | 1178 | 18 |
| 64 | L | C | 332 | 902 | 1153 | 22 |
| 64 | L | O | 338 | 912 | 1153 | 18 |
| 65 | A | N | 318 | 901 | 1154 | 21 |
| 65 | A | CA | 310 | 913 | 1155 | 19 |
| 65 | A | CB | 296 | 909 | 1155 | 23 |
| 65 | A | C | 314 | 920 | 1168 | 21 |
| 65 | A | O | 314 | 914 | 1179 | 22 |
| 66 | G | N | 317 | 933 | 1167 | 22 |
| 66 | G | CA | 320 | 941 | 1178 | 21 |
| 66 | G | C | 313 | 954 | 1179 | 22 |
| 66 | G | O | 306 | 958 | 1169 | 25 |
| 67 | P | N | 315 | 962 | 1189 | 22 |
| 67 | P | CD | 325 | 959 | 1200 | 21 |
| 67 | P | CA | 309 | 975 | 1191 | 26 |
| 67 | P | CB | 313 | 979 | 1205 | 25 |
| 67 | P | CG | 326 | 972 | 1207 | 30 |
| 67 | P | C | 313 | 986 | 1181 | 33 |
| 67 | P | O | 305 | 995 | 1178 | 35 |
| 68 | K | N | 325 | 985 | 1176 | 35 |
| 68 | K | CA | 329 | 995 | 1166 | 38 |
| 68 | K | CB | 343 | 1000 | 1169 | 38 |
| 68 | K | CG | 344 | 1015 | 1172 | 47 |
| 68 | K | CD | 338 | 1019 | 1185 | 54 |
| 68 | K | CE | 340 | 1035 | 1186 | 60 |
| 68 | K | NZ | 335 | 1040 | 1199 | 62 |
| 68 | K | C | 328 | 990 | 1152 | 38 |
| 68 | K | O | 332 | 997 | 1142 | 41 |
| 69 | G | N | 323 | 978 | 1151 | 36 |
| 69 | G | CA | 322 | 971 | 1138 | 31 |
| 69 | G | C | 330 | 958 | 1139 | 27 |
| 69 | G | O | 336 | 955 | 1150 | 27 |
| 70 | P | N | 331 | 950 | 1128 | 25 |
| 70 | P | CD | 325 | 954 | 1115 | 24 |
| 70 | P | CA | 338 | 937 | 1128 | 24 |
| 70 | P | CB | 337 | 933 | 1113 | 23 |
| 70 | P | CG | 331 | 945 | 1105 | 18 |
| 70 | P | C | 353 | 938 | 1132 | 26 |
| 70 | P | O | 360 | 946 | 1127 | 26 |
| 71 | I | N | 356 | 929 | 1141 | 29 |
| 71 | I | CA | 370 | 928 | 1146 | 25 |
| 71 | I | CB | 370 | 922 | 1161 | 26 |
| 71 | I | CG2 | 385 | 919 | 1165 | 21 |
| 71 | I | CG1 | 364 | 932 | 1170 | 23 |
| 71 | I | CD1 | 357 | 926 | 1182 | 31 |
| 71 | I | C | 377 | 917 | 1138 | 27 |
| 71 | I | O | 372 | 906 | 1136 | 30 |
| 72 | T | N | 389 | 921 | 1132 | 22 |
| 72 | T | CA | 396 | 911 | 1123 | 22 |
| 72 | T | CB | 405 | 917 | 1113 | 21 |
| 72 | T | OG1 | 415 | 925 | 1119 | 34 |
| 72 | T | CG2 | 398 | 925 | 1103 | 20 |
| 72 | T | C | 404 | 901 | 1132 | 17 |
| 72 | T | O | 407 | 905 | 1143 | 19 |
| 73 | Q | N | 406 | 889 | 1127 | 15 |
| 73 | Q | CA | 414 | 879 | 1135 | 17 |
| 73 | Q | CB | 414 | 866 | 1128 | 12 |
| 73 | Q | CG | 400 | 861 | 1125 | 15 |
| 73 | Q | CD | 400 | 846 | 1123 | 18 |
| 73 | Q | OE1 | 410 | 839 | 1122 | 21 |
| 73 | Q | NE2 | 388 | 840 | 1124 | 15 |
| 73 | Q | C | 428 | 884 | 1137 | 18 |
| 73 | Q | O | 435 | 888 | 1128 | 16 |
| 74 | M | N | 432 | 884 | 1150 | 25 |
| 74 | M | CA | 446 | 888 | 1153 | 28 |
| 74 | M | CB | 447 | 892 | 1167 | 26 |
| 74 | M | CG | 460 | 896 | 1172 | 33 |
| 74 | M | SD | 460 | 905 | 1187 | 44 |
| 74 | M | CE | 451 | 919 | 1182 | 51 |
| 74 | M | C | 455 | 876 | 1150 | 28 |
| 74 | M | O | 467 | 878 | 1145 | 26 |
| 75 | Y | N | 450 | 864 | 1152 | 25 |
| 75 | Y | CA | 458 | 852 | 1150 | 21 |
| 75 | Y | CB | 462 | 846 | 1163 | 22 |
| 75 | Y | CG | 470 | 855 | 1171 | 26 |
| 75 | Y | CD1 | 483 | 859 | 1167 | 25 |
| 75 | Y | CE1 | 491 | 868 | 1175 | 25 |
| 75 | Y | CD2 | 465 | 860 | 1184 | 20 |
| 75 | Y | CE2 | 473 | 869 | 1191 | 27 |
| 75 | Y | CZ | 486 | 873 | 1187 | 25 |
| 75 | Y | OH | 493 | 882 | 1195 | 28 |
| 75 | Y | C | 450 | 841 | 1142 | 23 |
| 75 | Y | O | 438 | 840 | 1144 | 21 |
| 76 | T | N | 457 | 834 | 1134 | 20 |
| 76 | T | CA | 451 | 823 | 1126 | 19 |
| 76 | T | CB | 446 | 829 | 1112 | 17 |
| 76 | T | OG1 | 437 | 840 | 1115 | 25 |
| 76 | T | CG2 | 439 | 819 | 1103 | 13 |
| 76 | T | C | 461 | 812 | 1123 | 19 |
| 76 | T | O | 468 | 812 | 1114 | 24 |
| 77 | N | N | 461 | 802 | 1132 | 22 |
| 77 | N | CA | 469 | 791 | 1130 | 23 |
| 77 | N | CB | 476 | 787 | 1143 | 26 |
| 77 | N | CG | 489 | 779 | 1141 | 29 |
| 77 | N | OD1 | 489 | 769 | 1134 | 28 |
| 77 | N | ND2 | 499 | 784 | 1148 | 30 |
| 77 | N | C | 461 | 779 | 1125 | 22 |
| 77 | N | O | 456 | 771 | 1133 | 26 |
| 78 | V | N | 461 | 777 | 1112 | 23 |
| 78 | V | CA | 453 | 766 | 1107 | 21 |

TABLE 2-continued

| | | | | | |
|---|---|---|---|---|---|
| 78 | V | CB | 452 | 766 | 1091 | 22 |
| 78 | V | CG1 | 446 | 753 | 1086 | 14 |
| 78 | V | CG2 | 444 | 778 | 1087 | 20 |
| 78 | V | C | 459 | 752 | 1111 | 25 |
| 78 | V | O | 452 | 743 | 1112 | 23 |
| 79 | D | N | 472 | 752 | 1114 | 23 |
| 79 | D | CA | 478 | 739 | 1118 | 24 |
| 79 | D | CB | 493 | 740 | 1117 | 26 |
| 79 | D | CG | 498 | 740 | 1102 | 33 |
| 79 | D | OD1 | 495 | 731 | 1095 | 36 |
| 79 | D | OD2 | 504 | 750 | 1098 | 40 |
| 79 | D | C | 474 | 735 | 1132 | 26 |
| 79 | D | O | 473 | 723 | 1135 | 22 |
| 80 | Q | N | 472 | 744 | 1141 | 24 |
| 80 | Q | CA | 467 | 741 | 1155 | 22 |
| 80 | Q | CB | 474 | 750 | 1165 | 26 |
| 80 | Q | CG | 488 | 752 | 1163 | 35 |
| 80 | Q | CD | 494 | 762 | 1172 | 38 |
| 80 | Q | OE1 | 506 | 765 | 1172 | 40 |
| 80 | Q | NE2 | 485 | 768 | 1180 | 29 |
| 80 | Q | C | 452 | 741 | 1156 | 20 |
| 80 | Q | O | 447 | 738 | 1167 | 23 |
| 81 | D | N | 446 | 746 | 1146 | 14 |
| 81 | D | CA | 432 | 748 | 1146 | 18 |
| 81 | D | CB | 425 | 734 | 1149 | 20 |
| 81 | D | CG | 411 | 733 | 1145 | 23 |
| 81 | D | OD1 | 404 | 723 | 1149 | 32 |
| 81 | D | OD2 | 407 | 742 | 1137 | 31 |
| 81 | D | C | 428 | 759 | 1156 | 20 |
| 81 | D | O | 418 | 758 | 1163 | 20 |
| 82 | L | N | 435 | 770 | 1156 | 20 |
| 82 | L | CA | 433 | 780 | 1165 | 22 |
| 82 | L | CB | 444 | 780 | 1176 | 28 |
| 82 | L | CG | 441 | 781 | 1191 | 37 |
| 82 | L | CD1 | 451 | 789 | 1199 | 40 |
| 82 | L | CD2 | 427 | 786 | 1193 | 41 |
| 82 | L | C | 433 | 794 | 1159 | 22 |
| 82 | L | O | 442 | 798 | 1152 | 20 |
| 83 | V | N | 422 | 802 | 1162 | 22 |
| 83 | V | CA | 422 | 816 | 1157 | 17 |
| 83 | V | CB | 410 | 818 | 1147 | 23 |
| 83 | V | CG1 | 413 | 811 | 1135 | 22 |
| 83 | V | CG2 | 397 | 815 | 1153 | 24 |
| 83 | V | C | 420 | 824 | 1170 | 19 |
| 83 | V | O | 415 | 820 | 1180 | 18 |
| 84 | G | N | 423 | 837 | 1169 | 20 |
| 84 | G | CA | 421 | 846 | 1180 | 19 |
| 84 | G | C | 418 | 860 | 1176 | 18 |
| 84 | G | O | 424 | 864 | 1166 | 18 |
| 85 | W | N | 410 | 867 | 1183 | 17 |
| 85 | W | CA | 406 | 881 | 1180 | 19 |
| 85 | W | CB | 391 | 883 | 1178 | 16 |
| 85 | W | CG | 385 | 876 | 1166 | 17 |
| 85 | W | CD2 | 377 | 863 | 1167 | 9 |
| 85 | W | CE2 | 372 | 861 | 1154 | 14 |
| 85 | W | CE3 | 374 | 854 | 1177 | 14 |
| 85 | W | CD1 | 384 | 880 | 1153 | 10 |
| 85 | W | NE1 | 377 | 871 | 1146 | 17 |
| 85 | W | CZ2 | 364 | 850 | 1151 | 14 |
| 85 | W | CZ3 | 366 | 843 | 1174 | 14 |
| 85 | W | CH2 | 361 | 841 | 1161 | 15 |
| 85 | W | C | 410 | 888 | 1193 | 22 |
| 85 | W | O | 409 | 882 | 1203 | 25 |
| 86 | Q | N | 413 | 901 | 1192 | 26 |
| 86 | Q | CA | 415 | 909 | 1203 | 30 |
| 86 | Q | CB | 420 | 923 | 1200 | 34 |
| 86 | Q | CG | 430 | 929 | 1210 | 45 |
| 86 | Q | CD | 435 | 942 | 1205 | 56 |
| 86 | Q | OE1 | 442 | 943 | 1195 | 63 |
| 86 | Q | NE2 | 432 | 952 | 1213 | 58 |
| 86 | Q | C | 402 | 910 | 1210 | 31 |
| 86 | Q | O | 392 | 915 | 1204 | 29 |
| 87 | A | N | 401 | 905 | 1223 | 30 |
| 87 | A | CA | 388 | 906 | 1230 | 34 |
| 87 | A | CB | 390 | 901 | 1244 | 31 |
| 87 | A | C | 381 | 920 | 1231 | 38 |
| 87 | A | O | 388 | 930 | 1233 | 37 |
| 88 | P | N | 368 | 920 | 1228 | 43 |
| 88 | P | CD | 359 | 909 | 1225 | 47 |
| 88 | P | CA | 361 | 933 | 1229 | 48 |
| 88 | P | CB | 347 | 930 | 1223 | 45 |
| 88 | P | CG | 348 | 916 | 1218 | 45 |
| 88 | P | C | 360 | 937 | 1243 | 51 |
| 88 | P | O | 361 | 929 | 1252 | 54 |
| 89 | P | N | 358 | 950 | 1246 | 53 |
| 89 | P | CD | 356 | 961 | 1236 | 51 |
| 89 | P | CA | 356 | 955 | 1259 | 53 |
| 89 | P | CB | 353 | 970 | 1257 | 53 |
| 89 | P | CG | 348 | 971 | 1243 | 53 |
| 89 | P | C | 346 | 947 | 1267 | 54 |
| 89 | P | O | 336 | 943 | 1261 | 51 |
| 90 | G | N | 347 | 945 | 1280 | 54 |
| 90 | G | CA | 337 | 938 | 1287 | 52 |
| 90 | G | C | 341 | 923 | 1289 | 53 |
| 90 | G | O | 335 | 916 | 1297 | 54 |
| 91 | A | N | 351 | 919 | 1281 | 55 |
| 91 | A | CA | 355 | 905 | 1281 | 53 |
| 91 | A | CB | 362 | 901 | 1268 | 52 |
| 91 | A | C | 364 | 902 | 1293 | 50 |
| 91 | A | O | 374 | 909 | 1294 | 54 |
| 92 | R | N | 361 | 893 | 1301 | 47 |
| 92 | R | CA | 369 | 889 | 1312 | 43 |
| 92 | R | CB | 360 | 883 | 1323 | 50 |
| 92 | R | CG | 347 | 889 | 1325 | 62 |
| 92 | R | CD | 348 | 903 | 1332 | 69 |
| 92 | R | NE | 356 | 902 | 1345 | 76 |
| 92 | R | CZ | 354 | 894 | 1355 | 81 |
| 92 | R | NH1 | 344 | 885 | 1354 | 81 |
| 92 | R | NH2 | 362 | 894 | 1365 | 85 |
| 92 | R | C | 377 | 878 | 1306 | 37 |
| 92 | R | O | 373 | 872 | 1296 | 36 |
| 93 | S | N | 389 | 875 | 1312 | 33 |
| 93 | S | CA | 398 | 865 | 1307 | 26 |
| 93 | S | CB | 411 | 872 | 1301 | 24 |
| 93 | S | OG | 410 | 876 | 1288 | 29 |
| 93 | S | C | 402 | 855 | 1317 | 27 |
| 93 | S | O | 402 | 858 | 1329 | 28 |
| 94 | L | N | 405 | 843 | 1312 | 24 |
| 94 | L | CA | 410 | 833 | 1321 | 22 |
| 94 | L | CB | 406 | 819 | 1315 | 24 |
| 94 | L | CG | 392 | 815 | 1314 | 23 |
| 94 | L | CD1 | 391 | 803 | 1305 | 22 |
| 94 | L | CD2 | 386 | 811 | 1328 | 17 |
| 94 | L | C | 425 | 835 | 1319 | 28 |
| 94 | L | O | 429 | 843 | 1310 | 28 |
| 95 | T | N | 433 | 829 | 1327 | 30 |
| 95 | T | CA | 448 | 830 | 1326 | 29 |
| 95 | T | CB | 453 | 839 | 1338 | 29 |
| 95 | T | OG1 | 451 | 831 | 1350 | 23 |
| 95 | T | CG2 | 446 | 852 | 1339 | 32 |
| 95 | T | C | 454 | 817 | 1326 | 28 |
| 95 | T | O | 448 | 807 | 1332 | 33 |
| 96 | P | N | 466 | 815 | 1321 | 29 |
| 96 | P | CD | 475 | 825 | 1314 | 31 |
| 96 | P | CA | 472 | 802 | 1322 | 29 |
| 96 | P | CB | 486 | 803 | 1315 | 28 |
| 96 | P | CG | 488 | 818 | 1315 | 29 |
| 96 | P | C | 473 | 795 | 1336 | 28 |
| 96 | P | O | 473 | 802 | 1346 | 24 |
| 97 | C | N | 473 | 782 | 1336 | 29 |
| 97 | C | CA | 474 | 774 | 1348 | 30 |
| 97 | C | CB | 468 | 760 | 1346 | 31 |
| 97 | C | SG | 475 | 747 | 1357 | 30 |
| 97 | C | C | 489 | 773 | 1352 | 32 |
| 97 | C | O | 497 | 770 | 1344 | 30 |
| 98 | T | N | 492 | 776 | 1365 | 32 |
| 98 | T | CA | 506 | 774 | 1370 | 32 |
| 98 | T | CB | 510 | 786 | 1378 | 31 |
| 98 | T | OG1 | 500 | 789 | 1388 | 33 |
| 98 | T | CG2 | 513 | 798 | 1370 | 28 |
| 98 | T | C | 508 | 762 | 1378 | 36 |
| 98 | T | O | 519 | 757 | 1379 | 38 |
| 99 | C | N | 497 | 756 | 1384 | 34 |
| 99 | C | CA | 498 | 745 | 1392 | 32 |
| 99 | C | CB | 485 | 742 | 1400 | 33 |
| 99 | C | SG | 472 | 734 | 1390 | 35 |
| 99 | C | C | 502 | 731 | 1386 | 35 |
| 99 | C | O | 507 | 722 | 1392 | 35 |

TABLE 2-continued

| | | | | | | |
|---|---|---|---|---|---|---|
| 100 | G | N | 501 | 730 | 1373 | 39 |
| 100 | G | CA | 504 | 718 | 1366 | 37 |
| 100 | G | C | 496 | 706 | 1370 | 39 |
| 100 | G | O | 501 | 695 | 1368 | 37 |
| 101 | S | N | 484 | 708 | 1374 | 38 |
| 101 | S | CA | 475 | 696 | 1378 | 39 |
| 101 | S | CB | 462 | 701 | 1384 | 43 |
| 101 | S | OG | 453 | 691 | 1387 | 42 |
| 101 | S | C | 472 | 687 | 1366 | 37 |
| 101 | S | O | 473 | 692 | 1354 | 39 |
| 102 | S | N | 469 | 675 | 1369 | 36 |
| 102 | S | CA | 466 | 665 | 1358 | 35 |
| 102 | S | CB | 473 | 652 | 1359 | 35 |
| 102 | S | OG | 484 | 652 | 1350 | 42 |
| 102 | S | C | 451 | 663 | 1358 | 35 |
| 102 | S | O | 445 | 656 | 1350 | 38 |
| 103 | D | N | 444 | 669 | 1368 | 29 |
| 103 | D | CA | 430 | 667 | 1370 | 29 |
| 103 | D | CB | 426 | 667 | 1385 | 34 |
| 103 | D | CG | 430 | 655 | 1392 | 37 |
| 103 | D | OD1 | 430 | 654 | 1404 | 43 |
| 103 | D | OD2 | 433 | 645 | 1384 | 39 |
| 103 | D | C | 423 | 679 | 1363 | 29 |
| 103 | D | O | 423 | 690 | 1368 | 24 |
| 104 | L | N | 418 | 677 | 1351 | 29 |
| 104 | L | CA | 412 | 687 | 1342 | 27 |
| 104 | L | CB | 417 | 685 | 1328 | 29 |
| 104 | L | CG | 430 | 692 | 1323 | 33 |
| 104 | L | CD1 | 440 | 695 | 1334 | 35 |
| 104 | L | CD2 | 436 | 683 | 1312 | 34 |
| 104 | L | C | 397 | 687 | 1342 | 24 |
| 104 | L | O | 390 | 678 | 1346 | 24 |
| 105 | Y | N | 391 | 698 | 1337 | 27 |
| 105 | Y | CA | 377 | 700 | 1336 | 27 |
| 105 | Y | CB | 372 | 708 | 1348 | 27 |
| 105 | Y | CG | 374 | 701 | 1361 | 30 |
| 105 | Y | CD1 | 366 | 690 | 1364 | 33 |
| 105 | Y | CE1 | 369 | 682 | 1375 | 37 |
| 105 | Y | CD2 | 386 | 703 | 1369 | 27 |
| 105 | Y | CE2 | 389 | 695 | 1380 | 30 |
| 105 | Y | CZ | 380 | 684 | 1383 | 38 |
| 105 | Y | OH | 384 | 675 | 1393 | 37 |
| 105 | Y | C | 373 | 707 | 1323 | 30 |
| 105 | Y | O | 377 | 718 | 1320 | 30 |
| 106 | L | N | 365 | 700 | 1315 | 26 |
| 106 | L | CA | 360 | 705 | 1302 | 26 |
| 106 | L | CB | 360 | 694 | 1291 | 27 |
| 106 | L | CG | 351 | 695 | 1279 | 28 |
| 106 | L | CD1 | 351 | 709 | 1273 | 32 |
| 106 | L | CD2 | 355 | 685 | 1269 | 24 |
| 106 | L | C | 346 | 712 | 1304 | 28 |
| 106 | L | O | 337 | 706 | 1309 | 27 |
| 107 | V | N | 345 | 724 | 1299 | 31 |
| 107 | V | CA | 332 | 732 | 1299 | 30 |
| 107 | V | CB | 335 | 747 | 1303 | 30 |
| 107 | V | CG1 | 322 | 754 | 1304 | 23 |
| 107 | V | CG2 | 342 | 747 | 1316 | 34 |
| 107 | V | C | 325 | 731 | 1286 | 29 |
| 107 | V | O | 331 | 735 | 1276 | 27 |
| 108 | T | N | 313 | 725 | 1285 | 28 |
| 108 | T | CA | 305 | 724 | 1273 | 27 |
| 108 | T | CB | 297 | 710 | 1274 | 28 |
| 108 | T | OG1 | 288 | 711 | 1285 | 31 |
| 108 | T | CG2 | 307 | 699 | 1276 | 18 |
| 108 | T | C | 295 | 735 | 1271 | 28 |
| 108 | T | O | 292 | 743 | 1280 | 29 |
| 109 | R | N | 290 | 736 | 1259 | 32 |
| 109 | R | CA | 280 | 746 | 1255 | 34 |
| 109 | R | CB | 276 | 745 | 1240 | 32 |
| 109 | R | CG | 268 | 733 | 1237 | 34 |
| 109 | R | CD | 263 | 735 | 1223 | 33 |
| 109 | R | NE | 270 | 744 | 1215 | 42 |
| 109 | R | CZ | 266 | 756 | 1211 | 43 |
| 109 | R | NH1 | 253 | 760 | 1214 | 45 |
| 109 | R | NH2 | 274 | 764 | 1205 | 50 |
| 109 | R | C | 268 | 745 | 1264 | 36 |
| 109 | R | O | 260 | 755 | 1265 | 35 |
| 110 | H | N | 265 | 734 | 1270 | 35 |
| 110 | H | CA | 254 | 732 | 1279 | 40 |
| 110 | H | CB | 248 | 718 | 1277 | 45 |
| 110 | H | CG | 243 | 715 | 1263 | 52 |
| 110 | H | CD2 | 232 | 720 | 1257 | 54 |
| 110 | H | ND1 | 250 | 707 | 1254 | 51 |
| 110 | H | CE1 | 243 | 707 | 1243 | 52 |
| 110 | H | NE2 | 233 | 715 | 1244 | 57 |
| 110 | H | C | 258 | 734 | 1293 | 39 |
| 110 | H | O | 251 | 729 | 1302 | 44 |
| 111 | A | N | 269 | 741 | 1295 | 34 |
| 111 | A | CA | 273 | 744 | 1309 | 30 |
| 111 | A | CB | 264 | 754 | 1316 | 26 |
| 111 | A | C | 275 | 731 | 1317 | 28 |
| 111 | A | O | 271 | 730 | 1329 | 27 |
| 112 | D | N | 280 | 721 | 1311 | 29 |
| 112 | D | CA | 283 | 708 | 1318 | 29 |
| 112 | D | CB | 280 | 696 | 1309 | 38 |
| 112 | D | CG | 265 | 693 | 1307 | 41 |
| 112 | D | OD1 | 258 | 693 | 1317 | 42 |
| 112 | D | OD2 | 261 | 691 | 1295 | 42 |
| 112 | D | C | 297 | 709 | 1321 | 31 |
| 112 | D | O | 305 | 714 | 1312 | 31 |
| 113 | V | N | 302 | 704 | 1332 | 32 |
| 113 | V | CA | 316 | 705 | 1336 | 30 |
| 113 | V | CB | 318 | 712 | 1349 | 27 |
| 113 | V | CG1 | 332 | 710 | 1354 | 25 |
| 113 | V | CG2 | 316 | 727 | 1347 | 22 |
| 113 | V | C | 321 | 690 | 1337 | 29 |
| 113 | V | O | 318 | 684 | 1347 | 32 |
| 114 | I | N | 327 | 685 | 1327 | 30 |
| 114 | I | CA | 332 | 671 | 1326 | 31 |
| 114 | I | CB | 331 | 666 | 1311 | 35 |
| 114 | I | CG2 | 336 | 652 | 1311 | 35 |
| 114 | I | CG1 | 317 | 667 | 1306 | 35 |
| 114 | I | CD1 | 306 | 664 | 1316 | 43 |
| 114 | I | C | 346 | 669 | 1330 | 31 |
| 114 | I | O | 355 | 677 | 1325 | 32 |
| 115 | P | N | 349 | 660 | 1339 | 25 |
| 115 | P | CD | 339 | 652 | 1346 | 24 |
| 115 | P | CA | 363 | 657 | 1344 | 25 |
| 115 | P | CB | 360 | 648 | 1356 | 24 |
| 115 | P | CG | 345 | 649 | 1359 | 28 |
| 115 | P | C | 371 | 650 | 1333 | 25 |
| 115 | P | O | 366 | 640 | 1327 | 21 |
| 116 | V | N | 383 | 654 | 1332 | 26 |
| 116 | V | CA | 392 | 648 | 1322 | 27 |
| 116 | V | CB | 394 | 657 | 1309 | 25 |
| 116 | V | CG1 | 405 | 652 | 1300 | 24 |
| 116 | V | CG2 | 381 | 658 | 1302 | 28 |
| 116 | V | C | 406 | 646 | 1328 | 27 |
| 116 | V | O | 410 | 654 | 1336 | 30 |
| 117 | R | N | 412 | 634 | 1325 | 29 |
| 117 | R | CA | 425 | 631 | 1331 | 29 |
| 117 | R | CB | 427 | 617 | 1334 | 29 |
| 117 | R | CG | 440 | 613 | 1339 | 27 |
| 117 | R | CD | 443 | 620 | 1352 | 34 |
| 117 | R | NE | 457 | 621 | 1355 | 45 |
| 117 | R | CZ | 462 | 623 | 1368 | 49 |
| 117 | R | NH1 | 453 | 624 | 1378 | 47 |
| 117 | R | NH2 | 475 | 625 | 1370 | 55 |
| 117 | R | C | 436 | 635 | 1320 | 27 |
| 117 | R | O | 436 | 630 | 1309 | 27 |
| 118 | R | N | 444 | 645 | 1323 | 27 |
| 118 | R | CA | 454 | 649 | 1314 | 32 |
| 118 | R | CB | 464 | 659 | 1320 | 35 |
| 118 | R | CG | 466 | 672 | 1312 | 36 |
| 118 | R | CD | 480 | 672 | 1305 | 33 |
| 118 | R | NE | 486 | 685 | 1306 | 45 |
| 118 | R | CZ | 488 | 693 | 1295 | 46 |
| 118 | R | NH1 | 483 | 690 | 1283 | 53 |
| 118 | R | NH2 | 494 | 705 | 1297 | 46 |
| 118 | R | C | 462 | 637 | 1310 | 36 |
| 118 | R | O | 464 | 628 | 1318 | 35 |
| 119 | R | N | 465 | 636 | 1297 | 41 |
| 119 | R | CA | 472 | 624 | 1292 | 45 |
| 119 | R | CB | 462 | 616 | 1284 | 48 |
| 119 | R | CG | 453 | 608 | 1292 | 51 |
| 119 | R | CD | 460 | 595 | 1296 | 57 |
| 119 | R | NE | 463 | 595 | 1311 | 61 |
| 119 | R | CZ | 455 | 590 | 1320 | 67 |

TABLE 2-continued

| | | | | | | |
|---|---|---|---|---|---|---|
| 119 | R | NH1 | 443 | 584 | 1316 | 66 |
| 119 | R | NH2 | 458 | 590 | 1332 | 68 |
| 119 | R | C | 484 | 628 | 1283 | 46 |
| 119 | R | O | 492 | 619 | 1279 | 49 |
| 120 | G | N | 485 | 640 | 1280 | 47 |
| 120 | G | CA | 497 | 645 | 1271 | 49 |
| 120 | G | C | 497 | 660 | 1272 | 51 |
| 120 | G | O | 493 | 666 | 1282 | 51 |
| 121 | D | N | 501 | 666 | 1261 | 51 |
| 121 | D | CA | 501 | 681 | 1261 | 50 |
| 121 | D | CB | 513 | 686 | 1252 | 55 |
| 121 | D | CG | 521 | 696 | 1259 | 64 |
| 121 | D | OD1 | 531 | 693 | 1266 | 67 |
| 121 | D | OD2 | 517 | 708 | 1258 | 65 |
| 121 | D | C | 489 | 687 | 1255 | 46 |
| 121 | D | O | 485 | 698 | 1258 | 42 |
| 122 | S | N | 482 | 679 | 1247 | 40 |
| 122 | S | CA | 470 | 683 | 1240 | 39 |
| 122 | S | CB | 474 | 685 | 1226 | 39 |
| 122 | S | OG | 483 | 675 | 1222 | 43 |
| 122 | S | C | 460 | 672 | 1240 | 36 |
| 122 | S | O | 450 | 672 | 1233 | 33 |
| 123 | R | N | 461 | 662 | 1250 | 33 |
| 123 | R | CA | 452 | 651 | 1250 | 34 |
| 123 | R | CB | 458 | 639 | 1243 | 33 |
| 123 | R | CG | 448 | 628 | 1241 | 40 |
| 123 | R | CD | 451 | 621 | 1228 | 43 |
| 123 | R | NE | 448 | 630 | 1217 | 47 |
| 123 | R | CZ | 447 | 625 | 1204 | 39 |
| 123 | R | NH1 | 448 | 612 | 1202 | 40 |
| 123 | R | NH2 | 444 | 633 | 1194 | 45 |
| 123 | R | C | 448 | 647 | 1265 | 33 |
| 123 | R | O | 456 | 647 | 1274 | 33 |
| 124 | G | N | 435 | 643 | 1266 | 31 |
| 124 | G | CA | 430 | 638 | 1279 | 31 |
| 124 | G | C | 420 | 628 | 1279 | 31 |
| 124 | G | O | 412 | 627 | 1269 | 31 |
| 125 | S | N | 419 | 619 | 1289 | 31 |
| 125 | S | CA | 409 | 609 | 1290 | 27 |
| 125 | S | CB | 415 | 596 | 1297 | 22 |
| 125 | S | OG | 426 | 591 | 1289 | 33 |
| 125 | S | C | 397 | 613 | 1297 | 26 |
| 125 | S | O | 398 | 619 | 1308 | 25 |
| 126 | L | N | 385 | 610 | 1292 | 26 |
| 126 | L | CA | 372 | 612 | 1298 | 29 |
| 126 | L | CB | 361 | 611 | 1287 | 30 |
| 126 | L | CG | 353 | 623 | 1283 | 33 |
| 126 | L | CD1 | 362 | 636 | 1283 | 29 |
| 126 | L | CD2 | 348 | 621 | 1269 | 35 |
| 126 | L | C | 370 | 602 | 1309 | 28 |
| 126 | L | O | 370 | 590 | 1306 | 34 |
| 127 | L | N | 368 | 606 | 1321 | 31 |
| 127 | L | CA | 366 | 596 | 1332 | 29 |
| 127 | L | CB | 364 | 603 | 1345 | 27 |
| 127 | L | CG | 377 | 606 | 1354 | 33 |
| 127 | L | CD1 | 389 | 609 | 1345 | 29 |
| 127 | L | CD2 | 374 | 617 | 1363 | 35 |
| 127 | L | C | 354 | 588 | 1328 | 32 |
| 127 | L | O | 353 | 576 | 1332 | 36 |
| 128 | S | N | 344 | 594 | 1321 | 31 |
| 128 | S | CA | 333 | 587 | 1316 | 27 |
| 128 | S | CB | 320 | 591 | 1324 | 19 |
| 128 | S | OG | 324 | 594 | 1337 | 24 |
| 128 | S | C | 330 | 589 | 1301 | 25 |
| 128 | S | O | 326 | 599 | 1297 | 28 |
| 129 | P | N | 333 | 578 | 1293 | 27 |
| 129 | P | CD | 338 | 565 | 1297 | 29 |
| 129 | P | CA | 331 | 580 | 1279 | 28 |
| 129 | P | CB | 334 | 566 | 1274 | 31 |
| 129 | P | CG | 343 | 560 | 1283 | 29 |
| 129 | P | C | 316 | 583 | 1276 | 35 |
| 129 | P | O | 307 | 579 | 1283 | 34 |
| 130 | R | N | 314 | 592 | 1266 | 38 |
| 130 | R | CA | 301 | 596 | 1262 | 40 |
| 130 | R | CB | 298 | 610 | 1267 | 45 |
| 130 | R | CG | 296 | 611 | 1282 | 54 |
| 130 | R | CD | 305 | 622 | 1288 | 60 |
| 130 | R | NE | 301 | 626 | 1301 | 59 |
| 130 | R | CZ | 309 | 627 | 1311 | 61 |
| 130 | R | NH1 | 322 | 624 | 1310 | 57 |
| 130 | R | NH2 | 304 | 632 | 1323 | 60 |
| 130 | R | C | 300 | 596 | 1247 | 37 |
| 130 | R | O | 310 | 597 | 1240 | 34 |
| 131 | P | N | 288 | 596 | 1241 | 35 |
| 131 | P | CD | 275 | 595 | 1249 | 32 |
| 131 | P | CA | 285 | 596 | 1227 | 33 |
| 131 | P | CB | 270 | 595 | 1226 | 33 |
| 131 | P | CG | 266 | 589 | 1239 | 29 |
| 131 | P | C | 290 | 609 | 1222 | 33 |
| 131 | P | O | 289 | 619 | 1228 | 34 |
| 132 | V | N | 296 | 609 | 1210 | 34 |
| 132 | V | CA | 302 | 622 | 1204 | 37 |
| 132 | V | CB | 308 | 620 | 1190 | 39 |
| 132 | V | CG1 | 320 | 629 | 1189 | 37 |
| 132 | V | CG2 | 312 | 606 | 1188 | 41 |
| 132 | V | C | 291 | 633 | 1203 | 35 |
| 132 | V | O | 295 | 645 | 1204 | 39 |
| 133 | S | N | 279 | 629 | 1201 | 30 |
| 133 | S | CA | 268 | 640 | 1200 | 32 |
| 133 | S | CB | 254 | 633 | 1200 | 33 |
| 133 | S | OG | 253 | 625 | 1211 | 33 |
| 133 | S | C | 268 | 649 | 1212 | 31 |
| 133 | S | O | 265 | 661 | 1211 | 35 |
| 134 | Y | N | 272 | 644 | 1224 | 31 |
| 134 | Y | CA | 273 | 652 | 1236 | 30 |
| 134 | Y | CB | 275 | 643 | 1248 | 39 |
| 134 | Y | CG | 276 | 649 | 1261 | 50 |
| 134 | Y | CD1 | 270 | 662 | 1264 | 57 |
| 134 | Y | CE1 | 271 | 668 | 1276 | 60 |
| 134 | Y | CD2 | 284 | 643 | 1271 | 56 |
| 134 | Y | CE2 | 285 | 650 | 1284 | 61 |
| 134 | Y | CZ | 278 | 662 | 1286 | 60 |
| 134 | Y | OH | 279 | 667 | 1298 | 67 |
| 134 | Y | C | 283 | 664 | 1236 | 30 |
| 134 | Y | O | 281 | 674 | 1242 | 22 |
| 135 | L | N | 294 | 661 | 1229 | 26 |
| 135 | L | CA | 305 | 671 | 1229 | 26 |
| 135 | L | CB | 318 | 664 | 1229 | 25 |
| 135 | L | CG | 321 | 656 | 1242 | 19 |
| 135 | L | CD1 | 334 | 648 | 1240 | 22 |
| 135 | L | CD2 | 323 | 667 | 1253 | 24 |
| 135 | L | C | 305 | 681 | 1217 | 23 |
| 135 | L | O | 312 | 691 | 1217 | 22 |
| 136 | K | N | 296 | 678 | 1207 | 25 |
| 136 | K | CA | 295 | 686 | 1195 | 28 |
| 136 | K | CB | 286 | 679 | 1185 | 35 |
| 136 | K | CG | 290 | 665 | 1182 | 46 |
| 136 | K | CD | 295 | 662 | 1168 | 48 |
| 136 | K | CE | 310 | 666 | 1166 | 58 |
| 136 | K | NZ | 312 | 675 | 1155 | 64 |
| 136 | K | C | 289 | 700 | 1199 | 30 |
| 136 | K | O | 279 | 700 | 1206 | 32 |
| 137 | G | N | 295 | 710 | 1194 | 28 |
| 137 | G | CA | 291 | 724 | 1197 | 22 |
| 137 | G | C | 299 | 729 | 1209 | 18 |
| 137 | G | O | 297 | 741 | 1213 | 17 |
| 138 | S | N | 309 | 721 | 1213 | 20 |
| 138 | S | CA | 317 | 725 | 1224 | 26 |
| 138 | S | CB | 318 | 714 | 1235 | 24 |
| 138 | S | OG | 305 | 713 | 1241 | 28 |
| 138 | S | C | 331 | 729 | 1220 | 25 |
| 138 | S | O | 340 | 732 | 1228 | 28 |
| 139 | S | N | 334 | 729 | 1207 | 24 |
| 139 | S | CA | 346 | 733 | 1201 | 25 |
| 139 | S | CB | 346 | 732 | 1186 | 21 |
| 139 | S | OG | 356 | 724 | 1181 | 33 |
| 139 | S | C | 349 | 747 | 1205 | 23 |
| 139 | S | O | 340 | 756 | 1205 | 15 |
| 140 | G | N | 361 | 750 | 1210 | 21 |
| 140 | G | CA | 364 | 764 | 1214 | 20 |
| 140 | G | C | 363 | 765 | 1229 | 20 |
| 140 | G | O | 366 | 775 | 1235 | 20 |
| 141 | G | N | 358 | 755 | 1236 | 16 |
| 141 | G | CA | 357 | 755 | 1250 | 20 |
| 141 | G | C | 370 | 753 | 1258 | 22 |
| 141 | G | O | 379 | 747 | 1253 | 17 |
| 142 | P | N | 370 | 758 | 1271 | 26 |
| 142 | P | CD | 360 | 765 | 1279 | 29 |

TABLE 2-continued

| | | | | | | |
|---|---|---|---|---|---|---|
| 142 | P | CA | 383 | 756 | 1278 | 29 |
| 142 | P | CB | 383 | 768 | 1288 | 27 |
| 142 | P | CG | 368 | 769 | 1291 | 29 |
| 142 | P | C | 384 | 743 | 1285 | 29 |
| 142 | P | O | 374 | 736 | 1288 | 27 |
| 143 | L | N | 397 | 739 | 1288 | 27 |
| 143 | L | CA | 400 | 728 | 1297 | 26 |
| 143 | L | CB | 411 | 719 | 1291 | 26 |
| 143 | L | CG | 407 | 705 | 1284 | 28 |
| 143 | L | CD1 | 401 | 696 | 1294 | 30 |
| 143 | L | CD2 | 397 | 708 | 1273 | 35 |
| 143 | L | C | 405 | 735 | 1309 | 24 |
| 143 | L | O | 415 | 742 | 1308 | 24 |
| 144 | L | N | 398 | 734 | 1320 | 27 |
| 144 | L | CA | 403 | 741 | 1332 | 26 |
| 144 | L | CB | 391 | 747 | 1339 | 27 |
| 144 | L | CG | 382 | 757 | 1331 | 30 |
| 144 | L | CD1 | 370 | 761 | 1340 | 29 |
| 144 | L | CD2 | 389 | 769 | 1327 | 26 |
| 144 | L | C | 410 | 732 | 1342 | 28 |
| 144 | L | O | 407 | 719 | 1342 | 29 |
| 145 | C | N | 418 | 737 | 1350 | 25 |
| 145 | C | CA | 425 | 730 | 1361 | 27 |
| 145 | C | CB | 439 | 735 | 1363 | 31 |
| 145 | C | SG | 440 | 750 | 1373 | 28 |
| 145 | C | C | 417 | 731 | 1374 | 28 |
| 145 | C | O | 408 | 740 | 1374 | 29 |
| 146 | P | N | 420 | 723 | 1384 | 30 |
| 146 | P | CD | 430 | 713 | 1386 | 31 |
| 146 | P | CA | 412 | 725 | 1396 | 29 |
| 146 | P | CB | 418 | 716 | 1406 | 25 |
| 146 | P | CG | 425 | 705 | 1398 | 27 |
| 146 | P | C | 410 | 740 | 1401 | 30 |
| 146 | P | O | 400 | 743 | 1407 | 32 |
| 147 | S | N | 420 | 748 | 1398 | 33 |
| 147 | S | CA | 420 | 762 | 1403 | 35 |
| 147 | S | CB | 434 | 767 | 1405 | 37 |
| 147 | S | OG | 442 | 758 | 1413 | 44 |
| 147 | S | C | 413 | 771 | 1393 | 35 |
| 147 | S | O | 412 | 783 | 1395 | 30 |
| 148 | G | N | 407 | 765 | 1383 | 34 |
| 148 | G | CA | 400 | 772 | 1373 | 28 |
| 148 | G | C | 408 | 780 | 1363 | 31 |
| 148 | G | O | 403 | 790 | 1357 | 31 |
| 149 | H | N | 420 | 776 | 1361 | 30 |
| 149 | H | CA | 429 | 783 | 1352 | 30 |
| 149 | H | CB | 443 | 785 | 1358 | 30 |
| 149 | H | CG | 443 | 797 | 1368 | 28 |
| 149 | H | CD2 | 445 | 797 | 1381 | 33 |
| 149 | H | ND1 | 439 | 809 | 1365 | 37 |
| 149 | H | CE1 | 439 | 817 | 1376 | 33 |
| 149 | H | NE2 | 443 | 809 | 1386 | 30 |
| 149 | H | C | 429 | 776 | 1339 | 25 |
| 149 | H | O | 427 | 764 | 1339 | 25 |
| 150 | A | N | 432 | 783 | 1328 | 23 |
| 150 | A | CA | 432 | 776 | 1315 | 24 |
| 150 | A | CB | 430 | 787 | 1304 | 21 |
| 150 | A | C | 443 | 767 | 1311 | 23 |
| 150 | A | O | 455 | 772 | 1312 | 26 |
| 151 | V | N | 440 | 755 | 1307 | 20 |
| 151 | V | CA | 450 | 745 | 1303 | 22 |
| 151 | V | CB | 446 | 732 | 1310 | 23 |
| 151 | V | CG1 | 455 | 721 | 1305 | 23 |
| 151 | V | CG2 | 446 | 733 | 1325 | 19 |
| 151 | V | C | 450 | 743 | 1288 | 21 |
| 151 | V | O | 461 | 740 | 1282 | 17 |
| 152 | G | N | 439 | 745 | 1281 | 18 |
| 152 | G | CA | 439 | 744 | 1266 | 20 |
| 152 | G | C | 425 | 746 | 1261 | 23 |
| 152 | G | O | 415 | 748 | 1269 | 24 |
| 153 | I | N | 423 | 747 | 1248 | 20 |
| 153 | I | CA | 410 | 749 | 1242 | 22 |
| 153 | I | CB | 408 | 761 | 1233 | 28 |
| 153 | I | CG2 | 414 | 774 | 1240 | 24 |
| 153 | I | CG1 | 415 | 759 | 1220 | 40 |
| 153 | I | CD1 | 408 | 768 | 1209 | 46 |
| 153 | I | C | 407 | 736 | 1235 | 22 |
| 153 | I | O | 414 | 731 | 1227 | 21 |
| 154 | F | N | 395 | 731 | 1238 | 20 |
| 154 | F | CA | 389 | 719 | 1232 | 18 |
| 154 | F | CB | 376 | 716 | 1239 | 19 |
| 154 | F | CG | 369 | 704 | 1235 | 18 |
| 154 | F | CD1 | 375 | 692 | 1234 | 21 |
| 154 | F | CD2 | 356 | 705 | 1231 | 25 |
| 154 | F | CE1 | 369 | 681 | 1229 | 29 |
| 154 | F | CE2 | 349 | 694 | 1226 | 27 |
| 154 | F | CZ | 355 | 682 | 1226 | 28 |
| 154 | F | C | 387 | 721 | 1217 | 20 |
| 154 | F | O | 383 | 731 | 1213 | 18 |
| 155 | R | N | 391 | 711 | 1209 | 19 |
| 155 | R | CA | 389 | 711 | 1195 | 17 |
| 155 | R | CB | 402 | 716 | 1188 | 21 |
| 155 | R | CG | 414 | 707 | 1188 | 22 |
| 155 | R | CD | 422 | 708 | 1175 | 18 |
| 155 | R | NE | 424 | 695 | 1170 | 27 |
| 155 | R | CZ | 419 | 690 | 1159 | 32 |
| 155 | R | NH1 | 411 | 697 | 1151 | 31 |
| 155 | R | NH2 | 423 | 678 | 1155 | 39 |
| 155 | R | C | 384 | 698 | 1189 | 19 |
| 155 | R | O | 379 | 698 | 1178 | 22 |
| 156 | A | N | 386 | 687 | 1196 | 16 |
| 156 | A | CA | 381 | 674 | 1190 | 21 |
| 156 | A | CB | 391 | 670 | 1178 | 16 |
| 156 | A | C | 381 | 663 | 1200 | 25 |
| 156 | A | O | 387 | 663 | 1210 | 27 |
| 157 | A | N | 373 | 653 | 1197 | 23 |
| 157 | A | CA | 371 | 641 | 1205 | 23 |
| 157 | A | CB | 355 | 638 | 1207 | 20 |
| 157 | A | C | 377 | 629 | 1198 | 21 |
| 157 | A | O | 377 | 628 | 1186 | 20 |
| 158 | V | N | 382 | 619 | 1206 | 22 |
| 158 | V | CA | 388 | 608 | 1201 | 22 |
| 158 | V | CB | 402 | 605 | 1207 | 20 |
| 158 | V | CG1 | 407 | 592 | 1202 | 21 |
| 158 | V | CG2 | 411 | 617 | 1204 | 29 |
| 158 | V | C | 378 | 597 | 1204 | 27 |
| 158 | V | O | 376 | 593 | 1216 | 28 |
| 159 | C | N | 372 | 591 | 1193 | 21 |
| 159 | C | CA | 362 | 581 | 1195 | 28 |
| 159 | C | CB | 350 | 585 | 1187 | 23 |
| 159 | C | SG | 343 | 601 | 1190 | 29 |
| 159 | C | C | 366 | 567 | 1191 | 30 |
| 159 | C | O | 376 | 564 | 1185 | 34 |
| 160 | T | N | 357 | 558 | 1196 | 29 |
| 160 | T | CA | 359 | 544 | 1194 | 30 |
| 160 | T | CB | 364 | 536 | 1206 | 30 |
| 160 | T | CG1 | 377 | 540 | 1209 | 32 |
| 160 | T | CG2 | 363 | 521 | 1204 | 22 |
| 160 | T | C | 344 | 540 | 1191 | 29 |
| 160 | T | O | 336 | 539 | 1200 | 31 |
| 161 | R | N | 342 | 538 | 1178 | 28 |
| 161 | R | CA | 328 | 534 | 1173 | 26 |
| 161 | R | CB | 325 | 520 | 1177 | 28 |
| 161 | R | CG | 329 | 509 | 1167 | 35 |
| 161 | R | CD | 331 | 495 | 1172 | 33 |
| 161 | R | NE | 340 | 494 | 1184 | 39 |
| 161 | R | CZ | 336 | 491 | 1196 | 39 |
| 161 | R | NH1 | 323 | 487 | 1197 | 40 |
| 161 | R | NH2 | 344 | 491 | 1206 | 37 |
| 161 | R | C | 318 | 544 | 1178 | 23 |
| 161 | R | O | 307 | 539 | 1183 | 22 |
| 162 | G | N | 320 | 556 | 1176 | 23 |
| 162 | G | CA | 311 | 567 | 1179 | 21 |
| 162 | G | C | 310 | 571 | 1194 | 29 |
| 162 | G | O | 304 | 581 | 1197 | 30 |
| 163 | V | N | 317 | 564 | 1203 | 27 |
| 163 | V | CA | 318 | 568 | 1217 | 29 |
| 163 | V | CB | 317 | 556 | 1227 | 33 |
| 163 | V | CG1 | 317 | 561 | 1241 | 29 |
| 163 | V | CG2 | 304 | 548 | 1224 | 31 |
| 163 | V | C | 331 | 576 | 1220 | 31 |
| 163 | V | o | 342 | 571 | 1216 | 32 |
| 164 | A | N | 330 | 587 | 1226 | 29 |
| 164 | A | CA | 343 | 595 | 1229 | 27 |
| 164 | A | CB | 340 | 610 | 1230 | 18 |
| 164 | A | C | 349 | 590 | 1242 | 30 |
| 164 | A | O | 342 | 588 | 1252 | 30 |
| 165 | K | N | 362 | 587 | 1241 | 29 |

TABLE 2-continued

| | | | | | | | | | | | | |
|---|---|---|---|---|---|---|---|---|---|---|---|---|
| 165 | K | CA | 369 | 582 | 1253 | 28 | 175 | M | SD | 451 | 786 | 1240 | 34 |
| 165 | K | CB | 376 | 569 | 1249 | 35 | 175 | M | CE | 444 | 802 | 1246 | 26 |
| 165 | K | CG | 385 | 570 | 1237 | 41 | 175 | M | C | 496 | 813 | 1232 | 29 |
| 165 | K | CD | 389 | 556 | 1232 | 47 | 175 | M | O | 497 | 824 | 1226 | 29 |
| 165 | K | CE | 405 | 555 | 1232 | 51 | 176 | E | N | 504 | 810 | 1243 | 31 |
| 165 | K | NZ | 409 | 541 | 1237 | 52 | 176 | E | CA | 513 | 820 | 1248 | 35 |
| 165 | K | C | 380 | 592 | 1257 | 28 | 176 | E | CB | 518 | 815 | 1262 | 39 |
| 165 | K | O | 385 | 592 | 1269 | 28 | 176 | E | CG | 511 | 820 | 1274 | 47 |
| 166 | A | N | 383 | 602 | 1248 | 24 | 176 | E | CD | 516 | 814 | 1287 | 57 |
| 166 | A | CA | 393 | 612 | 1251 | 23 | 176 | E | OE1 | 525 | 821 | 1293 | 63 |
| 166 | A | CB | 407 | 607 | 1249 | 24 | 176 | E | OE2 | 511 | 804 | 1291 | 60 |
| 166 | A | C | 390 | 624 | 1243 | 23 | 176 | E | C | 524 | 823 | 1238 | 37 |
| 166 | A | O | 382 | 624 | 1233 | 23 | 176 | E | O | 528 | 834 | 1237 | 40 |
| 167 | V | N | 397 | 635 | 1247 | 25 | 177 | T | N | 528 | 812 | 1232 | 35 |
| 167 | V | CA | 396 | 647 | 1240 | 20 | 177 | T | CA | 539 | 814 | 1222 | 35 |
| 167 | V | CB | 388 | 658 | 1248 | 23 | 177 | T | CB | 543 | 801 | 1216 | 35 |
| 167 | V | CG1 | 374 | 653 | 1252 | 17 | 177 | T | OG1 | 549 | 793 | 1226 | 39 |
| 167 | V | CG2 | 396 | 661 | 1261 | 21 | 177 | T | CG2 | 552 | 802 | 1204 | 36 |
| 167 | V | C | 410 | 653 | 1236 | 26 | 177 | T | C | 534 | 823 | 1210 | 37 |
| 167 | V | O | 420 | 651 | 1243 | 24 | 177 | T | O | 541 | 831 | 1205 | 38 |
| 168 | D | N | 409 | 661 | 1225 | 23 | 178 | T | N | 521 | 820 | 1206 | 36 |
| 168 | D | CA | 421 | 667 | 1220 | 24 | 178 | T | CA | 515 | 827 | 1196 | 31 |
| 168 | D | CB | 423 | 665 | 1205 | 26 | 178 | T | CB | 500 | 822 | 1193 | 30 |
| 168 | D | CG | 436 | 669 | 1200 | 34 | 178 | T | OG1 | 501 | 809 | 1187 | 33 |
| 168 | D | OD1 | 446 | 662 | 1202 | 37 | 178 | T | CG2 | 492 | 831 | 1184 | 26 |
| 168 | D | OD2 | 437 | 680 | 1193 | 34 | 178 | T | C | 514 | 842 | 1199 | 29 |
| 168 | D | C | 419 | 682 | 1222 | 24 | 178 | T | O | 515 | 850 | 1190 | 32 |
| 168 | D | O | 408 | 687 | 1221 | 25 | 179 | M | N | 512 | 845 | 1212 | 24 |
| 169 | F | N | 430 | 689 | 1226 | 20 | 179 | M | CA | 511 | 859 | 1216 | 27 |
| 169 | F | CA | 428 | 703 | 1228 | 20 | 179 | M | CB | 503 | 860 | 1229 | 21 |
| 169 | F | CB | 424 | 705 | 1243 | 17 | 179 | M | CG | 488 | 856 | 1227 | 23 |
| 169 | F | CG | 433 | 699 | 1253 | 24 | 179 | M | SD | 478 | 859 | 1241 | 29 |
| 169 | F | CD1 | 445 | 705 | 1257 | 20 | 179 | M | CE | 479 | 877 | 1242 | 31 |
| 169 | F | CD2 | 429 | 687 | 1259 | 18 | 179 | M | C | 524 | 865 | 1217 | 30 |
| 169 | F | CE1 | 453 | 700 | 1266 | 17 | 179 | M | O | 525 | 878 | 1217 | 33 |
| 169 | F | CE2 | 438 | 682 | 1269 | 21 | 180 | R | N | 535 | 857 | 1218 | 34 |
| 169 | F | CZ | 450 | 688 | 1273 | 19 | 180 | R | CA | 548 | 863 | 1219 | 38 |
| 169 | F | C | 441 | 710 | 1226 | 25 | 180 | R | CB | 557 | 854 | 1228 | 39 |
| 169 | F | O | 452 | 705 | 1227 | 27 | 180 | R | CG | 556 | 858 | 1242 | 44 |
| 170 | V | N | 440 | 723 | 1222 | 24 | 180 | R | CD | 564 | 849 | 1251 | 51 |
| 170 | V | CA | 452 | 731 | 1219 | 21 | 180 | R | NE | 556 | 838 | 1256 | 59 |
| 170 | V | CB | 448 | 744 | 1211 | 23 | 180 | R | CZ | 558 | 825 | 1253 | 64 |
| 170 | V | CG1 | 461 | 752 | 1208 | 20 | 180 | R | NH1 | 568 | 821 | 1246 | 67 |
| 170 | V | CG2 | 441 | 740 | 1199 | 22 | 180 | R | NH2 | 550 | 816 | 1259 | 66 |
| 170 | V | C | 458 | 735 | 1233 | 23 | 180 | R | C | 555 | 864 | 1205 | 38 |
| 170 | V | O | 451 | 742 | 1241 | 24 | 180 | R | O | 565 | 871 | 1203 | 43 |
| 171 | P | N | 470 | 732 | 1236 | 25 | 181 | S | N | 548 | 859 | 1195 | 33 |
| 171 | P | CD | 480 | 725 | 1227 | 21 | 181 | S | CA | 553 | 859 | 1181 | 30 |
| 171 | P | CA | 476 | 735 | 1249 | 24 | 181 | S | CB | 552 | 845 | 1175 | 27 |
| 171 | P | CB | 490 | 728 | 1249 | 24 | 181 | S | OG | 556 | 836 | 1185 | 33 |
| 171 | P | CG | 493 | 726 | 1235 | 25 | 181 | S | C | 547 | 870 | 1172 | 26 |
| 171 | P | C | 478 | 750 | 1250 | 26 | 181 | S | O | 537 | 876 | 1175 | 26 |
| 171 | P | O | 481 | 757 | 1241 | 27 | 182 | P | N | 553 | 872 | 1160 | 21 |
| 172 | V | N | 476 | 755 | 1263 | 27 | 182 | P | CD | 566 | 865 | 1156 | 19 |
| 172 | V | CA | 477 | 769 | 1266 | 30 | 182 | P | CA | 549 | 881 | 1150 | 20 |
| 172 | V | CB | 474 | 772 | 1281 | 30 | 182 | P | CB | 560 | 880 | 1139 | 14 |
| 172 | V | CG1 | 485 | 767 | 1290 | 25 | 182 | P | CG | 571 | 874 | 1146 | 18 |
| 172 | V | CG2 | 470 | 786 | 1282 | 29 | 182 | P | C | 535 | 878 | 1145 | 19 |
| 172 | V | C | 491 | 775 | 1262 | 32 | 182 | P | O | 531 | 867 | 1143 | 21 |
| 172 | V | O | 492 | 787 | 1259 | 33 | 183 | V | N | 528 | 889 | 1142 | 18 |
| 173 | E | N | 501 | 766 | 1263 | 31 | 183 | V | CA | 514 | 888 | 1137 | 21 |
| 173 | E | CA | 515 | 771 | 1260 | 30 | 183 | V | CB | 506 | 900 | 1142 | 27 |
| 173 | E | CB | 525 | 759 | 1263 | 39 | 183 | V | CG1 | 495 | 904 | 1132 | 15 |
| 173 | E | CG | 528 | 757 | 1277 | 48 | 183 | V | CG2 | 501 | 898 | 1157 | 17 |
| 173 | E | CD | 516 | 754 | 1286 | 56 | 183 | V | C | 515 | 888 | 1122 | 26 |
| 173 | E | OE1 | 507 | 746 | 1281 | 57 | 183 | V | O | 506 | 882 | 1115 | 27 |
| 173 | E | OE2 | 515 | 759 | 1298 | 57 | 184 | F | N | 525 | 894 | 1116 | 23 |
| 173 | E | C | 517 | 775 | 1246 | 30 | 184 | F | CA | 527 | 894 | 1102 | 17 |
| 173 | E | O | 524 | 785 | 1243 | 26 | 184 | F | CB | 526 | 908 | 1096 | 14 |
| 174 | S | N | 510 | 769 | 1237 | 29 | 184 | F | CG | 515 | 916 | 1101 | 14 |
| 174 | S | CA | 510 | 772 | 1223 | 28 | 184 | F | CD1 | 503 | 918 | 1093 | 24 |
| 174 | S | CB | 501 | 763 | 1215 | 25 | 184 | F | CD2 | 516 | 923 | 1113 | 18 |
| 174 | S | OG | 506 | 750 | 1213 | 27 | 184 | F | CE1 | 493 | 926 | 1098 | 29 |
| 174 | S | C | 505 | 787 | 1221 | 31 | 184 | F | CE2 | 506 | 931 | 1117 | 23 |
| 174 | S | O | 511 | 795 | 1214 | 32 | 184 | F | CZ | 494 | 933 | 1110 | 24 |
| 175 | M | N | 494 | 789 | 1227 | 26 | 184 | F | C | 540 | 887 | 1098 | 20 |
| 175 | M | CA | 487 | 802 | 1227 | 29 | 184 | F | O | 550 | 889 | 1104 | 19 |
| 175 | M | CB | 474 | 802 | 1235 | 25 | 185 | T | N | 540 | 878 | 1088 | 20 |
| 175 | M | CG | 464 | 793 | 1229 | 30 | 185 | T | CA | 552 | 871 | 1084 | 30 |

TABLE 2-continued

| | | | | | | |
|---|---|---|---|---|---|---|
| 185 | T | CB | 550 | 856 | 1086 | 35 |
| 185 | T | CG1 | 545 | 854 | 1099 | 44 |
| 185 | T | CG2 | 564 | 849 | 1085 | 41 |
| 185 | T | C | 554 | 873 | 1069 | 34 |
| 185 | T | O | 544 | 873 | 1061 | 33 |
| 186 | D | N | 566 | 874 | 1065 | 34 |
| 186 | D | CA | 569 | 876 | 1051 | 34 |
| 186 | D | CB | 582 | 885 | 1049 | 38 |
| 186 | D | CG | 583 | 890 | 1035 | 40 |
| 186 | D | OD1 | 595 | 892 | 1031 | 50 |
| 186 | D | OD2 | 573 | 893 | 1029 | 43 |
| 186 | D | C | 571 | 862 | 1044 | 32 |
| 186 | D | O | 579 | 854 | 1048 | 36 |
| 187 | N | N | 564 | 860 | 1033 | 32 |
| 187 | N | CA | 565 | 848 | 1025 | 31 |
| 187 | N | CB | 554 | 838 | 1029 | 32 |
| 187 | N | CG | 557 | 832 | 1043 | 34 |
| 187 | N | OD1 | 567 | 825 | 1045 | 31 |
| 187 | N | ND2 | 547 | 834 | 1052 | 29 |
| 187 | N | C | 562 | 852 | 1010 | 32 |
| 187 | N | O | 559 | 844 | 1002 | 35 |
| 188 | S | N | 563 | 865 | 1008 | 30 |
| 188 | S | CA | 561 | 870 | 994 | 31 |
| 188 | S | CB | 557 | 885 | 995 | 35 |
| 188 | S | OG | 563 | 891 | 1006 | 45 |
| 188 | S | C | 572 | 868 | 984 | 33 |
| 188 | S | O | 569 | 869 | 972 | 38 |
| 189 | S | N | 584 | 866 | 989 | 32 |
| 189 | S | CA | 595 | 865 | 979 | 35 |
| 189 | S | CB | 605 | 876 | 981 | 39 |
| 189 | S | OG | 598 | 888 | 980 | 45 |
| 189 | S | C | 602 | 851 | 978 | 36 |
| 189 | S | O | 603 | 844 | 989 | 34 |
| 190 | P | N | 606 | 847 | 966 | 36 |
| 190 | P | CD | 605 | 855 | 954 | 35 |
| 190 | P | CA | 613 | 835 | 965 | 36 |
| 190 | P | CB | 617 | 835 | 950 | 36 |
| 190 | P | CG | 607 | 844 | 944 | 33 |
| 190 | P | C | 626 | 835 | 974 | 37 |
| 190 | P | O | 634 | 844 | 974 | 34 |
| 191 | P | N | 627 | 824 | 982 | 37 |
| 191 | P | CD | 618 | 813 | 983 | 33 |
| 191 | P | CA | 638 | 823 | 991 | 38 |
| 191 | P | CB | 634 | 811 | 1000 | 37 |
| 191 | P | CG | 626 | 803 | 991 | 33 |
| 191 | P | C | 652 | 820 | 984 | 41 |
| 191 | P | O | 652 | 815 | 973 | 40 |
| 192 | A | N | 662 | 825 | 991 | 44 |
| 192 | A | CA | 676 | 823 | 985 | 40 |
| 192 | A | CB | 686 | 831 | 992 | 39 |
| 192 | A | C | 678 | 808 | 988 | 38 |
| 192 | A | O | 672 | 803 | 998 | 37 |
| 193 | V | N | 686 | 801 | 981 | 34 |
| 193 | V | CA | 689 | 787 | 983 | 36 |
| 193 | V | CB | 695 | 780 | 971 | 33 |
| 193 | V | CG1 | 694 | 765 | 973 | 33 |
| 193 | V | CG2 | 688 | 784 | 958 | 25 |
| 193 | V | C | 697 | 786 | 995 | 37 |
| 193 | V | O | 708 | 793 | 996 | 40 |
| 194 | P | N | 693 | 778 | 1005 | 40 |
| 194 | P | CD | 681 | 770 | 1006 | 40 |
| 194 | P | CA | 701 | 776 | 1017 | 41 |
| 194 | P | CB | 691 | 772 | 1027 | 39 |
| 194 | P | CG | 682 | 763 | 1019 | 35 |
| 194 | P | C | 712 | 767 | 1016 | 41 |
| 194 | P | O | 714 | 760 | 1006 | 42 |
| 195 | Q | N | 721 | 766 | 1026 | 40 |
| 195 | Q | CA | 732 | 757 | 1027 | 43 |
| 195 | Q | CB | 740 | 760 | 1040 | 49 |
| 195 | Q | CG | 754 | 754 | 1040 | 56 |
| 195 | Q | CD | 764 | 765 | 1037 | 63 |
| 195 | Q | OE1 | 774 | 767 | 1044 | 66 |
| 195 | Q | NE2 | 762 | 772 | 1025 | 63 |
| 195 | Q | C | 728 | 743 | 1028 | 40 |
| 195 | Q | O | 733 | 734 | 1021 | 41 |
| 196 | S | N | 718 | 740 | 1037 | 37 |
| 196 | S | CA | 713 | 727 | 1039 | 35 |
| 196 | S | CB | 715 | 722 | 1053 | 33 |
| 196 | S | OG | 713 | 733 | 1062 | 44 |
| 196 | S | C | 698 | 727 | 1036 | 33 |
| 196 | S | O | 692 | 738 | 1036 | 28 |
| 197 | F | N | 692 | 715 | 1034 | 33 |
| 197 | F | CA | 678 | 714 | 1031 | 30 |
| 197 | F | CB | 674 | 699 | 1032 | 29 |
| 197 | F | CG | 659 | 697 | 1029 | 28 |
| 197 | F | CD1 | 655 | 697 | 1016 | 25 |
| 197 | F | CD2 | 651 | 694 | 1040 | 28 |
| 197 | F | CE1 | 641 | 695 | 1013 | 32 |
| 197 | F | CE2 | 637 | 691 | 1037 | 29 |
| 197 | F | CZ | 632 | 692 | 1024 | 27 |
| 197 | F | C | 668 | 723 | 1039 | 31 |
| 197 | F | O | 668 | 722 | 1051 | 31 |
| 198 | Q | N | 660 | 730 | 1032 | 34 |
| 198 | Q | CA | 651 | 739 | 1039 | 35 |
| 198 | Q | CB | 656 | 753 | 1040 | 40 |
| 198 | Q | CG | 655 | 758 | 1055 | 54 |
| 198 | Q | CD | 667 | 754 | 1063 | 56 |
| 198 | Q | OE1 | 679 | 755 | 1060 | 59 |
| 198 | Q | NE2 | 663 | 748 | 1075 | 54 |
| 198 | Q | C | 637 | 738 | 1032 | 33 |
| 198 | Q | O | 637 | 738 | 1019 | 32 |
| 199 | V | N | 626 | 738 | 1039 | 33 |
| 199 | V | CA | 613 | 738 | 1033 | 28 |
| 199 | V | CB | 603 | 728 | 1040 | 29 |
| 199 | V | CG1 | 589 | 729 | 1034 | 32 |
| 199 | V | CG2 | 608 | 714 | 1040 | 21 |
| 199 | V | C | 608 | 752 | 1034 | 24 |
| 199 | V | O | 607 | 757 | 1045 | 25 |
| 200 | A | N | 604 | 759 | 1023 | 25 |
| 200 | A | CA | 599 | 772 | 1024 | 29 |
| 200 | A | CB | 610 | 782 | 1018 | 18 |
| 200 | A | C | 586 | 775 | 1018 | 27 |
| 200 | A | O | 581 | 768 | 1009 | 29 |
| 201 | H | N | 579 | 785 | 1022 | 29 |
| 201 | H | CA | 566 | 789 | 1017 | 28 |
| 201 | H | CB | 556 | 791 | 1029 | 19 |
| 201 | H | CG | 552 | 779 | 1036 | 22 |
| 201 | H | CD2 | 557 | 774 | 1048 | 21 |
| 201 | H | ND1 | 543 | 770 | 1032 | 24 |
| 201 | H | CE1 | 543 | 760 | 1040 | 27 |
| 201 | H | NE2 | 551 | 762 | 1050 | 26 |
| 201 | H | C | 567 | 801 | 1008 | 27 |
| 201 | H | O | 574 | 810 | 1010 | 27 |
| 202 | L | N | 559 | 800 | 997 | 28 |
| 202 | L | CA | 559 | 811 | 987 | 27 |
| 202 | L | CB | 566 | 807 | 974 | 26 |
| 202 | L | CG | 565 | 817 | 963 | 30 |
| 202 | L | CD1 | 570 | 831 | 968 | 32 |
| 202 | L | CD2 | 573 | 813 | 950 | 26 |
| 202 | L | C | 545 | 814 | 984 | 29 |
| 202 | L | O | 538 | 807 | 978 | 32 |
| 203 | H | N | 540 | 826 | 989 | 29 |
| 203 | H | CA | 526 | 830 | 987 | 31 |
| 203 | R | CB | 519 | 833 | 1000 | 34 |
| 203 | H | CG | 520 | 821 | 1010 | 32 |
| 203 | H | CD2 | 524 | 808 | 1008 | 28 |
| 203 | H | ND1 | 518 | 822 | 1023 | 34 |
| 203 | R | CE1 | 520 | 811 | 1029 | 24 |
| 203 | H | NE2 | 524 | 802 | 1020 | 27 |
| 203 | H | C | 527 | 843 | 978 | 31 |
| 203 | H | O | 529 | 854 | 983 | 32 |
| 204 | A | N | 524 | 841 | 966 | 34 |
| 204 | A | CA | 524 | 852 | 956 | 34 |
| 204 | A | CB | 537 | 853 | 949 | 32 |
| 204 | A | C | 513 | 851 | 947 | 32 |
| 204 | A | O | 509 | 840 | 942 | 32 |
| 205 | P | N | 507 | 863 | 943 | 34 |
| 205 | P | CD | 511 | 876 | 947 | 34 |
| 205 | P | CA | 496 | 863 | 933 | 36 |
| 205 | P | CB | 494 | 878 | 930 | 32 |
| 205 | P | CG | 505 | 885 | 937 | 34 |
| 205 | P | C | 499 | 855 | 921 | 40 |
| 205 | P | O | 510 | 851 | 918 | 44 |
| 206 | T | N | 488 | 853 | 913 | 42 |
| 206 | T | CA | 490 | 846 | 900 | 46 |
| 206 | T | CB | 476 | 842 | 894 | 50 |
| 206 | T | OG1 | 468 | 836 | 904 | 50 |
| 206 | T | CG2 | 478 | 832 | 883 | 47 |

TABLE 2-continued

| | | | | | | |
|---|---|---|---|---|---|---|
| 206 | T | C | 496 | 856 | 891 | 47 |
| 206 | T | O | 494 | 868 | 892 | 47 |
| 207 | G | N | 503 | 851 | 881 | 51 |
| 207 | G | CA | 510 | 860 | 871 | 51 |
| 207 | G | C | 521 | 867 | 879 | 51 |
| 207 | G | O | 524 | 879 | 878 | 52 |
| 208 | S | N | 529 | 859 | 886 | 49 |
| 208 | S | CA | 540 | 864 | 894 | 46 |
| 208 | S | CB | 538 | 863 | 909 | 48 |
| 208 | S | OG | 527 | 871 | 912 | 52 |
| 208 | S | C | 552 | 856 | 890 | 45 |
| 208 | S | O | 563 | 857 | 895 | 45 |
| 209 | G | N | 550 | 847 | 880 | 43 |
| 209 | G | CA | 561 | 839 | 875 | 42 |
| 209 | G | C | 566 | 829 | 886 | 38 |
| 209 | G | O | 577 | 824 | 885 | 39 |
| 210 | K | N | 557 | 825 | 895 | 41 |
| 210 | K | CA | 559 | 816 | 905 | 39 |
| 210 | K | CB | 546 | 814 | 913 | 39 |
| 210 | K | CG | 547 | 815 | 928 | 40 |
| 210 | K | CD | 534 | 818 | 935 | 43 |
| 210 | K | CE | 523 | 809 | 929 | 42 |
| 210 | K | NZ | 511 | 817 | 924 | 39 |
| 210 | K | C | 563 | 803 | 899 | 36 |
| 210 | K | O | 571 | 795 | 903 | 34 |
| 211 | S | N | 556 | 800 | 887 | 37 |
| 211 | S | CA | 558 | 788 | 879 | 38 |
| 211 | S | CB | 545 | 783 | 875 | 41 |
| 211 | S | OG | 543 | 769 | 878 | 47 |
| 211 | S | C | 567 | 791 | 868 | 33 |
| 211 | S | O | 571 | 781 | 861 | 29 |
| 212 | T | N | 570 | 803 | 865 | 34 |
| 212 | T | CA | 579 | 806 | 853 | 36 |
| 212 | T | CB | 571 | 814 | 842 | 33 |
| 212 | T | OG1 | 562 | 824 | 848 | 41 |
| 212 | T | CG2 | 562 | 804 | 835 | 31 |
| 212 | T | C | 591 | 814 | 857 | 34 |
| 212 | T | O | 602 | 810 | 855 | 35 |
| 213 | K | N | 589 | 827 | 861 | 35 |
| 213 | K | CA | 600 | 835 | 865 | 38 |
| 213 | K | CB | 595 | 849 | 869 | 34 |
| 213 | K | CG | 601 | 860 | 860 | 41 |
| 213 | K | CD | 607 | 871 | 869 | 45 |
| 213 | K | CE | 596 | 878 | 878 | 43 |
| 213 | K | NZ | 602 | 889 | 886 | 42 |
| 213 | K | C | 609 | 830 | 877 | 38 |
| 213 | K | O | 621 | 829 | 875 | 42 |
| 214 | V | N | 603 | 826 | 888 | 35 |
| 214 | V | CA | 612 | 822 | 899 | 37 |
| 214 | V | CB | 605 | 820 | 913 | 33 |
| 214 | V | CG1 | 592 | 827 | 912 | 35 |
| 214 | V | CG2 | 604 | 806 | 916 | 36 |
| 214 | V | C | 621 | 809 | 895 | 38 |
| 214 | V | O | 632 | 809 | 898 | 40 |
| 215 | P | N | 615 | 799 | 888 | 38 |
| 215 | P | CD | 600 | 798 | 884 | 41 |
| 215 | P | CA | 623 | 788 | 884 | 38 |
| 215 | P | CB | 613 | 779 | 877 | 36 |
| 215 | P | CG | 600 | 783 | 880 | 40 |
| 215 | P | C | 634 | 792 | 875 | 36 |
| 215 | P | O | 646 | 788 | 877 | 34 |
| 216 | A | N | 631 | 801 | 866 | 37 |
| 216 | A | CA | 641 | 806 | 856 | 41 |
| 216 | A | CB | 634 | 816 | 847 | 41 |
| 216 | A | C | 653 | 813 | 863 | 44 |
| 216 | A | O | 665 | 811 | 860 | 42 |
| 217 | A | N | 650 | 822 | 873 | 46 |
| 217 | A | CA | 660 | 829 | 880 | 43 |
| 217 | A | CB | 654 | 838 | 890 | 43 |
| 217 | A | C | 669 | 819 | 888 | 43 |
| 217 | A | O | 681 | 820 | 887 | 45 |
| 218 | Y | N | 663 | 809 | 894 | 44 |
| 218 | Y | CA | 671 | 799 | 901 | 43 |
| 218 | Y | CB | 663 | 789 | 909 | 43 |
| 218 | Y | CG | 656 | 794 | 921 | 50 |
| 218 | Y | CD1 | 663 | 799 | 932 | 47 |
| 218 | Y | CE1 | 656 | 803 | 944 | 46 |
| 218 | Y | CD2 | 642 | 794 | 922 | 49 |
| 218 | Y | CE2 | 635 | 797 | 934 | 47 |
| 218 | Y | CZ | 643 | 802 | 945 | 48 |
| 218 | Y | OH | 636 | 805 | 956 | 48 |
| 218 | Y | C | 680 | 791 | 892 | 41 |
| 218 | Y | O | 692 | 789 | 895 | 43 |
| 219 | A | N | 675 | 788 | 880 | 41 |
| 219 | A | CA | 683 | 780 | 870 | 44 |
| 219 | A | CB | 674 | 775 | 859 | 38 |
| 219 | A | C | 694 | 789 | 865 | 43 |
| 219 | A | O | 705 | 785 | 862 | 43 |
| 220 | A | N | 691 | 802 | 864 | 43 |
| 220 | A | CA | 700 | 812 | 859 | 46 |
| 220 | A | CB | 692 | 825 | 855 | 45 |
| 220 | A | C | 710 | 816 | 870 | 49 |
| 220 | A | O | 716 | 826 | 870 | 56 |
| 221 | Q | N | 711 | 806 | 880 | 51 |
| 221 | Q | CA | 720 | 808 | 891 | 47 |
| 221 | Q | CB | 713 | 810 | 904 | 50 |
| 221 | Q | CG | 708 | 823 | 907 | 53 |
| 221 | Q | CD | 702 | 824 | 921 | 60 |
| 221 | Q | OE1 | 708 | 819 | 930 | 59 |
| 221 | Q | NE2 | 690 | 830 | 922 | 65 |
| 221 | Q | C | 728 | 795 | 892 | 44 |
| 221 | Q | O | 736 | 793 | 900 | 46 |
| 222 | G | N | 725 | 786 | 882 | 42 |
| 222 | G | CA | 731 | 774 | 882 | 43 |
| 222 | G | C | 725 | 762 | 890 | 43 |
| 222 | G | O | 733 | 753 | 893 | 48 |
| 223 | Y | N | 712 | 763 | 893 | 41 |
| 223 | Y | CA | 707 | 752 | 901 | 37 |
| 223 | Y | CB | 699 | 757 | 912 | 37 |
| 223 | Y | CG | 707 | 764 | 923 | 35 |
| 223 | Y | CD1 | 714 | 757 | 933 | 34 |
| 223 | Y | CE1 | 721 | 763 | 943 | 33 |
| 223 | Y | CD2 | 707 | 778 | 924 | 36 |
| 223 | Y | CE2 | 714 | 784 | 935 | 36 |
| 223 | Y | CZ | 721 | 777 | 944 | 38 |
| 223 | Y | OH | 727 | 783 | 954 | 39 |
| 223 | Y | C | 697 | 743 | 892 | 34 |
| 223 | Y | O | 692 | 749 | 882 | 32 |
| 224 | K | N | 697 | 730 | 895 | 34 |
| 224 | K | CA | 688 | 721 | 887 | 35 |
| 224 | K | CB | 693 | 707 | 889 | 40 |
| 224 | K | CG | 708 | 705 | 885 | 44 |
| 224 | K | CD | 716 | 702 | 898 | 50 |
| 224 | K | CE | 716 | 687 | 902 | 51 |
| 224 | K | NZ | 728 | 680 | 898 | 46 |
| 224 | K | C | 674 | 722 | 894 | 37 |
| 224 | K | O | 673 | 717 | 905 | 36 |
| 225 | V | N | 665 | 729 | 888 | 34 |
| 225 | V | CA | 651 | 730 | 894 | 33 |
| 225 | V | CB | 648 | 745 | 896 | 34 |
| 225 | V | CG1 | 653 | 753 | 885 | 39 |
| 225 | V | CG2 | 633 | 747 | 898 | 30 |
| 225 | V | C | 640 | 723 | 888 | 33 |
| 225 | V | O | 637 | 724 | 875 | 30 |
| 226 | L | N | 632 | 715 | 896 | 28 |
| 226 | L | CA | 620 | 708 | 892 | 26 |
| 226 | L | CB | 621 | 694 | 898 | 23 |
| 226 | L | CG | 608 | 686 | 897 | 22 |
| 226 | L | CD1 | 606 | 681 | 882 | 15 |
| 226 | L | CD2 | 609 | 674 | 906 | 11 |
| 226 | L | C | 608 | 715 | 897 | 25 |
| 226 | L | O | 606 | 718 | 908 | 26 |
| 227 | V | N | 599 | 718 | 887 | 25 |
| 227 | V | CA | 586 | 725 | 890 | 22 |
| 227 | V | CB | 584 | 737 | 881 | 23 |
| 227 | V | CG1 | 572 | 745 | 885 | 22 |
| 227 | V | CG2 | 597 | 745 | 882 | 22 |
| 227 | V | C | 574 | 715 | 889 | 25 |
| 227 | V | O | 571 | 710 | 878 | 22 |
| 228 | L | N | 567 | 713 | 900 | 18 |
| 228 | L | CA | 555 | 704 | 900 | 21 |
| 228 | L | CB | 556 | 694 | 912 | 14 |
| 228 | L | CG | 567 | 684 | 913 | 13 |
| 228 | L | CD1 | 565 | 677 | 926 | 13 |
| 228 | L | CD2 | 567 | 674 | 902 | 16 |
| 228 | L | C | 542 | 711 | 900 | 21 |
| 228 | L | O | 540 | 720 | 907 | 25 |
| 229 | N | N | 533 | 707 | 891 | 22 |

TABLE 2-continued

| | | | | | | |
|---|---|---|---|---|---|---|
| 229 | N | CA | 520 | 713 | 890 | 27 |
| 229 | N | CB | 519 | 722 | 877 | 30 |
| 229 | N | CG | 513 | 735 | 880 | 37 |
| 229 | N | OD1 | 519 | 744 | 886 | 40 |
| 229 | N | ND2 | 500 | 736 | 877 | 42 |
| 229 | N | C | 509 | 702 | 889 | 26 |
| 229 | N | O | 511 | 691 | 883 | 28 |
| 230 | P | N | 497 | 704 | 895 | 28 |
| 230 | P | CD | 494 | 716 | 903 | 29 |
| 230 | P | CA | 486 | 695 | 894 | 32 |
| 230 | P | CB | 476 | 700 | 904 | 27 |
| 230 | P | CG | 480 | 714 | 907 | 29 |
| 230 | P | C | 480 | 693 | 880 | 32 |
| 230 | P | O | 474 | 683 | 877 | 37 |
| 231 | S | N | 481 | 703 | 872 | 34 |
| 231 | S | CA | 475 | 703 | 858 | 34 |
| 231 | S | CB | 469 | 716 | 856 | 34 |
| 231 | S | OG | 466 | 719 | 842 | 30 |
| 231 | S | C | 484 | 699 | 847 | 36 |
| 231 | S | O | 495 | 705 | 845 | 36 |
| 232 | V | N | 480 | 689 | 838 | 35 |
| 232 | V | CA | 488 | 685 | 827 | 36 |
| 232 | V | CB | 484 | 671 | 821 | 36 |
| 232 | V | CG1 | 469 | 669 | 822 | 40 |
| 232 | V | CG2 | 488 | 670 | 807 | 37 |
| 232 | V | C | 488 | 696 | 816 | 38 |
| 232 | V | O | 497 | 698 | 809 | 37 |
| 233 | A | N | 477 | 704 | 816 | 36 |
| 233 | A | CA | 475 | 715 | 806 | 33 |
| 233 | A | CB | 461 | 719 | 806 | 36 |
| 233 | A | C | 484 | 726 | 810 | 34 |
| 233 | A | O | 490 | 733 | 802 | 38 |
| 234 | A | N | 485 | 729 | 823 | 32 |
| 234 | A | CA | 493 | 740 | 828 | 36 |
| 234 | A | CB | 490 | 743 | 843 | 37 |
| 234 | A | C | 508 | 736 | 827 | 37 |
| 234 | A | O | 516 | 745 | 823 | 38 |
| 235 | T | N | 512 | 724 | 830 | 36 |
| 235 | T | CA | 525 | 719 | 829 | 36 |
| 235 | T | CB | 526 | 704 | 834 | 33 |
| 235 | T | OG1 | 524 | 703 | 848 | 35 |
| 235 | T | CG2 | 539 | 697 | 830 | 30 |
| 235 | T | C | 531 | 719 | 815 | 39 |
| 235 | T | O | 542 | 724 | 813 | 38 |
| 236 | L | N | 523 | 715 | 806 | 43 |
| 236 | L | CA | 527 | 715 | 792 | 46 |
| 236 | L | CB | 517 | 707 | 783 | 43 |
| 236 | L | CG | 516 | 692 | 785 | 45 |
| 236 | L | CD1 | 508 | 686 | 774 | 43 |
| 236 | L | CD2 | 531 | 687 | 784 | 46 |
| 236 | L | C | 528 | 729 | 787 | 46 |
| 236 | L | O | 537 | 732 | 778 | 48 |
| 237 | G | N | 520 | 738 | 792 | 48 |
| 237 | G | CA | 521 | 752 | 788 | 47 |
| 237 | G | C | 534 | 759 | 792 | 49 |
| 237 | G | O | 541 | 765 | 783 | 52 |
| 238 | F | N | 539 | 757 | 804 | 50 |
| 238 | F | CA | 551 | 763 | 809 | 48 |
| 238 | F | CB | 554 | 759 | 823 | 48 |
| 238 | F | CG | 544 | 763 | 833 | 46 |
| 238 | F | CD1 | 539 | 776 | 833 | 47 |
| 238 | F | CD2 | 539 | 754 | 842 | 46 |
| 238 | F | CE1 | 529 | 781 | 842 | 41 |
| 238 | F | CE2 | 529 | 759 | 852 | 44 |
| 238 | F | CZ | 524 | 772 | 851 | 43 |
| 238 | F | C | 563 | 760 | 800 | 51 |
| 238 | F | O | 569 | 769 | 794 | 54 |
| 239 | G | N | 567 | 747 | 799 | 50 |
| 239 | G | CA | 578 | 744 | 791 | 52 |
| 239 | G | C | 578 | 749 | 777 | 54 |
| 239 | G | O | 588 | 749 | 770 | 56 |
| 240 | A | N | 566 | 754 | 773 | 55 |
| 240 | A | CA | 564 | 759 | 760 | 55 |
| 240 | A | CB | 550 | 756 | 755 | 54 |
| 240 | A | C | 566 | 774 | 760 | 56 |
| 240 | A | O | 569 | 781 | 750 | 59 |
| 241 | Y | N | 564 | 780 | 772 | 55 |
| 241 | Y | CA | 565 | 794 | 774 | 56 |
| 241 | Y | CB | 555 | 799 | 784 | 58 |
| 241 | Y | CG | 558 | 811 | 791 | 59 |
| 241 | Y | CD1 | 552 | 823 | 788 | 59 |
| 241 | Y | CE1 | 555 | 835 | 794 | 60 |
| 241 | Y | CD2 | 568 | 811 | 801 | 59 |
| 241 | Y | CE2 | 572 | 823 | 807 | 63 |
| 241 | Y | CZ | 565 | 835 | 804 | 63 |
| 241 | Y | OH | 569 | 847 | 810 | 65 |
| 241 | Y | C | 579 | 797 | 779 | 56 |
| 241 | Y | O | 584 | 808 | 776 | 58 |
| 242 | M | N | 585 | 789 | 787 | 56 |
| 242 | M | CA | 598 | 792 | 793 | 55 |
| 242 | M | CB | 602 | 781 | 803 | 58 |
| 242 | M | CG | 606 | 788 | 816 | 60 |
| 242 | M | SD | 593 | 795 | 825 | 64 |
| 242 | M | CE | 579 | 783 | 821 | 61 |
| 242 | M | C | 608 | 791 | 781 | 58 |
| 242 | M | O | 619 | 798 | 782 | 60 |
| 243 | S | N | 606 | 783 | 771 | 60 |
| 243 | S | CA | 615 | 782 | 760 | 63 |
| 243 | S | CB | 613 | 769 | 752 | 62 |
| 243 | S | CG | 606 | 772 | 740 | 62 |
| 243 | S | C | 614 | 794 | 751 | 65 |
| 243 | S | O | 624 | 799 | 745 | 68 |
| 244 | K | N | 602 | 800 | 750 | 65 |
| 244 | K | CA | 600 | 812 | 741 | 66 |
| 244 | K | CB | 587 | 810 | 733 | 68 |
| 244 | K | CG | 574 | 811 | 741 | 70 |
| 244 | K | CD | 563 | 817 | 732 | 72 |
| 244 | K | CE | 559 | 831 | 737 | 76 |
| 244 | K | NZ | 546 | 830 | 744 | 80 |
| 244 | K | C | 599 | 825 | 749 | 66 |
| 244 | K | O | 596 | 835 | 743 | 66 |
| 245 | A | N | 602 | 824 | 762 | 68 |
| 245 | A | CA | 601 | 836 | 770 | 65 |
| 245 | A | CB | 588 | 837 | 777 | 65 |
| 245 | A | C | 612 | 838 | 780 | 63 |
| 245 | A | O | 615 | 848 | 785 | 65 |
| 246 | H | N | 619 | 826 | 783 | 60 |
| 246 | H | CA | 630 | 827 | 792 | 59 |
| 246 | H | CB | 627 | 819 | 805 | 61 |
| 246 | R | CG | 617 | 826 | 814 | 64 |
| 246 | H | CD2 | 618 | 838 | 821 | 64 |
| 246 | H | ND1 | 604 | 821 | 816 | 62 |
| 246 | H | CE1 | 598 | 830 | 824 | 61 |
| 246 | H | NE2 | 606 | 840 | 827 | 63 |
| 246 | H | C | 643 | 821 | 786 | 59 |
| 246 | H | O | 653 | 820 | 792 | 60 |
| 247 | G | N | 642 | 817 | 773 | 58 |
| 247 | G | CA | 653 | 812 | 766 | 58 |
| 247 | G | C | 658 | 798 | 770 | 60 |
| 247 | G | O | 670 | 796 | 773 | 62 |
| 248 | I | N | 649 | 788 | 771 | 61 |
| 248 | I | CA | 653 | 775 | 775 | 61 |
| 248 | I | CB | 659 | 175 | 789 | 62 |
| 248 | I | CG2 | 648 | 779 | 800 | 63 |
| 248 | I | CG1 | 665 | 761 | 793 | 64 |
| 248 | I | CD1 | 674 | 755 | 782 | 61 |
| 248 | I | C | 642 | 764 | 774 | 58 |
| 248 | I | O | 631 | 765 | 779 | 59 |
| 249 | D | N | 646 | 753 | 767 | 55 |
| 249 | D | CA | 636 | 742 | 766 | 52 |
| 249 | D | CB | 639 | 735 | 752 | 59 |
| 249 | D | CG | 628 | 738 | 742 | 68 |
| 249 | D | OD1 | 632 | 739 | 730 | 72 |
| 249 | D | OD2 | 616 | 739 | 746 | 74 |
| 249 | D | C | 639 | 732 | 777 | 47 |
| 249 | D | O | 649 | 725 | 777 | 43 |
| 250 | P | N | 629 | 732 | 787 | 43 |
| 250 | P | CD | 617 | 740 | 786 | 38 |
| 250 | P | CA | 630 | 723 | 799 | 40 |
| 250 | P | CB | 621 | 731 | 808 | 39 |
| 250 | P | CG | 610 | 736 | 799 | 39 |
| 250 | P | C | 625 | 709 | 796 | 37 |
| 250 | P | O | 618 | 707 | 786 | 39 |
| 251 | N | N | 628 | 700 | 805 | 36 |
| 251 | N | CA | 623 | 687 | 803 | 38 |
| 251 | N | CB | 631 | 677 | 812 | 35 |
| 251 | N | CG | 646 | 680 | 812 | 43 |
| 251 | N | OD1 | 651 | 689 | 818 | 39 |

TABLE 2-continued

| | | | | | | | | | | | | |
|---|---|---|---|---|---|---|---|---|---|---|---|---|
| 251 | N | ND2 | 653 | 672 | 804 | 40 | 261 | T | O | 685 | 685 | 767 | 50 |
| 251 | N | C | 608 | 687 | 807 | 33 | 262 | G | N | 677 | 679 | 786 | 45 |
| 251 | N | O | 604 | 696 | 815 | 31 | 262 | G | CA | 690 | 680 | 793 | 44 |
| 252 | I | N | 600 | 679 | 800 | 33 | 262 | G | C | 691 | 694 | 799 | 45 |
| 252 | I | CA | 586 | 678 | 803 | 33 | 262 | G | O | 702 | 698 | 803 | 46 |
| 252 | I | CB | 578 | 683 | 791 | 33 | 263 | A | N | 680 | 701 | 800 | 44 |
| 252 | I | CG2 | 563 | 684 | 794 | 36 | 263 | A | CA | 680 | 714 | 806 | 42 |
| 252 | I | CG1 | 583 | 697 | 786 | 32 | 263 | A | CB | 668 | 722 | 802 | 44 |
| 252 | I | CD1 | 582 | 707 | 797 | 33 | 263 | A | C | 681 | 713 | 821 | 41 |
| 252 | I | C | 582 | 664 | 806 | 33 | 263 | A | O | 680 | 701 | 826 | 37 |
| 252 | I | O | 585 | 655 | 798 | 33 | 264 | P | N | 683 | 724 | 829 | 41 |
| 253 | R | N | 575 | 662 | 817 | 33 | 264 | P | CD | 685 | 737 | 824 | 40 |
| 253 | R | CA | 571 | 649 | 821 | 31 | 264 | P | CA | 684 | 723 | 843 | 40 |
| 253 | R | CB | 579 | 644 | 833 | 28 | 264 | P | CB | 694 | 735 | 847 | 39 |
| 253 | R | CG | 594 | 645 | 830 | 32 | 264 | P | CG | 691 | 745 | 836 | 40 |
| 253 | R | CD | 602 | 637 | 841 | 28 | 264 | P | C | 670 | 725 | 850 | 43 |
| 253 | R | NE | 600 | 623 | 840 | 33 | 264 | P | O | 669 | 726 | 862 | 40 |
| 253 | R | CZ | 604 | 615 | 830 | 34 | 265 | V | N | 660 | 727 | 841 | 42 |
| 253 | R | NH1 | 610 | 620 | 819 | 38 | 265 | V | CA | 647 | 729 | 845 | 44 |
| 253 | R | NH2 | 602 | 602 | 830 | 33 | 265 | V | CB | 641 | 743 | 841 | 44 |
| 253 | R | C | 556 | 649 | 824 | 33 | 265 | V | CG1 | 628 | 746 | 848 | 46 |
| 253 | R | O | 552 | 654 | 834 | 34 | 265 | V | CG2 | 652 | 753 | 843 | 45 |
| 254 | T | N | 548 | 642 | 816 | 34 | 265 | V | C | 637 | 718 | 840 | 43 |
| 254 | T | CA | 534 | 641 | 818 | 30 | 265 | V | O | 636 | 716 | 828 | 45 |
| 254 | T | CB | 525 | 652 | 811 | 32 | 266 | T | N | 631 | 711 | 849 | 35 |
| 254 | T | OG1 | 528 | 652 | 797 | 32 | 266 | T | CA | 621 | 701 | 845 | 31 |
| 254 | T | CG2 | 528 | 665 | 816 | 29 | 266 | T | CB | 625 | 687 | 851 | 29 |
| 254 | T | C | 531 | 627 | 812 | 30 | 266 | T | OG1 | 637 | 683 | 845 | 37 |
| 254 | T | O | 538 | 623 | 803 | 26 | 266 | T | CG2 | 614 | 677 | 847 | 33 |
| 255 | G | N | 520 | 621 | 816 | 33 | 266 | T | C | 607 | 704 | 850 | 27 |
| 255 | G | CA | 517 | 608 | 810 | 32 | 266 | T | O | 606 | 707 | 862 | 24 |
| 255 | G | C | 515 | 609 | 795 | 33 | 267 | Y | N | 598 | 704 | 841 | 27 |
| 255 | G | O | 518 | 600 | 787 | 35 | 267 | Y | CA | 584 | 707 | 845 | 25 |
| 256 | V | N | 510 | 621 | 790 | 30 | 267 | Y | CB | 577 | 716 | 835 | 27 |
| 256 | V | CA | 507 | 623 | 776 | 33 | 267 | Y | CG | 580 | 730 | 838 | 25 |
| 256 | V | CB | 496 | 633 | 775 | 30 | 267 | Y | CD1 | 571 | 738 | 845 | 30 |
| 256 | V | CG1 | 501 | 645 | 767 | 35 | 267 | Y | CE1 | 573 | 751 | 848 | 34 |
| 256 | V | CG2 | 484 | 626 | 768 | 33 | 267 | Y | CD2 | 591 | 736 | 833 | 31 |
| 256 | V | C | 519 | 627 | 768 | 34 | 267 | Y | CE2 | 594 | 750 | 835 | 35 |
| 256 | V | O | 521 | 622 | 757 | 36 | 267 | Y | CZ | 585 | 757 | 843 | 36 |
| 257 | R | N | 528 | 636 | 774 | 33 | 267 | Y | OH | 587 | 770 | 846 | 36 |
| 257 | R | CA | 540 | 640 | 767 | 34 | 267 | Y | C | 576 | 693 | 845 | 26 |
| 257 | R | CB | 537 | 653 | 760 | 31 | 267 | Y | O | 575 | 686 | 835 | 25 |
| 257 | R | CG | 550 | 659 | 755 | 33 | 268 | S | N | 571 | 690 | 857 | 27 |
| 257 | R | CD | 548 | 674 | 753 | 44 | 268 | S | CA | 564 | 678 | 859 | 23 |
| 257 | R | NE | 535 | 677 | 747 | 49 | 268 | S | CB | 572 | 668 | 867 | 27 |
| 257 | R | CZ | 533 | 687 | 740 | 55 | 268 | S | OG | 567 | 655 | 865 | 30 |
| 257 | R | NH1 | 542 | 695 | 736 | 60 | 268 | S | C | 550 | 680 | 865 | 27 |
| 257 | R | NH2 | 520 | 689 | 735 | 54 | 268 | S | O | 546 | 690 | 871 | 20 |
| 257 | R | C | 552 | 641 | 776 | 33 | 269 | T | N | 542 | 669 | 865 | 23 |
| 257 | R | O | 552 | 649 | 785 | 33 | 269 | T | CA | 529 | 668 | 870 | 25 |
| 258 | T | N | 563 | 634 | 772 | 32 | 269 | T | CB | 520 | 661 | 859 | 27 |
| 258 | T | CA | 575 | 634 | 780 | 31 | 269 | T | OG1 | 508 | 668 | 857 | 25 |
| 258 | T | CB | 579 | 620 | 785 | 35 | 269 | T | CG2 | 518 | 647 | 864 | 19 |
| 258 | T | OG1 | 569 | 616 | 795 | 36 | 269 | T | C | 531 | 660 | 883 | 25 |
| 258 | T | CG2 | 593 | 619 | 791 | 30 | 269 | T | O | 540 | 652 | 884 | 25 |
| 258 | T | C | 587 | 639 | 770 | 31 | 270 | Y | N | 522 | 663 | 893 | 20 |
| 258 | T | O | 588 | 634 | 759 | 28 | 270 | Y | CA | 524 | 655 | 905 | 22 |
| 259 | I | N | 594 | 648 | 775 | 30 | 270 | Y | CB | 514 | 659 | 916 | 20 |
| 259 | I | CA | 606 | 653 | 767 | 30 | 270 | Y | CG | 518 | 672 | 922 | 22 |
| 259 | I | CB | 602 | 667 | 761 | 27 | 270 | Y | CD1 | 527 | 673 | 932 | 18 |
| 259 | I | CG2 | 614 | 672 | 753 | 34 | 270 | Y | CE1 | 530 | 686 | 938 | 21 |
| 259 | I | CG1 | 590 | 665 | 751 | 28 | 270 | Y | CD2 | 511 | 684 | 918 | 22 |
| 259 | I | CD1 | 584 | 678 | 747 | 26 | 270 | Y | CE2 | 514 | 697 | 923 | 19 |
| 259 | I | C | 618 | 655 | 776 | 31 | 270 | Y | CZ | 524 | 697 | 933 | 20 |
| 259 | I | O | 617 | 662 | 786 | 30 | 270 | Y | OH | 528 | 710 | 939 | 18 |
| 260 | T | N | 629 | 649 | 772 | 35 | 270 | Y | C | 523 | 640 | 902 | 23 |
| 260 | T | CA | 641 | 650 | 780 | 37 | 270 | Y | O | 530 | 631 | 907 | 25 |
| 260 | T | CB | 648 | 637 | 782 | 39 | 271 | G | N | 513 | 637 | 893 | 21 |
| 260 | T | OG1 | 639 | 627 | 787 | 42 | 271 | G | CA | 510 | 623 | 889 | 23 |
| 260 | T | CG2 | 660 | 638 | 792 | 41 | 271 | G | C | 522 | 616 | 882 | 25 |
| 260 | T | C | 650 | 659 | 771 | 41 | 271 | G | O | 525 | 605 | 885 | 23 |
| 260 | T | O | 654 | 655 | 760 | 40 | 272 | K | N | 529 | 624 | 873 | 23 |
| 261 | T | N | 653 | 671 | 775 | 42 | 272 | K | CA | 540 | 618 | 866 | 22 |
| 261 | T | CA | 662 | 680 | 767 | 46 | 272 | K | CB | 544 | 627 | 854 | 20 |
| 261 | T | CB | 656 | 694 | 766 | 47 | 272 | K | CG | 552 | 620 | 843 | 27 |
| 261 | T | OG1 | 657 | 701 | 778 | 48 | 272 | K | CD | 551 | 605 | 845 | 25 |
| 261 | T | CG2 | 642 | 693 | 762 | 51 | 272 | K | CE | 560 | 598 | 833 | 29 |
| 261 | T | C | 676 | 682 | 774 | 46 | 272 | K | NZ | 551 | 590 | 825 | 31 |

TABLE 2-continued

| | | | | | | |
|---|---|---|---|---|---|---|
| 272 | K | C | 551 | 616 | 876 | 23 |
| 272 | K | O | 559 | 606 | 875 | 24 |
| 273 | F | N | 553 | 626 | 884 | 18 |
| 273 | F | CA | 563 | 625 | 894 | 17 |
| 273 | F | CB | 563 | 637 | 903 | 13 |
| 273 | F | CG | 572 | 637 | 915 | 15 |
| 273 | F | CD1 | 586 | 639 | 914 | 12 |
| 273 | F | CD2 | 567 | 635 | 928 | 17 |
| 273 | F | CE1 | 595 | 639 | 925 | 13 |
| 273 | F | CE2 | 575 | 635 | 939 | 14 |
| 273 | F | CZ | 589 | 637 | 938 | 18 |
| 273 | F | C | 561 | 612 | 902 | 21 |
| 273 | F | O | 570 | 604 | 904 | 22 |
| 274 | L | N | 548 | 610 | 906 | 21 |
| 274 | L | CA | 545 | 598 | 914 | 21 |
| 274 | L | CB | 530 | 598 | 918 | 20 |
| 274 | L | CG | 529 | 608 | 930 | 17 |
| 274 | L | CD1 | 514 | 612 | 931 | 17 |
| 274 | L | CD2 | 535 | 601 | 942 | 16 |
| 274 | L | C | 548 | 586 | 906 | 20 |
| 274 | L | O | 553 | 576 | 911 | 22 |
| 275 | A | N | 544 | 586 | 893 | 17 |
| 275 | A | CA | 546 | 575 | 884 | 21 |
| 275 | A | CB | 540 | 578 | 870 | 25 |
| 275 | A | C | 561 | 572 | 882 | 22 |
| 275 | A | O | 565 | 560 | 880 | 27 |
| 276 | D | N | 569 | 582 | 883 | 26 |
| 276 | D | CA | 583 | 580 | 881 | 31 |
| 276 | D | CB | 590 | 593 | 877 | 31 |
| 276 | D | CG | 587 | 597 | 862 | 29 |
| 276 | D | OD1 | 587 | 587 | 854 | 29 |
| 276 | D | OD2 | 585 | 608 | 859 | 34 |
| 276 | D | C | 590 | 575 | 894 | 29 |
| 276 | D | O | 602 | 571 | 893 | 35 |
| 277 | G | N | 582 | 574 | 904 | 27 |
| 277 | G | CA | 588 | 568 | 917 | 32 |
| 277 | G | C | 592 | 579 | 926 | 36 |
| 277 | G | O | 597 | 577 | 938 | 38 |
| 278 | G | N | 591 | 592 | 922 | 38 |
| 278 | G | CA | 595 | 603 | 931 | 39 |
| 278 | G | C | 608 | 610 | 928 | 41 |
| 278 | G | O | 612 | 613 | 917 | 40 |
| 279 | C | N | 615 | 612 | 939 | 41 |
| 279 | C | CA | 628 | 619 | 939 | 41 |
| 279 | C | CB | 630 | 625 | 953 | 40 |
| 279 | C | SG | 620 | 639 | 958 | 40 |
| 279 | C | C | 640 | 610 | 935 | 43 |
| 279 | C | O | 642 | 600 | 942 | 41 |
| 280 | S | N | 646 | 614 | 925 | 45 |
| 280 | S | CA | 658 | 607 | 920 | 47 |
| 280 | S | CB | 659 | 607 | 904 | 46 |
| 280 | S | OG | 652 | 619 | 900 | 51 |
| 280 | S | C | 671 | 613 | 925 | 46 |
| 280 | S | O | 673 | 626 | 925 | 48 |
| 281 | G | N | 680 | 605 | 931 | 43 |
| 281 | G | CA | 692 | 610 | 937 | 43 |
| 281 | G | C | 700 | 621 | 930 | 40 |
| 281 | G | O | 704 | 619 | 918 | 40 |
| 282 | G | N | 702 | 631 | 937 | 42 |
| 282 | G | CA | 710 | 643 | 932 | 41 |
| 282 | G | C | 705 | 647 | 918 | 41 |
| 282 | G | O | 714 | 651 | 910 | 43 |
| 283 | A | N | 693 | 647 | 915 | 38 |
| 283 | A | CA | 688 | 652 | 902 | 34 |
| 283 | A | CB | 676 | 644 | 898 | 35 |
| 283 | A | C | 684 | 667 | 903 | 34 |
| 283 | A | O | 685 | 674 | 893 | 35 |
| 284 | Y | N | 680 | 671 | 915 | 30 |
| 284 | Y | CA | 677 | 686 | 916 | 29 |
| 284 | Y | CB | 661 | 687 | 915 | 24 |
| 284 | Y | CG | 656 | 681 | 902 | 26 |
| 284 | Y | CD1 | 655 | 688 | 891 | 24 |
| 284 | Y | CE1 | 649 | 682 | 879 | 23 |
| 284 | Y | CD2 | 651 | 667 | 903 | 29 |
| 284 | Y | CE2 | 646 | 662 | 891 | 26 |
| 284 | Y | CZ | 645 | 669 | 879 | 27 |
| 284 | Y | OH | 640 | 663 | 868 | 32 |
| 284 | Y | C | 681 | 692 | 930 | 30 |
| 284 | Y | O | 681 | 686 | 940 | 31 |
| 285 | D | N | 684 | 705 | 929 | 30 |
| 285 | D | CA | 687 | 712 | 941 | 36 |
| 285 | D | CB | 698 | 723 | 940 | 36 |
| 285 | D | CG | 707 | 721 | 92$ | 38 |
| 285 | D | OD1 | 707 | 728 | 918 | 40 |
| 285 | D | OD2 | 715 | 711 | 928 | 39 |
| 285 | D | C | 675 | 719 | 947 | 37 |
| 285 | D | O | 673 | 722 | 959 | 39 |
| 286 | I | N | 665 | 721 | 938 | 29 |
| 286 | I | CA | 653 | 728 | 941 | 31 |
| 286 | I | CB | 652 | 743 | 936 | 27 |
| 286 | I | CG2 | 640 | 750 | 942 | 27 |
| 286 | I | CG1 | 665 | 750 | 941 | 26 |
| 286 | I | CD1 | 665 | 765 | 936 | 24 |
| 286 | I | C | 640 | 721 | 936 | 31 |
| 286 | I | O | 640 | 718 | 924 | 30 |
| 287 | I | N | 630 | 719 | 944 | 29 |
| 287 | I | CA | 618 | 714 | 940 | 24 |
| 287 | I | CB | 615 | 700 | 946 | 20 |
| 287 | I | CG2 | 602 | 694 | 940 | 17 |
| 287 | I | CG1 | 627 | 691 | 943 | 15 |
| 287 | I | CD1 | 627 | 678 | 950 | 14 |
| 287 | I | C | 606 | 723 | 943 | 27 |
| 287 | I | O | 604 | 727 | 955 | 27 |
| 288 | I | N | 600 | 729 | 933 | 23 |
| 288 | I | CA | 589 | 738 | 935 | 25 |
| 288 | I | CB | 589 | 749 | 926 | 25 |
| 288 | I | CG2 | 577 | 758 | 929 | 29 |
| 288 | I | CG1 | 602 | 757 | 927 | 30 |
| 288 | I | CD1 | 604 | 768 | 917 | 32 |
| 288 | I | C | 575 | 731 | 934 | 26 |
| 288 | I | O | 572 | 726 | 923 | 19 |
| 289 | C | N | 568 | 730 | 945 | 24 |
| 289 | C | CA | 555 | 724 | 945 | 21 |
| 289 | C | CB | 552 | 717 | 958 | 21 |
| 289 | C | SG | 565 | 704 | 963 | 26 |
| 289 | C | C | 544 | 735 | 943 | 21 |
| 289 | C | O | 539 | 741 | 953 | 24 |
| 290 | D | N | 542 | 739 | 931 | 20 |
| 290 | D | CA | 532 | 749 | 928 | 27 |
| 290 | D | CB | 534 | 754 | 913 | 30 |
| 290 | D | CG | 527 | 767 | 910 | 34 |
| 290 | D | OD1 | 519 | 772 | 919 | 32 |
| 290 | D | OD2 | 529 | 773 | 899 | 38 |
| 290 | D | C | 518 | 744 | 930 | 25 |
| 290 | D | O | 515 | 732 | 930 | 22 |
| 291 | E | N | 509 | 754 | 932 | 23 |
| 291 | E | CA | 495 | 751 | 934 | 29 |
| 291 | E | CB | 489 | 744 | 922 | 31 |
| 291 | E | CG | 480 | 752 | 913 | 45 |
| 291 | E | CD | 485 | 766 | 909 | 53 |
| 291 | E | OE1 | 485 | 774 | 918 | 57 |
| 291 | E | OE2 | 488 | 768 | 898 | 58 |
| 291 | E | C | 493 | 742 | 947 | 28 |
| 291 | E | O | 484 | 734 | 947 | 30 |
| 292 | C | N | 502 | 744 | 957 | 25 |
| 292 | C | CA | 502 | 736 | 969 | 26 |
| 292 | C | CB | 515 | 738 | 977 | 20 |
| 292 | C | SG | 515 | 754 | 986 | 29 |
| 292 | C | C | 490 | 737 | 978 | 30 |
| 292 | C | O | 489 | 731 | 988 | 33 |
| 293 | H | N | 480 | 745 | 974 | 32 |
| 293 | H | CA | 468 | 746 | 982 | 32 |
| 293 | R | CB | 462 | 760 | 978 | 32 |
| 293 | H | CG | 460 | 762 | 964 | 33 |
| 293 | H | CD2 | 468 | 768 | 954 | 31 |
| 293 | H | ND1 | 450 | 755 | 956 | 36 |
| 293 | H | CE1 | 452 | 758 | 944 | 34 |
| 293 | H | NE2 | 462 | 766 | 942 | 35 |
| 293 | H | C | 458 | 735 | 977 | 29 |
| 293 | H | O | 448 | 733 | 984 | 34 |
| 294 | S | N | 461 | 729 | 966 | 32 |
| 294 | S | CA | 453 | 718 | 961 | 30 |
| 294 | S | CB | 459 | 713 | 948 | 30 |
| 294 | S | OG | 460 | 724 | 939 | 40 |
| 294 | S | C | 451 | 706 | 970 | 30 |
| 294 | S | O | 461 | 700 | 974 | 28 |
| 295 | T | N | 439 | 703 | 974 | 28 |
| 295 | T | CA | 436 | 692 | 983 | 28 |

TABLE 2-continued

| | | | | | | |
|---|---|---|---|---|---|---|
| 295 | T | CB | 425 | 694 | 993 | 26 |
| 295 | T | OG1 | 414 | 699 | 986 | 28 |
| 295 | T | CG2 | 430 | 706 | 1003 | 22 |
| 295 | T | C | 432 | 679 | 975 | 29 |
| 295 | T | O | 426 | 670 | 981 | 31 |
| 296 | D | N | 435 | 678 | 962 | 26 |
| 296 | D | CA | 431 | 666 | 955 | 27 |
| 296 | D | CB | 431 | 668 | 940 | 29 |
| 296 | D | CG | 445 | 670 | 935 | 36 |
| 296 | D | OD1 | 452 | 660 | 931 | 48 |
| 296 | D | OD2 | 450 | 682 | 934 | 41 |
| 296 | D | C | 442 | 656 | 959 | 26 |
| 296 | D | O | 453 | 659 | 962 | 27 |
| 297 | S | N | 439 | 643 | 958 | 25 |
| 297 | S | CA | 447 | 632 | 962 | 28 |
| 297 | S | CB | 440 | 619 | 961 | 28 |
| 297 | S | OG | 435 | 618 | 948 | 39 |
| 297 | S | C | 461 | 632 | 956 | 27 |
| 297 | S | O | 471 | 629 | 963 | 26 |
| 298 | T | N | 462 | 633 | 943 | 27 |
| 298 | T | CA | 475 | 632 | 936 | 27 |
| 298 | T | CB | 473 | 631 | 921 | 31 |
| 298 | T | OG1 | 468 | 618 | 918 | 37 |
| 298 | T | CG2 | 487 | 633 | 914 | 36 |
| 298 | T | C | 485 | 644 | 940 | 24 |
| 298 | T | O | 497 | 642 | 940 | 24 |
| 299 | T | N | 479 | 655 | 944 | 19 |
| 299 | T | CA | 488 | 666 | 948 | 16 |
| 299 | T | CB | 481 | 680 | 948 | 15 |
| 299 | T | OG1 | 477 | 683 | 935 | 17 |
| 299 | T | CG2 | 491 | 691 | 953 | 13 |
| 299 | T | C | 494 | 663 | 962 | 19 |
| 299 | T | O | 505 | 665 | 965 | 21 |
| 300 | I | N | 484 | 659 | 971 | 22 |
| 300 | I | CA | 488 | 656 | 985 | 18 |
| 300 | I | CB | 476 | 652 | 993 | 21 |
| 300 | I | CG2 | 480 | 646 | 1007 | 12 |
| 300 | I | CG1 | 467 | 665 | 997 | 22 |
| 300 | I | CD1 | 453 | 662 | 997 | 20 |
| 300 | I | C | 498 | 645 | 986 | 21 |
| 300 | I | O | 508 | 646 | 993 | 19 |
| 301 | L | N | 495 | 634 | 979 | 21 |
| 301 | L | CA | 504 | 623 | 978 | 23 |
| 301 | L | CB | 498 | 611 | 971 | 15 |
| 301 | L | CG | 505 | 598 | 971 | 19 |
| 301 | L | CD1 | 510 | 595 | 985 | 14 |
| 301 | L | CD2 | 496 | 587 | 966 | 11 |
| 301 | L | C | 517 | 627 | 972 | 25 |
| 301 | L | O | 528 | 623 | 976 | 24 |
| 302 | G | N | 516 | 636 | 962 | 24 |
| 302 | G | CA | 528 | 641 | 955 | 22 |
| 302 | G | C | 537 | 649 | 963 | 24 |
| 302 | G | O | 549 | 647 | 963 | 23 |
| 303 | I | N | 531 | 659 | 971 | 19 |
| 303 | I | CA | 539 | 667 | 980 | 16 |
| 303 | I | CB | 530 | 679 | 985 | 18 |
| 303 | I | CG2 | 538 | 687 | 995 | 11 |
| 303 | I | CG1 | 525 | 686 | 973 | 19 |
| 303 | I | CD1 | 521 | 701 | 975 | 21 |
| 303 | I | C | 544 | 660 | 992 | 20 |
| 303 | I | O | 556 | 662 | 997 | 18 |
| 304 | G | N | 537 | 651 | 998 | 19 |
| 304 | G | CA | 542 | 643 | 1009 | 22 |
| 304 | G | C | 554 | 635 | 1005 | 26 |
| 304 | G | O | 563 | 633 | 1012 | 24 |
| 305 | T | N | 553 | 630 | 992 | 26 |
| 305 | T | CA | 565 | 622 | 987 | 26 |
| 305 | T | CB | 561 | 616 | 973 | 29 |
| 305 | T | OG1 | 550 | 607 | 975 | 29 |
| 305 | T | CG2 | 573 | 609 | 967 | 33 |
| 305 | T | C | 577 | 631 | 986 | 23 |
| 305 | T | O | 588 | 626 | 989 | 23 |
| 306 | V | N | 576 | 643 | 981 | 18 |
| 306 | V | CA | 587 | 652 | 980 | 15 |
| 306 | V | CB | 583 | 666 | 974 | 19 |
| 306 | V | CG1 | 593 | 676 | 977 | 7 |
| 306 | V | CG2 | 581 | 664 | 959 | 15 |
| 306 | V | C | 592 | 655 | 994 | 24 |
| 306 | V | O | 605 | 655 | 997 | 27 |
| 307 | L | N | 583 | 658 | 1004 | 18 |
| 307 | L | CA | 587 | 661 | 1018 | 23 |
| 307 | L | CB | 575 | 665 | 1026 | 19 |
| 307 | L | CG | 568 | 677 | 1020 | 25 |
| 307 | L | CD1 | 555 | 680 | 1027 | 17 |
| 307 | L | CD2 | 578 | 689 | 1022 | 21 |
| 307 | L | C | 594 | 649 | 1024 | 18 |
| 307 | L | O | 603 | 651 | 1032 | 21 |
| 308 | D | N | 590 | 637 | 1020 | 19 |
| 308 | D | CA | 597 | 626 | 1026 | 22 |
| 308 | D | CB | 587 | 614 | 1025 | 25 |
| 308 | D | CG | 594 | 601 | 1028 | 29 |
| 308 | D | OD1 | 597 | 599 | 1040 | 26 |
| 308 | D | OD2 | 596 | 593 | 1019 | 36 |
| 308 | D | C | 610 | 622 | 1019 | 25 |
| 308 | D | O | 618 | 615 | 1024 | 23 |
| 309 | Q | N | 612 | 628 | 1007 | 21 |
| 309 | Q | CA | 624 | 624 | 999 | 25 |
| 309 | Q | CB | 620 | 615 | 987 | 17 |
| 309 | Q | CG | 613 | 603 | 990 | 20 |
| 309 | Q | CD | 607 | 597 | 978 | 24 |
| 309 | Q | OE1 | 608 | 603 | 967 | 28 |
| 309 | Q | NE2 | 600 | 585 | 979 | 20 |
| 309 | Q | C | 634 | 634 | 994 | 24 |
| 309 | Q | O | 644 | 630 | 989 | 29 |
| 310 | A | N | 631 | 647 | 994 | 30 |
| 310 | A | CA | 640 | 657 | 989 | 28 |
| 310 | A | CB | 633 | 670 | 988 | 26 |
| 310 | A | C | 653 | 658 | 996 | 31 |
| 310 | A | O | 664 | 661 | 990 | 35 |
| 311 | E | N | 653 | 657 | 1009 | 34 |
| 311 | E | CA | 666 | 658 | 1017 | 36 |
| 311 | E | CB | 663 | 658 | 1032 | 36 |
| 311 | E | CG | 672 | 669 | 1039 | 44 |
| 311 | E | CD | 674 | 666 | 1054 | 44 |
| 311 | E | OE1 | 685 | 669 | 1059 | 49 |
| 311 | E | OE2 | 665 | 661 | 1060 | 46 |
| 311 | E | C | 675 | 647 | 1013 | 36 |
| 311 | E | O | 687 | 650 | 1010 | 35 |
| 312 | T | N | 671 | 635 | 1014 | 34 |
| 312 | T | CA | 679 | 624 | 1011 | 37 |
| 312 | T | CB | 673 | 610 | 1015 | 39 |
| 312 | T | OG1 | 669 | 611 | 1029 | 43 |
| 312 | T | CG2 | 683 | 599 | 1014 | 38 |
| 312 | T | C | 682 | 623 | 996 | 37 |
| 312 | T | O | 692 | 616 | 992 | 38 |
| 313 | A | N | 675 | 630 | 988 | 37 |
| 313 | A | CA | 677 | 629 | 973 | 36 |
| 313 | A | CB | 664 | 632 | 966 | 35 |
| 313 | A | C | 687 | 640 | 970 | 35 |
| 313 | A | O | 690 | 642 | 958 | 36 |
| 314 | G | N | 691 | 647 | 980 | 36 |
| 314 | G | CA | 701 | 658 | 978 | 32 |
| 314 | G | C | 697 | 672 | 975 | 32 |
| 314 | G | O | 705 | 680 | 972 | 33 |
| 315 | A | N | 684 | 674 | 976 | 31 |
| 315 | A | CA | 679 | 688 | 974 | 30 |
| 315 | A | CB | 663 | 688 | 972 | 32 |
| 315 | A | C | 683 | 697 | 985 | 29 |
| 315 | A | O | 686 | 692 | 996 | 23 |
| 316 | R | N | 683 | 710 | 983 | 29 |
| 316 | R | CA | 687 | 719 | 993 | 33 |
| 316 | R | CB | 698 | 729 | 988 | 40 |
| 316 | R | CG | 712 | 726 | 994 | 47 |
| 316 | R | CD | 722 | 735 | 988 | 51 |
| 316 | R | NE | 733 | 728 | 983 | 64 |
| 316 | R | CZ | 746 | 732 | 986 | 66 |
| 316 | R | NH1 | 749 | 742 | 994 | 68 |
| 316 | R | NH2 | 756 | 725 | 981 | 67 |
| 316 | R | C | 674 | 728 | 996 | 34 |
| 316 | R | O | 673 | 733 | 1007 | 30 |
| 317 | L | N | 665 | 728 | 987 | 29 |
| 317 | L | CA | 653 | 736 | 989 | 33 |
| 317 | L | CB | 656 | 750 | 983 | 26 |
| 317 | L | CG | 644 | 760 | 984 | 24 |
| 317 | L | CD1 | 642 | 764 | 999 | 26 |
| 317 | L | CD2 | 647 | 772 | 976 | 24 |
| 317 | L | C | 640 | 730 | 983 | 33 |
| 317 | L | O | 640 | 725 | 972 | 36 |

TABLE 2-continued

| | | | | | | |
|---|---|---|---|---|---|---|
| 318 | V | N | 629 | 732 | 991 | 31 |
| 318 | V | CA | 616 | 728 | 986 | 27 |
| 318 | V | CB | 611 | 716 | 994 | 25 |
| 318 | V | CG1 | 596 | 715 | 992 | 20 |
| 318 | V | CG2 | 617 | 703 | 988 | 27 |
| 318 | V | C | 607 | 740 | 989 | 25 |
| 318 | V | O | 606 | 745 | 1000 | 24 |
| 319 | V | N | 602 | 745 | 978 | 22 |
| 319 | V | CA | 593 | 757 | 978 | 22 |
| 319 | V | CB | 597 | 767 | 967 | 24 |
| 319 | V | CG1 | 589 | 779 | 968 | 25 |
| 319 | V | CG2 | 612 | 771 | 969 | 22 |
| 319 | V | C | 579 | 752 | 976 | 25 |
| 319 | V | O | 576 | 745 | 967 | 22 |
| 320 | L | N | 571 | 756 | 986 | 24 |
| 320 | L | CK | 556 | 752 | 986 | 24 |
| 320 | L | CB | 551 | 748 | 1000 | 23 |
| 320 | L | CG | 557 | 735 | 1005 | 25 |
| 320 | L | CD1 | 554 | 734 | 1020 | 24 |
| 320 | L | CD2 | 552 | 724 | 997 | 18 |
| 320 | L | C | 550 | 765 | 981 | 22 |
| 320 | L | O | 548 | 774 | 989 | 24 |
| 321 | A | N | 546 | 765 | 968 | 22 |
| 321 | A | CA | 540 | 778 | 963 | 23 |
| 321 | A | CB | 548 | 782 | 951 | 17 |
| 321 | A | C | 525 | 778 | 960 | 25 |
| 321 | A | O | 520 | 769 | 954 | 29 |
| 322 | T | N | 519 | 789 | 965 | 25 |
| 322 | T | CA | 504 | 791 | 962 | 30 |
| 322 | T | CB | 496 | 782 | 972 | 33 |
| 322 | T | OG1 | 482 | 785 | 970 | 37 |
| 322 | T | CG2 | 500 | 785 | 986 | 29 |
| 322 | T | C | 500 | 805 | 964 | 31 |
| 322 | T | O | 507 | 813 | 972 | 29 |
| 323 | A | N | 490 | 809 | 957 | 29 |
| 323 | A | CA | 485 | 823 | 958 | 30 |
| 323 | A | CB | 479 | 827 | 944 | 34 |
| 323 | A | C | 474 | 823 | 969 | 29 |
| 323 | A | O | 470 | 833 | 973 | 36 |
| 324 | T | N | 469 | 811 | 973 | 26 |
| 324 | T | CA | 459 | 811 | 983 | 23 |
| 324 | T | CB | 445 | 808 | 976 | 19 |
| 324 | T | OG1 | 447 | 795 | 970 | 20 |
| 324 | T | CG2 | 441 | 818 | 966 | 12 |
| 324 | T | C | 462 | 801 | 994 | 24 |
| 324 | T | O | 457 | 790 | 994 | 29 |
| 325 | P | N | 471 | 805 | 1003 | 23 |
| 325 | P | CD | 477 | 818 | 1004 | 22 |
| 325 | P | CA | 474 | 795 | 1014 | 26 |
| 325 | P | CB | 486 | 803 | 1021 | 19 |
| 325 | P | CG | 484 | 817 | 1018 | 24 |
| 325 | P | C | 463 | 793 | 1024 | 26 |
| 325 | P | O | 453 | 801 | 1025 | 25 |
| 326 | P | N | 464 | 782 | 1032 | 26 |
| 326 | P | CD | 474 | 772 | 1031 | 18 |
| 326 | P | CA | 453 | 779 | 1042 | 28 |
| 326 | P | CB | 460 | 768 | 1050 | 24 |
| 326 | P | CG | 470 | 761 | 1040 | 21 |
| 326 | P | C | 449 | 791 | 1050 | 31 |
| 326 | P | O | 458 | 798 | 1056 | 34 |
| 327 | G | N | 436 | 793 | 1051 | 34 |
| 327 | G | CA | 431 | 804 | 1059 | 27 |
| 327 | G | C | 431 | 817 | 1050 | 30 |
| 327 | G | O | 427 | 828 | 1055 | 32 |
| 328 | S | N | 434 | 816 | 1038 | 30 |
| 328 | S | CA | 433 | 827 | 1029 | 36 |
| 328 | S | CB | 441 | 825 | 1016 | 34 |
| 328 | S | OG | 433 | 817 | 1007 | 42 |
| 328 | S | C | 419 | 831 | 1027 | 38 |
| 328 | S | O | 410 | 823 | 1028 | 40 |
| 329 | V | N | 416 | 843 | 1023 | 38 |
| 329 | V | CA | 403 | 848 | 1020 | 42 |
| 329 | V | CB | 398 | 857 | 1032 | 43 |
| 329 | V | CG1 | 397 | 872 | 1028 | 47 |
| 329 | V | CG2 | 385 | 852 | 1038 | 43 |
| 329 | V | C | 402 | 856 | 1007 | 41 |
| 329 | V | O | 410 | 864 | 1004 | 44 |
| 330 | T | N | 392 | 853 | 999 | 41 |
| 330 | T | CA | 390 | 860 | 986 | 44 |
| 330 | T | CB | 378 | 854 | 978 | 47 |
| 330 | T | OG1 | 382 | 840 | 974 | 49 |
| 330 | T | CG2 | 376 | 862 | 965 | 46 |
| 330 | T | C | 387 | 875 | 988 | 45 |
| 330 | T | O | 377 | 879 | 993 | 47 |
| 331 | V | N | 396 | 883 | 983 | 46 |
| 331 | V | CA | 395 | 897 | 983 | 46 |
| 331 | V | CB | 408 | 904 | 989 | 46 |
| 331 | V | CG1 | 408 | 902 | 1004 | 49 |
| 331 | V | CG2 | 420 | 898 | 982 | 47 |
| 331 | V | C | 393 | 903 | 969 | 46 |
| 331 | V | O | 395 | 896 | 959 | 45 |
| 332 | P | N | 389 | 916 | 968 | 48 |
| 332 | P | CD | 386 | 925 | 979 | 48 |
| 332 | P | CA | 387 | 923 | 955 | 49 |
| 332 | P | CB | 384 | 937 | 959 | 48 |
| 332 | P | CG | 387 | 938 | 973 | 49 |
| 332 | P | C | 399 | 922 | 945 | 51 |
| 332 | P | O | 411 | 922 | 949 | 50 |
| 333 | H | N | 395 | 921 | 932 | 52 |
| 333 | H | CA | 405 | 921 | 922 | 54 |
| 333 | H | CB | 404 | 908 | 913 | 55 |
| 333 | H | CG | 415 | 906 | 904 | 58 |
| 333 | H | CD2 | 422 | 895 | 900 | 60 |
| 333 | H | ND1 | 420 | 917 | 896 | 58 |
| 333 | H | CE1 | 429 | 912 | 888 | 57 |
| 333 | H | NE2 | 431 | 899 | 891 | 58 |
| 333 | H | C | 403 | 933 | 913 | 55 |
| 333 | H | O | 393 | 935 | 907 | 53 |
| 334 | P | N | 413 | 942 | 913 | 55 |
| 334 | P | CD | 426 | 940 | 919 | 54 |
| 334 | P | CA | 413 | 955 | 905 | 55 |
| 334 | P | CB | 427 | 960 | 906 | 53 |
| 334 | P | CG | 435 | 948 | 910 | 55 |
| 334 | P | C | 408 | 954 | 890 | 56 |
| 334 | P | O | 404 | 963 | 885 | 56 |
| 335 | N | N | 410 | 942 | 885 | 55 |
| 335 | N | CA | 406 | 940 | 871 | 55 |
| 335 | N | CB | 416 | 930 | 864 | 58 |
| 335 | N | CG | 425 | 937 | 854 | 62 |
| 335 | N | OD1 | 420 | 947 | 848 | 67 |
| 335 | N | ND2 | 436 | 932 | 851 | 63 |
| 335 | N | C | 393 | 933 | 869 | 54 |
| 335 | N | O | 387 | 933 | 858 | 54 |
| 336 | I | N | 387 | 929 | 880 | 53 |
| 336 | I | CA | 374 | 922 | 879 | 52 |
| 336 | I | CB | 376 | 908 | 884 | 52 |
| 336 | I | CG2 | 363 | 899 | 881 | 53 |
| 336 | I | CG1 | 388 | 901 | 878 | 52 |
| 336 | I | CD1 | 392 | 888 | 884 | 54 |
| 336 | I | C | 362 | 929 | 885 | 49 |
| 336 | I | O | 362 | 932 | 897 | 46 |
| 337 | E | N | 352 | 930 | 877 | 47 |
| 337 | E | CA | 339 | 936 | 882 | 46 |
| 337 | E | CB | 332 | 944 | 870 | 52 |
| 337 | E | CG | 321 | 953 | 875 | 57 |
| 337 | E | CD | 327 | 964 | 884 | 63 |
| 337 | E | OE1 | 321 | 966 | 895 | 68 |
| 337 | E | OE2 | 337 | 970 | 880 | 69 |
| 337 | E | C | 330 | 925 | 886 | 44 |
| 337 | E | O | 327 | 916 | 878 | 45 |
| 338 | E | N | 326 | 925 | 899 | 43 |
| 338 | E | CA | 318 | 914 | 904 | 45 |
| 338 | E | CB | 323 | 910 | 918 | 42 |
| 338 | E | CG | 337 | 905 | 917 | 45 |
| 338 | E | CD | 342 | 900 | 931 | 50 |
| 338 | E | OE1 | 333 | 894 | 938 | 49 |
| 338 | E | OE2 | 354 | 901 | 934 | 53 |
| 338 | E | C | 303 | 919 | 905 | 45 |
| 338 | E | O | 300 | 929 | 912 | 44 |
| 339 | V | N | 294 | 912 | 898 | 46 |
| 339 | V | CA | 280 | 916 | 899 | 45 |
| 339 | V | CB | 276 | 922 | 886 | 44 |
| 339 | V | CG1 | 261 | 923 | 886 | 44 |
| 339 | V | CG2 | 283 | 935 | 883 | 44 |
| 339 | V | C | 271 | 904 | 902 | 46 |
| 339 | V | O | 271 | 894 | 895 | 47 |
| 340 | A | N | 264 | 906 | 913 | 46 |
| 340 | A | CA | 254 | 896 | 918 | 47 |

TABLE 2-continued

| | | | | | | | | | | | | |
|---|---|---|---|---|---|---|---|---|---|---|---|---|
| 340 | A | CB | 249 | 900 | 932 | 45 | 350 | Y | CZ | 245 | 749 | 890 | 31 |
| 340 | A | C | 243 | 894 | 908 | 47 | 350 | Y | OH | 252 | 739 | 884 | 30 |
| 340 | A | O | 237 | 903 | 903 | 51 | 350 | Y | C | 198 | 788 | 912 | 32 |
| 341 | L | N | 240 | 881 | 906 | 48 | 350 | Y | O | 203 | 794 | 922 | 34 |
| 341 | L | CA | 230 | 877 | 897 | 46 | 351 | G | N | 185 | 789 | 908 | 31 |
| 341 | L | CB | 230 | 862 | 894 | 46 | 351 | G | CA | 176 | 797 | 916 | 34 |
| 341 | L | CG | 233 | 857 | 880 | 50 | 351 | G | C | 176 | 812 | 912 | 37 |
| 341 | L | CD1 | 241 | 867 | 872 | 46 | 351 | G | O | 168 | 820 | 916 | 39 |
| 341 | L | CD2 | 240 | 843 | 881 | 47 | 352 | K | N | 185 | 815 | 903 | 35 |
| 341 | L | C | 216 | 881 | 904 | 47 | 352 | K | CA | 186 | 828 | 897 | 36 |
| 341 | L | O | 216 | 885 | 915 | 50 | 352 | K | CB | 200 | 835 | 900 | 39 |
| 342 | S | N | 206 | 880 | 896 | 49 | 352 | K | CG | 202 | 840 | 914 | 42 |
| 342 | S | CA | 192 | 883 | 902 | 50 | 352 | K | CD | 189 | 847 | 919 | 47 |
| 342 | S | CB | 189 | 898 | 900 | 48 | 352 | K | CE | 189 | 847 | 934 | 48 |
| 342 | S | CG | 184 | 900 | 887 | 53 | 352 | K | NZ | 175 | 851 | 939 | 49 |
| 342 | S | C | 182 | 875 | 895 | 50 | 352 | K | C | 185 | 828 | 882 | 34 |
| 342 | S | O | 185 | 866 | 887 | 52 | 352 | K | O | 180 | 817 | 877 | 32 |
| 343 | N | N | 169 | 877 | 899 | 50 | 353 | A | N | 188 | 838 | 875 | 38 |
| 343 | N | CA | 158 | 869 | 894 | 51 | 353 | A | CA | 187 | 839 | 861 | 42 |
| 343 | N | CB | 147 | 869 | 903 | 49 | 353 | A | CB | 174 | 845 | 856 | 42 |
| 343 | N | CG | 149 | 861 | 916 | 50 | 353 | A | C | 199 | 847 | 855 | 41 |
| 343 | N | OD1 | 151 | 866 | 927 | 52 | 353 | A | O | 206 | 854 | 861 | 42 |
| 343 | N | ND2 | 149 | 848 | 914 | 46 | 354 | I | N | 201 | 844 | 842 | 44 |
| 343 | N | C | 154 | 874 | 880 | 51 | 354 | I | CA | 212 | 851 | 834 | 46 |
| 343 | N | O | 147 | 867 | 873 | 52 | 354 | I | CB | 223 | 841 | 830 | 45 |
| 344 | T | N | 159 | 886 | 876 | 52 | 354 | I | CG2 | 233 | 848 | 821 | 43 |
| 344 | T | CA | 155 | 891 | 863 | 52 | 354 | I | CG1 | 230 | 836 | 842 | 48 |
| 344 | T | CB | 155 | 906 | 862 | 55 | 354 | I | CD1 | 237 | 823 | 840 | 47 |
| 344 | T | OG1 | 169 | 911 | 860 | 59 | 354 | I | C | 206 | 857 | 822 | 49 |
| 344 | T | CG2 | 150 | 913 | 875 | 55 | 354 | I | O | 201 | 850 | 813 | 49 |
| 344 | T | C | 165 | 885 | 853 | 49 | 355 | P | N | 207 | 871 | 820 | 50 |
| 344 | T | O | 177 | 887 | 855 | 52 | 355 | P | CD | 214 | 880 | 830 | 49 |
| 345 | G | N | 161 | 878 | 843 | 47 | 355 | P | CA | 202 | 878 | 809 | 50 |
| 345 | G | CA | 170 | 872 | 834 | 44 | 355 | P | CB | 202 | 892 | 813 | 49 |
| 345 | G | C | 163 | 862 | 826 | 44 | 355 | P | CG | 206 | 892 | 828 | 51 |
| 345 | G | O | 152 | 857 | 829 | 45 | 355 | P | C | 212 | 875 | 797 | 52 |
| 346 | E | N | 169 | 857 | 815 | 42 | 355 | P | O | 223 | 880 | 797 | 53 |
| 346 | E | CA | 163 | 848 | 806 | 46 | 356 | I | N | 207 | 867 | 787 | 54 |
| 346 | E | CB | 167 | 850 | 791 | 51 | 356 | I | CA | 216 | 864 | 775 | 55 |
| 346 | E | CG | 164 | 864 | 786 | 58 | 356 | I | CB | 207 | 859 | 764 | 60 |
| 346 | E | CD | 174 | 875 | 792 | 62 | 356 | I | CG2 | 211 | 844 | 761 | 62 |
| 346 | E | OE1 | 172 | 879 | 804 | 65 | 356 | I | CG1 | 192 | 860 | 766 | 62 |
| 346 | E | OE2 | 183 | 879 | 785 | 66 | 356 | I | CD1 | 184 | 856 | 755 | 61 |
| 346 | E | C | 166 | 834 | 810 | 45 | 356 | I | C | 223 | 876 | 770 | 56 |
| 346 | E | O | 157 | 825 | 812 | 47 | 356 | I | O | 234 | 875 | 764 | 55 |
| 347 | I | N | 179 | 831 | 810 | 44 | 357 | E | N | 218 | 888 | 773 | 56 |
| 347 | I | CA | 183 | 817 | 814 | 41 | 357 | E | CA | 225 | 901 | 769 | 57 |
| 347 | I | CB | 198 | 815 | 809 | 42 | 357 | E | CB | 216 | 912 | 773 | 59 |
| 347 | I | CG2 | 202 | 801 | 812 | 40 | 357 | E | CG | 207 | 918 | 762 | 65 |
| 347 | I | CG1 | 198 | 817 | 794 | 42 | 357 | E | CD | 215 | 922 | 750 | 67 |
| 347 | I | CD1 | 208 | 828 | 790 | 43 | 357 | E | OE1 | 216 | 914 | 740 | 68 |
| 347 | I | C | 183 | 815 | 829 | 36 | 357 | E | OE2 | 221 | 933 | 750 | 67 |
| 347 | I | O | 188 | 822 | 837 | 35 | 357 | E | C | 238 | 902 | 776 | 57 |
| 348 | P | N | 176 | 804 | 833 | 35 | 357 | E | O | 245 | 912 | 774 | 59 |
| 348 | P | CD | 168 | 794 | 825 | 34 | 358 | A | N | 242 | 892 | 784 | 55 |
| 348 | P | CA | 175 | 801 | 847 | 36 | 358 | A | CA | 255 | 893 | 791 | 54 |
| 348 | P | CB | 163 | 791 | 848 | 38 | 358 | A | CB | 253 | 890 | 806 | 52 |
| 348 | P | CG | 157 | 791 | 834 | 37 | 358 | A | C | 265 | 883 | 785 | 52 |
| 348 | P | C | 188 | 795 | 852 | 33 | 358 | A | O | 277 | 884 | 786 | 51 |
| 348 | P | O | 193 | 785 | 846 | 31 | 359 | I | N | 259 | 873 | 778 | 54 |
| 349 | F | N | 193 | 800 | 863 | 33 | 359 | I | CA | 268 | 863 | 772 | 55 |
| 349 | F | CA | 206 | 796 | 868 | 33 | 359 | I | CB | 264 | 849 | 779 | 56 |
| 349 | F | CB | 217 | 805 | 863 | 34 | 359 | I | CG2 | 267 | 850 | 793 | 52 |
| 349 | F | CG | 231 | 800 | 865 | 32 | 359 | I | CG1 | 249 | 847 | 777 | 57 |
| 349 | F | CD1 | 235 | 789 | 857 | 35 | 359 | I | CD1 | 245 | 832 | 781 | 54 |
| 349 | F | CD2 | 239 | 806 | 874 | 36 | 359 | I | C | 267 | 862 | 757 | 58 |
| 349 | F | CE1 | 248 | 784 | 859 | 35 | 359 | I | O | 274 | 854 | 750 | 58 |
| 349 | F | CE2 | 252 | 801 | 875 | 37 | 360 | R | N | 258 | 870 | 750 | 60 |
| 349 | F | CZ | 256 | 790 | 868 | 34 | 360 | R | CA | 256 | 869 | 736 | 63 |
| 349 | F | C | 207 | 794 | 884 | 33 | 360 | R | CB | 246 | 880 | 732 | 63 |
| 349 | F | O | 208 | 805 | 891 | 29 | 360 | R | CG | 251 | 895 | 733 | 68 |
| 350 | Y | N | 206 | 782 | 889 | 34 | 360 | R | CD | 256 | 898 | 747 | 74 |
| 350 | Y | CA | 207 | 780 | 903 | 29 | 360 | R | NE | 262 | 911 | 748 | 78 |
| 350 | Y | CB | 222 | 780 | 908 | 33 | 360 | R | CZ | 273 | 915 | 755 | 82 |
| 350 | Y | CG | 230 | 769 | 902 | 29 | 360 | R | NH1 | 278 | 905 | 763 | 81 |
| 350 | Y | CD1 | 235 | 771 | 889 | 30 | 360 | R | NH2 | 278 | 927 | 755 | 82 |
| 350 | Y | CE1 | 242 | 760 | 883 | 29 | 360 | R | C | 270 | 871 | 728 | 63 |
| 350 | Y | CD2 | 233 | 758 | 909 | 26 | 360 | R | O | 275 | 861 | 723 | 67 |
| 350 | Y | CE2 | 240 | 747 | 903 | 24 | 361 | G | N | 275 | 883 | 727 | 63 |

TABLE 2-continued

| | | | | | | |
|---|---|---|---|---|---|---|
| 361 | G | CA | 288 | 884 | 720 | 59 |
| 361 | G | C | 299 | 882 | 730 | 59 |
| 361 | G | O | 299 | 886 | 742 | 61 |
| 362 | G | N | 310 | 876 | 725 | 54 |
| 362 | G | CA | 322 | 874 | 734 | 52 |
| 362 | G | C | 324 | 859 | 738 | 50 |
| 362 | G | O | 318 | 850 | 733 | 47 |
| 363 | R | N | 334 | 858 | 747 | 48 |
| 363 | R | CA | 338 | 845 | 752 | 48 |
| 363 | R | CB | 353 | 842 | 749 | 44 |
| 363 | R | CG | 356 | 842 | 734 | 44 |
| 363 | R | CD | 371 | 842 | 732 | 44 |
| 363 | R | NE | 378 | 831 | 738 | 43 |
| 363 | R | CZ | 377 | 818 | 735 | 44 |
| 363 | R | NH1 | 369 | 815 | 724 | 47 |
| 363 | R | NH2 | 383 | 808 | 741 | 39 |
| 363 | R | C | 335 | 845 | 767 | 48 |
| 363 | R | O | 340 | 853 | 774 | 48 |
| 364 | H | N | 328 | 835 | 772 | 45 |
| 364 | H | CA | 325 | 834 | 786 | 43 |
| 364 | H | CB | 311 | 841 | 789 | 43 |
| 364 | H | CG | 309 | 853 | 781 | 42 |
| 364 | H | CD2 | 305 | 855 | 768 | 43 |
| 364 | H | ND1 | 310 | 866 | 787 | 38 |
| 364 | H | CE1 | 307 | 875 | 777 | 41 |
| 364 | H | NE2 | 304 | 869 | 766 | 46 |
| 364 | H | C | 324 | 820 | 791 | 43 |
| 364 | H | O | 322 | 810 | 784 | 45 |
| 365 | L | N | 327 | 819 | 804 | 41 |
| 365 | L | CA | 327 | 807 | 811 | 36 |
| 365 | L | CB | 341 | 804 | 817 | 35 |
| 365 | L | CG | 343 | 792 | 826 | 30 |
| 365 | L | CD1 | 340 | 779 | 818 | 34 |
| 365 | L | CD2 | 357 | 792 | 831 | 36 |
| 365 | L | C | 317 | 807 | 822 | 34 |
| 365 | L | O | 316 | 816 | 830 | 32 |
| 366 | I | N | 308 | 797 | 822 | 34 |
| 366 | I | CA | 298 | 795 | 832 | 35 |
| 366 | I | CB | 284 | 793 | 826 | 32 |
| 366 | I | CG2 | 274 | 790 | 837 | 34 |
| 366 | I | CG1 | 280 | 806 | 819 | 31 |
| 366 | I | CD1 | 272 | 803 | 806 | 36 |
| 366 | I | C | 303 | 783 | 840 | 35 |
| 366 | I | O | 306 | 773 | 833 | 34 |
| 367 | F | N | 303 | 784 | 853 | 35 |
| 367 | F | CA | 308 | 772 | 861 | 33 |
| 367 | F | CB | 317 | 777 | 872 | 30 |
| 367 | F | CG | 331 | 777 | 869 | 29 |
| 367 | F | CD1 | 338 | 766 | 867 | 33 |
| 367 | F | CD2 | 338 | 790 | 867 | 30 |
| 367 | F | CE1 | 352 | 766 | 863 | 29 |
| 367 | F | CE2 | 351 | 790 | 863 | 30 |
| 367 | F | CZ | 358 | 778 | 861 | 28 |
| 367 | F | C | 296 | 765 | 867 | 33 |
| 367 | F | O | 288 | 771 | 875 | 35 |
| 368 | C | N | 294 | 752 | 865 | 35 |
| 368 | C | CA | 283 | 744 | 870 | 40 |
| 368 | C | CB | 275 | 738 | 858 | 45 |
| 368 | C | SG | 269 | 750 | 847 | 54 |
| 368 | C | C | 289 | 733 | 879 | 38 |
| 368 | C | O | 299 | 727 | 876 | 35 |
| 369 | H | N | 281 | 729 | 889 | 38 |
| 369 | H | CA | 285 | 719 | 899 | 37 |
| 369 | H | CB | 275 | 719 | 911 | 39 |
| 369 | H | CG | 263 | 710 | 908 | 42 |
| 369 | H | CD2 | 254 | 709 | 898 | 41 |
| 369 | H | ND1 | 259 | 700 | 918 | 47 |
| 369 | H | CE1 | 248 | 694 | 913 | 46 |
| 369 | H | NE2 | 245 | 700 | 902 | 45 |
| 369 | H | C | 286 | 705 | 893 | 40 |
| 369 | H | O | 294 | 697 | 898 | 42 |
| 370 | S | N | 278 | 702 | 883 | 40 |
| 370 | S | CA | 279 | 688 | 877 | 44 |
| 370 | S | CB | 266 | 681 | 880 | 46 |
| 370 | S | OG | 256 | 683 | 871 | 49 |
| 370 | S | C | 280 | 689 | 862 | 47 |
| 370 | S | O | 279 | 699 | 855 | 45 |
| 371 | K | N | 283 | 677 | 856 | 49 |
| 371 | K | CA | 284 | 676 | 841 | 53 |
| 371 | K | CB | 293 | 664 | 838 | 54 |
| 371 | K | CG | 285 | 651 | 836 | 57 |
| 371 | K | CD | 292 | 641 | 827 | 57 |
| 371 | K | CE | 282 | 636 | 816 | 61 |
| 371 | K | NZ | 289 | 626 | 808 | 62 |
| 371 | K | C | 270 | 675 | 835 | 54 |
| 371 | K | O | 269 | 679 | 823 | 51 |
| 372 | K | N | 261 | 671 | 843 | 56 |
| 372 | K | CA | 247 | 670 | 838 | 56 |
| 372 | K | CB | 238 | 663 | 849 | 57 |
| 372 | K | CG | 224 | 660 | 844 | 59 |
| 372 | K | CD | 216 | 654 | 856 | 58 |
| 372 | K | CE | 201 | 659 | 856 | 57 |
| 372 | K | NZ | 197 | 663 | 870 | 56 |
| 372 | K | C | 241 | 684 | 836 | 56 |
| 372 | K | O | 234 | 686 | 826 | 59 |
| 373 | K | N | 244 | 694 | 845 | 55 |
| 373 | K | CA | 239 | 707 | 843 | 55 |
| 373 | K | CB | 241 | 715 | 856 | 55 |
| 373 | K | CG | 227 | 717 | 864 | 62 |
| 373 | K | CD | 219 | 704 | 864 | 64 |
| 373 | K | CE | 214 | 701 | 878 | 64 |
| 373 | K | NZ | 218 | 688 | 884 | 64 |
| 373 | K | C | 246 | 715 | 832 | 51 |
| 373 | K | O | 241 | 725 | 827 | 52 |
| 374 | C | N | 257 | 710 | 827 | 53 |
| 374 | C | CA | 264 | 716 | 816 | 55 |
| 374 | C | CB | 279 | 712 | 816 | 55 |
| 374 | C | SG | 287 | 712 | 831 | 59 |
| 374 | C | C | 257 | 711 | 804 | 55 |
| 374 | C | O | 253 | 719 | 795 | 57 |
| 375 | D | N | 255 | 698 | 803 | 55 |
| 375 | D | CA | 248 | 692 | 792 | 55 |
| 375 | D | CB | 246 | 677 | 795 | 57 |
| 375 | D | CG | 257 | 668 | 790 | 58 |
| 375 | D | OD1 | 256 | 656 | 792 | 60 |
| 375 | D | OD2 | 266 | 673 | 783 | 58 |
| 375 | D | C | 235 | 699 | 790 | 55 |
| 375 | D | O | 230 | 700 | 779 | 59 |
| 376 | E | N | 228 | 703 | 801 | 55 |
| 376 | E | CA | 216 | 710 | 801 | 55 |
| 376 | E | CB | 209 | 710 | 815 | 55 |
| 376 | E | CG | 200 | 698 | 817 | 58 |
| 376 | E | CD | 199 | 694 | 832 | 64 |
| 376 | E | OE1 | 198 | 682 | 835 | 65 |
| 376 | E | OE2 | 198 | 703 | 841 | 67 |
| 376 | E | C | 217 | 724 | 796 | 55 |
| 376 | E | O | 212 | 727 | 785 | 57 |
| 377 | L | N | 224 | 732 | 803 | 55 |
| 377 | L | CA | 226 | 746 | 800 | 53 |
| 377 | L | CB | 236 | 753 | 809 | 52 |
| 377 | L | CG | 235 | 768 | 812 | 46 |
| 377 | L | CD1 | 221 | 773 | 810 | 39 |
| 377 | L | CD2 | 240 | 771 | 826 | 45 |
| 377 | L | C | 232 | 748 | 786 | 53 |
| 377 | L | O | 226 | 756 | 778 | 53 |
| 378 | A | N | 242 | 740 | 782 | 54 |
| 378 | A | CA | 248 | 741 | 769 | 56 |
| 378 | A | CB | 258 | 730 | 767 | 54 |
| 378 | A | C | 237 | 740 | 759 | 58 |
| 378 | A | O | 236 | 747 | 749 | 59 |
| 379 | A | N | 227 | 731 | 761 | 59 |
| 379 | A | CA | 216 | 728 | 752 | 59 |
| 379 | A | CB | 208 | 717 | 757 | 59 |
| 379 | A | C | 207 | 741 | 751 | 59 |
| 379 | A | O | 206 | 747 | 741 | 61 |
| 380 | K | N | 202 | 745 | 763 | 58 |
| 380 | K | CA | 193 | 757 | 763 | 58 |
| 380 | K | CB | 189 | 760 | 778 | 54 |
| 380 | K | CG | 184 | 774 | 780 | 54 |
| 380 | K | CD | 170 | 774 | 786 | 55 |
| 380 | K | CE | 162 | 786 | 782 | 58 |
| 380 | K | NZ | 149 | 787 | 790 | 59 |
| 380 | K | C | 201 | 769 | 758 | 58 |
| 380 | K | O | 195 | 777 | 750 | 60 |
| 381 | L | N | 214 | 770 | 761 | 60 |
| 381 | L | CA | 222 | 782 | 757 | 62 |
| 381 | L | CB | 236 | 781 | 763 | 60 |
| 381 | L | CG | 237 | 788 | 776 | 61 |

TABLE 2-continued

| | | | | | | | | | | | | |
|---|---|---|---|---|---|---|---|---|---|---|---|---|
| 381 | L | CD1 | 252 | 788 | 781 | 60 | 392 | Y | CZ | 298 | 663 | 796 | 57 |
| 381 | L | CD2 | 232 | 802 | 776 | 59 | 392 | Y | OH | 289 | 658 | 786 | 54 |
| 381 | L | C | 222 | 781 | 741 | 64 | 392 | Y | C | 349 | 669 | 817 | 59 |
| 381 | L | O | 220 | 791 | 734 | 65 | 392 | Y | O | 354 | 666 | 807 | 59 |
| 382 | S | N | 225 | 769 | 736 | 65 | 393 | R | N | 351 | 661 | 828 | 61 |
| 382 | S | CA | 226 | 767 | 722 | 66 | 393 | R | CA | 359 | 649 | 827 | 60 |
| 382 | S | CB | 229 | 752 | 719 | 65 | 393 | R | CB | 359 | 642 | 841 | 60 |
| 382 | S | OG | 242 | 751 | 713 | 69 | 393 | R | CG | 373 | 635 | 844 | 59 |
| 382 | S | C | 212 | 771 | 716 | 68 | 393 | R | CD | 372 | 626 | 856 | 59 |
| 382 | S | O | 211 | 779 | 707 | 65 | 393 | R | NE | 362 | 616 | 855 | 62 |
| 383 | G | N | 202 | 764 | 721 | 69 | 393 | R | CZ | 364 | 605 | 846 | 62 |
| 383 | G | CA | 188 | 767 | 717 | 68 | 393 | R | NH1 | 374 | 605 | 838 | 64 |
| 383 | G | C | 184 | 781 | 715 | 66 | 393 | R | NH2 | 354 | 596 | 846 | 66 |
| 383 | G | O | 177 | 785 | 706 | 68 | 393 | R | C | 354 | 639 | 817 | 60 |
| 384 | L | N | 189 | 790 | 725 | 65 | 393 | R | O | 342 | 636 | 816 | 63 |
| 384 | L | CA | 187 | 804 | 724 | 63 | 394 | G | N | 363 | 635 | 808 | 59 |
| 384 | L | CB | 190 | 811 | 737 | 64 | 394 | G | CA | 360 | 626 | 798 | 61 |
| 384 | L | CG | 179 | 812 | 747 | 63 | 394 | G | C | 359 | 632 | 784 | 62 |
| 384 | L | CD1 | 173 | 798 | 751 | 64 | 394 | G | O | 359 | 624 | 774 | 63 |
| 384 | L | CD2 | 183 | 820 | 759 | 64 | 395 | L | N | 360 | 645 | 783 | 60 |
| 384 | L | C | 195 | 810 | 713 | 63 | 395 | L | CA | 360 | 652 | 770 | 61 |
| 384 | L | O | 197 | 822 | 712 | 61 | 395 | L | CB | 350 | 664 | 770 | 56 |
| 385 | G | N | 201 | 801 | 705 | 63 | 395 | L | CG | 336 | 661 | 767 | 54 |
| 385 | G | CA | 210 | 805 | 695 | 64 | 395 | L | CD1 | 331 | 648 | 774 | 48 |
| 385 | G | C | 224 | 808 | 699 | 66 | 395 | L | CD2 | 327 | 672 | 771 | 50 |
| 385 | G | O | 233 | 809 | 690 | 69 | 395 | L | C | 374 | 656 | 768 | 65 |
| 386 | I | N | 227 | 808 | 712 | 66 | 395 | L | O | 382 | 657 | 777 | 66 |
| 386 | I | CA | 240 | 810 | 717 | 66 | 396 | D | N | 376 | 660 | 756 | 68 |
| 386 | I | CB | 240 | 813 | 732 | 67 | 396 | D | CA | 390 | 665 | 752 | 72 |
| 386 | I | CG2 | 253 | 819 | 736 | 70 | 396 | D | CB | 395 | 659 | 739 | 76 |
| 386 | I | CG1 | 229 | 822 | 736 | 69 | 396 | D | CG | 397 | 669 | 728 | 81 |
| 386 | I | CD1 | 229 | 835 | 728 | 70 | 396 | D | OD1 | 408 | 675 | 728 | 82 |
| 386 | I | C | 249 | 798 | 714 | 66 | 396 | D | OD2 | 387 | 672 | 721 | 85 |
| 386 | I | O | 245 | 787 | 715 | 67 | 396 | D | C | 388 | 680 | 750 | 73 |
| 387 | N | N | 262 | 801 | 710 | 64 | 396 | D | O | 377 | 685 | 747 | 71 |
| 387 | N | CA | 271 | 790 | 707 | 63 | 397 | V | N | 398 | 688 | 751 | 74 |
| 387 | N | CB | 281 | 795 | 697 | 65 | 397 | V | CA | 397 | 702 | 749 | 77 |
| 387 | N | CG | 292 | 784 | 694 | 63 | 397 | V | CB | 411 | 709 | 751 | 77 |
| 387 | N | OD1 | 289 | 772 | 694 | 63 | 397 | V | CG1 | 409 | 724 | 751 | 78 |
| 387 | N | ND2 | 304 | 788 | 692 | 60 | 397 | V | CG2 | 417 | 705 | 765 | 75 |
| 387 | N | C | 278 | 786 | 720 | 62 | 397 | V | C | 392 | 704 | 735 | 78 |
| 387 | N | O | 289 | 791 | 724 | 63 | 397 | V | O | 400 | 705 | 725 | 79 |
| 388 | A | N | 272 | 776 | 727 | 60 | 398 | S | N | 379 | 705 | 734 | 78 |
| 388 | A | CA | 278 | 771 | 740 | 58 | 398 | S | CA | 372 | 707 | 721 | 74 |
| 388 | A | CB | 267 | 770 | 750 | 58 | 398 | S | CB | 360 | 698 | 720 | 76 |
| 388 | A | C | 285 | 758 | 738 | 57 | 398 | S | OG | 355 | 694 | 733 | 73 |
| 388 | A | O | 283 | 751 | 727 | 58 | 398 | S | C | 367 | 722 | 722 | 73 |
| 389 | V | N | 292 | 753 | 748 | 54 | 398 | S | O | 358 | 726 | 715 | 72 |
| 389 | V | CA | 299 | 740 | 747 | 53 | 399 | V | N | 373 | 729 | 731 | 73 |
| 389 | V | CB | 312 | 741 | 739 | 52 | 399 | V | CA | 369 | 743 | 733 | 72 |
| 389 | V | CG1 | 309 | 736 | 725 | 52 | 399 | V | CB | 375 | 748 | 746 | 72 |
| 389 | V | CG2 | 316 | 756 | 739 | 55 | 399 | V | CG1 | 373 | 764 | 748 | 71 |
| 389 | V | C | 302 | 735 | 761 | 51 | 399 | V | CG2 | 369 | 741 | 758 | 69 |
| 389 | V | O | 310 | 741 | 768 | 49 | 399 | V | C | 375 | 751 | 722 | 73 |
| 390 | A | N | 296 | 724 | 765 | 52 | 399 | V | O | 386 | 747 | 717 | 72 |
| 390 | A | CA | 298 | 718 | 778 | 53 | 400 | I | N | 369 | 762 | 718 | 75 |
| 390 | A | CB | 287 | 709 | 782 | 50 | 400 | I | CA | 374 | 771 | 707 | 78 |
| 390 | A | C | 311 | 711 | 779 | 54 | 400 | I | CB | 362 | 777 | 700 | 78 |
| 390 | A | O | 316 | 705 | 769 | 52 | 400 | I | CG2 | 357 | 769 | 689 | 78 |
| 391 | Y | N | 318 | 712 | 791 | 56 | 400 | I | CG1 | 351 | 780 | 710 | 81 |
| 391 | Y | CA | 331 | 706 | 792 | 56 | 400 | I | CD1 | 343 | 768 | 714 | 82 |
| 391 | Y | CB | 342 | 716 | 790 | 53 | 400 | I | C | 383 | 781 | 712 | 81 |
| 391 | Y | CG | 356 | 710 | 792 | 57 | 400 | I | O | 379 | 792 | 716 | 81 |
| 391 | Y | CD1 | 361 | 701 | 782 | 53 | 401 | P | N | 396 | 779 | 713 | 85 |
| 391 | Y | CE1 | 373 | 694 | 784 | 53 | 401 | P | CD | 403 | 766 | 708 | 87 |
| 391 | Y | CD2 | 363 | 711 | 804 | 56 | 401 | P | CA | 406 | 789 | 717 | 87 |
| 391 | Y | CE2 | 375 | 704 | 806 | 56 | 401 | P | CB | 419 | 781 | 719 | 87 |
| 391 | Y | CZ | 380 | 696 | 796 | 55 | 401 | P | CG | 415 | 767 | 717 | 88 |
| 391 | Y | OH | 392 | 689 | 798 | 57 | 401 | P | C | 407 | 799 | 706 | 88 |
| 391 | Y | C | 333 | 700 | 806 | 56 | 401 | P | O | 412 | 810 | 708 | 88 |
| 391 | Y | O | 330 | 706 | 816 | 56 | 402 | T | N | 402 | 795 | 695 | 91 |
| 392 | Y | N | 338 | 688 | 807 | 57 | 402 | T | CA | 402 | 804 | 683 | 94 |
| 392 | Y | CA | 340 | 681 | 819 | 58 | 402 | T | CB | 396 | 797 | 671 | 95 |
| 392 | Y | CB | 326 | 677 | 825 | 56 | 402 | T | OG1 | 398 | 783 | 671 | 95 |
| 392 | Y | CG | 317 | 672 | 815 | 57 | 402 | T | CG2 | 402 | 802 | 658 | 96 |
| 392 | Y | CD1 | 318 | 659 | 809 | 57 | 402 | T | C | 394 | 816 | 686 | 94 |
| 392 | Y | CE1 | 309 | 655 | 800 | 57 | 402 | T | O | 389 | 823 | 676 | 94 |
| 392 | Y | CD2 | 306 | 680 | 811 | 56 | 403 | I | N | 394 | 820 | 698 | 94 |
| 392 | Y | CE2 | 297 | 675 | 801 | 57 | 403 | I | CA | 387 | 832 | 703 | 94 |

TABLE 2-continued

| | | | | | | |
|---|---|---|---|---|---|---|
| 403 | I | CB | 395 | 845 | 700 | 94 |
| 403 | I | CG2 | 388 | 857 | 706 | 96 |
| 403 | I | CG1 | 409 | 843 | 708 | 94 |
| 403 | I | CD1 | 407 | 844 | 723 | 92 |
| 403 | I | C | 373 | 834 | 695 | 93 |
| 403 | I | O | 368 | 845 | 694 | 92 |
| 404 | G | N | 368 | 823 | 690 | 90 |
| 404 | G | CA | 356 | 823 | 683 | 85 |
| 404 | G | C | 345 | 825 | 693 | 82 |
| 404 | G | O | 344 | 817 | 702 | 84 |
| 405 | D | N | 337 | 835 | 691 | 75 |
| 405 | D | CA | 326 | 838 | 700 | 69 |
| 405 | D | CB | 314 | 845 | 693 | 70 |
| 405 | D | CG | 311 | 859 | 697 | 71 |
| 405 | D | OD1 | 300 | 864 | 695 | 72 |
| 405 | D | OD2 | 320 | 865 | 703 | 73 |
| 405 | D | C | 321 | 825 | 707 | 65 |
| 405 | D | O | 318 | 816 | 699 | 64 |
| 406 | V | N | 320 | 825 | 720 | 60 |
| 406 | V | CA | 315 | 813 | 726 | 53 |
| 406 | V | CB | 325 | 801 | 724 | 50 |
| 406 | V | CG1 | 338 | 803 | 733 | 51 |
| 406 | V | CG2 | 319 | 788 | 727 | 48 |
| 406 | V | C | 313 | 814 | 741 | 49 |
| 406 | V | O | 317 | 823 | 748 | 46 |
| 407 | V | N | 305 | 804 | 746 | 49 |
| 407 | V | CA | 302 | 803 | 761 | 50 |
| 407 | V | CB | 287 | 807 | 764 | 51 |
| 407 | V | CG1 | 286 | 815 | 777 | 50 |
| 407 | V | CG2 | 281 | 814 | 752 | 52 |
| 407 | V | C | 305 | 789 | 764 | 49 |
| 407 | V | O | 298 | 780 | 758 | 48 |
| 408 | V | N | 314 | 786 | 773 | 48 |
| 408 | V | CA | 317 | 773 | 777 | 46 |
| 408 | V | CB | 333 | 771 | 778 | 46 |
| 408 | V | CG1 | 338 | 772 | 764 | 46 |
| 408 | V | CG2 | 339 | 781 | 787 | 53 |
| 408 | V | C | 311 | 770 | 791 | 45 |
| 408 | V | O | 314 | 777 | 801 | 47 |
| 409 | V | N | 302 | 761 | 791 | 43 |
| 409 | V | CA | 295 | 757 | 804 | 42 |
| 409 | V | CB | 281 | 752 | 802 | 39 |
| 409 | V | CG1 | 275 | 750 | 815 | 42 |
| 409 | V | CG2 | 273 | 762 | 794 | 41 |
| 409 | V | C | 304 | 746 | 809 | 42 |
| 409 | V | O | 305 | 736 | 804 | 43 |
| 410 | A | N | 311 | 749 | 820 | 41 |
| 410 | A | CA | 321 | 740 | 825 | 40 |
| 410 | A | CB | 335 | 744 | 822 | 38 |
| 410 | A | C | 320 | 735 | 840 | 40 |
| 410 | A | O | 314 | 742 | 848 | 38 |
| 411 | T | N | 326 | 724 | 842 | 41 |
| 411 | T | CA | 327 | 718 | 855 | 41 |
| 411 | T | CB | 326 | 703 | 853 | 37 |
| 411 | T | OG1 | 316 | 698 | 863 | 35 |
| 411 | T | CG2 | 339 | 696 | 856 | 34 |
| 411 | T | C | 341 | 723 | 860 | 43 |
| 411 | T | O | 348 | 730 | 853 | 43 |
| 412 | D | N | 345 | 719 | 872 | 45 |
| 412 | D | CA | 358 | 723 | 877 | 47 |
| 412 | D | CB | 359 | 720 | 892 | 43 |
| 412 | D | CG | 357 | 732 | 901 | 50 |
| 412 | D | OD1 | 355 | 743 | 895 | 56 |
| 412 | D | OD2 | 356 | 730 | 913 | 52 |
| 412 | D | C | 369 | 718 | 869 | 46 |
| 412 | D | O | 381 | 722 | 870 | 47 |
| 413 | A | N | 366 | 707 | 861 | 45 |
| 413 | A | CA | 376 | 701 | 852 | 47 |
| 413 | A | CB | 370 | 690 | 844 | 47 |
| 413 | A | C | 383 | 711 | 843 | 46 |
| 413 | A | O | 393 | 708 | 836 | 52 |
| 414 | L | N | 378 | 723 | 842 | 45 |
| 414 | L | CA | 383 | 733 | 834 | 45 |
| 414 | L | CB | 375 | 746 | 836 | 40 |
| 414 | L | CG | 373 | 755 | 823 | 38 |
| 414 | L | CD1 | 383 | 766 | 823 | 36 |
| 414 | L | CD2 | 373 | 747 | 810 | 37 |
| 414 | L | C | 398 | 736 | 838 | 51 |
| 414 | L | O | 407 | 735 | 830 | 52 |
| 415 | M | N | 400 | 739 | 851 | 53 |
| 415 | M | CA | 414 | 742 | 856 | 56 |
| 415 | M | CB | 414 | 743 | 871 | 64 |
| 415 | M | CG | 425 | 735 | 878 | 73 |
| 415 | M | SD | 440 | 744 | 880 | 87 |
| 415 | M | CE | 450 | 732 | 890 | 81 |
| 415 | M | C | 424 | 732 | 852 | 54 |
| 415 | M | O | 436 | 735 | 851 | 57 |
| 416 | T | N | 420 | 719 | 849 | 53 |
| 416 | T | CA | 430 | 709 | 845 | 51 |
| 416 | T | CB | 428 | 696 | 853 | 54 |
| 416 | T | OG1 | 418 | 698 | 863 | 57 |
| 416 | T | CG2 | 441 | 690 | 858 | 54 |
| 416 | T | C | 431 | 706 | 831 | 49 |
| 416 | T | O | 441 | 701 | 826 | 51 |
| 417 | G | N | 421 | 710 | 823 | 48 |
| 417 | G | CA | 421 | 707 | 809 | 47 |
| 417 | G | C | 424 | 719 | 800 | 47 |
| 417 | G | O | 429 | 717 | 789 | 48 |
| 418 | Y | N | 420 | 731 | 804 | 47 |
| 418 | Y | CA | 422 | 742 | 796 | 46 |
| 418 | Y | CB | 408 | 746 | 790 | 47 |
| 418 | Y | CG | 407 | 759 | 782 | 44 |
| 418 | Y | CD1 | 407 | 759 | 768 | 45 |
| 418 | Y | CE1 | 407 | 771 | 761 | 47 |
| 418 | Y | CD2 | 406 | 771 | 789 | 44 |
| 418 | Y | CE2 | 405 | 783 | 782 | 46 |
| 418 | Y | CZ | 405 | 783 | 768 | 49 |
| 418 | Y | OR | 405 | 795 | 760 | 53 |
| 418 | Y | C | 428 | 754 | 803 | 48 |
| 418 | Y | O | 426 | 757 | 815 | 48 |
| 419 | T | N | 437 | 761 | 796 | 51 |
| 419 | T | CA | 443 | 773 | 801 | 53 |
| 419 | T | CB | 459 | 772 | 799 | 51 |
| 419 | T | OG1 | 462 | 768 | 785 | 46 |
| 419 | T | CG2 | 465 | 762 | 808 | 49 |
| 419 | T | C | 438 | 785 | 792 | 54 |
| 419 | T | O | 440 | 785 | 780 | 58 |
| 420 | G | N | 431 | 794 | 799 | 53 |
| 420 | G | CA | 426 | 805 | 791 | 52 |
| 420 | G | C | 416 | 814 | 799 | 54 |
| 420 | G | O | 408 | 808 | 807 | 57 |
| 421 | D | N | 416 | 827 | 797 | 53 |
| 421 | D | CA | 407 | 835 | 805 | 53 |
| 421 | D | CB | 414 | 848 | 810 | 60 |
| 421 | D | CG | 420 | 857 | 799 | 67 |
| 421 | D | OD1 | 426 | 852 | 790 | 68 |
| 421 | D | OD2 | 417 | 869 | 799 | 74 |
| 421 | D | C | 395 | 838 | 796 | 48 |
| 421 | D | O | 394 | 833 | 785 | 47 |
| 422 | F | N | 386 | 847 | 801 | 41 |
| 422 | F | CA | 374 | 851 | 794 | 40 |
| 422 | F | CB | 363 | 841 | 798 | 39 |
| 422 | F | CG | 365 | 827 | 793 | 39 |
| 422 | F | CD1 | 374 | 819 | 800 | 40 |
| 422 | F | CD2 | 358 | 821 | 783 | 42 |
| 422 | F | CE1 | 377 | 806 | 796 | 44 |
| 422 | F | CE2 | 360 | 808 | 779 | 43 |
| 422 | F | CZ | 369 | 800 | 786 | 48 |
| 422 | F | C | 370 | 865 | 797 | 41 |
| 422 | F | O | 375 | 872 | 806 | 40 |
| 423 | D | N | 361 | 870 | 789 | 41 |
| 423 | D | CA | 356 | 884 | 791 | 45 |
| 423 | D | CB | 347 | 888 | 779 | 46 |
| 423 | D | CG | 354 | 885 | 766 | 52 |
| 423 | D | OD1 | 347 | 878 | 757 | 55 |
| 423 | D | OD2 | 365 | 889 | 763 | 52 |
| 423 | D | C | 348 | 884 | 804 | 45 |
| 423 | D | O | 349 | 893 | 812 | 44 |
| 424 | S | N | 340 | 874 | 806 | 45 |
| 424 | S | CA | 331 | 872 | 818 | 44 |
| 424 | S | CB | 317 | 876 | 815 | 48 |
| 424 | S | OG | 308 | 868 | 823 | 52 |
| 424 | S | C | 332 | 858 | 824 | 41 |
| 424 | S | O | 337 | 849 | 817 | 43 |
| 425 | V | N | 328 | 856 | 836 | 38 |
| 425 | V | CA | 327 | 844 | 843 | 35 |
| 425 | V | CB | 340 | 841 | 852 | 34 |
| 425 | V | CG1 | 338 | 829 | 861 | 32 |

TABLE 2-continued

| | | | | | | |
|---|---|---|---|---|---|---|
| 425 | V | CG2 | 352 | 839 | 843 | 33 |
| 425 | V | C | 315 | 843 | 852 | 35 |
| 425 | V | O | 313 | 853 | 860 | 35 |
| 426 | I | N | 307 | 833 | 851 | 35 |
| 426 | I | CA | 295 | 831 | 859 | 36 |
| 426 | I | CB | 282 | 830 | 850 | 34 |
| 426 | I | CG2 | 270 | 829 | 859 | 36 |
| 426 | I | CG1 | 281 | 842 | 841 | 35 |
| 426 | I | CD1 | 271 | 840 | 830 | 32 |
| 426 | I | C | 297 | 819 | 867 | 36 |
| 426 | I | O | 299 | 808 | 862 | 36 |
| 427 | D | N | 297 | 821 | 881 | 37 |
| 427 | D | CA | 299 | 811 | 890 | 34 |
| 427 | D | CB | 309 | 816 | 901 | 33 |
| 427 | D | CG | 314 | 805 | 910 | 35 |
| 427 | D | OD1 | 309 | 793 | 909 | 39 |
| 427 | D | OD2 | 324 | 807 | 917 | 37 |
| 427 | D | C | 285 | 807 | 897 | 35 |
| 427 | D | O | 277 | 815 | 901 | 34 |
| 428 | C | N | 283 | 794 | 898 | 35 |
| 428 | C | CA | 271 | 789 | 905 | 32 |
| 428 | C | CB | 268 | 774 | 901 | 36 |
| 428 | C | SG | 281 | 762 | 904 | 33 |
| 428 | C | C | 274 | 789 | 920 | 33 |
| 428 | C | O | 265 | 788 | 929 | 32 |
| 429 | N | N | 287 | 790 | 923 | 32 |
| 429 | N | CA | 292 | 791 | 937 | 33 |
| 429 | N | CB | 285 | 802 | 944 | 36 |
| 429 | N | CG | 286 | 816 | 938 | 33 |
| 429 | N | OD1 | 276 | 823 | 936 | 31 |
| 429 | N | ND2 | 299 | 819 | 934 | 30 |
| 429 | N | C | 291 | 778 | 945 | 34 |
| 429 | N | O | 293 | 778 | 957 | 35 |
| 430 | T | N | 287 | 767 | 938 | 31 |
| 430 | T | CA | 286 | 754 | 945 | 33 |
| 430 | T | CB | 272 | 748 | 944 | 27 |
| 430 | T | OG1 | 268 | 745 | 931 | 33 |
| 430 | T | CG2 | 262 | 757 | 950 | 30 |
| 430 | T | C | 296 | 744 | 939 | 33 |
| 430 | T | O | 301 | 747 | 928 | 35 |
| 431 | C | N | 298 | 734 | 945 | 35 |
| 431 | C | CA | 307 | 723 | 940 | 37 |
| 431 | C | CB | 322 | 726 | 942 | 40 |
| 431 | C | SG | 326 | 730 | 959 | 53 |
| 431 | C | C | 304 | 710 | 946 | 38 |
| 431 | C | O | 296 | 709 | 956 | 39 |
| 432 | V | N | 309 | 699 | 941 | 37 |
| 432 | V | CA | 306 | 686 | 946 | 35 |
| 432 | V | CB | 302 | 676 | 935 | 37 |
| 432 | V | CG1 | 302 | 662 | 940 | 36 |
| 432 | V | CG2 | 288 | 680 | 929 | 33 |
| 432 | V | C | 318 | 680 | 954 | 35 |
| 432 | V | O | 329 | 680 | 948 | 34 |
| 433 | T | N | 316 | 676 | 966 | 29 |
| 433 | T | CA | 326 | 671 | 974 | 33 |
| 433 | T | CB | 330 | 680 | 986 | 38 |
| 433 | T | OG1 | 339 | 674 | 995 | 47 |
| 433 | T | CG2 | 317 | 684 | 993 | 41 |
| 433 | T | C | 323 | 657 | 980 | 35 |
| 433 | T | O | 312 | 652 | 979 | 35 |
| 434 | Q | N | 333 | 650 | 985 | 33 |
| 434 | Q | CA | 331 | 637 | 991 | 30 |
| 434 | Q | CB | 340 | 626 | 984 | 34 |
| 434 | Q | CG | 333 | 622 | 971 | 42 |
| 434 | Q | CD | 343 | 615 | 962 | 46 |
| 434 | Q | OE1 | 355 | 618 | 962 | 47 |
| 434 | Q | NE2 | 338 | 607 | 953 | 48 |
| 434 | Q | C | 335 | 637 | 1005 | 29 |
| 434 | Q | O | 344 | 644 | 1009 | 31 |
| 435 | T | N | 328 | 630 | 1013 | 27 |
| 435 | T | CA | 330 | 630 | 1028 | 31 |
| 435 | T | CB | 320 | 639 | 1035 | 36 |
| 435 | T | OG1 | 308 | 640 | 1027 | 44 |
| 435 | T | CG2 | 326 | 653 | 1036 | 38 |
| 435 | T | C | 328 | 616 | 1032 | 32 |
| 435 | T | O | 320 | 608 | 1027 | 30 |
| 436 | V | N | 335 | 612 | 1043 | 27 |
| 436 | V | CA | 333 | 598 | 1048 | 29 |
| 436 | V | CB | 347 | 592 | 1050 | 27 |
| 436 | V | CG1 | 356 | 600 | 1059 | 28 |
| 436 | V | CG2 | 345 | 578 | 1057 | 24 |
| 436 | V | C | 325 | 599 | 1060 | 27 |
| 436 | V | O | 327 | 608 | 1068 | 24 |
| 437 | D | N | 317 | 589 | 1062 | 25 |
| 437 | D | CA | 309 | 587 | 1074 | 22 |
| 437 | D | CB | 294 | 588 | 1071 | 30 |
| 437 | D | CG | 286 | 589 | 1083 | 38 |
| 437 | D | OD1 | 287 | 599 | 1091 | 50 |
| 437 | D | OD2 | 277 | 580 | 1086 | 43 |
| 437 | D | C | 312 | 574 | 1080 | 20 |
| 437 | D | O | 311 | 563 | 1073 | 21 |
| 438 | F | N | 317 | 573 | 1092 | 21 |
| 438 | F | CA | 319 | 561 | 1099 | 22 |
| 438 | F | CB | 330 | 563 | 1110 | 23 |
| 438 | F | CG | 343 | 569 | 1105 | 24 |
| 438 | F | CD1 | 348 | 581 | 1110 | 24 |
| 438 | F | CD2 | 349 | 564 | 1094 | 23 |
| 438 | F | CE1 | 359 | 587 | 1105 | 31 |
| 438 | F | CE2 | 361 | 570 | 1089 | 27 |
| 438 | F | CZ | 366 | 581 | 1095 | 25 |
| 438 | F | C | 306 | 555 | 1104 | 27 |
| 438 | F | O | 304 | 554 | 1116 | 33 |
| 439 | S | N | 297 | 553 | 1095 | 24 |
| 439 | S | CA | 284 | 548 | 1098 | 24 |
| 439 | S | CB | 276 | 549 | 1085 | 21 |
| 439 | S | CG | 283 | 543 | 1074 | 22 |
| 439 | S | C | 281 | 535 | 1104 | 26 |
| 439 | S | O | 270 | 531 | 1108 | 27 |
| 440 | L | N | 292 | 526 | 1104 | 26 |
| 440 | L | CA | 291 | 513 | 1110 | 25 |
| 440 | L | CB | 290 | 514 | 1125 | 24 |
| 440 | L | CG | 300 | 522 | 1132 | 28 |
| 440 | L | CD1 | 298 | 521 | 1147 | 21 |
| 440 | L | CD2 | 314 | 516 | 1129 | 23 |
| 440 | L | C | 280 | 504 | 1104 | 25 |
| 440 | L | O | 275 | 496 | 1112 | 26 |
| 441 | D | N | 277 | 506 | 1091 | 24 |
| 441 | D | CA | 266 | 498 | 1085 | 23 |
| 441 | D | CB | 254 | 507 | 1083 | 26 |
| 441 | D | CG | 257 | 519 | 1074 | 32 |
| 441 | D | OD1 | 269 | 521 | 1072 | 40 |
| 441 | D | OD2 | 248 | 525 | 1069 | 35 |
| 441 | D | C | 269 | 491 | 1072 | 23 |
| 441 | D | O | 263 | 494 | 1062 | 27 |
| 442 | P | N | 278 | 481 | 1073 | 22 |
| 442 | P | CD | 281 | 473 | 1061 | 21 |
| 442 | P | CA | 285 | 475 | 1085 | 22 |
| 442 | P | CB | 288 | 461 | 1081 | 20 |
| 442 | P | CG | 291 | 463 | 1066 | 24 |
| 442 | P | C | 297 | 483 | 1088 | 19 |
| 442 | P | O | 302 | 482 | 1099 | 22 |
| 443 | T | N | 303 | 490 | 1078 | 20 |
| 443 | T | CA | 316 | 497 | 1081 | 19 |
| 443 | T | CB | 327 | 491 | 1072 | 12 |
| 443 | T | OG1 | 322 | 490 | 1058 | 15 |
| 443 | T | CG2 | 330 | 477 | 1077 | 9 |
| 443 | T | C | 316 | 513 | 1079 | 14 |
| 443 | T | O | 314 | 519 | 1089 | 18 |
| 444 | F | N | 318 | 518 | 1067 | 17 |
| 444 | F | CA | 319 | 532 | 1065 | 18 |
| 444 | F | CB | 333 | 538 | 1066 | 13 |
| 444 | F | CG | 342 | 532 | 1055 | 14 |
| 444 | F | CD1 | 351 | 521 | 1057 | 13 |
| 444 | F | CD2 | 342 | 538 | 1042 | 9 |
| 444 | F | CE1 | 358 | 516 | 1047 | 11 |
| 444 | F | CE2 | 350 | 532 | 1031 | 16 |
| 444 | F | CZ | 358 | 521 | 1034 | 17 |
| 444 | F | C | 312 | 536 | 1052 | 15 |
| 444 | F | O | 309 | 527 | 1044 | 16 |
| 445 | T | N | 310 | 549 | 1050 | 20 |
| 445 | T | CA | 303 | 554 | 1038 | 18 |
| 445 | T | CB | 289 | 558 | 1041 | 21 |
| 445 | T | OG1 | 281 | 546 | 1046 | 17 |
| 445 | T | CG2 | 282 | 563 | 1029 | 14 |
| 445 | T | C | 311 | 566 | 1033 | 21 |
| 445 | T | O | 316 | 574 | 1040 | 19 |
| 446 | I | N | 311 | 566 | 1019 | 22 |
| 446 | I | CA | 318 | 577 | 1012 | 26 |

TABLE 2-continued

| | | | | | | |
|---|---|---|---|---|---|---|
| 446 | I | CB | 327 | 572 | 1001 | 27 |
| 446 | I | CG2 | 331 | 584 | 992 | 19 |
| 446 | I | CG1 | 340 | 565 | 1007 | 24 |
| 446 | I | CD1 | 349 | 574 | 1014 | 28 |
| 446 | I | C | 306 | 583 | 1005 | 26 |
| 446 | I | O | 300 | 578 | 997 | 31 |
| 447 | E | N | 302 | 595 | 1010 | 29 |
| 447 | E | CA | 290 | 602 | 1004 | 34 |
| 447 | E | CB | 281 | 607 | 1014 | 41 |
| 447 | E | CG | 289 | 613 | 1026 | 54 |
| 447 | E | CD | 280 | 614 | 1038 | 62 |
| 447 | E | OE1 | 284 | 621 | 1048 | 64 |
| 447 | E | OE2 | 270 | 607 | 1039 | 65 |
| 447 | E | C | 294 | 613 | 994 | 36 |
| 447 | E | O | 304 | 620 | 997 | 35 |
| 448 | T | N | 287 | 615 | 983 | 35 |
| 448 | T | CA | 290 | 626 | 974 | 36 |
| 448 | T | CB | 289 | 621 | 960 | 32 |
| 448 | T | OG1 | 301 | 612 | 957 | 38 |
| 448 | T | CG2 | 290 | 632 | 950 | 35 |
| 448 | T | C | 278 | 636 | 976 | 37 |
| 448 | T | O | 267 | 632 | 975 | 39 |
| 449 | T | N | 282 | 648 | 978 | 37 |
| 449 | T | CA | 272 | 659 | 980 | 37 |
| 449 | T | CB | 270 | 661 | 995 | 40 |
| 449 | T | CG1 | 281 | 669 | 1001 | 48 |
| 449 | T | CG2 | 269 | 647 | 1003 | 41 |
| 449 | T | C | 277 | 672 | 975 | 36 |
| 449 | T | O | 289 | 675 | 974 | 39 |
| 450 | T | N | 268 | 681 | 971 | 33 |
| 450 | T | CA | 271 | 694 | 966 | 34 |
| 450 | T | CB | 263 | 699 | 954 | 36 |
| 450 | T | OG1 | 252 | 707 | 959 | 37 |
| 450 | T | CG2 | 258 | 687 | 946 | 29 |
| 450 | T | C | 271 | 704 | 978 | 34 |
| 450 | T | O | 261 | 705 | 985 | 30 |
| 451 | V | N | 282 | 712 | 979 | 32 |
| 451 | V | CA | 283 | 722 | 989 | 31 |
| 451 | V | CB | 294 | 718 | 999 | 31 |
| 451 | V | CG1 | 291 | 705 | 1006 | 34 |
| 451 | V | CG2 | 307 | 717 | 992 | 29 |
| 451 | V | C | 287 | 735 | 984 | 33 |
| 451 | V | O | 292 | 737 | 973 | 36 |
| 452 | P | N | 286 | 746 | 993 | 34 |
| 452 | P | CD | 279 | 746 | 1006 | 34 |
| 452 | P | CA | 290 | 760 | 989 | 30 |
| 452 | P | CB | 286 | 768 | 1001 | 29 |
| 452 | P | CG | 276 | 760 | 1008 | 33 |
| 452 | P | C | 305 | 759 | 987 | 29 |
| 452 | P | O | 312 | 753 | 994 | 26 |
| 453 | Q | N | 310 | 766 | 977 | 26 |
| 453 | Q | CA | 324 | 767 | 974 | 29 |
| 453 | Q | CB | 326 | 774 | 961 | 26 |
| 453 | Q | CG | 322 | 788 | 961 | 28 |
| 453 | Q | CD | 325 | 796 | 948 | 24 |
| 453 | Q | OE1 | 322 | 808 | 947 | 33 |
| 453 | Q | NE2 | 330 | 789 | 938 | 22 |
| 453 | Q | C | 331 | 774 | 985 | 28 |
| 453 | Q | O | 326 | 782 | 993 | 25 |
| 454 | D | N | 344 | 771 | 986 | 29 |
| 454 | D | CA | 353 | 778 | 996 | 30 |
| 454 | D | CB | 363 | 767 | 1002 | 39 |
| 454 | D | CG | 375 | 766 | 993 | 45 |
| 454 | D | OD1 | 374 | 759 | 983 | 50 |
| 454 | D | OD2 | 385 | 772 | 997 | 54 |
| 454 | D | C | 360 | 789 | 989 | 29 |
| 454 | D | O | 359 | 790 | 977 | 26 |
| 455 | A | N | 369 | 796 | 996 | 29 |
| 455 | A | CA | 376 | 807 | 990 | 24 |
| 455 | A | CB | 384 | 815 | 1001 | 24 |
| 455 | A | C | 386 | 803 | 978 | 29 |
| 455 | A | O | 387 | 810 | 968 | 34 |
| 456 | V | N | 392 | 792 | 980 | 31 |
| 456 | V | CA | 40I | 788 | 970 | 28 |
| 456 | V | CB | 408 | 775 | 973 | 26 |
| 456 | V | CG1 | 414 | 768 | 961 | 28 |
| 456 | V | CG2 | 419 | 777 | 983 | 27 |
| 456 | V | C | 393 | 787 | 957 | 31 |
| 456 | V | O | 396 | 793 | 947 | 35 |
| 457 | S | N | 382 | 779 | 958 | 33 |
| 457 | S | CA | 373 | 777 | 947 | 29 |
| 457 | S | CB | 360 | 770 | 952 | 30 |
| 457 | S | OG | 351 | 767 | 941 | 34 |
| 457 | S | C | 368 | 790 | 940 | 30 |
| 457 | S | O | 369 | 792 | 928 | 25 |
| 458 | R | N | 364 | 800 | 949 | 30 |
| 458 | R | CA | 360 | 813 | 944 | 33 |
| 458 | R | CB | 355 | 821 | 955 | 37 |
| 458 | R | CG | 345 | 832 | 951 | 35 |
| 458 | R | CD | 337 | 838 | 962 | 38 |
| 458 | R | NE | 328 | 848 | 957 | 41 |
| 458 | R | CZ | 315 | 846 | 955 | 44 |
| 458 | R | NH1 | 310 | 834 | 957 | 46 |
| 458 | R | NH2 | 307 | 856 | 950 | 46 |
| 458 | R | C | 371 | 820 | 936 | 34 |
| 458 | R | O | 369 | 824 | 924 | 35 |
| 459 | S | N | 383 | 821 | 942 | 34 |
| 459 | S | CA | 394 | 827 | 935 | 35 |
| 459 | S | CB | 406 | 827 | 944 | 32 |
| 459 | S | CG | 403 | 832 | 957 | 42 |
| 459 | S | C | 398 | 821 | 922 | 33 |
| 459 | S | O | 398 | 828 | 912 | 36 |
| 460 | Q | N | 399 | 808 | 922 | 34 |
| 460 | Q | CA | 403 | 800 | 910 | 34 |
| 460 | Q | CB | 405 | 786 | 914 | 35 |
| 460 | Q | CG | 418 | 780 | 909 | 44 |
| 460 | Q | CD | 429 | 779 | 920 | 49 |
| 460 | Q | OE1 | 428 | 770 | 929 | 51 |
| 460 | Q | NE2 | 438 | 788 | 919 | 49 |
| 460 | Q | C | 392 | 801 | 899 | 31 |
| 460 | Q | O | 396 | 802 | 887 | 33 |
| 461 | R | N | 380 | 801 | 903 | 32 |
| 461 | R | CA | 369 | 802 | 893 | 32 |
| 461 | R | CB | 356 | 798 | 900 | 32 |
| 461 | R | CG | 354 | 783 | 904 | 28 |
| 461 | R | CD | 340 | 779 | 903 | 29 |
| 461 | R | NE | 338 | 764 | 905 | 23 |
| 461 | R | CZ | 327 | 759 | 911 | 25 |
| 461 | R | NH1 | 318 | 767 | 915 | 30 |
| 461 | R | NH2 | 327 | 746 | 913 | 20 |
| 461 | R | C | 368 | 816 | 888 | 35 |
| 461 | R | O | 367 | 818 | 876 | 35 |
| 462 | R | N | 369 | 825 | 898 | 34 |
| 462 | R | CA | 369 | 840 | 894 | 35 |
| 462 | R | CB | 368 | 848 | 907 | 32 |
| 462 | R | CG | 367 | 863 | 904 | 39 |
| 462 | R | CD | 370 | 872 | 916 | 40 |
| 462 | R | NE | 384 | 871 | 921 | 43 |
| 462 | R | CZ | 389 | 878 | 931 | 41 |
| 462 | R | NH1 | 382 | 886 | 938 | 34 |
| 462 | R | NH2 | 402 | 876 | 934 | 40 |
| 462 | R | C | 381 | 844 | 886 | 37 |
| 462 | R | O | 380 | 853 | 878 | 37 |
| 463 | G | N | 392 | 837 | 889 | 38 |
| 463 | G | CA | 404 | 840 | 883 | 36 |
| 463 | G | C | 405 | 838 | 868 | 37 |
| 463 | G | O | 414 | 842 | 861 | 35 |
| 464 | R | N | 395 | 831 | 862 | 38 |
| 464 | R | CA | 395 | 828 | 848 | 43 |
| 464 | R | CB | 386 | 815 | 846 | 45 |
| 464 | R | CG | 393 | 803 | 851 | 49 |
| 464 | R | CD | 407 | 801 | 844 | 51 |
| 464 | R | NE | 411 | 787 | 843 | 56 |
| 464 | R | CZ | 412 | 780 | 832 | 58 |
| 464 | R | NH1 | 409 | 785 | 821 | 58 |
| 464 | R | NH2 | 415 | 767 | 833 | 56 |
| 464 | R | C | 390 | 840 | 840 | 46 |
| 464 | R | O | 387 | 838 | 828 | 46 |
| 465 | T | N | 389 | 851 | 846 | 47 |
| 465 | T | CA | 385 | 864 | 840 | 49 |
| 465 | T | CB | 370 | 867 | 841 | 52 |
| 465 | T | OG1 | 366 | 877 | 832 | 54 |
| 465 | T | CG2 | 366 | 870 | 855 | 51 |
| 465 | T | C | 393 | 875 | 846 | 48 |
| 465 | T | O | 400 | 874 | 856 | 46 |
| 466 | G | N | 393 | 887 | 839 | 50 |
| 466 | G | CA | 400 | 899 | 844 | 54 |
| 466 | G | C | 415 | 897 | 845 | 54 |

TABLE 2-continued

| | | | | | | |
|---|---|---|---|---|---|---|
| 466 | G | O | 422 | 904 | 852 | 53 |
| 467 | R | N | 421 | 887 | 837 | 57 |
| 467 | R | CA | 435 | 885 | 838 | 59 |
| 467 | R | CB | 439 | 871 | 833 | 60 |
| 467 | R | CG | 431 | 860 | 840 | 67 |
| 467 | R | CD | 440 | 848 | 845 | 70 |
| 467 | R | NE | 443 | 839 | 834 | 71 |
| 467 | R | CZ | 438 | 827 | 833 | 71 |
| 467 | R | NH1 | 429 | 822 | 842 | 70 |
| 467 | R | NH2 | 441 | 819 | 823 | 66 |
| 467 | R | C | 442 | 895 | 829 | 60 |
| 467 | R | O | 442 | 893 | 816 | 61 |
| 468 | G | N | 448 | 905 | 835 | 62 |
| 468 | G | CA | 455 | 915 | 827 | 63 |
| 468 | G | C | 446 | 925 | 820 | 66 |
| 468 | G | O | 450 | 936 | 817 | 69 |
| 469 | R | N | 434 | 920 | 817 | 65 |
| 469 | R | CA | 424 | 929 | 810 | 63 |
| 469 | R | CB | 421 | 924 | 796 | 64 |
| 469 | R | CG | 413 | 910 | 796 | 69 |
| 469 | R | CD | 418 | 901 | 785 | 68 |
| 469 | R | NE | 408 | 891 | 782 | 73 |
| 469 | R | CZ | 395 | 893 | 780 | 73 |
| 469 | R | NH1 | 390 | 905 | 779 | 77 |
| 469 | R | NH2 | 387 | 882 | 778 | 74 |
| 469 | R | C | 411 | 929 | 819 | 62 |
| 469 | R | O | 411 | 923 | 829 | 59 |
| 470 | R | N | 402 | 937 | 815 | 60 |
| 470 | R | CA | 389 | 938 | 822 | 59 |
| 470 | R | CB | 381 | 950 | 817 | 62 |
| 470 | R | CG | 381 | 962 | 825 | 65 |
| 470 | R | CD | 382 | 959 | 840 | 71 |
| 470 | R | NE | 371 | 965 | 848 | 76 |
| 470 | R | CZ | 370 | 967 | 861 | 77 |
| 470 | R | NH1 | 380 | 963 | 868 | 79 |
| 470 | R | NH2 | 360 | 972 | 867 | 76 |
| 470 | R | C | 381 | 925 | 822 | 57 |
| 470 | R | O | 382 | 918 | 812 | 61 |
| 471 | G | N | 373 | 923 | 832 | 50 |
| 471 | G | CA | 365 | 911 | 832 | 47 |
| 471 | G | C | 353 | 912 | 841 | 46 |
| 471 | G | O | 353 | 921 | 850 | 43 |
| 472 | I | N | 343 | 904 | 839 | 44 |
| 472 | I | CA | 331 | 905 | 848 | 42 |
| 472 | I | CB | 318 | 908 | 840 | 45 |
| 472 | I | CG2 | 306 | 907 | 850 | 39 |
| 472 | I | CG1 | 319 | 923 | 835 | 45 |
| 472 | I | CD1 | 319 | 923 | 820 | 46 |
| 472 | I | C | 329 | 891 | 855 | 37 |
| 472 | I | O | 330 | 881 | 849 | 36 |
| 473 | Y | N | 327 | 892 | 868 | 34 |
| 473 | Y | CA | 324 | 880 | 876 | 34 |
| 473 | Y | CB | 335 | 879 | 888 | 32 |
| 473 | Y | CG | 332 | 867 | 897 | 34 |
| 473 | Y | CD1 | 333 | 854 | 892 | 32 |
| 473 | Y | CE1 | 330 | 843 | 900 | 31 |
| 473 | Y | CD2 | 329 | 869 | 910 | 34 |
| 473 | Y | CE2 | 326 | 858 | 919 | 36 |
| 473 | Y | CZ | 327 | 845 | 913 | 32 |
| 473 | Y | OR | 324 | 834 | 921 | 34 |
| 473 | Y | C | 310 | 880 | 882 | 32 |
| 473 | Y | O | 307 | 887 | 891 | 33 |
| 474 | R | N | 301 | 872 | 876 | 33 |
| 474 | R | CA | 288 | 871 | 881 | 37 |
| 474 | R | CB | 278 | 870 | 869 | 41 |
| 474 | R | CG | 279 | 881 | 859 | 47 |
| 474 | R | CD | 267 | 891 | 859 | 48 |
| 474 | R | NE | 268 | 900 | 847 | 45 |
| 474 | R | CZ | 271 | 896 | 835 | 45 |
| 474 | R | NH1 | 273 | 883 | 832 | 39 |
| 474 | R | NH2 | 272 | 905 | 825 | 45 |
| 474 | R | C | 287 | 859 | 890 | 35 |
| 474 | R | O | 292 | 849 | 887 | 35 |
| 475 | F | N | 280 | 861 | 901 | 35 |
| 475 | F | CA | 279 | 850 | 910 | 38 |
| 475 | F | CB | 288 | 853 | 922 | 37 |
| 475 | F | CG | 285 | 866 | 929 | 41 |
| 475 | F | CD1 | 289 | 878 | 924 | 41 |
| 475 | F | CD2 | 277 | 866 | 941 | 40 |
| 475 | F | CE1 | 286 | 890 | 930 | 40 |
| 475 | F | CE2 | 274 | 878 | 947 | 39 |
| 475 | F | CZ | 278 | 890 | 941 | 40 |
| 475 | F | C | 264 | 848 | 916 | 37 |
| 475 | F | O | 256 | 858 | 916 | 37 |
| 476 | V | N | 261 | 836 | 919 | 35 |
| 476 | V | CA | 248 | 833 | 925 | 34 |
| 476 | V | CB | 244 | 818 | 923 | 34 |
| 476 | V | CG1 | 232 | 815 | 931 | 30 |
| 476 | V | CG2 | 242 | 815 | 909 | 35 |
| 476 | V | C | 247 | 837 | 939 | 35 |
| 476 | V | O | 237 | 842 | 945 | 37 |
| 477 | T | N | 258 | 835 | 946 | 37 |
| 477 | T | CA | 259 | 837 | 961 | 36 |
| 477 | T | CB | 259 | 824 | 969 | 35 |
| 477 | T | OG1 | 248 | 816 | 964 | 40 |
| 477 | T | CG2 | 257 | 827 | 983 | 37 |
| 477 | T | C | 272 | 845 | 965 | 39 |
| 477 | T | O | 282 | 843 | 958 | 41 |
| 478 | P | N | 271 | 853 | 975 | 39 |
| 478 | P | CD | 259 | 857 | 982 | 40 |
| 478 | P | CA | 282 | 861 | 980 | 42 |
| 478 | P | CB | 276 | 873 | 987 | 41 |
| 478 | P | CG | 263 | 867 | 992 | 41 |
| 478 | P | C | 292 | 854 | 990 | 44 |
| 478 | P | O | 304 | 856 | 990 | 47 |
| 479 | G | N | 286 | 845 | 998 | 44 |
| 479 | G | CA | 294 | 837 | 1007 | 49 |
| 479 | G | C | 307 | 832 | 1003 | 50 |
| 479 | G | O | 313 | 835 | 993 | 51 |
| 480 | E | N | 312 | 822 | 1011 | 52 |
| 480 | E | CA | 325 | 815 | 1008 | 48 |
| 480 | E | CB | 335 | 825 | 1003 | 53 |
| 480 | E | CG | 349 | 824 | 1009 | 56 |
| 480 | E | CD | 358 | 836 | 1003 | 59 |
| 480 | E | OE1 | 357 | 839 | 991 | 59 |
| 480 | E | OE2 | 366 | 841 | 1011 | 61 |
| 480 | E | C | 329 | 808 | 1021 | 46 |
| 480 | E | O | 330 | 815 | 1032 | 43 |
| 481 | R | N | 332 | 795 | 1020 | 43 |
| 481 | R | CA | 336 | 787 | 1032 | 43 |
| 481 | R | CB | 331 | 773 | 1030 | 45 |
| 481 | R | CG | 316 | 771 | 1031 | 51 |
| 481 | R | CD | 312 | 757 | 1028 | 58 |
| 481 | R | NE | 322 | 751 | 1018 | 64 |
| 481 | R | CZ | 326 | 738 | 1019 | 68 |
| 481 | R | NH1 | 322 | 730 | 1028 | 68 |
| 481 | R | NH2 | 336 | 734 | 1010 | 66 |
| 481 | R | C | 351 | 788 | 1033 | 38 |
| 481 | R | O | 358 | 791 | 1023 | 37 |
| 482 | P | N | 356 | 786 | 1045 | 35 |
| 482 | P | CD | 349 | 783 | 1058 | 32 |
| 482 | P | CA | 371 | 787 | 1048 | 32 |
| 482 | P | CB | 372 | 784 | 1063 | 30 |
| 482 | P | CG | 360 | 777 | 1067 | 29 |
| 482 | P | C | 379 | 777 | 1040 | 31 |
| 482 | P | O | 375 | 766 | 1036 | 33 |
| 483 | S | N | 391 | 782 | 1037 | 30 |
| 483 | S | CA | 401 | 775 | 1029 | 31 |
| 483 | S | CB | 410 | 785 | 1022 | 36 |
| 483 | S | OG | 416 | 794 | 1031 | 32 |
| 483 | S | C | 410 | 767 | 1038 | 31 |
| 483 | S | O | 410 | 768 | 1050 | 29 |
| 484 | G | N | 418 | 758 | 1032 | 28 |
| 484 | G | CA | 428 | 750 | 1039 | 30 |
| 484 | G | C | 425 | 737 | 1045 | 27 |
| 484 | G | O | 434 | 731 | 1050 | 29 |
| 485 | M | N | 413 | 733 | 1046 | 27 |
| 485 | M | CA | 410 | 720 | 1052 | 22 |
| 485 | M | CB | 400 | 721 | 1063 | 22 |
| 485 | M | CG | 404 | 730 | 1074 | 24 |
| 485 | M | SD | 390 | 735 | 1084 | 37 |
| 485 | M | CE | 382 | 747 | 1074 | 28 |
| 485 | M | C | 404 | 710 | 1041 | 25 |
| 485 | M | O | 398 | 714 | 1031 | 22 |
| 486 | F | N | 406 | 697 | 1044 | 21 |
| 486 | F | CA | 400 | 687 | 1035 | 22 |
| 486 | F | CB | 410 | 684 | 1023 | 19 |
| 486 | F | CG | 423 | 677 | 1028 | 19 |

TABLE 2-continued

| | | | | | | |
|---|---|---|---|---|---|---|
| 486 | F | CD1 | 435 | 684 | 1030 | 20 |
| 486 | F | CD2 | 423 | 663 | 1030 | 16 |
| 486 | F | CE1 | 447 | 678 | 1033 | 18 |
| 486 | F | CE2 | 435 | 657 | 1034 | 23 |
| 486 | F | CZ | 447 | 664 | 1035 | 16 |
| 486 | F | C | 396 | 675 | 1043 | 22 |
| 486 | F | O | 401 | 672 | 1054 | 23 |
| 487 | D | N | 387 | 667 | 1037 | 23 |
| 487 | D | CA | 381 | 655 | 1044 | 24 |
| 487 | D | CB | 368 | 652 | 1038 | 20 |
| 487 | D | CG | 360 | 642 | 1046 | 24 |
| 487 | D | OD1 | 353 | 646 | 1056 | 31 |
| 487 | D | OD2 | 360 | 630 | 1043 | 22 |
| 487 | D | C | 390 | 643 | 1045 | 19 |
| 487 | D | O | 399 | 641 | 1036 | 25 |
| 488 | S | N | 387 | 634 | 1054 | 19 |
| 488 | S | CA | 394 | 622 | 1057 | 22 |
| 488 | S | CB | 389 | 615 | 1069 | 22 |
| 488 | S | CG | 395 | 603 | 1072 | 28 |
| 488 | S | C | 393 | 613 | 1044 | 23 |
| 488 | S | O | 401 | 604 | 1042 | 21 |
| 489 | S | N | 382 | 614 | 1037 | 21 |
| 489 | S | CA | 379 | 606 | 1025 | 21 |
| 489 | S | CB | 365 | 609 | 1020 | 28 |
| 489 | S | OG | 365 | 620 | 1011 | 36 |
| 489 | S | C | 390 | 609 | 1015 | 16 |
| 489 | S | O | 393 | 601 | 1006 | 16 |
| 490 | V | N | 397 | 621 | 1016 | 13 |
| 490 | V | CA | 407 | 624 | 1006 | 15 |
| 490 | V | CB | 412 | 638 | 1007 | 15 |
| 490 | V | CG1 | 424 | 640 | 998 | 11 |
| 490 | V | CG2 | 401 | 648 | 1002 | 8 |
| 490 | V | C | 419 | 615 | 1009 | 16 |
| 490 | V | O | 426 | 610 | 1000 | 20 |
| 491 | L | N | 421 | 612 | 1022 | 16 |
| 491 | L | CA | 432 | 604 | 1026 | 18 |
| 491 | L | CB | 434 | 603 | 1041 | 16 |
| 491 | L | CG | 438 | 617 | 1048 | 24 |
| 491 | L | CD1 | 439 | 615 | 1062 | 19 |
| 491 | L | CD2 | 452 | 621 | 1042 | 13 |
| 491 | L | C | 429 | 590 | 1021 | 21 |
| 491 | L | O | 439 | 583 | 1017 | 24 |
| 492 | C | N | 417 | 586 | 1021 | 22 |
| 492 | C | CA | 413 | 573 | 1016 | 21 |
| 492 | C | CB | 398 | 570 | 1019 | 21 |
| 492 | C | SG | 391 | 556 | 1010 | 20 |
| 492 | C | C | 416 | 572 | 1001 | 21 |
| 492 | C | O | 420 | 562 | 996 | 20 |
| 493 | E | N | 414 | 583 | 994 | 19 |
| 493 | E | CA | 417 | 584 | 980 | 21 |
| 493 | E | CB | 413 | 598 | 975 | 24 |
| 493 | E | CG | 400 | 598 | 966 | 39 |
| 493 | E | CD | 395 | 612 | 963 | 44 |
| 493 | E | OE1 | 385 | 613 | 956 | 47 |
| 493 | E | OE2 | 400 | 622 | 969 | 44 |
| 493 | E | C | 432 | 582 | 978 | 23 |
| 493 | E | O | 436 | 576 | 968 | 27 |
| 494 | C | N | 440 | 587 | 987 | 20 |
| 494 | C | CA | 454 | 586 | 986 | 21 |
| 494 | C | CB | 461 | 594 | 997 | 23 |
| 494 | C | SG | 460 | 612 | 995 | 19 |
| 494 | C | C | 459 | 572 | 986 | 21 |
| 494 | C | O | 467 | 567 | 978 | 18 |
| 495 | Y | N | 454 | 564 | 996 | 20 |
| 495 | Y | CA | 457 | 550 | 997 | 22 |
| 495 | Y | CB | 450 | 544 | 1010 | 22 |
| 495 | Y | CG | 458 | 548 | 1022 | 17 |
| 495 | Y | CD1 | 468 | 540 | 1027 | 13 |
| 495 | Y | CE1 | 476 | 544 | 1038 | 11 |
| 495 | Y | CD2 | 454 | 560 | 1029 | 12 |
| 495 | Y | CE2 | 462 | 564 | 1040 | 16 |
| 495 | Y | CZ | 472 | 556 | 1045 | 17 |
| 495 | Y | OH | 480 | 560 | 1056 | 15 |
| 495 | Y | C | 453 | 542 | 985 | 23 |
| 495 | Y | O | 459 | 533 | 981 | 26 |
| 496 | D | N | 441 | 546 | 980 | 21 |
| 496 | D | CA | 435 | 541 | 968 | 18 |
| 496 | D | CB | 422 | 547 | 965 | 24 |
| 496 | D | CG | 412 | 539 | 956 | 22 |
| 496 | D | OD1 | 414 | 538 | 944 | 26 |
| 496 | D | OD2 | 403 | 532 | 962 | 20 |
| 496 | D | C | 445 | 543 | 956 | 18 |
| 496 | D | O | 448 | 533 | 949 | 19 |
| 497 | A | N | 449 | 555 | 954 | 16 |
| 497 | A | CA | 458 | 559 | 943 | 17 |
| 497 | A | CB | 460 | 574 | 942 | 14 |
| 497 | A | C | 471 | 551 | 945 | 22 |
| 497 | A | O | 477 | 547 | 935 | 23 |
| 498 | G | N | 476 | 550 | 957 | 23 |
| 498 | G | CA | 488 | 544 | 960 | 20 |
| 498 | G | C | 488 | 529 | 956 | 26 |
| 498 | G | O | 497 | 524 | 949 | 25 |
| 499 | C | N | 476 | 523 | 959 | 22 |
| 499 | C | CA | 474 | 509 | 956 | 19 |
| 499 | C | CB | 462 | 504 | 964 | 20 |
| 499 | C | SG | 466 | 501 | 982 | 29 |
| 499 | C | C | 471 | 506 | 941 | 20 |
| 499 | C | O | 476 | 497 | 936 | 23 |
| 500 | A | N | 463 | 515 | 935 | 19 |
| 500 | A | CA | 459 | 513 | 921 | 16 |
| 500 | A | CB | 446 | 520 | 919 | 13 |
| 500 | A | C | 469 | 518 | 910 | 20 |
| 500 | A | O | 470 | 512 | 900 | 25 |
| 501 | W | N | 476 | 529 | 913 | 22 |
| 501 | W | CA | 485 | 535 | 903 | 20 |
| 501 | W | CB | 481 | 550 | 901 | 23 |
| 501 | W | CG | 468 | 552 | 894 | 22 |
| 501 | W | CD2 | 465 | 551 | 881 | 20 |
| 501 | W | CE2 | 452 | 554 | 879 | 24 |
| 501 | W | CE3 | 473 | 548 | 869 | 23 |
| 501 | W | CD1 | 456 | 556 | 901 | 21 |
| 501 | W | NE1 | 447 | 557 | 891 | 27 |
| 501 | W | CZ2 | 445 | 554 | 866 | 22 |
| 501 | W | CZ3 | 467 | 548 | 857 | 22 |
| 501 | W | CH2 | 453 | 551 | 855 | 27 |
| 501 | W | C | 500 | 535 | 906 | 25 |
| 501 | W | O | 507 | 532 | 896 | 25 |
| 502 | Y | N | 504 | 537 | 918 | 23 |
| 502 | Y | CA | 518 | 538 | 921 | 21 |
| 502 | Y | CB | 520 | 551 | 929 | 17 |
| 502 | Y | CG | 513 | 562 | 923 | 21 |
| 502 | Y | CD1 | 515 | 566 | 910 | 22 |
| 502 | Y | CE1 | 508 | 576 | 904 | 19 |
| 502 | Y | CD2 | 503 | 569 | 931 | 21 |
| 502 | Y | CE2 | 496 | 580 | 925 | 20 |
| 502 | Y | CZ | 498 | 583 | 912 | 20 |
| 502 | Y | OH | 492 | 594 | 906 | 27 |
| 502 | Y | C | 525 | 526 | 928 | 23 |
| 502 | Y | O | 536 | 528 | 934 | 22 |
| 503 | E | N | 518 | 515 | 928 | 29 |
| 503 | E | CA | 524 | 503 | 934 | 29 |
| 503 | E | CB | 535 | 496 | 925 | 35 |
| 503 | E | CG | 535 | 500 | 911 | 47 |
| 503 | E | CD | 544 | 491 | 903 | 55 |
| 503 | E | OE1 | 548 | 481 | 908 | 58 |
| 503 | E | OE2 | 548 | 495 | 891 | 58 |
| 503 | E | C | 530 | 506 | 948 | 28 |
| 503 | E | O | 541 | 502 | 951 | 32 |
| 504 | L | N | 524 | 514 | 956 | 27 |
| 504 | L | CA | 529 | 517 | 969 | 21 |
| 504 | L | CB | 526 | 532 | 973 | 21 |
| 504 | L | CG | 532 | 543 | 964 | 21 |
| 504 | L | CD1 | 525 | 556 | 966 | 21 |
| 504 | L | CD2 | 547 | 545 | 968 | 19 |
| 504 | L | C | 522 | 509 | 979 | 24 |
| 504 | L | O | 510 | 507 | 978 | 29 |
| 505 | T | N | 529 | 503 | 989 | 23 |
| 505 | T | CA | 522 | 495 | 999 | 24 |
| 505 | T | CB | 531 | 487 | 1008 | 28 |
| 505 | T | OG1 | 540 | 497 | 1015 | 24 |
| 505 | T | CG2 | 540 | 477 | 1001 | 35 |
| 505 | T | C | 515 | 505 | 1008 | 26 |
| 505 | T | O | 518 | 517 | 1008 | 22 |
| 506 | P | N | 505 | 501 | 1015 | 23 |
| 506 | P | CD | 498 | 488 | 1015 | 22 |
| 506 | P | CA | 498 | 510 | 1024 | 23 |
| 506 | P | CB | 487 | 502 | 1031 | 24 |
| 506 | P | CG | 484 | 491 | 1021 | 23 |

TABLE 2-continued

| | | | | | | |
|---|---|---|---|---|---|---|
| 506 | P | C | 508 | 517 | 1034 | 22 |
| 506 | P | O | 507 | 529 | 1036 | 22 |
| 507 | A | N | 517 | 509 | 1039 | 24 |
| 507 | A | CA | 527 | 514 | 1048 | 26 |
| 507 | A | CB | 536 | 502 | 1052 | 24 |
| 507 | A | C | 535 | 525 | 1042 | 25 |
| 507 | A | O | 538 | 535 | 1048 | 29 |
| 508 | E | N | 539 | 523 | 1029 | 25 |
| 508 | E | CA | 547 | 533 | 1022 | 25 |
| 508 | E | CB | 551 | 528 | 1008 | 24 |
| 508 | E | CG | 559 | 516 | 1008 | 37 |
| 508 | E | CD | 563 | 512 | 994 | 44 |
| 508 | E | OE1 | 560 | 500 | 990 | 46 |
| 508 | E | OE2 | 569 | 520 | 987 | 51 |
| 508 | E | C | 538 | 546 | 1020 | 24 |
| 508 | E | O | 543 | 557 | 1023 | 27 |
| 509 | T | N | 525 | 544 | 1017 | 21 |
| 509 | T | CA | 517 | 556 | 1015 | 21 |
| 509 | T | CB | 503 | 552 | 1011 | 19 |
| 509 | T | OG1 | 503 | 545 | 998 | 27 |
| 509 | T | CG2 | 494 | 564 | 1010 | 15 |
| 509 | T | C | 516 | 563 | 1028 | 22 |
| 509 | T | O | 517 | 576 | 1028 | 25 |
| 510 | S | N | 516 | 556 | 1040 | 19 |
| 510 | S | CA | 515 | 563 | 1053 | 23 |
| 510 | S | CB | 514 | 553 | 1064 | 20 |
| 510 | S | OG | 501 | 548 | 1065 | 25 |
| 510 | S | C | 528 | 572 | 1056 | 22 |
| 510 | S | O | 527 | 583 | 1061 | 18 |
| 511 | V | N | 540 | 567 | 1052 | 23 |
| 511 | V | CA | 552 | 575 | 1054 | 21 |
| 511 | V | CB | 564 | 567 | 1049 | 25 |
| 511 | V | CG1 | 576 | 576 | 1050 | 21 |
| 511 | V | CG2 | 565 | 554 | 1055 | 16 |
| 511 | V | C | 550 | 588 | 1046 | 20 |
| 511 | V | O | 552 | 599 | 1052 | 21 |
| 512 | R | N | 547 | 587 | 1034 | 15 |
| 512 | R | CA | 545 | 599 | 1026 | 23 |
| 512 | R | CB | 542 | 596 | 1011 | 19 |
| 512 | R | CG | 554 | 588 | 1005 | 25 |
| 512 | R | CD | 550 | 583 | 991 | 28 |
| 512 | R | NE | 559 | 573 | 987 | 28 |
| 512 | R | CZ | 563 | 572 | 974 | 31 |
| 512 | R | NH1 | 559 | 580 | 965 | 34 |
| 512 | R | NH2 | 572 | 562 | 971 | 33 |
| 512 | R | C | 534 | 609 | 1031 | 22 |
| 512 | R | O | 537 | 621 | 1032 | 27 |
| 513 | L | N | 523 | 603 | 1035 | 23 |
| 513 | L | CA | 512 | 612 | 1041 | 23 |
| 513 | L | CB | 499 | 604 | 1042 | 26 |
| 513 | L | CG | 493 | 600 | 1029 | 28 |
| 513 | L | CD1 | 480 | 593 | 1032 | 29 |
| 513 | L | CD2 | 491 | 612 | 1020 | 25 |
| 513 | L | C | 517 | 618 | 1054 | 22 |
| 513 | L | O | 513 | 629 | 1057 | 24 |
| 514 | R | N | 524 | 610 | 1062 | 23 |
| 514 | R | CA | 529 | 615 | 1075 | 24 |
| 514 | R | CB | 537 | 604 | 1082 | 26 |
| 514 | R | CG | 529 | 595 | 1091 | 34 |
| 514 | R | CD | 531 | 598 | 1106 | 40 |
| 514 | R | NE | 525 | 611 | 1109 | 42 |
| 514 | R | CZ | 513 | 611 | 1115 | 42 |
| 514 | R | NH1 | 506 | 600 | 1118 | 29 |
| 514 | R | NH2 | 507 | 623 | 1117 | 43 |
| 514 | R | C | 538 | 627 | 1073 | 22 |
| 514 | R | O | 537 | 637 | 1080 | 25 |
| 515 | A | N | 546 | 627 | 1063 | 21 |
| 515 | A | CA | 555 | 638 | 1060 | 20 |
| 515 | A | CB | 564 | 635 | 1048 | 6 |
| 515 | A | C | 546 | 650 | 1057 | 20 |
| 515 | A | O | 548 | 662 | 1062 | 25 |
| 516 | Y | N | 536 | 648 | 1049 | 22 |
| 516 | Y | CA | 527 | 659 | 1045 | 20 |
| 516 | Y | CB | 516 | 653 | 1036 | 21 |
| 516 | Y | CG | 506 | 664 | 1031 | 21 |
| 516 | Y | CD1 | 496 | 668 | 1039 | 21 |
| 516 | Y | CE1 | 487 | 678 | 1034 | 14 |
| 516 | Y | CD2 | 508 | 670 | 1018 | 16 |
| 516 | Y | CE2 | 499 | 680 | 1014 | 21 |
| 516 | Y | CZ | 489 | 684 | 1022 | 22 |
| 516 | Y | OH | 480 | 694 | 1017 | 20 |
| 516 | Y | C | 520 | 665 | 1058 | 21 |
| 516 | Y | O | 521 | 676 | 1060 | 23 |
| 517 | L | N | 514 | 656 | 1065 | 26 |
| 517 | L | CA | 507 | 660 | 1078 | 23 |
| 517 | L | CB | 50i | 648 | 1085 | 29 |
| 517 | L | CG | 486 | 646 | 1083 | 25 |
| 517 | L | CD1 | 482 | 650 | 1069 | 28 |
| 517 | L | CD2 | 482 | 631 | 1085 | 29 |
| 517 | L | C | 516 | 667 | 1087 | 27 |
| 517 | L | O | 512 | 678 | 1093 | 31 |
| 518 | N | N | 528 | 662 | 1089 | 27 |
| 518 | N | CA | 537 | 669 | 1098 | 27 |
| 518 | N | CB | 549 | 659 | 1101 | 33 |
| 518 | N | CG | 544 | 647 | 1110 | 37 |
| 518 | N | OD1 | 534 | 648 | 1117 | 35 |
| 518 | N | ND2 | 552 | 637 | 1110 | 41 |
| 518 | N | C | 543 | 682 | 1094 | 25 |
| 518 | N | O | 547 | 690 | 1102 | 32 |
| 519 | T | N | 543 | 685 | 1081 | 21 |
| 519 | T | CA | 548 | 698 | 1076 | 22 |
| 519 | T | CB | 551 | 697 | 1061 | 20 |
| 519 | T | CG1 | 559 | 685 | 1059 | 23 |
| 519 | T | CG2 | 559 | 710 | 1057 | 18 |
| 519 | T | C | 537 | 709 | 1077 | 23 |
| 519 | T | O | 526 | 709 | 1071 | 29 |
| 520 | P | N | 541 | 720 | 1084 | 24 |
| 520 | P | CD | 554 | 722 | 1090 | 27 |
| 520 | P | CA | 532 | 732 | 1086 | 23 |
| 520 | P | CB | 540 | 740 | 1096 | 29 |
| 520 | P | CG | 551 | 731 | 1102 | 24 |
| 520 | P | C | 530 | 740 | 1073 | 26 |
| 520 | P | O | 537 | 739 | 1064 | 25 |
| 521 | G | N | 519 | 748 | 1073 | 20 |
| 521 | G | CA | 516 | 756 | 1062 | 19 |
| 521 | G | C | 507 | 750 | 1051 | 26 |
| 521 | G | O | 503 | 757 | 1041 | 31 |
| 522 | L | N | 506 | 737 | 1051 | 23 |
| 522 | L | CA | 498 | 730 | 1041 | 24 |
| 522 | L | CB | 504 | 716 | 1039 | 23 |
| 522 | L | CG | 518 | 716 | 1032 | 23 |
| 522 | L | CD1 | 523 | 701 | 1032 | 15 |
| 522 | L | CD2 | 517 | 721 | 1018 | 19 |
| 522 | L | C | 483 | 728 | 1046 | 24 |
| 522 | L | O | 480 | 730 | 1057 | 25 |
| 523 | P | N | 474 | 725 | 1036 | 20 |
| 523 | P | CD | 477 | 724 | 1022 | 17 |
| 523 | P | CA | 460 | 723 | 1039 | 17 |
| 523 | P | CB | 454 | 718 | 1026 | 18 |
| 523 | P | CG | 463 | 725 | 1016 | 20 |
| 523 | P | C | 460 | 712 | 1050 | 16 |
| 523 | P | O | 468 | 703 | 1050 | 18 |
| 524 | V | N | 450 | 713 | 1059 | 14 |
| 524 | V | CA | 450 | 703 | 1070 | 18 |
| 524 | V | CB | 450 | 709 | 1084 | 21 |
| 524 | V | CG1 | 462 | 719 | 1085 | 25 |
| 524 | V | CG2 | 437 | 717 | 1085 | 13 |
| 524 | V | C | 439 | 692 | 1069 | 18 |
| 524 | V | O | 429 | 694 | 1062 | 21 |
| 525 | C | N | 440 | 682 | 1077 | 18 |
| 525 | C | CA | 430 | 671 | 1077 | 17 |
| 525 | C | CB | 433 | 662 | 1066 | 19 |
| 525 | C | SG | 421 | 650 | 1064 | 40 |
| 525 | C | C | 432 | 663 | 1090 | 19 |
| 525 | C | O | 442 | 664 | 1097 | 25 |
| 526 | Q | N | 422 | 656 | 1094 | 20 |
| 526 | Q | CA | 422 | 648 | 1106 | 19 |
| 526 | Q | CB | 408 | 641 | 1109 | 22 |
| 526 | Q | CG | 398 | 651 | 1115 | 27 |
| 526 | Q | CD | 402 | 656 | 1129 | 29 |
| 526 | Q | OE1 | 400 | 649 | 1139 | 35 |
| 526 | Q | NE2 | 409 | 668 | 1130 | 30 |
| 526 | Q | C | 432 | 636 | 1104 | 24 |
| 526 | Q | O | 433 | 631 | 1093 | 25 |
| 527 | D | N | 440 | 633 | 1114 | 23 |
| 527 | D | CA | 450 | 622 | 1112 | 24 |
| 527 | D | CB | 461 | 623 | 1122 | 24 |
| 527 | D | CG | 472 | 612 | 1120 | 27 |

TABLE 2-continued

| | | | | | | |
|---|---|---|---|---|---|---|
| 527 | D | OD1 | 481 | 612 | 1128 | 30 |
| 527 | D | OD2 | 470 | 604 | 1111 | 29 |
| 527 | D | C | 443 | 608 | 1114 | 25 |
| 527 | D | O | 442 | 603 | 1125 | 28 |
| 528 | H | N | 439 | 603 | 1102 | 23 |
| 528 | H | CA | 432 | 590 | 1102 | 23 |
| 528 | H | CB | 419 | 591 | 1095 | 26 |
| 528 | H | CG | 408 | 598 | 1103 | 26 |
| 528 | H | CD2 | 408 | 602 | 1116 | 28 |
| 528 | H | ND1 | 397 | 603 | 1098 | 24 |
| 528 | H | CE1 | 390 | 610 | 1107 | 26 |
| 528 | H | NE2 | 397 | 609 | 1119 | 27 |
| 528 | H | C | 441 | 580 | 1094 | 25 |
| 528 | H | O | 437 | 570 | 1089 | 26 |
| 529 | L | N | 454 | 583 | 1094 | 24 |
| 529 | L | CA | 464 | 576 | 1087 | 23 |
| 529 | L | CB | 478 | 582 | 1089 | 21 |
| 529 | L | CG | 483 | 591 | 1078 | 27 |
| 529 | L | CD1 | 472 | 599 | 1072 | 24 |
| 529 | L | CD2 | 494 | 600 | 1084 | 17 |
| 529 | L | C | 465 | 561 | 1091 | 24 |
| 529 | L | O | 464 | 552 | 1083 | 25 |
| 530 | E | N | 466 | 559 | 1104 | 24 |
| 530 | E | CA | 466 | 545 | 1109 | 26 |
| 530 | E | CB | 468 | 545 | 1124 | 28 |
| 530 | E | CG | 477 | 533 | 1128 | 43 |
| 530 | E | CD | 484 | 536 | 1141 | 50 |
| 530 | E | OE1 | 479 | 532 | 1152 | 49 |
| 530 | E | OE2 | 494 | 543 | 1141 | 54 |
| 530 | E | C | 453 | 537 | 1105 | 24 |
| 530 | E | O | 454 | 526 | 1101 | 22 |
| 531 | F | N | 442 | 544 | 1106 | 22 |
| 531 | F | CA | 429 | 536 | 1103 | 18 |
| 531 | F | CB | 417 | 545 | 1107 | 20 |
| 531 | F | CG | 404 | 540 | 1100 | 11 |
| 531 | F | CD1 | 397 | 530 | 1104 | 13 |
| 531 | F | CD2 | 400 | 546 | 1088 | 15 |
| 531 | F | CE1 | 385 | 525 | 1098 | 16 |
| 531 | F | CE2 | 389 | 542 | 1081 | 19 |
| 531 | F | CZ | 381 | 532 | 1086 | 19 |
| 531 | F | C | 428 | 533 | 1089 | 18 |
| 531 | F | O | 426 | 521 | 1085 | 15 |
| 532 | W | N | 431 | 542 | 1080 | 16 |
| 532 | W | CA | 431 | 539 | 1066 | 15 |
| 532 | W | CB | 432 | 552 | 1057 | 16 |
| 532 | W | CG | 419 | 560 | 1057 | 17 |
| 532 | W | CD2 | 406 | 556 | 1053 | 19 |
| 532 | W | CE2 | 397 | 567 | 1055 | 18 |
| 532 | W | CE3 | 401 | 544 | 1047 | 16 |
| 532 | W | CD1 | 418 | 573 | 1061 | 18 |
| 532 | W | NE1 | 405 | 577 | 1060 | 22 |
| 532 | W | CZ2 | 384 | 566 | 1052 | 15 |
| 532 | W | CZ3 | 388 | 543 | 1045 | 21 |
| 532 | W | CH2 | 379 | 554 | 1047 | 19 |
| 532 | W | C | 441 | 529 | 1061 | 15 |
| 532 | W | O | 437 | 519 | 1054 | 21 |
| 533 | E | N | 453 | 530 | 1066 | 21 |
| 533 | E | CA | 463 | 520 | 1063 | 21 |
| 533 | E | CB | 476 | 523 | 1071 | 28 |
| 533 | E | CG | 487 | 514 | 1066 | 26 |
| 533 | E | CD | 500 | 516 | 1074 | 23 |
| 533 | E | OE1 | 507 | 506 | 1076 | 24 |
| 533 | E | OE2 | 502 | 527 | 1079 | 30 |
| 533 | E | C | 459 | 506 | 1066 | 19 |
| 533 | E | O | 461 | 497 | 1057 | 19 |
| 534 | S | N | 452 | 504 | 1077 | 18 |
| 534 | S | CA | 447 | 491 | 1081 | 22 |
| 534 | S | CB | 443 | 491 | 1096 | 18 |
| 534 | S | OG | 431 | 499 | 1097 | 22 |
| 534 | S | C | 436 | 485 | 1072 | 24 |
| 534 | S | O | 436 | 473 | 1070 | 24 |
| 535 | V | N | 427 | 493 | 1067 | 24 |
| 535 | V | CA | 417 | 487 | 1058 | 21 |
| 535 | V | CB | 404 | 496 | 1056 | 21 |
| 535 | V | CG1 | 404 | 508 | 1065 | 19 |
| 535 | V | CG2 | 402 | 500 | 1042 | 17 |
| 535 | V | C | 423 | 483 | 1045 | 22 |
| 535 | V | O | 419 | 473 | 1040 | 25 |
| 536 | F | N | 432 | 491 | 1040 | 23 |
| 536 | F | CA | 437 | 488 | 1027 | 22 |
| 536 | F | CB | 444 | 500 | 1020 | 19 |
| 536 | F | CG | 434 | 509 | 1013 | 22 |
| 536 | F | CD1 | 432 | 508 | 999 | 15 |
| 536 | F | CD2 | 426 | 519 | 1019 | 18 |
| 536 | F | CE1 | 423 | 516 | 992 | 20 |
| 536 | F | CE2 | 417 | 527 | 1013 | 13 |
| 536 | F | CZ | 415 | 525 | 999 | 16 |
| 536 | F | C | 447 | 476 | 1028 | 21 |
| 536 | F | O | 448 | 468 | 1018 | 21 |
| 537 | T | N | 453 | 475 | 1039 | 22 |
| 537 | T | CA | 463 | 463 | 1042 | 19 |
| 537 | T | CB | 469 | 464 | 1056 | 23 |
| 537 | T | OG1 | 476 | 476 | 1057 | 21 |
| 537 | T | CG2 | 479 | 453 | 1057 | 18 |
| 537 | T | C | 455 | 450 | 1040 | 20 |
| 537 | T | O | 462 | 440 | 1036 | 18 |
| 538 | G | N | 442 | 450 | 1043 | 24 |
| 538 | G | CA | 435 | 438 | 1042 | 16 |
| 538 | G | C | 429 | 435 | 1028 | 18 |
| 538 | G | O | 425 | 424 | 1025 | 17 |
| 539 | L | N | 429 | 445 | 1019 | 19 |
| 539 | L | CA | 423 | 444 | 1006 | 18 |
| 539 | L | CB | 419 | 458 | 1001 | 17 |
| 539 | L | CG | 406 | 463 | 1003 | 21 |
| 539 | L | CD1 | 399 | 457 | 1015 | 20 |
| 539 | L | CD2 | 407 | 478 | 1005 | 14 |
| 539 | L | C | 434 | 438 | 997 | 24 |
| 539 | L | O | 439 | 445 | 988 | 24 |
| 540 | T | N | 436 | 425 | 998 | 21 |
| 540 | T | CA | 446 | 418 | 990 | 18 |
| 540 | T | CB | 455 | 409 | 999 | 16 |
| 540 | T | OG1 | 447 | 400 | 1007 | 19 |
| 540 | T | CG2 | 462 | 418 | 1009 | 17 |
| 540 | T | C | 440 | 408 | 979 | 20 |
| 540 | T | O | 428 | 404 | 980 | 30 |
| 541 | H | N | 448 | 405 | 969 | 19 |
| 541 | H | CA | 444 | 397 | 958 | 18 |
| 541 | H | CB | 441 | 383 | 963 | 16 |
| 541 | H | CG | 452 | 377 | 972 | 20 |
| 541 | H | CD2 | 452 | 374 | 985 | 22 |
| 541 | H | ND1 | 464 | 374 | 967 | 22 |
| 541 | H | CE1 | 472 | 370 | 976 | 19 |
| 541 | H | NE2 | 465 | 370 | 988 | 19 |
| 541 | H | C | 432 | 402 | 950 | 17 |
| 541 | H | O | 422 | 395 | 948 | 22 |
| 542 | I | N | 433 | 415 | 946 | 18 |
| 542 | I | CA | 423 | 421 | 938 | 15 |
| 542 | I | CB | 425 | 436 | 937 | 15 |
| 542 | I | CG2 | 437 | 440 | 928 | 13 |
| 542 | I | CG1 | 413 | 443 | 931 | 18 |
| 542 | I | CD1 | 411 | 457 | 935 | 24 |
| 542 | I | C | 424 | 415 | 924 | 21 |
| 542 | I | O | 435 | 411 | 920 | 22 |
| 543 | D | N | 413 | 416 | 917 | 24 |
| 543 | D | CA | 413 | 411 | 903 | 25 |
| 543 | D | CB | 398 | 408 | 899 | 28 |
| 543 | D | CG | 397 | 404 | 885 | 29 |
| 543 | D | OD1 | 396 | 391 | 883 | 41 |
| 543 | D | OD2 | 398 | 412 | 875 | 37 |
| 543 | D | C | 419 | 421 | 894 | 28 |
| 543 | D | O | 414 | 432 | 892 | 29 |
| 544 | A | N | 431 | 418 | 889 | 23 |
| 544 | A | CA | 439 | 427 | 881 | 19 |
| 544 | A | CB | 451 | 419 | 875 | 17 |
| 544 | A | C | 431 | 433 | 869 | 19 |
| 544 | A | O | 432 | 444 | 866 | 16 |
| 545 | H | N | 422 | 424 | 864 | 15 |
| 545 | H | CA | 414 | 430 | 853 | 17 |
| 545 | H | CB | 407 | 418 | 845 | 18 |
| 545 | H | CG | 399 | 423 | 833 | 22 |
| 545 | H | CD2 | 403 | 431 | 824 | 22 |
| 545 | H | ND1 | 386 | 420 | 831 | 20 |
| 545 | H | CE1 | 382 | 426 | 820 | 24 |
| 545 | H | NE2 | 393 | 434 | 815 | 28 |
| 545 | H | C | 403 | 440 | 857 | 20 |
| 545 | H | O | 402 | 451 | 850 | 20 |
| 546 | F | N | 396 | 438 | 868 | 17 |
| 546 | F | CA | 386 | 448 | 872 | 21 |

TABLE 2-continued

| | | | | | | |
|---|---|---|---|---|---|---|
| 546 | F | CB | 378 | 442 | 884 | 19 |
| 546 | F | CG | 369 | 431 | 881 | 24 |
| 546 | F | CD1 | 363 | 430 | 869 | 19 |
| 546 | F | CD2 | 365 | 422 | 891 | 19 |
| 546 | F | CE1 | 353 | 420 | 866 | 22 |
| 546 | F | CE2 | 356 | 412 | 888 | 26 |
| 546 | F | CZ | 350 | 411 | 875 | 19 |
| 546 | F | C | 393 | 461 | 876 | 22 |
| 546 | F | O | 388 | 472 | 874 | 22 |
| 547 | L | N | 405 | 460 | 882 | 19 |
| 547 | L | CA | 412 | 472 | 886 | 15 |
| 547 | L | CB | 424 | 467 | 894 | 17 |
| 547 | L | CG | 433 | 479 | 900 | 16 |
| 547 | L | CD1 | 424 | 488 | 909 | 15 |
| 547 | L | CD2 | 444 | 473 | 907 | 15 |
| 547 | L | C | 417 | 479 | 874 | 14 |
| 547 | L | O | 417 | 492 | 874 | 14 |
| 548 | S | N | 420 | 472 | 864 | 17 |
| 548 | S | CA | 425 | 479 | 851 | 18 |
| 548 | S | CB | 430 | 469 | 842 | 20 |
| 548 | S | OG | 430 | 474 | 829 | 32 |
| 548 | S | C | 413 | 487 | 845 | 19 |
| 548 | S | O | 416 | 498 | 840 | 17 |
| 549 | Q | N | 401 | 481 | 845 | 17 |
| 549 | Q | CA | 390 | 488 | 839 | 19 |
| 549 | Q | CB | 378 | 479 | 838 | 19 |
| 549 | Q | CG | 381 | 466 | 831 | 26 |
| 549 | Q | CD | 369 | 458 | 828 | 23 |
| 549 | Q | OE1 | 365 | 449 | 835 | 27 |
| 549 | Q | NE2 | 363 | 462 | 817 | 30 |
| 549 | Q | C | 386 | 501 | 847 | 21 |
| 549 | Q | O | 383 | 511 | 841 | 24 |
| 550 | T | N | 386 | 500 | 860 | 21 |
| 550 | T | CA | 382 | 511 | 868 | 20 |
| 550 | T | CB | 380 | 508 | 883 | 17 |
| 550 | T | OG1 | 392 | 502 | 888 | 25 |
| 550 | T | CG2 | 368 | 498 | 885 | 20 |
| 550 | T | C | 393 | 522 | 867 | 23 |
| 550 | T | O | 390 | 534 | 866 | 26 |
| 551 | K | N | 405 | 518 | 866 | 23 |
| 551 | K | CA | 416 | 528 | 865 | 27 |
| 551 | K | CB | 429 | 522 | 866 | 23 |
| 551 | K | CG | 434 | 518 | 879 | 19 |
| 551 | K | CD | 447 | 510 | 878 | 21 |
| 551 | K | CE | 458 | 518 | 872 | 19 |
| 551 | K | NZ | 470 | 510 | 874 | 25 |
| 551 | K | C | 414 | 536 | 852 | 27 |
| 551 | K | O | 416 | 548 | 852 | 29 |
| 552 | Q | N | 410 | 529 | 842 | 31 |
| 552 | Q | CA | 408 | 535 | 829 | 29 |
| 552 | Q | CB | 409 | 525 | 818 | 27 |
| 552 | Q | CG | 409 | 531 | 804 | 40 |
| 552 | Q | CD | 396 | 535 | 798 | 50 |
| 552 | Q | OE1 | 386 | 527 | 799 | 55 |
| 552 | Q | NE2 | 395 | 547 | 792 | 55 |
| 552 | Q | C | 396 | 543 | 828 | 32 |
| 552 | Q | O | 395 | 554 | 821 | 35 |
| 553 | A | N | 385 | 539 | 834 | 31 |
| 553 | A | CA | 373 | 546 | 833 | 28 |
| 553 | A | CB | 362 | 538 | 840 | 20 |
| 553 | A | C | 373 | 560 | 840 | 28 |
| 553 | A | O | 365 | 568 | 837 | 30 |
| 554 | G | N | 383 | 562 | 848 | 30 |
| 554 | G | CA | 385 | 576 | 854 | 26 |
| 554 | G | C | 377 | 579 | 867 | 29 |
| 554 | G | O | 380 | 589 | 874 | 23 |
| 555 | D | N | 368 | 570 | 871 | 32 |
| 555 | D | CA | 360 | 571 | 883 | 34 |
| 555 | D | CB | 352 | 559 | 886 | 41 |
| 555 | D | CG | 361 | 546 | 886 | 41 |
| 555 | D | OD1 | 365 | 541 | 875 | 36 |
| 555 | D | OD2 | 363 | 540 | 897 | 33 |
| 555 | D | C | 369 | 574 | 896 | 32 |
| 555 | D | O | 381 | 572 | 895 | 39 |
| 556 | N | N | 363 | 578 | 907 | 33 |
| 556 | N | CA | 370 | 581 | 919 | 31 |
| 556 | N | CB | 361 | 590 | 928 | 28 |
| 556 | N | CG | 364 | 605 | 926 | 31 |
| 556 | N | OD1 | 357 | 613 | 932 | 25 |
| 556 | N | ND2 | 373 | 608 | 917 | 27 |
| 556 | N | C | 377 | 571 | 928 | 35 |
| 556 | N | O | 388 | 574 | 933 | 41 |
| 557 | F | N | 371 | 560 | 931 | 32 |
| 557 | F | CA | 378 | 550 | 940 | 30 |
| 557 | F | CB | 370 | 548 | 952 | 28 |
| 557 | F | CG | 369 | 559 | 961 | 27 |
| 557 | F | CD1 | 378 | 560 | 972 | 27 |
| 557 | F | CD2 | 360 | 570 | 959 | 25 |
| 557 | F | CE1 | 378 | 572 | 980 | 27 |
| 557 | F | CE2 | 360 | 581 | 967 | 23 |
| 557 | F | CZ | 369 | 582 | 977 | 21 |
| 557 | F | C | 380 | 537 | 932 | 29 |
| 557 | F | O | 374 | 527 | 935 | 27 |
| 558 | P | N | 389 | 537 | 922 | 25 |
| 558 | P | CD | 398 | 549 | 920 | 21 |
| 558 | P | CA | 393 | 526 | 913 | 24 |
| 558 | P | CB | 405 | 531 | 906 | 26 |
| 558 | P | CG | 411 | 543 | 914 | 22 |
| 558 | P | C | 395 | 513 | 921 | 21 |
| 558 | P | O | 390 | 503 | 917 | 22 |
| 559 | Y | N | 403 | 514 | 931 | 19 |
| 559 | Y | CA | 407 | 503 | 939 | 19 |
| 559 | Y | CB | 419 | 506 | 948 | 16 |
| 559 | Y | CG | 426 | 493 | 953 | 19 |
| 559 | Y | CD1 | 422 | 487 | 964 | 13 |
| 559 | Y | CE1 | 428 | 475 | 969 | 18 |
| 559 | Y | CD2 | 437 | 488 | 945 | 21 |
| 559 | Y | CE2 | 443 | 476 | 949 | 15 |
| 559 | Y | CZ | 439 | 470 | 961 | 19 |
| 559 | Y | OH | 444 | 457 | 964 | 18 |
| 559 | Y | C | 395 | 497 | 947 | 12 |
| 559 | Y | O | 393 | 486 | 947 | 11 |
| 560 | L | N | 389 | 506 | 955 | 10 |
| 560 | L | CA | 377 | 502 | 963 | 14 |
| 560 | L | CB | 372 | 513 | 972 | 17 |
| 560 | L | CG | 380 | 519 | 983 | 24 |
| 560 | L | CD1 | 372 | 529 | 991 | 19 |
| 560 | L | CD2 | 385 | 507 | 992 | 25 |
| 560 | L | C | 366 | 496 | 954 | 13 |
| 560 | L | O | 360 | 486 | 958 | 14 |
| 561 | V | N | 364 | 502 | 943 | 8 |
| 561 | V | CA | 353 | 498 | 934 | 9 |
| 561 | V | CB | 351 | 508 | 922 | 14 |
| 561 | V | CG1 | 341 | 502 | 912 | 13 |
| 561 | V | CG2 | 344 | 521 | 928 | 17 |
| 561 | V | C | 357 | 484 | 928 | 14 |
| 561 | V | O | 349 | 475 | 929 | 14 |
| 562 | A | N | 369 | 483 | 923 | 13 |
| 562 | A | CA | 374 | 470 | 917 | 11 |
| 562 | A | CB | 387 | 472 | 910 | 9 |
| 562 | A | C | 375 | 460 | 928 | 14 |
| 562 | A | O | 373 | 448 | 925 | 12 |
| 563 | Y | N | 378 | 464 | 940 | 13 |
| 563 | Y | CA | 379 | 454 | 951 | 13 |
| 563 | Y | CB | 386 | 459 | 963 | 14 |
| 563 | Y | CG | 392 | 447 | 971 | 15 |
| 563 | Y | CD1 | 405 | 442 | 969 | 20 |
| 563 | Y | CE1 | 409 | 431 | 975 | 18 |
| 563 | Y | CD2 | 383 | 440 | 980 | 16 |
| 563 | Y | CE2 | 388 | 428 | 986 | 16 |
| 563 | Y | CZ | 401 | 424 | 984 | 17 |
| 563 | Y | OH | 405 | 412 | 990 | 20 |
| 563 | Y | C | 365 | 448 | 954 | 19 |
| 563 | Y | O | 363 | 436 | 955 | 18 |
| 564 | Q | N | 355 | 457 | 956 | 18 |
| 564 | Q | CA | 342 | 452 | 959 | 17 |
| 564 | Q | CB | 332 | 464 | 960 | 21 |
| 564 | Q | CG | 317 | 460 | 960 | 16 |
| 564 | Q | CD | 313 | 453 | 973 | 23 |
| 564 | Q | OE1 | 311 | 459 | 984 | 21 |
| 564 | Q | NE2 | 313 | 440 | 973 | 20 |
| 564 | Q | C | 337 | 443 | 947 | 20 |
| 564 | Q | O | 330 | 433 | 950 | 16 |
| 565 | A | N | 340 | 447 | 935 | 19 |
| 565 | A | CA | 336 | 439 | 923 | 22 |
| 565 | A | CB | 340 | 446 | 911 | 10 |
| 565 | A | C | 343 | 425 | 923 | 23 |
| 565 | A | O | 337 | 415 | 920 | 25 |

TABLE 2-continued

| | | | | | | |
|---|---|---|---|---|---|---|
| 566 | T | N | 355 | 425 | 928 | 22 |
| 566 | T | CA | 363 | 413 | 929 | 18 |
| 566 | T | CB | 377 | 416 | 934 | 17 |
| 566 | T | OG1 | 384 | 423 | 924 | 19 |
| 566 | T | CG2 | 385 | 403 | 936 | 13 |
| 566 | T | C | 356 | 403 | 938 | 18 |
| 566 | T | O | 354 | 392 | 935 | 19 |
| 567 | V | N | 352 | 408 | 951 | 16 |
| 567 | V | CA | 346 | 398 | 960 | 18 |
| 567 | V | CB | 344 | 404 | 974 | 18 |
| 567 | V | CG1 | 357 | 405 | 982 | 18 |
| 567 | V | CG2 | 339 | 419 | 973 | 31 |
| 567 | V | C | 332 | 394 | 954 | 18 |
| 567 | V | O | 329 | 382 | 955 | 17 |
| 568 | C | N | 325 | 403 | 948 | 17 |
| 568 | C | CA | 312 | 399 | 943 | 23 |
| 568 | C | CB | 305 | 412 | 936 | 17 |
| 568 | C | SG | 299 | 424 | 948 | 29 |
| 568 | C | C | 313 | 389 | 932 | 27 |
| 568 | C | O | 306 | 379 | 932 | 29 |
| 569 | A | N | 321 | 391 | 922 | 23 |
| 569 | A | CA | 323 | 382 | 911 | 22 |
| 569 | A | CB | 332 | 388 | 900 | 21 |
| 569 | A | C | 328 | 368 | 915 | 20 |
| 569 | A | O | 324 | 358 | 910 | 23 |
| 570 | R | N | 337 | 368 | 925 | 22 |
| 570 | R | CA | 343 | 355 | 930 | 22 |
| 570 | R | CB | 354 | 357 | 939 | 25 |
| 570 | R | CG | 368 | 357 | 933 | 20 |
| 570 | R | CD | 378 | 365 | 941 | 25 |
| 570 | R | NE | 390 | 367 | 933 | 28 |
| 570 | R | CZ | 400 | 374 | 938 | 29 |
| 570 | R | NH1 | 400 | 380 | 950 | 25 |
| 570 | R | NH2 | 411 | 376 | 930 | 23 |
| 570 | R | C | 332 | 347 | 937 | 26 |
| 570 | R | O | 332 | 335 | 937 | 30 |
| 571 | A | N | 322 | 354 | 942 | 22 |
| 571 | A | CA | 311 | 348 | 949 | 23 |
| 571 | A | CB | 306 | 356 | 961 | 15 |
| 571 | A | C | 299 | 346 | 939 | 29 |
| 571 | A | O | 289 | 341 | 943 | 33 |
| 572 | Q | N | 301 | 351 | 927 | 30 |
| 572 | Q | CA | 291 | 351 | 917 | 33 |
| 572 | Q | CB | 286 | 337 | 914 | 37 |
| 572 | Q | CG | 296 | 329 | 906 | 47 |
| 572 | Q | CD | 298 | 315 | 913 | 59 |
| 572 | Q | OE1 | 292 | 305 | 910 | 62 |
| 572 | Q | NE2 | 308 | 315 | 922 | 62 |
| 572 | Q | C | 278 | 358 | 923 | 33 |
| 572 | Q | O | 267 | 353 | 921 | 36 |
| 573 | A | N | 281 | 369 | 929 | 29 |
| 573 | A | CA | 270 | 377 | 935 | 23 |
| 573 | A | CB | 271 | 379 | 950 | 15 |
| 573 | A | C | 269 | 390 | 927 | 26 |
| 573 | A | O | 279 | 394 | 921 | 17 |
| 574 | P | N | 258 | 397 | 927 | 22 |
| 574 | P | CD | 245 | 393 | 934 | 21 |
| 574 | P | CA | 256 | 410 | 921 | 22 |
| 574 | P | CB | 241 | 411 | 919 | 27 |
| 574 | P | CG | 235 | 400 | 926 | 27 |
| 574 | P | C | 262 | 422 | 928 | 22 |
| 574 | P | O | 264 | 421 | 940 | 24 |
| 575 | P | N | 266 | 433 | 921 | 18 |
| 575 | P | CD | 264 | 435 | 907 | 14 |
| 575 | P | CA | 272 | 444 | 929 | 19 |
| 575 | P | CB | 276 | 454 | 918 | 16 |
| 575 | P | CG | 268 | 450 | 905 | 15 |
| 575 | P | C | 261 | 450 | 938 | 18 |
| 575 | P | O | 250 | 446 | 938 | 25 |
| 576 | P | N | 265 | 460 | 946 | 20 |
| 576 | P | CD | 278 | 466 | 947 | 21 |
| 576 | P | CA | 255 | 467 | 954 | 21 |
| 576 | P | CB | 263 | 478 | 962 | 21 |
| 576 | P | CG | 277 | 473 | 960 | 21 |
| 576 | P | C | 243 | 473 | 947 | 20 |
| 576 | P | O | 232 | 473 | 952 | 20 |
| 577 | S | N | 245 | 477 | 935 | 20 |
| 577 | S | CA | 234 | 482 | 926 | 21 |
| 577 | S | CB | 232 | 497 | 930 | 22 |
| 577 | S | OG | 241 | 505 | 924 | 32 |
| 577 | S | C | 239 | 481 | 912 | 26 |
| 577 | S | O | 251 | 477 | 910 | 27 |
| 578 | W | N | 231 | 485 | 902 | 24 |
| 578 | W | CA | 236 | 484 | 888 | 25 |
| 578 | W | CB | 226 | 477 | 879 | 18 |
| 578 | W | CG | 227 | 462 | 881 | 21 |
| 578 | W | CD2 | 238 | 453 | 878 | 23 |
| 578 | W | CE2 | 235 | 440 | 883 | 24 |
| 578 | W | CE3 | 250 | 455 | 871 | 21 |
| 578 | W | CD1 | 218 | 454 | 888 | 20 |
| 578 | W | NE1 | 223 | 441 | 889 | 23 |
| 578 | W | CZ2 | 244 | 430 | 881 | 20 |
| 578 | W | CZ3 | 258 | 445 | 869 | 24 |
| 578 | W | CH2 | 255 | 432 | 874 | 23 |
| 578 | W | C | 239 | 498 | 883 | 28 |
| 578 | W | O | 237 | 501 | 871 | 29 |
| 579 | D | N | 244 | 506 | 892 | 34 |
| 579 | D | CA | 247 | 520 | 888 | 37 |
| 579 | D | CB | 251 | 528 | 901 | 41 |
| 579 | D | CG | 256 | 542 | 898 | 47 |
| 579 | D | OD1 | 247 | 551 | 896 | 56 |
| 579 | D | OD2 | 268 | 544 | 897 | 49 |
| 579 | D | C | 259 | 519 | 879 | 34 |
| 579 | D | O | 266 | 509 | 878 | 37 |
| 580 | Q | N | 262 | 530 | 872 | 31 |
| 580 | Q | CA | 273 | 530 | 863 | 32 |
| 580 | Q | CB | 275 | 544 | 856 | 32 |
| 580 | Q | CG | 268 | 544 | 842 | 44 |
| 580 | Q | CD | 273 | 533 | 833 | 50 |
| 580 | Q | OE1 | 283 | 536 | 825 | 51 |
| 580 | Q | NE2 | 267 | 521 | 834 | 49 |
| 580 | Q | C | 286 | 526 | 870 | 31 |
| 580 | Q | O | 295 | 520 | 864 | 31 |
| 581 | M | N | 287 | 530 | 882 | 25 |
| 581 | M | CA | 299 | 527 | 890 | 27 |
| 581 | M | CB | 296 | 531 | 905 | 25 |
| 581 | M | CG | 306 | 525 | 915 | 25 |
| 581 | M | SD | 303 | 529 | 932 | 32 |
| 581 | M | CE | 305 | 547 | 931 | 24 |
| 581 | M | C | 303 | 513 | 889 | 26 |
| 581 | M | O | 315 | 510 | 890 | 26 |
| 582 | W | N | 293 | 504 | 887 | 25 |
| 582 | W | CA | 296 | 490 | 887 | 24 |
| 582 | W | CB | 286 | 482 | 896 | 22 |
| 582 | W | CG | 286 | 488 | 911 | 25 |
| 582 | W | CD2 | 296 | 487 | 920 | 24 |
| 582 | W | CE2 | 293 | 495 | 932 | 19 |
| 582 | W | CE3 | 309 | 480 | 920 | 22 |
| 582 | W | CD1 | 276 | 496 | 916 | 24 |
| 582 | W | NE1 | 280 | 500 | 929 | 21 |
| 582 | W | CZ2 | 301 | 496 | 943 | 17 |
| 582 | W | CZ3 | 317 | 481 | 932 | 16 |
| 582 | W | CH2 | 313 | 489 | 943 | 15 |
| 582 | W | C | 295 | 483 | 873 | 24 |
| 582 | W | O | 293 | 471 | 872 | 27 |
| 583 | K | N | 298 | 491 | 863 | 25 |
| 583 | K | CA | 297 | 486 | 849 | 24 |
| 583 | K | CB | 299 | 497 | 839 | 28 |
| 583 | K | CG | 312 | 505 | 840 | 33 |
| 583 | K | CD | 309 | 519 | 834 | 39 |
| 583 | K | CE | 322 | 525 | 829 | 38 |
| 583 | K | NZ | 322 | 529 | 815 | 47 |
| 583 | K | C | 307 | 474 | 845 | 26 |
| 583 | K | O | 304 | 467 | 836 | 25 |
| 584 | C | N | 318 | 473 | 852 | 27 |
| 584 | C | CA | 327 | 462 | 849 | 30 |
| 584 | C | CB | 341 | 464 | 856 | 28 |
| 584 | C | SG | 341 | 461 | 874 | 31 |
| 584 | C | C | 321 | 449 | 851 | 30 |
| 584 | C | O | 327 | 438 | 848 | 30 |
| 585 | L | N | 309 | 449 | 857 | 29 |
| 585 | L | CA | 302 | 436 | 860 | 25 |
| 585 | L | CB | 298 | 436 | 875 | 22 |
| 585 | L | CG | 306 | 430 | 886 | 21 |
| 585 | L | CD1 | 318 | 423 | 880 | 22 |
| 585 | L | CD2 | 310 | 440 | 896 | 14 |
| 585 | L | C | 290 | 435 | 851 | 27 |
| 585 | L | O | 284 | 424 | 851 | 29 |

TABLE 2-continued

| | | | | | | | | | | | | |
|---|---|---|---|---|---|---|---|---|---|---|---|---|
| 586 | I | N | 286 | 445 | 844 | 28 | 596 | T | N | 246 | 407 | 979 | 24 |
| 586 | I | CA | 274 | 444 | 835 | 28 | 596 | T | CA | 260 | 410 | 977 | 24 |
| 586 | I | CB | 273 | 456 | 825 | 31 | 596 | T | CB | 261 | 424 | 968 | 26 |
| 586 | I | CG2 | 262 | 453 | 815 | 23 | 596 | T | OG1 | 268 | 434 | 976 | 27 |
| 586 | I | CG1 | 270 | 470 | 832 | 28 | 596 | T | CG2 | 247 | 429 | 965 | 18 |
| 586 | I | CD1 | 264 | 469 | 845 | 35 | 596 | T | C | 267 | 411 | 990 | 23 |
| 586 | I | C | 273 | 431 | 827 | 28 | 596 | T | O | 262 | 417 | 1000 | 25 |
| 586 | I | O | 263 | 425 | 826 | 32 | 597 | P | N | 279 | 406 | 990 | 23 |
| 587 | R | N | 284 | 427 | 822 | 29 | 597 | P | CD | 286 | 399 | 979 | 23 |
| 587 | R | CA | 285 | 415 | 813 | 35 | 597 | P | CA | 288 | 406 | 1002 | 25 |
| 587 | R | CB | 297 | 415 | 805 | 38 | 597 | P | CB | 299 | 396 | 999 | 16 |
| 587 | R | CG | 310 | 417 | 812 | 42 | 597 | P | CG | 300 | 396 | 984 | 20 |
| 587 | R | CD | 322 | 415 | 803 | 41 | 597 | P | C | 294 | 420 | 1003 | 26 |
| 587 | R | NE | 335 | 415 | 811 | 46 | 597 | P | O | 304 | 423 | 997 | 23 |
| 587 | R | CZ | 341 | 404 | 813 | 44 | 598 | L | N | 287 | 428 | 1011 | 24 |
| 587 | R | NH1 | 337 | 392 | 809 | 42 | 598 | L | CA | 290 | 442 | 1012 | 23 |
| 587 | R | NH2 | 352 | 404 | 821 | 45 | 598 | L | CB | 279 | 450 | 1018 | 25 |
| 587 | R | C | 283 | 402 | 821 | 33 | 598 | L | CG | 280 | 466 | 1019 | 27 |
| 587 | R | O | 281 | 391 | 815 | 35 | 598 | L | CD1 | 281 | 472 | 1005 | 22 |
| 588 | L | N | 284 | 402 | 834 | 32 | 598 | L | CD2 | 267 | 471 | 1025 | 27 |
| 588 | L | CA | 283 | 390 | 842 | 28 | 598 | L | C | 303 | 445 | 1021 | 25 |
| 588 | L | CB | 293 | 390 | 854 | 28 | 598 | L | O | 304 | 439 | 1031 | 29 |
| 588 | L | CG | 306 | 384 | 851 | 32 | 599 | L | N | 312 | 453 | 1015 | 25 |
| 588 | L | CD1 | 309 | 384 | 836 | 30 | 599 | L | CA | 325 | 456 | 1022 | 22 |
| 588 | L | CD2 | 317 | 393 | 859 | 28 | 599 | L | CB | 336 | 456 | 1011 | 20 |
| 588 | L | C | 269 | 389 | 848 | 31 | 599 | L | CG | 338 | 443 | 1003 | 23 |
| 588 | L | O | 265 | 379 | 855 | 33 | 599 | L | CD1 | 351 | 443 | 996 | 18 |
| 589 | K | N | 261 | 399 | 845 | 34 | 599 | L | CD2 | 337 | 431 | 1013 | 21 |
| 589 | K | CA | 247 | 400 | 850 | 35 | 599 | L | C | 324 | 470 | 1028 | 19 |
| 589 | K | CB | 240 | 412 | 843 | 31 | 599 | L | O | 329 | 473 | 1039 | 18 |
| 589 | K | CG | 227 | 416 | 850 | 26 | 600 | Y | N | 317 | 479 | 1021 | 19 |
| 589 | K | CD | 225 | 431 | 848 | 32 | 600 | Y | CA | 316 | 493 | 1025 | 18 |
| 589 | K | CE | 212 | 436 | 853 | 39 | 600 | Y | CB | 329 | 501 | 1024 | 16 |
| 589 | K | NZ | 208 | 449 | 846 | 43 | 600 | Y | CG | 338 | 496 | 1014 | 17 |
| 589 | K | C | 238 | 387 | 850 | 37 | 600 | Y | CD1 | 336 | 497 | 1000 | 11 |
| 589 | K | O | 232 | 384 | 860 | 35 | 600 | Y | CE1 | 344 | 492 | 990 | 9 |
| 590 | P | N | 238 | 380 | 838 | 37 | 600 | Y | CD2 | 350 | 488 | 1017 | 17 |
| 590 | P | CD | 246 | 383 | 826 | 41 | 600 | Y | CE2 | 358 | 483 | 1007 | 9 |
| 590 | P | CA | 230 | 368 | 838 | 39 | 600 | Y | CZ | 355 | 485 | 994 | 14 |
| 590 | P | CB | 232 | 363 | 823 | 38 | 600 | Y | OH | 363 | 480 | 984 | 13 |
| 590 | P | CG | 245 | 369 | 819 | 42 | 600 | Y | C | 305 | 500 | 1015 | 19 |
| 590 | P | C | 234 | 358 | 848 | 37 | 600 | Y | O | 301 | 494 | 1006 | 13 |
| 590 | P | O | 226 | 351 | 854 | 41 | 601 | R | N | 301 | 512 | 1018 | 18 |
| 591 | T | N | 247 | 357 | 851 | 37 | 601 | R | CA | 291 | 519 | 1009 | 21 |
| 591 | T | CA | 253 | 347 | 860 | 37 | 601 | R | CB | 279 | 523 | 1018 | 21 |
| 591 | T | CB | 268 | 345 | 856 | 41 | 601 | R | CG | 274 | 511 | 1027 | 28 |
| 591 | T | OG1 | 276 | 355 | 862 | 46 | 601 | R | CD | 264 | 516 | 1037 | 31 |
| 591 | T | CG2 | 270 | 345 | 841 | 43 | 601 | R | NE | 251 | 514 | 1031 | 37 |
| 591 | T | C | 254 | 351 | 875 | 38 | 601 | R | CZ | 241 | 506 | 1035 | 32 |
| 591 | T | O | 257 | 343 | 883 | 32 | 601 | R | NH1 | 244 | 498 | 1045 | 30 |
| 592 | L | N | 251 | 364 | 877 | 40 | 601 | R | NH2 | 230 | 505 | 1028 | 36 |
| 592 | L | CA | 252 | 369 | 891 | 36 | 601 | R | C | 297 | 530 | 1002 | 20 |
| 592 | L | CB | 256 | 383 | 891 | 35 | 601 | R | O | 303 | 540 | 1007 | 24 |
| 592 | L | CG | 271 | 386 | 891 | 37 | 602 | L | N | 296 | 529 | 989 | 19 |
| 592 | L | CD1 | 280 | 374 | 889 | 33 | 602 | L | CA | 302 | 539 | 980 | 27 |
| 592 | L | CD2 | 274 | 396 | 880 | 39 | 602 | L | CB | 310 | 533 | 969 | 25 |
| 592 | L | C | 239 | 367 | 898 | 34 | 602 | L | CG | 325 | 530 | 971 | 30 |
| 592 | L | O | 229 | 371 | 893 | 38 | 602 | L | CD1 | 329 | 531 | 986 | 24 |
| 593 | H | N | 239 | 362 | 910 | 35 | 602 | L | CD2 | 329 | 517 | 966 | 28 |
| 593 | H | CA | 228 | 359 | 918 | 33 | 602 | L | C | 290 | 547 | 973 | 31 |
| 593 | H | CB | 222 | 345 | 915 | 40 | 602 | L | O | 292 | 556 | 965 | 37 |
| 593 | H | CG | 217 | 344 | 901 | 52 | 603 | G | N | 278 | 542 | 976 | 31 |
| 593 | H | CD2 | 206 | 349 | 895 | 56 | 603 | G | CA | 266 | 548 | 970 | 30 |
| 593 | H | ND1 | 225 | 338 | 891 | 57 | 603 | G | C | 254 | 541 | 975 | 29 |
| 593 | H | CE1 | 218 | 339 | 879 | 59 | 603 | G | O | 254 | 535 | 986 | 27 |
| 593 | H | NE2 | 207 | 345 | 881 | 62 | 604 | A | N | 243 | 540 | 967 | 28 |
| 593 | H | C | 230 | 360 | 933 | 32 | 604 | A | CA | 231 | 533 | 971 | 28 |
| 593 | H | O | 241 | 357 | 938 | 34 | 604 | A | CB | 219 | 539 | 963 | 26 |
| 594 | G | N | 219 | 363 | 941 | 29 | 604 | A | C | 232 | 519 | 969 | 28 |
| 594 | G | CA | 221 | 363 | 956 | 25 | 604 | A | O | 236 | 514 | 958 | 33 |
| 594 | G | C | 224 | 377 | 962 | 24 | 605 | V | N | 229 | 511 | 979 | 26 |
| 594 | G | O | 225 | 387 | 956 | 28 | 605 | V | CA | 229 | 497 | 979 | 29 |
| 595 | P | N | 226 | 377 | 975 | 20 | 605 | V | CB | 235 | 491 | 992 | 29 |
| 595 | F | CD | 226 | 365 | 985 | 18 | 605 | V | CG1 | 234 | 475 | 992 | 22 |
| 595 | P | CA | 229 | 389 | 982 | 22 | 605 | V | CG2 | 250 | 495 | 993 | 27 |
| 595 | P | CB | 227 | 386 | 997 | 22 | 605 | V | C | 214 | 493 | 977 | 29 |
| 595 | P | CG | 229 | 371 | 998 | 22 | 605 | V | O | 206 | 494 | 986 | 31 |
| 595 | P | C | 243 | 394 | 979 | 24 | 606 | Q | N | 211 | 488 | 965 | 30 |
| 595 | P | O | 252 | 385 | 978 | 24 | 606 | Q | CA | 197 | 484 | 961 | 29 |

TABLE 2-continued

| | | | | | | |
|---|---|---|---|---|---|---|
| 606 | Q | CB | 194 | 488 | 947 | 32 |
| 606 | Q | CG | 188 | 502 | 946 | 39 |
| 606 | Q | CD | 190 | 508 | 932 | 46 |
| 606 | Q | OE1 | 199 | 516 | 929 | 51 |
| 606 | Q | NE2 | 181 | 504 | 923 | 46 |
| 606 | Q | C | 195 | 469 | 963 | 32 |
| 606 | Q | O | 184 | 464 | 965 | 34 |
| 607 | N | N | 206 | 461 | 963 | 34 |
| 607 | N | CA | 205 | 447 | 964 | 31 |
| 607 | N | CB | 216 | 440 | 957 | 31 |
| 607 | N | CG | 214 | 424 | 957 | 34 |
| 607 | N | OD1 | 203 | 420 | 958 | 38 |
| 607 | N | ND2 | 225 | 417 | 955 | 34 |
| 607 | N | C | 205 | 443 | 979 | 33 |
| 607 | N | O | 209 | 451 | 987 | 38 |
| 608 | E | N | 201 | 431 | 982 | 29 |
| 608 | E | CA | 201 | 426 | 995 | 33 |
| 608 | E | CB | 194 | 412 | 996 | 43 |
| 608 | E | CG | 189 | 407 | 983 | 57 |
| 608 | E | CD | 175 | 413 | 980 | 64 |
| 608 | E | OE1 | 173 | 417 | 968 | 66 |
| 608 | E | OE2 | 167 | 413 | 989 | 69 |
| 608 | E | C | 216 | 423 | 998 | 30 |
| 608 | E | O | 224 | 421 | 989 | 22 |
| 609 | V | N | 220 | 423 | 1010 | 26 |
| 609 | V | CA | 234 | 421 | 1013 | 31 |
| 609 | V | CB | 240 | 434 | 1017 | 32 |
| 609 | V | CG1 | 239 | 444 | 1005 | 39 |
| 609 | V | CG2 | 233 | 440 | 1029 | 28 |
| 609 | V | C | 236 | 412 | 1025 | 31 |
| 609 | V | O | 228 | 409 | 1033 | 32 |
| 610 | T | N | 248 | 406 | 1025 | 28 |
| 610 | T | CA | 252 | 397 | 1035 | 27 |
| 610 | T | CB | 255 | 383 | 1030 | 32 |
| 610 | T | OG1 | 259 | 374 | 1041 | 35 |
| 610 | T | CG2 | 266 | 383 | 1020 | 33 |
| 610 | T | C | 265 | 402 | 1041 | 27 |
| 610 | T | O | 273 | 408 | 1034 | 31 |
| 611 | L | N | 267 | 401 | 1054 | 28 |
| 611 | L | CA | 279 | 406 | 1061 | 25 |
| 611 | L | CB | 275 | 415 | 1072 | 29 |
| 611 | L | CG | 271 | 430 | 1070 | 30 |
| 611 | L | CD1 | 268 | 433 | 1055 | 33 |
| 611 | L | CD2 | 259 | 433 | 1079 | 36 |
| 611 | L | C | 288 | 395 | 1065 | 26 |
| 611 | L | O | 297 | 398 | 1074 | 26 |
| 612 | T | N | 287 | 384 | 1060 | 26 |
| 612 | T | CA | 295 | 372 | 1064 | 29 |
| 612 | T | CB | 288 | 359 | 1060 | 30 |
| 612 | T | OG1 | 285 | 360 | 1046 | 24 |
| 612 | T | CG2 | 276 | 357 | 1068 | 33 |
| 612 | T | C | 310 | 371 | 1058 | 28 |
| 612 | T | O | 318 | 365 | 1064 | 30 |
| 613 | H | N | 312 | 378 | 1047 | 28 |
| 613 | H | CA | 325 | 377 | 1041 | 24 |
| 613 | H | CB | 325 | 385 | 1028 | 23 |
| 613 | H | CG | 337 | 383 | 1019 | 26 |
| 613 | H | CD2 | 338 | 375 | 1008 | 25 |
| 613 | H | ND1 | 349 | 389 | 1021 | 24 |
| 613 | H | CE1 | 357 | 385 | 1011 | 22 |
| 613 | H | NE2 | 351 | 376 | 1003 | 22 |
| 613 | H | C | 336 | 382 | 1050 | 24 |
| 613 | H | O | 335 | 392 | 1057 | 25 |
| 614 | P | N | 348 | 374 | 1050 | 23 |
| 614 | P | CD | 349 | 362 | 1042 | 16 |
| 614 | P | CA | 359 | 378 | 1058 | 21 |
| 614 | P | CB | 370 | 367 | 1053 | 20 |
| 614 | P | CG | 362 | 356 | 1048 | 22 |
| 614 | P | C | 365 | 392 | 1057 | 19 |
| 614 | P | O | 369 | 398 | 1066 | 21 |
| 615 | I | N | 365 | 397 | 1045 | 20 |
| 615 | I | CA | 369 | 411 | 1043 | 20 |
| 615 | I | CB | 370 | 415 | 1028 | 22 |
| 615 | I | CG2 | 376 | 430 | 1027 | 18 |
| 615 | I | CG1 | 380 | 406 | 1021 | 22 |
| 615 | I | CD1 | 394 | 407 | 1026 | 10 |
| 615 | I | C | 360 | 421 | 1050 | 25 |
| 615 | I | O | 364 | 430 | 1057 | 27 |
| 616 | T | N | 347 | 418 | 1049 | 22 |
| 616 | T | CA | 337 | 427 | 1056 | 19 |
| 616 | T | CB | 322 | 423 | 1054 | 22 |
| 616 | T | OG1 | 319 | 422 | 1040 | 18 |
| 616 | T | CG2 | 313 | 433 | 1061 | 18 |
| 616 | T | C | 340 | 427 | 1071 | 19 |
| 616 | T | O | 340 | 437 | 1077 | 22 |
| 617 | K | N | 342 | 415 | 1076 | 19 |
| 617 | K | CA | 345 | 413 | 1091 | 23 |
| 617 | K | CB | 345 | 398 | 1094 | 23 |
| 617 | K | CG | 332 | 391 | 1091 | 30 |
| 617 | K | CD | 333 | 376 | 1093 | 38 |
| 617 | K | CE | 320 | 370 | 1097 | 36 |
| 617 | K | NZ | 320 | 365 | 1111 | 45 |
| 617 | K | C | 358 | 420 | 1095 | 24 |
| 617 | K | O | 359 | 425 | 1106 | 24 |
| 618 | Y | N | 368 | 419 | 1086 | 23 |
| 618 | Y | CA | 381 | 425 | 1088 | 20 |
| 618 | Y | CB | 390 | 421 | 1077 | 21 |
| 618 | Y | CG | 403 | 429 | 1078 | 20 |
| 618 | Y | CD1 | 414 | 425 | 1086 | 22 |
| 618 | Y | CE1 | 425 | 433 | 1088 | 16 |
| 618 | Y | CD2 | 405 | 441 | 1070 | 22 |
| 618 | Y | CE2 | 417 | 448 | 1071 | 19 |
| 618 | Y | CZ | 427 | 444 | 1080 | 19 |
| 618 | Y | OH | 438 | 451 | 1082 | 15 |
| 618 | Y | C | 379 | 440 | 1088 | 23 |
| 618 | Y | O | 384 | 447 | 1097 | 24 |
| 619 | I | N | 373 | 446 | 1078 | 21 |
| 619 | I | CA | 371 | 460 | 1078 | 23 |
| 619 | I | CB | 364 | 465 | 1064 | 15 |
| 619 | I | CG2 | 361 | 480 | 1065 | 11 |
| 619 | I | CG1 | 375 | 463 | 1053 | 21 |
| 619 | I | CD1 | 369 | 466 | 1039 | 15 |
| 619 | I | C | 362 | 464 | 1090 | 24 |
| 619 | I | O | 364 | 475 | 1095 | 26 |
| 620 | M | N | 353 | 456 | 1094 | 26 |
| 620 | M | CA | 344 | 460 | 1106 | 29 |
| 620 | M | CB | 334 | 449 | 1108 | 21 |
| 620 | M | CG | 321 | 451 | 1100 | 35 |
| 620 | M | SD | 308 | 438 | 1099 | 34 |
| 620 | M | CE | 311 | 429 | 1114 | 42 |
| 620 | M | C | 354 | 461 | 1118 | 27 |
| 620 | M | O | 353 | 471 | 1125 | 29 |
| 621 | A | N | 363 | 451 | 1119 | 24 |
| 621 | A | CA | 372 | 451 | 1130 | 22 |
| 621 | A | CB | 381 | 439 | 1130 | 16 |
| 621 | A | C | 381 | 464 | 1130 | 21 |
| 621 | A | O | 384 | 470 | 1140 | 23 |
| 622 | C | N | 384 | 469 | 1118 | 21 |
| 622 | C | CA | 392 | 481 | 1116 | 25 |
| 622 | C | CB | 396 | 483 | 1102 | 24 |
| 622 | C | SG | 408 | 472 | 1095 | 33 |
| 622 | C | C | 384 | 493 | 1121 | 25 |
| 622 | C | O | 390 | 504 | 1124 | 32 |
| 623 | M | N | 371 | 492 | 1123 | 26 |
| 623 | M | CA | 363 | 504 | 1127 | 25 |
| 623 | M | CB | 348 | 502 | 1124 | 27 |
| 623 | M | CG | 345 | 498 | 1110 | 21 |
| 623 | M | SD | 350 | 511 | 1099 | 29 |
| 623 | M | CE | 345 | 526 | 1108 | 23 |
| 623 | M | C | 365 | 507 | 1142 | 24 |
| 623 | M | O | 360 | 517 | 1147 | 25 |
| 624 | S | N | 372 | 498 | 1149 | 23 |
| 624 | S | CA | 374 | 500 | 1164 | 20 |
| 624 | S | CB | 374 | 486 | 1171 | 20 |
| 624 | S | OG | 362 | 479 | 1167 | 30 |
| 624 | S | C | 386 | 508 | 1167 | 27 |
| 624 | S | O | 389 | 510 | 1179 | 25 |
| 625 | A | N | 393 | 513 | 1157 | 27 |
| 625 | A | CA | 405 | 521 | 1159 | 32 |
| 625 | A | CB | 412 | 524 | 1146 | 26 |
| 625 | A | C | 401 | 535 | 1165 | 30 |
| 625 | A | O | 389 | 539 | 1164 | 33 |
| 626 | D | N | 410 | 541 | 1172 | 31 |
| 626 | D | CA | 408 | 554 | 1178 | 35 |
| 626 | D | CB | 419 | 559 | 1187 | 38 |
| 626 | D | CG | 420 | 552 | 1200 | 43 |
| 626 | D | OD1 | 411 | 544 | 1203 | 48 |
| 626 | D | OD2 | 430 | 554 | 1207 | 49 |

TABLE 2-continued

| | | | | | | |
|---|---|---|---|---|---|---|
| 626 | D | C | 407 | 564 | 1166 | 36 |
| 626 | D | O | 417 | 565 | 1159 | 37 |
| 627 | L | N | 396 | 571 | 1164 | 36 |
| 627 | L | CA | 394 | 580 | 1153 | 34 |
| 627 | L | CB | 382 | 576 | 1144 | 36 |
| 627 | L | CG | 384 | 570 | 1130 | 39 |
| 627 | L | CD1 | 398 | 569 | 1126 | 36 |
| 627 | L | CD2 | 376 | 557 | 1130 | 40 |
| 627 | L | C | 391 | 594 | 1159 | 33 |
| 627 | L | O | 382 | 595 | 1168 | 38 |
| 628 | E | N | 398 | 604 | 1155 | 35 |
| 628 | E | CA | 396 | 617 | 1161 | 32 |
| 628 | E | CB | 409 | 625 | 1162 | 39 |
| 628 | E | CG | 409 | 638 | 1169 | 41 |
| 628 | E | CD | 419 | 648 | 1165 | 47 |
| 628 | E | OE1 | 420 | 650 | 1152 | 54 |
| 628 | E | OE2 | 425 | 655 | 1173 | 47 |
| 628 | E | C | 387 | 625 | 1152 | 31 |
| 628 | E | O | 389 | 627 | 1140 | 29 |
| 629 | V | N | 375 | 630 | 1157 | 29 |
| 629 | V | CA | 366 | 638 | 1149 | 31 |
| 629 | V | CB | 352 | 630 | 1148 | 30 |
| 629 | V | CG1 | 354 | 618 | 1139 | 34 |
| 629 | V | CG2 | 347 | 627 | 1162 | 26 |
| 629 | V | C | 364 | 651 | 1156 | 29 |
| 629 | V | O | 364 | 653 | 1168 | 33 |
| 630 | V | N | 362 | 661 | 1147 | 29 |
| 630 | V | CA | 360 | 675 | 1153 | 34 |
| 630 | V | CB | 362 | 686 | 1142 | 31 |
| 630 | V | CG1 | 376 | 685 | 1135 | 34 |
| 630 | V | CG2 | 351 | 685 | 1132 | 37 |
| 630 | V | C | 347 | 677 | 1159 | 37 |
| 630 | V | O | 337 | 670 | 1155 | 38 |
| 631 | T | N | 346 | 685 | 1169 | 39 |
| 631 | T | CA | 334 | 688 | 1176 | 42 |
| 631 | T | CB | 335 | 682 | 1190 | 43 |
| 631 | T | OG1 | 348 | 684 | 1196 | 40 |
| 631 | T | CG2 | 331 | 667 | 1190 | 42 |
| 631 | T | C | 331 | 703 | 1177 | 42 |
| 631 | T | O | 336 | 711 | 1169 | 43 |
| 631 | T | OT | 324 | 707 | 1186 | 43 |
| 999 | Z | ZN | 463 | 751 | 1377 | 38 |
| 1999 | Z | ZN | −52 | 642 | 837 | 69 |
| 800 | P | P | 520 | 820 | 887 | 77 |
| 800 | P | O1 | 510 | 827 | 879 | 76 |
| 800 | P | O2 | 514 | 807 | 892 | 77 |
| 800 | P | O3 | 532 | 816 | 879 | 77 |
| 800 | P | O4 | 524 | 828 | 899 | 75 |
| 1800 | P | P | −130 | 685 | 1323 | 37 |
| 1800 | P | O1 | −116 | 691 | 1324 | 38 |
| 1800 | P | O2 | −135 | 690 | 1310 | 37 |
| 1800 | P | O3 | −129 | 670 | 1323 | 36 |
| 1800 | P | O4 | −139 | 690 | 1334 | 38 |
| 998 | X | OH2 | 469 | 772 | 1385 | 12 |
| 1998 | X | OH2 | −156 | 672 | 902 | 59 |
| 750 | X | OH2 | 379 | 384 | 1087 | 25 |
| 751 | X | OH2 | 516 | 567 | 1106 | 44 |
| 752 | X | OH2 | 593 | 481 | 968 | 52 |
| 754 | X | OH2 | 314 | 477 | 1138 | 47 |
| 755 | X | OH2 | 300 | 404 | 1035 | 26 |
| 756 | X | OH2 | 282 | 700 | 1231 | 20 |
| 757 | X | OH2 | 605 | 754 | 1317 | 65 |
| 759 | X | OH2 | 245 | 530 | 1199 | 26 |
| 760 | X | OH2 | 571 | 605 | 1072 | 38 |
| 761 | X | OH2 | 402 | 618 | 859 | 64 |
| 762 | X | OH2 | 484 | 812 | 909 | 42 |
| 764 | X | OH2 | 666 | 836 | 941 | 45 |
| 765 | X | OH2 | 713 | 715 | 774 | 54 |
| 766 | X | OH2 | 725 | 679 | 930 | 52 |
| 767 | X | OH2 | 609 | 572 | 849 | 52 |
| 768 | X | OH2 | 620 | 591 | 798 | 36 |
| 770 | X | OH2 | 502 | 693 | 1068 | 37 |
| 771 | X | OH2 | 291 | 931 | 1002 | 71 |
| 772 | X | OH2 | 411 | 1035 | 1150 | 43 |
| 773 | X | OH2 | 405 | 645 | 1364 | 30 |
| 774 | X | OH2 | 326 | 834 | 1345 | 43 |
| 775 | X | OH2 | 437 | 553 | 1146 | 63 |
| 776 | X | OH2 | 664 | 870 | 1199 | 54 |
| 777 | X | OH2 | 694 | 532 | 894 | 58 |
| 778 | X | OH2 | 173 | 883 | 932 | 55 |
| 779 | X | OH2 | 151 | 818 | 883 | 55 |
| 781 | X | OH2 | 168 | 883 | 1181 | 41 |
| 782 | X | OH2 | 419 | 821 | 1352 | 47 |
| 783 | X | OH2 | 387 | 891 | 1351 | 37 |
| 784 | X | OH2 | 204 | 750 | 1387 | 27 |
| 785 | X | OH2 | 206 | 792 | 1325 | 23 |
| 787 | X | OH2 | 255 | 733 | 1184 | 30 |
| 788 | X | OH2 | 475 | 862 | 1323 | 49 |
| 789 | X | OH2 | 487 | 838 | 1130 | 42 |
| 790 | X | OH2 | 486 | 730 | 1282 | 45 |
| 791 | X | OH2 | 469 | 815 | 1166 | 48 |
| 794 | X | OH2 | 520 | 789 | 1189 | 40 |
| 795 | X | OH2 | 443 | 900 | 1369 | 45 |
| 796 | X | OH2 | 448 | 935 | 1375 | 40 |
| 797 | X | OH2 | 427 | 946 | 1356 | 47 |
| 801 | X | OH2 | 292 | 893 | 1188 | 32 |
| 802 | X | OH2 | 326 | 832 | 1315 | 46 |
| 803 | X | OH2 | 435 | 1014 | 1385 | 36 |
| 805 | X | OH2 | 358 | 707 | 1405 | 37 |
| 807 | X | OH2 | 225 | 656 | 1629 | 68 |
| 808 | X | OH2 | 223 | 768 | 1400 | 52 |
| 809 | X | OH2 | 226 | 766 | 1327 | 23 |
| 810 | X | OH2 | 214 | 699 | 1339 | 54 |
| 811 | X | OH2 | 191 | 759 | 1341 | 34 |
| 812 | X | OH2 | 211 | 824 | 1325 | 31 |
| 821 | X | OH2 | 278 | 647 | 1121 | 64 |
| 822 | X | OH2 | 447 | 888 | 1311 | 43 |
| 824 | X | OH2 | 381 | 934 | 1266 | 48 |
| 825 | X | OH2 | 418 | 911 | 1165 | 9 |
| 826 | X | OH2 | 354 | 830 | 1051 | 57 |
| 827 | X | OH2 | 394 | 885 | 1105 | 30 |
| 830 | X | OH2 | 399 | 947 | 1139 | 21 |
| 831 | X | OH2 | 518 | 886 | 1189 | 34 |
| 832 | X | OH2 | 485 | 779 | 1075 | 32 |
| 835 | X | OH2 | 519 | 752 | 1142 | 59 |
| 837 | X | OH2 | 478 | 818 | 1367 | 44 |
| 845 | X | OH2 | 343 | 626 | 1323 | 28 |
| 846 | X | OH2 | 545 | 379 | 1345 | 73 |
| 847 | X | OH2 | 503 | 729 | 1328 | 65 |
| 848 | X | OH2 | 438 | 598 | 1169 | 49 |
| 852 | X | OH2 | 546 | 795 | 1277 | 41 |
| 853 | X | OH2 | 544 | 916 | 1131 | 2 |
| 854 | X | OH2 | 573 | 916 | 1146 | 12 |
| 856 | X | OH2 | 475 | 791 | 1094 | 28 |
| 859 | X | OH2 | 712 | 760 | 861 | 47 |
| 860 | X | OH2 | 681 | 674 | 859 | 45 |
| 861 | X | OH2 | 677 | 657 | 938 | 37 |
| 862 | X | OH2 | 504 | 632 | 840 | 7 |
| 864 | X | OH2 | 490 | 658 | 891 | 41 |
| 866 | X | OH2 | 550 | 717 | 761 | 33 |
| 869 | X | OH2 | 549 | 600 | 780 | 39 |
| 872 | X | OH2 | 481 | 458 | 986 | 57 |
| 874 | X | OH2 | 622 | 642 | 810 | 30 |
| 875 | X | OH2 | 526 | 777 | 1011 | 33 |
| 876 | X | OH2 | 443 | 768 | 1009 | 25 |
| 877 | X | OH2 | 432 | 746 | 1004 | 20 |
| 878 | X | OH2 | 390 | 760 | 884 | 52 |
| 880 | X | OH2 | 325 | 581 | 947 | 43 |
| 881 | X | OH2 | 483 | 702 | 988 | 26 |
| 882 | X | OH2 | 645 | 632 | 1027 | 30 |
| 884 | X | OH2 | 695 | 672 | 1009 | 45 |
| 885 | X | OH2 | 480 | 749 | 1075 | 20 |
| 888 | X | OH2 | 392 | 763 | 862 | 44 |
| 889 | X | OH2 | 448 | 786 | 834 | 62 |
| 890 | X | OH2 | 211 | 942 | 773 | 46 |
| 892 | X | OH2 | 235 | 874 | 943 | 49 |
| 893 | X | OH2 | 0 | 882 | 976 | 57 |
| 895 | X | OH2 | 339 | 564 | 920 | 54 |
| 896 | X | OH2 | 323 | 724 | 887 | 38 |
| 897 | X | OH2 | 471 | 745 | 878 | 52 |
| 900 | X | OH2 | 280 | 476 | 1136 | 61 |
| 901 | X | OH2 | 419 | 578 | 906 | 35 |
| 902 | X | OH2 | 515 | 482 | 1037 | 19 |
| 903 | X | OH2 | 406 | 706 | 1114 | 45 |
| 905 | X | OH2 | 425 | 591 | 1149 | 24 |
| 906 | X | OH2 | 439 | 567 | 1124 | 21 |
| 907 | X | OH2 | 426 | 401 | 1050 | 58 |
| 908 | X | OH2 | 440 | 527 | 1232 | 64 |

TABLE 2-continued

| | | | | | | |
|---|---|---|---|---|---|---|
| 909 | X | OH2 | 424 | 448 | 1129 | 30 |
| 912 | X | OH2 | 414 | 720 | 954 | 35 |
| 914 | X | OH2 | 485 | 591 | 792 | 65 |
| 915 | X | OH2 | 400 | 559 | 881 | 18 |
| 916 | X | OH2 | 323 | 335 | 1034 | 61 |
| 918 | X | OH2 | 264 | 511 | 951 | 45 |
| 919 | X | OH2 | 239 | 332 | 931 | 46 |
| 920 | X | OH2 | 305 | 487 | 977 | 26 |
| 921 | X | OH2 | 199 | 609 | 876 | 50 |
| 922 | X | OH2 | 202 | 548 | 992 | 54 |
| 923 | X | OH2 | 209 | 562 | 924 | 60 |
| 924 | X | OH2 | 198 | 431 | 1028 | 36 |
| 925 | X | OH2 | 170 | 486 | 987 | 26 |
| 926 | X | OH2 | 303 | 400 | 1130 | 37 |
| 928 | X | OH2 | 413 | 384 | 1061 | 36 |
| 930 | X | OH2 | 312 | 127 | 1059 | 61 |
| 935 | X | OH2 | 398 | 779 | 1468 | 58 |
| 937 | X | OH2 | 413 | 967 | 1318 | 54 |
| 938 | X | OH2 | 311 | 802 | 1057 | 58 |
| 939 | X | OH2 | 389 | 813 | 1047 | 55 |
| 942 | X | OH2 | 546 | 914 | 1226 | 56 |
| 948 | X | OH2 | 266 | 565 | 1209 | 28 |
| 950 | X | OH2 | 274 | 556 | 1145 | 42 |
| 951 | X | OH2 | 304 | 465 | 1278 | 45 |
| 952 | X | OH2 | 575 | 881 | 1104 | 29 |
| 953 | X | OH2 | 502 | 763 | 1016 | 23 |
| 954 | X | OH2 | 482 | 791 | 932 | 37 |
| 955 | X | OH2 | 752 | 779 | 914 | 59 |
| 956 | X | OH2 | 490 | 634 | 808 | 37 |
| 957 | X | OH2 | 553 | 565 | 792 | 42 |
| 958 | X | OH2 | 585 | 632 | 869 | 32 |
| 959 | X | OH2 | 666 | 624 | 669 | 61 |
| 962 | X | OH2 | 375 | 648 | 908 | 45 |
| 965 | X | OH2 | 205 | 835 | 1027 | 39 |
| 966 | X | OH2 | 344 | 686 | 1032 | 53 |
| 967 | X | OH2 | 229 | 457 | 1068 | 43 |
| 968 | X | OH2 | 290 | 504 | 1053 | 18 |
| 969 | X | OH2 | 369 | 629 | 1098 | 31 |
| 970 | X | OH2 | 486 | 527 | 994 | 20 |
| 971 | X | OH2 | 508 | 530 | 857 | 52 |
| 972 | X | OH2 | 536 | 627 | 1167 | 69 |
| 973 | X | OH2 | 438 | 527 | 1175 | 41 |
| 974 | X | OH2 | 468 | 578 | 1125 | 29 |
| 975 | X | OH2 | 506 | 478 | 1067 | 25 |
| 976 | X | OH2 | 476 | 463 | 939 | 53 |
| 978 | X | OH2 | 348 | 506 | 854 | 37 |
| 980 | X | OH2 | 283 | 507 | 978 | 24 |
| 981 | X | OH2 | 156 | 480 | 959 | 59 |
| 982 | X | OH2 | 373 | 510 | 815 | 40 |
| 983 | X | OH2 | 333 | 450 | 809 | 16 |
| 984 | X | OH2 | 256 | 349 | 956 | 38 |
| 985 | X | OH2 | 254 | 549 | 1050 | 30 |
| 986 | X | OH2 | 206 | 498 | 1022 | 37 |
| 987 | X | OH2 | 522 | 783 | 1466 | 57 |
| 1801 | X | OH2 | 51 | 834 | 1024 | 41 |
| 1803 | X | OH2 | 57 | 830 | 946 | 51 |
| 1804 | X | OH2 | 155 | 883 | 1014 | 50 |
| 1806 | X | OH2 | 3 | 878 | 951 | 62 |
| 1809 | X | OH2 | 1 | 614 | 1093 | 57 |
| 1813 | X | OH2 | 27 | 615 | 1095 | 49 |
| 1814 | X | OH2 | 48 | 509 | 1061 | 40 |
| 1815 | X | OH2 | −62 | 631 | 1136 | 47 |
| 1816 | X | OH2 | −23 | 591 | 1066 | 56 |
| 1818 | X | OH2 | 146 | 565 | 1105 | 21 |
| 1820 | X | OH2 | −301 | 580 | 1062 | 46 |
| 1822 | X | OH2 | 117 | 575 | 888 | 26 |
| 1826 | X | OH2 | −110 | 636 | 1203 | 37 |
| 1827 | X | OH2 | −81 | 675 | 1116 | 45 |
| 1829 | X | OH2 | −17 | 689 | 1341 | 62 |
| 1830 | X | OH2 | −92 | 739 | 1276 | 33 |
| 1832 | X | OH2 | −185 | 686 | 1377 | 42 |
| 1833 | X | OH2 | −102 | 574 | 1355 | 44 |
| 1834 | X | OH2 | −4 | 552 | 1346 | 54 |
| 1835 | X | OH2 | 151 | 526 | 1295 | 57 |
| 1836 | X | OH2 | −19 | 559 | 1300 | 20 |
| 1837 | X | OH2 | −23 | 523 | 1369 | 10 |
| 1838 | X | OH2 | −69 | 799 | 1470 | 65 |
| 1839 | X | OH2 | −95 | 644 | 1395 | 56 |
| 1841 | X | OH2 | −101 | 488 | 1343 | 30 |
| 1844 | X | OH2 | −145 | 393 | 1463 | 55 |
| 1845 | X | OH2 | −130 | 475 | 1323 | 44 |
| 1846 | X | OH2 | −43 | 590 | 1223 | 20 |
| 1848 | X | OH2 | 25 | 679 | 1293 | 44 |
| 1849 | X | OH2 | 26 | 623 | 1255 | 44 |
| 1850 | X | OH2 | −52 | 688 | 1270 | 30 |
| 1852 | X | OH2 | −29 | 547 | 1325 | 36 |
| 1855 | X | OH2 | −56 | 684 | 1312 | 58 |
| 1858 | X | OH2 | −7 | 718 | 1168 | 35 |
| 1859 | X | OH2 | −25 | 711 | 1334 | 36 |
| 1860 | X | OH2 | −75 | 751 | 1142 | 65 |
| 1863 | X | OH2 | 124 | 849 | 1272 | 32 |
| 1864 | X | OH2 | 180 | 1033 | 1276 | 66 |
| 1866 | X | OH2 | 155 | 902 | 1396 | 52 |
| 1867 | X | OH2 | 107 | 758 | 1229 | 39 |
| 1869 | X | OH2 | 77 | 890 | 1412 | 43 |
| 1874 | X | OH2 | 96 | 671 | 1317 | 34 |
| 1875 | X | OH2 | 104 | 616 | 1353 | 14 |
| 1877 | X | OH2 | 250 | 547 | 1117 | 39 |
| 1882 | X | OH2 | 248 | 775 | 1654 | 49 |
| 1884 | X | OH2 | 92 | 561 | 1226 | 26 |
| 1886 | X | OH2 | 59 | 579 | 1130 | 44 |
| 1890 | X | OH2 | −45 | 718 | 1373 | 38 |
| 1891 | X | OH2 | −42 | 735 | 1450 | 57 |
| 1892 | X | OH2 | −90 | 840 | 1446 | 56 |
| 1894 | X | OH2 | 144 | 532 | 1344 | 49 |
| 1895 | X | OH2 | 5 | 490 | 1333 | 47 |
| 1896 | X | OH2 | 26 | 426 | 1224 | 32 |
| 1897 | X | OH2 | 72 | 372 | 1222 | 43 |
| 1900 | X | OH2 | −17 | 452 | 1112 | 50 |
| 1901 | X | OH2 | −159 | 459 | 1189 | 22 |
| 1902 | X | OH2 | 70 | 481 | 1282 | 55 |
| 1903 | X | OH2 | 80 | 425 | 1387 | 58 |
| 1904 | X | OH2 | 167 | 555 | 1243 | 48 |
| 1905 | X | OH2 | 220 | 490 | 1232 | 15 |
| 1906 | X | OH2 | 227 | 550 | 1152 | 58 |
| 1909 | X | OH2 | 248 | 386 | 1068 | 25 |
| 1911 | X | OH2 | −65 | 872 | 951 | 64 |
| 1912 | X | OH2 | 46 | 771 | 899 | 48 |
| 1914 | X | OH2 | 43 | 615 | 1113 | 42 |
| 1915 | X | OH2 | −108 | 684 | 1077 | 55 |
| 1916 | X | OH2 | −68 | 807 | 1046 | 44 |
| 1918 | X | OH2 | 19 | 826 | 869 | 60 |
| 1919 | X | OH2 | 133 | 488 | 1050 | 31 |
| 1921 | X | OH2 | −126 | 643 | 1148 | 50 |
| 1922 | X | OH2 | −115 | 733 | 1241 | 37 |
| 1923 | X | OH2 | −244 | 664 | 1356 | 42 |
| 1926 | X | OH2 | −26 | 657 | 1373 | 60 |
| 1929 | X | OH2 | −236 | 647 | 1473 | 57 |
| 1930 | X | OH2 | −120 | 336 | 1388 | 50 |
| 1932 | X | OH2 | −338 | 421 | 1359 | 43 |
| 1933 | X | OH2 | −37 | 670 | 1200 | 33 |
| 1934 | X | OH2 | 28 | 664 | 1177 | 34 |
| 1935 | X | OH2 | 8 | 646 | 1239 | 46 |
| 1936 | X | OH2 | −67 | 758 | 1187 | 39 |
| 1937 | X | OH2 | 79 | 800 | 1477 | 23 |
| 1941 | X | OH2 | 16 | 653 | 1478 | 23 |
| 1942 | X | OH2 | 71 | 674 | 1220 | 60 |
| 1943 | X | OH2 | 211 | 490 | 1152 | 17 |
| 1944 | X | OH2 | 216 | 530 | 1045 | 49 |
| 1946 | X | OH2 | 62 | 609 | 1197 | 30 |
| 1948 | X | OH2 | 94 | 566 | 1111 | 44 |
| 1949 | X | OH2 | 69 | 639 | 1283 | 53 |
| 1950 | X | OH2 | 96 | 324 | 1087 | 56 |
| 1951 | X | OH2 | −57 | 569 | 1141 | 39 |
| 1953 | X | OH2 | 23 | 482 | 1094 | 27 |
| 1957 | X | OH2 | 76 | 496 | 1376 | 43 |
| 1958 | X | OH2 | 95 | 433 | 1090 | 26 |
| 1959 | X | OH2 | 92 | 748 | 835 | 58 |
| 1960 | X | OH2 | −34 | 784 | 1108 | 35 |
| 1962 | X | OH2 | −57 | 435 | 1368 | 63 |
| 1963 | X | OH2 | −152 | 476 | 1387 | 47 |
| 1964 | X | OH2 | 51 | 482 | 1090 | 22 |
| 1965 | X | OH2 | 63 | 470 | 1069 | 34 |
| 1966 | X | OH2 | 142 | 857 | 1172 | 32 |
| 1972 | X | OH2 | 19 | 803 | 1125 | 44 |
| 1973 | X | OH2 | −82 | 634 | 1199 | 27 |
| 1974 | X | OH2 | −135 | 683 | 1379 | 53 |
| 1975 | X | OH2 | −143 | 474 | 1355 | 35 |

TABLE 2-continued

| | | | | | | |
|---|---|---|---|---|---|---|
| 1976 | X | OH2 | 14 | 811 | 1228 | 51 |
| 1977 | X | OH2 | 183 | 682 | 1451 | 31 |
| 1978 | X | OH2 | −43 | 877 | 1309 | 46 |
| 1979 | X | OH2 | 148 | 314 | 1056 | 51 |
| 1970 | X | OH2 | 211 | 464 | 1230 | 36 |
| END | | | | | | |

TABLE 3

The following table contains one line for each atom in one HCV scNS3/NS4A (S139A) monomer as well as solvent molecules. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor. The coordinates of the second monomer ($x_2$, $y_2$, $z_2$) are related to the coordinates of the first monomer ($x_1$, $y_1$, $z_1$) listed below according to the following operation:

$$x_2 = x_1 \cdot a_{11} + y_1 \cdot a_{12} + z_1 \cdot a_{13} + t_1$$
$$y_2 = x_1 \cdot a_{21} + y_1 \cdot a_{22} + z_1 \cdot a_{23} + t_2$$
$$z_2 = x_1 \cdot a_{31} + y_1 \cdot a_{32} + z_1 \cdot a_{33} + t_3$$

where

| | | | | | | |
|---|---|---|---|---|---|---|
| $a_{11}$ | $a_{12}$ | $a_{13}$ | | −0.9075 | −0.4200 | −0.0103 |
| $a_{21}$ | $a_{22}$ | $a_{23}$ | = | −0.4197 | 0.9074 | −0.0200 |
| $a_{31}$ | $a_{32}$ | $a_{33}$ | | 0.0178 | 0.0138 | −0.9997 and |
| $t_1$ | $t_2$ | $t_3$ | = | 70.69 | 17.44 | 220.99 |

The noncrystallographic operation described above should only be applied to the HCV scNS3/NS4A (S139A) protein atoms (residues 705 through 720 and residues 3 through 631). Following the protein atoms are listed all discrete solvent molecules (residue X, atom OH2) and phosphate ions (residue P, atoms P, O1, O2, O3 and O4) which were modeled into the asymmetric unit.

| | | | | | |
|---|---|---|---|---|---|
| 705 | G | C | 303 | 877 | 1085 | 25 |
| 705 | G | O | 314 | 872 | 1083 | 28 |
| 705 | G | N | 298 | 873 | 1061 | 30 |
| 705 | G | CA | 293 | 878 | 1074 | 25 |
| 706 | S | N | 300 | 882 | 1097 | 18 |
| 706 | S | CA | 309 | 881 | 1108 | 13 |
| 706 | S | CB | 308 | 895 | 1115 | 12 |
| 706 | S | OG | 312 | 906 | 1107 | 8 |
| 706 | S | C | 304 | 870 | 1117 | 12 |
| 706 | S | O | 293 | 865 | 1116 | 14 |
| 707 | V | N | 313 | 866 | 1126 | 11 |
| 707 | V | CA | 310 | 856 | 1136 | 10 |
| 707 | V | CB | 322 | 851 | 1144 | 5 |
| 707 | V | CG1 | 318 | 846 | 1157 | 9 |
| 707 | V | CG2 | 329 | 841 | 1135 | 4 |
| 707 | V | C | 302 | 865 | 1146 | 12 |
| 707 | V | O | 306 | 877 | 1148 | 18 |
| 708 | V | N | 292 | 860 | 1152 | 12 |
| 708 | V | CA | 284 | 868 | 1162 | 7 |
| 708 | V | CB | 270 | 871 | 1156 | 7 |
| 708 | V | CG1 | 261 | 878 | 1167 | 8 |
| 708 | V | CG2 | 270 | 879 | 1144 | 10 |
| 708 | V | C | 283 | 862 | 1175 | 7 |
| 708 | V | O | 282 | 850 | 1176 | 3 |
| 709 | I | N | 284 | 870 | 1186 | 7 |
| 709 | I | CA | 283 | 865 | 1199 | 8 |
| 709 | I | CB | 290 | 874 | 1209 | 8 |
| 709 | I | CG2 | 286 | 870 | 1224 | 8 |
| 709 | I | CG1 | 305 | 873 | 1207 | 11 |
| 709 | I | CD1 | 313 | 885 | 1214 | 3 |
| 709 | I | C | 268 | 866 | 1203 | 10 |
| 709 | I | O | 262 | 876 | 1203 | 19 |
| 710 | V | N | 262 | 854 | 1205 | 13 |
| 710 | V | CA | 248 | 853 | 1208 | 7 |
| 710 | V | CB | 241 | 843 | 1198 | 6 |
| 710 | V | CG1 | 243 | 848 | 1184 | 9 |
| 710 | V | CG2 | 248 | 829 | 1199 | 2 |
| 710 | V | C | 245 | 848 | 1222 | 8 |
| 710 | V | O | 234 | 844 | 1226 | 11 |
| 711 | G | N | 256 | 847 | 1230 | 5 |
| 711 | G | CA | 254 | 843 | 1244 | 3 |
| 711 | G | C | 268 | 841 | 1251 | 3 |
| 711 | G | O | 278 | 843 | 1245 | 3 |
| 712 | R | N | 268 | 837 | 1264 | 4 |
| 712 | R | CA | 280 | 835 | 1271 | 5 |
| 712 | R | CB | 285 | 848 | 1278 | 9 |

TABLE 3-continued

| | | | | | | |
|---|---|---|---|---|---|---|
| 712 | R | CG | 273 | 856 | 1283 | 19 |
| 712 | R | CD | 279 | 868 | 1291 | 18 |
| 712 | R | NE | 270 | 879 | 1290 | 28 |
| 712 | R | CZ | 269 | 888 | 1280 | 32 |
| 712 | R | NH1 | 278 | 887 | 1270 | 41 |
| 712 | R | NH2 | 261 | 898 | 1280 | 35 |
| 712 | R | C | 278 | 824 | 1281 | 4 |
| 712 | R | O | 267 | 821 | 1285 | 9 |
| 713 | I | N | 289 | 818 | 1286 | 6 |
| 713 | I | CA | 288 | 808 | 1297 | 8 |
| 713 | I | CB | 296 | 795 | 1292 | 13 |
| 713 | I | CG2 | 298 | 786 | 1303 | 9 |
| 713 | I | CG1 | 287 | 788 | 1281 | 11 |
| 713 | I | CD1 | 294 | 778 | 1273 | 27 |
| 713 | I | C | 296 | 814 | 1309 | 12 |
| 713 | I | O | 308 | 816 | 1309 | 14 |
| 714 | I | N | 288 | 816 | 1319 | 13 |
| 714 | I | CA | 293 | 822 | 1332 | 10 |
| 714 | I | CB | 282 | 830 | 1339 | 11 |
| 714 | I | CG2 | 289 | 838 | 1350 | 10 |
| 714 | I | CG1 | 274 | 838 | 1329 | 8 |
| 714 | I | CD1 | 283 | 848 | 1321 | 9 |
| 714 | I | C | 299 | 811 | 1341 | 11 |
| 714 | I | O | 292 | 802 | 1345 | 10 |
| 715 | L | N | 312 | 813 | 1344 | 15 |
| 715 | L | CA | 319 | 803 | 1353 | 17 |
| 715 | L | CB | 333 | 802 | 1349 | 13 |
| 715 | L | CG | 337 | 795 | 1337 | 19 |
| 715 | L | CD1 | 331 | 781 | 1337 | 20 |
| 715 | L | CD2 | 333 | 802 | 1324 | 16 |
| 715 | L | C | 318 | 808 | 1368 | 20 |
| 715 | L | O | 316 | 820 | 1370 | 22 |
| 716 | S | N | 320 | 799 | 1377 | 22 |
| 716 | S | CA | 319 | 802 | 1391 | 24 |
| 716 | S | CB | 316 | 790 | 1400 | 23 |
| 716 | S | OG | 324 | 779 | 1397 | 24 |
| 716 | S | C | 333 | 808 | 1396 | 27 |
| 716 | S | O | 343 | 803 | 1392 | 26 |
| 717 | G | N | 332 | 818 | 1404 | 28 |
| 717 | G | CA | 344 | 825 | 1409 | 23 |
| 717 | G | C | 350 | 819 | 1422 | 24 |
| 717 | G | O | 361 | 822 | 1427 | 22 |
| 718 | S | N | 342 | 809 | 1428 | 26 |
| 718 | S | CA | 346 | 803 | 1440 | 33 |
| 718 | S | CB | 341 | 810 | 1452 | 40 |
| 718 | S | OG | 351 | 817 | 1459 | 57 |
| 718 | S | C | 341 | 788 | 1440 | 31 |
| 718 | S | O | 335 | 784 | 1431 | 36 |
| 719 | G | N | 345 | 781 | 1451 | 28 |
| 719 | G | CA | 341 | 767 | 1452 | 30 |
| 719 | G | C | 345 | 759 | 1440 | 32 |
| 719 | G | O | 354 | 763 | 1433 | 37 |
| 720 | S | N | 338 | 748 | 1437 | 30 |
| 720 | S | CA | 341 | 740 | 1426 | 29 |
| 720 | S | CB | 333 | 727 | 1427 | 31 |
| 720 | S | OG | 320 | 728 | 1425 | 35 |
| 720 | S | C | 336 | 748 | 1414 | 28 |
| 720 | S | O | 328 | 756 | 1415 | 29 |
| 3 | I | N | 342 | 744 | 1402 | 25 |
| 3 | I | CA | 339 | 751 | 1390 | 20 |
| 3 | I | CB | 350 | 749 | 1379 | 21 |
| 3 | I | CG2 | 348 | 759 | 1368 | 25 |
| 3 | I | CG1 | 364 | 752 | 1386 | 18 |
| 3 | I | CD1 | 375 | 751 | 1376 | 17 |
| 3 | I | C | 325 | 747 | 1384 | 14 |
| 3 | I | O | 324 | 736 | 1380 | 14 |
| 4 | T | N | 316 | 756 | 1384 | 16 |
| 4 | T | CA | 303 | 754 | 1378 | 17 |
| 4 | T | CB | 291 | 755 | 1389 | 17 |
| 4 | T | OG1 | 292 | 768 | 1396 | 22 |
| 4 | T | CG2 | 293 | 744 | 1399 | 13 |
| 4 | T | C | 300 | 765 | 1368 | 19 |
| 4 | T | O | 308 | 774 | 1367 | 20 |
| 5 | A | N | 289 | 763 | 1360 | 18 |
| 5 | A | CA | 287 | 773 | 1350 | 15 |
| 5 | A | CB | 295 | 770 | 1338 | 13 |
| 5 | A | C | 272 | 774 | 1346 | 11 |
| 5 | A | O | 265 | 764 | 1348 | 13 |
| 6 | Y | N | 268 | 785 | 1340 | 7 |

TABLE 3-continued

| | | | | | | |
|---|---|---|---|---|---|---|
| 6 | Y | CA | 254 | 786 | 1335 | 10 |
| 6 | Y | CB | 245 | 792 | 1346 | 5 |
| 6 | Y | CG | 248 | 806 | 1351 | 4 |
| 6 | Y | CD1 | 243 | 817 | 1345 | 5 |
| 6 | Y | CE1 | 246 | 830 | 1349 | 6 |
| 6 | Y | CD2 | 257 | 808 | 1361 | 5 |
| 6 | Y | CE2 | 260 | 821 | 1366 | 2 |
| 6 | Y | CZ | 254 | 832 | 1360 | 9 |
| 6 | Y | OH | 258 | 845 | 1364 | 17 |
| 6 | Y | C | 255 | 796 | 1323 | 11 |
| 6 | Y | O | 263 | 805 | 1322 | 16 |
| 7 | S | N | 246 | 793 | 1314 | 14 |
| 7 | S | CA | 245 | 800 | 1301 | 12 |
| 7 | S | CB | 242 | 791 | 1290 | 15 |
| 7 | S | OG | 232 | 782 | 1294 | 30 |
| 7 | S | C | 235 | 812 | 1301 | 13 |
| 7 | S | O | 224 | 811 | 1307 | 15 |
| 8 | Q | N | 240 | 823 | 1295 | 9 |
| 8 | Q | CA | 231 | 835 | 1294 | 7 |
| 8 | Q | CB | 239 | 847 | 1299 | 8 |
| 8 | Q | CG | 236 | 849 | 1314 | 14 |
| 8 | Q | CD | 244 | 862 | 1319 | 22 |
| 8 | Q | OE1 | 251 | 868 | 1311 | 21 |
| 8 | Q | NE2 | 242 | 865 | 1332 | 24 |
| 8 | Q | C | 229 | 836 | 1279 | 8 |
| 8 | Q | O | 239 | 837 | 1271 | 13 |
| 9 | Q | N | 217 | 836 | 1274 | 10 |
| 9 | Q | CA | 214 | 837 | 1260 | 14 |
| 9 | Q | CB | 201 | 831 | 1257 | 17 |
| 9 | Q | CG | 201 | 825 | 1243 | 29 |
| 9 | Q | CD | 187 | 827 | 1235 | 35 |
| 9 | Q | OE1 | 181 | 818 | 1231 | 45 |
| 9 | Q | NE2 | 184 | 840 | 1233 | 34 |
| 9 | Q | C | 213 | 852 | 1259 | 17 |
| 9 | Q | O | 206 | 859 | 1266 | 22 |
| 10 | T | N | 219 | 858 | 1248 | 20 |
| 10 | T | CA | 219 | 872 | 1247 | 16 |
| 10 | T | CB | 232 | 879 | 1250 | 15 |
| 10 | T | OG1 | 241 | 876 | 1239 | 14 |
| 10 | T | CG2 | 238 | 874 | 1263 | 17 |
| 10 | T | C | 214 | 877 | 1233 | 19 |
| 10 | T | O | 211 | 889 | 1231 | 23 |
| 11 | R | N | 212 | 868 | 1224 | 23 |
| 11 | R | CA | 207 | 872 | 1211 | 22 |
| 11 | R | CB | 219 | 874 | 1201 | 20 |
| 11 | R | CG | 218 | 886 | 1193 | 13 |
| 11 | R | CD | 231 | 892 | 1189 | 23 |
| 11 | R | NE | 231 | 906 | 1188 | 30 |
| 11 | R | CZ | 240 | 914 | 1192 | 32 |
| 11 | R | NH1 | 251 | 909 | 1198 | 34 |
| 11 | R | NH2 | 239 | 927 | 1191 | 25 |
| 11 | R | C | 198 | 861 | 1205 | 23 |
| 11 | R | O | 200 | 849 | 1207 | 26 |
| 12 | G | N | 189 | 866 | 1196 | 23 |
| 12 | G | CA | 179 | 857 | 1190 | 25 |
| 12 | G | C | 183 | 855 | 1175 | 30 |
| 12 | G | O | 192 | 862 | 1170 | 33 |
| 13 | L | N | 176 | 846 | 1168 | 28 |
| 13 | L | CA | 179 | 843 | 1154 | 27 |
| 13 | L | CB | 169 | 834 | 1148 | 27 |
| 13 | L | CG | 173 | 823 | 1138 | 26 |
| 13 | L | CD1 | 161 | 820 | 1129 | 28 |
| 13 | L | CD2 | 185 | 828 | 1130 | 26 |
| 13 | L | C | 181 | 856 | 1145 | 26 |
| 13 | L | O | 191 | 858 | 1139 | 26 |
| 14 | L | N | 171 | 864 | 1146 | 25 |
| 14 | L | CA | 171 | 876 | 1137 | 21 |
| 14 | L | CB | 158 | 884 | 1139 | 18 |
| 14 | L | CG | 155 | 896 | 1130 | 18 |
| 14 | L | CD1 | 157 | 891 | 1115 | 17 |
| 14 | L | CD2 | 141 | 901 | 1132 | 23 |
| 14 | L | C | 183 | 885 | 1141 | 22 |
| 14 | L | O | 190 | 889 | 1132 | 23 |
| 15 | G | N | 184 | 888 | 1154 | 22 |
| 15 | G | CA | 195 | 897 | 1158 | 17 |
| 15 | G | C | 208 | 891 | 1153 | 16 |
| 15 | G | O | 216 | 898 | 1147 | 24 |
| 16 | C | N | 211 | 878 | 1156 | 18 |
| 16 | C | CA | 223 | 872 | 1152 | 22 |
| 16 | C | CB | 223 | 857 | 1154 | 24 |
| 16 | C | SG | 234 | 847 | 1144 | 27 |
| 16 | C | C | 225 | 875 | 1137 | 20 |
| 16 | C | O | 236 | 879 | 1133 | 20 |
| 17 | I | N | 215 | 872 | 1129 | 21 |
| 17 | I | CA | 215 | 874 | 1114 | 21 |
| 17 | I | CB | 202 | 871 | 1108 | 20 |
| 17 | I | CG2 | 201 | 878 | 1094 | 23 |
| 17 | I | CG1 | 200 | 856 | 1106 | 20 |
| 17 | I | CD1 | 187 | 853 | 1098 | 22 |
| 17 | I | C | 219 | 889 | 1110 | 21 |
| 17 | I | O | 228 | 891 | 1102 | 19 |
| 18 | I | N | 212 | 898 | 1115 | 20 |
| 18 | I | CA | 214 | 912 | 1112 | 22 |
| 18 | I | CB | 205 | 922 | 1120 | 18 |
| 18 | I | CG2 | 211 | 935 | 1122 | 19 |
| 18 | I | CG1 | 192 | 923 | 1111 | 16 |
| 18 | I | CD1 | 180 | 915 | 1116 | 15 |
| 18 | I | C | 229 | 916 | 1116 | 23 |
| 18 | I | O | 236 | 923 | 1109 | 28 |
| 19 | T | N | 233 | 912 | 1128 | 23 |
| 19 | T | CA | 246 | 915 | 1133 | 20 |
| 19 | T | CB | 247 | 910 | 1148 | 18 |
| 19 | T | OG1 | 238 | 918 | 1156 | 14 |
| 19 | T | CG2 | 262 | 912 | 1153 | 14 |
| 19 | T | C | 257 | 909 | 1124 | 19 |
| 19 | T | O | 268 | 915 | 1122 | 14 |
| 20 | S | N | 255 | 897 | 1119 | 18 |
| 20 | S | CA | 264 | 890 | 1110 | 21 |
| 20 | S | CB | 260 | 876 | 1107 | 24 |
| 20 | S | OG | 270 | 868 | 1101 | 32 |
| 20 | S | C | 266 | 898 | 1097 | 23 |
| 20 | S | O | 278 | 899 | 1092 | 23 |
| 21 | L | N | 256 | 904 | 1092 | 25 |
| 21 | L | CA | 256 | 912 | 1080 | 27 |
| 21 | L | CB | 242 | 914 | 1074 | 27 |
| 21 | L | CG | 234 | 901 | 1073 | 32 |
| 21 | L | CD1 | 221 | 904 | 1065 | 29 |
| 21 | L | CD2 | 242 | 890 | 1066 | 34 |
| 21 | L | C | 263 | 925 | 1081 | 29 |
| 21 | L | O | 272 | 929 | 1074 | 33 |
| 22 | T | N | 259 | 933 | 1091 | 26 |
| 22 | T | CA | 264 | 946 | 1094 | 28 |
| 22 | T | CB | 256 | 954 | 1104 | 23 |
| 22 | T | OG1 | 255 | 948 | 1116 | 21 |
| 22 | T | CG2 | 242 | 956 | 1098 | 22 |
| 22 | T | C | 278 | 945 | 1100 | 34 |
| 22 | T | O | 287 | 953 | 1097 | 37 |
| 23 | G | N | 280 | 935 | 1108 | 31 |
| 23 | G | CA | 293 | 933 | 1114 | 27 |
| 23 | G | C | 295 | 942 | 1126 | 29 |
| 23 | G | O | 306 | 944 | 1131 | 29 |
| 24 | R | N | 284 | 948 | 1131 | 31 |
| 24 | R | CA | 284 | 957 | 1142 | 32 |
| 24 | R | CB | 279 | 971 | 1138 | 37 |
| 24 | R | CG | 286 | 982 | 1146 | 46 |
| 24 | R | CD | 277 | 994 | 1146 | 55 |
| 24 | R | NE | 285 | 1006 | 1152 | 63 |
| 24 | R | CZ | 292 | 1014 | 1144 | 67 |
| 24 | R | NH1 | 293 | 1012 | 1131 | 70 |
| 24 | R | NH2 | 299 | 1024 | 1150 | 68 |
| 24 | R | C | 275 | 952 | 1153 | 28 |
| 24 | R | O | 263 | 952 | 1152 | 28 |
| 25 | D | N | 281 | 948 | 1164 | 29 |
| 25 | D | CA | 274 | 944 | 1176 | 30 |
| 25 | D | CB | 280 | 930 | 1181 | 33 |
| 25 | D | CG | 273 | 925 | 1193 | 34 |
| 25 | D | OD1 | 263 | 932 | 1198 | 32 |
| 25 | D | OD2 | 277 | 915 | 1199 | 33 |
| 25 | D | C | 277 | 954 | 1187 | 33 |
| 25 | D | O | 288 | 955 | 1192 | 34 |
| 26 | K | N | 266 | 962 | 1189 | 37 |
| 26 | K | CA | 267 | 973 | 1200 | 42 |
| 26 | K | CB | 257 | 983 | 1197 | 45 |
| 26 | K | CG | 259 | 993 | 1186 | 51 |
| 26 | K | CD | 274 | 998 | 1187 | 52 |
| 26 | K | CE | 274 | 1013 | 1183 | 50 |
| 26 | K | NZ | 287 | 1019 | 1186 | 48 |
| 26 | K | C | 266 | 967 | 1214 | 43 |

TABLE 3-continued

| | | | | | | |
|---|---|---|---|---|---|---|
| 26 | K | O | 269 | 974 | 1223 | 45 |
| 27 | N | N | 262 | 954 | 1215 | 41 |
| 27 | N | CA | 261 | 948 | 1228 | 39 |
| 27 | N | CB | 256 | 933 | 1226 | 38 |
| 27 | N | CG | 241 | 932 | 1225 | 39 |
| 27 | N | OD1 | 235 | 923 | 1232 | 44 |
| 27 | N | ND2 | 235 | 941 | 1218 | 39 |
| 27 | N | C | 274 | 948 | 1236 | 40 |
| 27 | N | O | 285 | 948 | 1230 | 44 |
| 28 | Q | N | 272 | 947 | 1249 | 44 |
| 28 | Q | CA | 284 | 947 | 1258 | 46 |
| 28 | Q | CB | 281 | 954 | 1271 | 52 |
| 28 | Q | CG | 268 | 948 | 1278 | 51 |
| 28 | Q | CD | 268 | 951 | 1293 | 52 |
| 28 | Q | OE1 | 272 | 962 | 1297 | 56 |
| 28 | Q | NE2 | 263 | 942 | 1301 | 51 |
| 28 | Q | C | 289 | 933 | 1260 | 44 |
| 28 | Q | O | 280 | 924 | 1262 | 46 |
| 29 | V | N | 302 | 931 | 1260 | 41 |
| 29 | V | CA | 307 | 918 | 1262 | 34 |
| 29 | V | CB | 322 | 917 | 1257 | 27 |
| 29 | V | CG1 | 330 | 906 | 1264 | 28 |
| 29 | V | CG2 | 322 | 914 | 1242 | 20 |
| 29 | V | C | 307 | 916 | 1277 | 34 |
| 29 | V | O | 307 | 925 | 1285 | 39 |
| 30 | E | N | 306 | 903 | 1281 | 32 |
| 30 | E | CA | 306 | 900 | 1296 | 29 |
| 30 | E | CB | 292 | 900 | 1301 | 31 |
| 30 | E | CG | 285 | 913 | 1300 | 36 |
| 30 | E | CD | 286 | 921 | 1313 | 46 |
| 30 | E | OE1 | 276 | 927 | 1317 | 50 |
| 30 | E | OE2 | 297 | 921 | 1319 | 53 |
| 30 | E | C | 312 | 885 | 1297 | 25 |
| 30 | E | O | 309 | 877 | 1289 | 29 |
| 31 | G | N | 319 | 883 | 1308 | 23 |
| 31 | G | CA | 325 | 870 | 1310 | 25 |
| 31 | G | C | 336 | 867 | 1300 | 24 |
| 31 | G | O | 339 | 875 | 1291 | 22 |
| 32 | E | N | 342 | 855 | 1301 | 25 |
| 32 | E | CA | 353 | 851 | 1292 | 28 |
| 32 | E | CB | 365 | 845 | 1300 | 32 |
| 32 | E | CG | 361 | 835 | 1310 | 40 |
| 32 | E | CD | 356 | 841 | 1323 | 47 |
| 32 | E | OE1 | 348 | 834 | 1330 | 47 |
| 32 | E | OE2 | 360 | 852 | 1326 | 53 |
| 32 | E | C | 349 | 842 | 1281 | 26 |
| 32 | E | O | 353 | 843 | 1269 | 26 |
| 33 | V | N | 341 | 832 | 1284 | 19 |
| 33 | V | CA | 336 | 822 | 1275 | 11 |
| 33 | V | CB | 333 | 809 | 1282 | 5 |
| 33 | V | CG1 | 330 | 798 | 1272 | 3 |
| 33 | V | CG2 | 345 | 805 | 1290 | 10 |
| 33 | V | C | 323 | 827 | 1268 | 10 |
| 33 | V | O | 313 | 828 | 1274 | 12 |
| 34 | Q | N | 325 | 830 | 1255 | 11 |
| 34 | Q | CA | 313 | 834 | 1247 | 8 |
| 34 | Q | CB | 317 | 846 | 1238 | 9 |
| 34 | Q | CG | 326 | 857 | 1245 | 18 |
| 34 | Q | CD | 319 | 865 | 1255 | 17 |
| 34 | Q | OE1 | 307 | 870 | 1253 | 15 |
| 34 | Q | NE2 | 324 | 867 | 1267 | 20 |
| 34 | Q | C | 308 | 824 | 1238 | 9 |
| 34 | Q | O | 315 | 815 | 1233 | 9 |
| 35 | V | N | 295 | 825 | 1235 | 3 |
| 35 | V | CA | 289 | 815 | 1226 | 3 |
| 35 | V | CB | 275 | 811 | 1231 | 5 |
| 35 | V | CG1 | 269 | 800 | 1222 | 5 |
| 35 | V | CG2 | 276 | 806 | 1245 | 2 |
| 35 | V | C | 287 | 823 | 1213 | 6 |
| 35 | V | O | 281 | 833 | 1212 | 9 |
| 36 | V | N | 294 | 818 | 1202 | 5 |
| 36 | V | CA | 293 | 824 | 1189 | 6 |
| 36 | V | CB | 307 | 828 | 1184 | 8 |
| 36 | V | CG1 | 314 | 837 | 1195 | 5 |
| 36 | V | CG2 | 316 | 816 | 1182 | 2 |
| 36 | V | C | 287 | 815 | 1179 | 13 |
| 36 | V | O | 286 | 803 | 1180 | 14 |
| 37 | S | N | 283 | 822 | 1168 | 15 |
| 37 | S | CA | 277 | 814 | 1157 | 19 |
| 37 | S | CB | 262 | 812 | 1161 | 23 |
| 37 | S | OG | 253 | 819 | 1153 | 34 |
| 37 | S | C | 278 | 822 | 1144 | 16 |
| 37 | S | O | 278 | 834 | 1144 | 13 |
| 38 | T | N | 279 | 815 | 1133 | 19 |
| 38 | T | CA | 279 | 821 | 1120 | 23 |
| 38 | T | CB | 290 | 814 | 1111 | 19 |
| 38 | T | OG1 | 286 | 800 | 1109 | 24 |
| 38 | T | CG2 | 304 | 814 | 1118 | 20 |
| 38 | T | C | 266 | 818 | 1115 | 31 |
| 38 | T | O | 257 | 813 | 1122 | 32 |
| 39 | A | N | 264 | 820 | 1102 | 38 |
| 39 | A | CA | 251 | 818 | 1096 | 40 |
| 39 | A | CB | 250 | 824 | 1082 | 45 |
| 39 | A | C | 246 | 803 | 1095 | 40 |
| 39 | A | O | 235 | 800 | 1094 | 40 |
| 40 | T | N | 256 | 794 | 1096 | 38 |
| 40 | T | CA | 253 | 780 | 1095 | 39 |
| 40 | T | CB | 256 | 775 | 1081 | 44 |
| 40 | T | OG1 | 269 | 779 | 1077 | 49 |
| 40 | T | CG2 | 246 | 780 | 1071 | 45 |
| 40 | T | C | 261 | 772 | 1105 | 35 |
| 40 | T | O | 264 | 760 | 1102 | 39 |
| 41 | Q | N | 264 | 777 | 1117 | 30 |
| 41 | Q | CA | 272 | 770 | 1127 | 25 |
| 41 | Q | CB | 286 | 767 | 1121 | 28 |
| 41 | Q | CG | 291 | 753 | 1124 | 44 |
| 41 | Q | CD | 306 | 752 | 1123 | 51 |
| 41 | Q | OE1 | 312 | 744 | 1131 | 50 |
| 41 | Q | NE2 | 312 | 759 | 1113 | 53 |
| 41 | Q | C | 273 | 778 | 1140 | 19 |
| 41 | Q | O | 274 | 790 | 1140 | 13 |
| 42 | S | N | 274 | 771 | 1151 | 14 |
| 42 | S | CA | 275 | 777 | 1164 | 16 |
| 42 | S | CB | 262 | 777 | 1172 | 14 |
| 42 | S | OG | 262 | 787 | 1182 | 16 |
| 42 | S | C | 286 | 770 | 1172 | 15 |
| 42 | S | O | 287 | 757 | 1171 | 11 |
| 43 | F | N | 294 | 777 | 1179 | 10 |
| 43 | F | CA | 305 | 772 | 1187 | 6 |
| 43 | F | CB | 317 | 768 | 1179 | 5 |
| 43 | F | CG | 320 | 779 | 1168 | 5 |
| 43 | F | CD1 | 312 | 780 | 1157 | 5 |
| 43 | F | CD2 | 331 | 787 | 1170 | 2 |
| 43 | F | CE1 | 315 | 790 | 1147 | 2 |
| 43 | F | CE2 | 334 | 797 | 1160 | 2 |
| 43 | F | CZ | 326 | 798 | 1149 | 2 |
| 43 | F | C | 308 | 782 | 1198 | 7 |
| 43 | F | O | 301 | 791 | 1201 | 2 |
| 44 | L | N | 320 | 779 | 1205 | 5 |
| 44 | L | CA | 324 | 788 | 1215 | 5 |
| 44 | L | CB | 327 | 780 | 1228 | 2 |
| 44 | L | CG | 316 | 770 | 1232 | 2 |
| 44 | L | CD1 | 321 | 761 | 1243 | 2 |
| 44 | L | CD2 | 304 | 778 | 1237 | 5 |
| 44 | L | C | 337 | 796 | 1212 | 6 |
| 44 | L | O | 345 | 793 | 1203 | 11 |
| 45 | A | N | 339 | 807 | 1220 | 8 |
| 45 | A | CA | 351 | 816 | 1219 | 4 |
| 45 | A | CB | 347 | 828 | 1211 | 2 |
| 45 | A | C | 355 | 819 | 1233 | 4 |
| 45 | A | O | 347 | 823 | 1241 | 10 |
| 46 | T | N | 368 | 818 | 1235 | 5 |
| 46 | T | CA | 373 | 821 | 1249 | 5 |
| 46 | T | CB | 380 | 809 | 1254 | 2 |
| 46 | T | OG1 | 371 | 798 | 1254 | 8 |
| 46 | T | CG2 | 385 | 811 | 1268 | 3 |
| 46 | T | C | 383 | 832 | 1249 | 7 |
| 46 | T | O | 393 | 832 | 1242 | 12 |
| 47 | C | N | 381 | 842 | 1258 | 9 |
| 47 | C | CA | 390 | 853 | 1259 | 7 |
| 47 | C | CB | 383 | 866 | 1264 | 4 |
| 47 | C | SG | 370 | 872 | 1253 | 26 |
| 47 | C | C | 401 | 850 | 1268 | 10 |
| 47 | C | O | 399 | 846 | 1280 | 12 |
| 48 | V | N | 413 | 850 | 1263 | 10 |
| 48 | V | CA | 425 | 847 | 1271 | 12 |
| 48 | V | CB | 431 | 833 | 1267 | 14 |
| 48 | V | CG1 | 442 | 829 | 1277 | 9 |

TABLE 3-continued

| | | | | | | |
|---|---|---|---|---|---|---|
| 48 | V | CG2 | 420 | 823 | 1267 | 9 |
| 48 | V | C | 436 | 858 | 1269 | 13 |
| 48 | V | O | 439 | 860 | 1257 | 13 |
| 49 | N | N | 440 | 864 | 1280 | 11 |
| 49 | N | CA | 450 | 874 | 1279 | 8 |
| 49 | N | CB | 464 | 868 | 1276 | 5 |
| 49 | N | CG | 469 | 860 | 1288 | 7 |
| 49 | N | OD1 | 463 | 860 | 1298 | 18 |
| 49 | N | ND2 | 481 | 854 | 1286 | 13 |
| 49 | N | C | 447 | 885 | 1269 | 7 |
| 49 | N | O | 456 | 890 | 1262 | 6 |
| 50 | G | N | 434 | 889 | 1268 | 7 |
| 50 | G | CA | 431 | 900 | 1259 | 12 |
| 50 | G | C | 427 | 897 | 1245 | 11 |
| 50 | G | O | 423 | 905 | 1237 | 10 |
| 51 | V | N | 428 | 884 | 1241 | 13 |
| 51 | V | CA | 424 | 879 | 1228 | 9 |
| 51 | V | CB | 435 | 872 | 1220 | 13 |
| 51 | V | CG1 | 432 | 870 | 1206 | 10 |
| 51 | V | CG2 | 448 | 881 | 1221 | 8 |
| 51 | V | C | 412 | 870 | 1229 | 7 |
| 51 | V | O | 411 | 862 | 1238 | 9 |
| 52 | C | N | 403 | 871 | 1220 | 9 |
| 52 | C | CA | 391 | 862 | 1219 | 8 |
| 52 | C | CB | 379 | 870 | 1215 | 12 |
| 52 | C | SG | 364 | 860 | 1213 | 27 |
| 52 | C | C | 395 | 851 | 1210 | 5 |
| 52 | C | O | 395 | 853 | 1197 | 5 |
| 53 | W | N | 398 | 839 | 1215 | 4 |
| 53 | W | CA | 402 | 827 | 1207 | 3 |
| 53 | W | CB | 412 | 819 | 1213 | 6 |
| 53 | W | CG | 424 | 827 | 1219 | 8 |
| 53 | W | CD2 | 436 | 830 | 1212 | 8 |
| 53 | W | CE2 | 444 | 837 | 1221 | 11 |
| 53 | W | CE3 | 441 | 828 | 1199 | 8 |
| 53 | W | CD1 | 425 | 832 | 1231 | 5 |
| 53 | W | NE1 | 438 | 838 | 1233 | 14 |
| 53 | W | CZ2 | 457 | 842 | 1217 | 16 |
| 53 | W | CZ3 | 453 | 832 | 1195 | 9 |
| 53 | W | CH2 | 461 | 839 | 1204 | 14 |
| 53 | W | C | 390 | 818 | 1203 | 5 |
| 53 | W | O | 381 | 817 | 1211 | 10 |
| 54 | T | N | 392 | 811 | 1192 | 8 |
| 54 | T | CA | 382 | 800 | 1188 | 7 |
| 54 | T | CB | 369 | 806 | 1182 | 6 |
| 54 | T | OG1 | 360 | 796 | 1181 | 2 |
| 54 | T | CG2 | 371 | 813 | 1169 | 8 |
| 54 | T | C | 389 | 792 | 1177 | 6 |
| 54 | T | O | 401 | 794 | 1174 | 10 |
| 55 | V | N | 382 | 782 | 1172 | 7 |
| 55 | V | CA | 388 | 773 | 1162 | 6 |
| 55 | V | CB | 381 | 759 | 1162 | 2 |
| 55 | V | CG1 | 388 | 750 | 1172 | 2 |
| 55 | V | CG2 | 366 | 761 | 1164 | 2 |
| 55 | V | C | 386 | 778 | 1148 | 6 |
| 55 | V | O | 377 | 785 | 1144 | 11 |
| 56 | Y | N | 396 | 775 | 1139 | 7 |
| 56 | Y | CA | 396 | 779 | 1125 | 7 |
| 56 | Y | CB | 410 | 778 | 1119 | 4 |
| 56 | Y | CG | 410 | 781 | 1104 | 6 |
| 56 | Y | CD1 | 410 | 795 | 1100 | 9 |
| 56 | Y | CE1 | 410 | 798 | 1087 | 5 |
| 56 | Y | CD2 | 409 | 771 | 1094 | 4 |
| 56 | Y | CE2 | 409 | 775 | 1081 | 6 |
| 56 | Y | CZ | 409 | 788 | 1077 | 6 |
| 56 | Y | OH | 409 | 791 | 1064 | 13 |
| 56 | Y | C | 385 | 771 | 1118 | 10 |
| 56 | Y | O | 379 | 777 | 1109 | 6 |
| 57 | H | N | 384 | 758 | 1121 | 7 |
| 57 | H | CA | 375 | 750 | 1114 | 8 |
| 57 | H | CB | 376 | 735 | 1118 | 8 |
| 57 | H | CG | 372 | 732 | 1132 | 9 |
| 57 | H | CD2 | 379 | 729 | 1143 | 4 |
| 57 | H | ND1 | 359 | 730 | 1136 | 4 |
| 57 | H | CE1 | 358 | 726 | 1149 | 2 |
| 57 | H | NE2 | 370 | 725 | 1153 | 2 |
| 57 | H | C | 360 | 755 | 1116 | 13 |
| 57 | H | O | 351 | 750 | 1110 | 13 |
| 58 | G | N | 359 | 764 | 1125 | 13 |
| 58 | G | CA | 346 | 770 | 1128 | 9 |
| 58 | G | C | 344 | 784 | 1123 | 9 |
| 58 | G | O | 334 | 788 | 1117 | 9 |
| 59 | A | N | 354 | 793 | 1126 | 8 |
| 59 | A | CA | 353 | 807 | 1123 | 13 |
| 59 | A | CB | 360 | 815 | 1134 | 11 |
| 59 | A | C | 360 | 810 | 1109 | 18 |
| 59 | A | O | 357 | 821 | 1103 | 20 |
| 60 | G | N | 369 | 802 | 1105 | 19 |
| 60 | G | CA | 376 | 805 | 1092 | 15 |
| 60 | G | C | 384 | 818 | 1094 | 18 |
| 60 | G | O | 390 | 820 | 1105 | 16 |
| 61 | S | N | 383 | 827 | 1084 | 18 |
| 61 | S | CA | 390 | 840 | 1085 | 18 |
| 61 | S | CB | 399 | 842 | 1073 | 14 |
| 61 | S | OG | 404 | 830 | 1069 | 21 |
| 61 | S | C | 379 | 851 | 1087 | 16 |
| 61 | S | O | 381 | 862 | 1082 | 18 |
| 62 | K | N | 368 | 848 | 1093 | 9 |
| 62 | K | CA | 358 | 857 | 1095 | 11 |
| 62 | K | CB | 345 | 850 | 1099 | 8 |
| 62 | K | CG | 337 | 844 | 1088 | 10 |
| 62 | K | CD | 326 | 835 | 1093 | 12 |
| 62 | K | CE | 320 | 826 | 1082 | 18 |
| 62 | K | NZ | 305 | 828 | 1082 | 34 |
| 62 | K | C | 360 | 868 | 1106 | 12 |
| 62 | K | O | 368 | 866 | 1115 | 15 |
| 63 | T | N | 355 | 880 | 1103 | 13 |
| 63 | T | CA | 356 | 891 | 1113 | 17 |
| 63 | T | CB | 353 | 905 | 1106 | 13 |
| 63 | T | OG1 | 339 | 905 | 1102 | 10 |
| 63 | T | CG2 | 362 | 908 | 1095 | 7 |
| 63 | T | C | 346 | 888 | 1124 | 11 |
| 63 | T | O | 338 | 880 | 1123 | 15 |
| 64 | L | N | 347 | 896 | 1135 | 11 |
| 64 | L | CA | 339 | 894 | 1147 | 6 |
| 64 | L | CB | 347 | 893 | 1159 | 2 |
| 64 | L | CG | 343 | 884 | 1171 | 2 |
| 64 | L | CD1 | 349 | 891 | 1183 | 2 |
| 64 | L | CD2 | 328 | 882 | 1173 | 5 |
| 64 | L | C | 331 | 907 | 1148 | 9 |
| 64 | L | O | 337 | 918 | 1148 | 11 |
| 65 | A | N | 318 | 907 | 1149 | 12 |
| 65 | A | CA | 310 | 919 | 1151 | 10 |
| 65 | A | CB | 295 | 915 | 1153 | 9 |
| 65 | A | C | 315 | 926 | 1163 | 13 |
| 65 | A | O | 317 | 920 | 1174 | 16 |
| 66 | G | N | 318 | 939 | 1161 | 15 |
| 66 | G | CA | 323 | 947 | 1172 | 9 |
| 66 | G | C | 315 | 960 | 1174 | 9 |
| 66 | G | O | 306 | 963 | 1166 | 7 |
| 67 | P | N | 317 | 967 | 1185 | 13 |
| 67 | P | CD | 328 | 964 | 1195 | 11 |
| 67 | P | CA | 310 | 980 | 1188 | 15 |
| 67 | P | CB | 315 | 984 | 1201 | 10 |
| 67 | P | CG | 329 | 977 | 1203 | 14 |
| 67 | P | C | 313 | 990 | 1177 | 16 |
| 67 | P | O | 303 | 998 | 1173 | 22 |
| 68 | K | N | 325 | 991 | 1172 | 21 |
| 68 | K | CA | 328 | 1001 | 1162 | 25 |
| 68 | K | CB | 342 | 1006 | 1164 | 27 |
| 68 | K | CG | 344 | 1016 | 1175 | 38 |
| 68 | K | CD | 334 | 1027 | 1175 | 51 |
| 68 | K | CE | 332 | 1033 | 1189 | 58 |
| 68 | K | NZ | 322 | 1044 | 1189 | 64 |
| 68 | K | C | 327 | 994 | 1148 | 25 |
| 68 | K | O | 328 | 1001 | 1138 | 31 |
| 69 | G | N | 323 | 982 | 1149 | 20 |
| 69 | G | CA | 322 | 974 | 1136 | 19 |
| 69 | G | C | 330 | 962 | 1136 | 17 |
| 69 | G | O | 336 | 958 | 1146 | 18 |
| 70 | P | N | 331 | 955 | 1125 | 14 |
| 70 | P | CD | 324 | 959 | 1112 | 14 |
| 70 | P | CA | 338 | 942 | 1123 | 11 |
| 70 | P | CB | 338 | 940 | 1108 | 17 |
| 70 | P | CG | 326 | 947 | 1103 | 16 |
| 70 | P | C | 352 | 942 | 1128 | 13 |
| 70 | P | O | 360 | 951 | 1125 | 16 |
| 71 | I | N | 356 | 932 | 1136 | 11 |

TABLE 3-continued

| | | | | | | |
|---|---|---|---|---|---|---|
| 71 | I | CA | 369 | 931 | 1142 | 12 |
| 71 | I | CB | 368 | 927 | 1157 | 11 |
| 71 | I | CG2 | 382 | 923 | 1162 | 2 |
| 71 | I | CG1 | 362 | 938 | 1165 | 11 |
| 71 | I | CD1 | 355 | 933 | 1177 | 2 |
| 71 | I | C | 377 | 921 | 1134 | 16 |
| 71 | I | O | 373 | 909 | 1133 | 14 |
| 72 | T | N | 388 | 925 | 1128 | 12 |
| 72 | T | CA | 396 | 916 | 1120 | 14 |
| 72 | T | CB | 406 | 924 | 1111 | 17 |
| 72 | T | OG1 | 399 | 932 | 1101 | 24 |
| 72 | T | CG2 | 415 | 914 | 1104 | 18 |
| 72 | T | C | 404 | 907 | 1128 | 9 |
| 72 | T | O | 409 | 910 | 1139 | 11 |
| 73 | Q | N | 406 | 894 | 1121 | 9 |
| 73 | Q | CA | 414 | 885 | 1131 | 9 |
| 73 | Q | CB | 414 | 871 | 1124 | 2 |
| 73 | Q | CG | 400 | 864 | 1123 | 2 |
| 73 | Q | CD | 401 | 850 | 1118 | 4 |
| 73 | Q | OE1 | 412 | 844 | 1118 | 14 |
| 73 | Q | NE2 | 390 | 844 | 1115 | 2 |
| 73 | Q | C | 428 | 890 | 1132 | 6 |
| 73 | Q | O | 433 | 895 | 1123 | 6 |
| 74 | M | N | 433 | 889 | 1145 | 4 |
| 74 | M | CA | 446 | 894 | 1147 | 7 |
| 74 | M | CB | 447 | 898 | 1162 | 3 |
| 74 | M | CG | 461 | 902 | 1166 | 12 |
| 74 | M | SD | 461 | 911 | 1181 | 21 |
| 74 | M | CE | 478 | 918 | 1180 | 23 |
| 74 | M | C | 456 | 882 | 1145 | 9 |
| 74 | M | O | 467 | 884 | 1141 | 10 |
| 75 | Y | N | 451 | 870 | 1147 | 12 |
| 75 | Y | CA | 459 | 858 | 1145 | 12 |
| 75 | Y | CB | 463 | 852 | 1158 | 9 |
| 75 | Y | CG | 471 | 862 | 1167 | 10 |
| 75 | Y | CD1 | 484 | 865 | 1164 | 9 |
| 75 | Y | CE1 | 491 | 874 | 1172 | 14 |
| 75 | Y | CD2 | 465 | 867 | 1178 | 5 |
| 75 | Y | CE2 | 472 | 876 | 1187 | 4 |
| 75 | Y | CZ | 486 | 879 | 1183 | 9 |
| 75 | Y | OH | 493 | 888 | 1191 | 18 |
| 75 | Y | C | 450 | 848 | 1137 | 16 |
| 75 | Y | O | 438 | 847 | 1138 | 19 |
| 76 | T | N | 457 | 840 | 1129 | 16 |
| 76 | T | CA | 451 | 829 | 1122 | 16 |
| 76 | T | CB | 447 | 835 | 1108 | 13 |
| 76 | T | OG1 | 440 | 847 | 1110 | 18 |
| 76 | T | CG2 | 437 | 825 | 1101 | 11 |
| 76 | T | C | 461 | 818 | 1120 | 14 |
| 76 | T | O | 470 | 820 | 1111 | 23 |
| 77 | N | N | 460 | 807 | 1127 | 10 |
| 77 | N | CA | 469 | 796 | 1126 | 6 |
| 77 | N | CB | 476 | 793 | 1139 | 8 |
| 77 | N | CG | 489 | 786 | 1137 | 18 |
| 77 | N | OD1 | 490 | 777 | 1129 | 26 |
| 77 | N | ND2 | 499 | 790 | 1144 | 20 |
| 77 | N | C | 461 | 784 | 1121 | 7 |
| 77 | N | O | 455 | 777 | 1130 | 14 |
| 78 | V | N | 461 | 781 | 1109 | 9 |
| 78 | V | CA | 454 | 770 | 1103 | 7 |
| 78 | V | CB | 454 | 770 | 1088 | 7 |
| 78 | V | CG1 | 445 | 759 | 1083 | 4 |
| 78 | V | CG2 | 448 | 783 | 1084 | 2 |
| 78 | V | C | 460 | 757 | 1108 | 11 |
| 78 | V | O | 453 | 746 | 1110 | 9 |
| 79 | D | N | 473 | 757 | 1110 | 15 |
| 79 | D | CA | 481 | 745 | 1115 | 17 |
| 79 | D | CB | 496 | 748 | 1115 | 21 |
| 79 | D | CG | 502 | 746 | 1101 | 25 |
| 79 | D | OD1 | 498 | 736 | 1094 | 24 |
| 79 | D | OD2 | 511 | 754 | 1097 | 36 |
| 79 | D | C | 477 | 741 | 1129 | 19 |
| 79 | D | O | 475 | 729 | 1132 | 23 |
| 80 | Q | N | 474 | 751 | 1137 | 19 |
| 80 | Q | CA | 470 | 749 | 1151 | 16 |
| 80 | Q | CB | 476 | 760 | 1160 | 19 |
| 80 | Q | CG | 491 | 762 | 1159 | 22 |
| 80 | Q | CD | 496 | 772 | 1169 | 14 |
| 80 | Q | OE1 | 508 | 774 | 1170 | 19 |
| 80 | Q | NE2 | 487 | 778 | 1177 | 11 |
| 80 | Q | C | 455 | 748 | 1152 | 16 |
| 80 | Q | O | 449 | 744 | 1162 | 16 |
| 81 | D | N | 448 | 753 | 1142 | 12 |
| 81 | D | CA | 434 | 754 | 1141 | 8 |
| 81 | D | CB | 428 | 740 | 1144 | 7 |
| 81 | D | CG | 413 | 739 | 1142 | 10 |
| 81 | D | OD1 | 408 | 746 | 1133 | 14 |
| 81 | D | OD2 | 407 | 730 | 1148 | 11 |
| 81 | D | C | 429 | 763 | 1151 | 11 |
| 81 | D | O | 420 | 760 | 1159 | 14 |
| 82 | L | N | 435 | 775 | 1151 | 10 |
| 82 | L | CA | 431 | 785 | 1161 | 9 |
| 82 | L | CB | 440 | 784 | 1173 | 8 |
| 82 | L | CG | 441 | 795 | 1183 | 16 |
| 82 | L | CD1 | 435 | 792 | 1196 | 10 |
| 82 | L | CD2 | 456 | 798 | 1185 | 15 |
| 82 | L | C | 432 | 799 | 1156 | 7 |
| 82 | L | O | 442 | 803 | 1149 | 13 |
| 83 | V | N | 422 | 808 | 1158 | 7 |
| 83 | V | CA | 422 | 822 | 1154 | 6 |
| 83 | V | CB | 411 | 825 | 1143 | 6 |
| 83 | V | CG1 | 413 | 816 | 1131 | 8 |
| 83 | V | CG2 | 397 | 823 | 1149 | 2 |
| 83 | V | C | 419 | 830 | 1166 | 8 |
| 83 | V | O | 414 | 826 | 1176 | 13 |
| 84 | G | N | 423 | 843 | 1165 | 7 |
| 84 | G | CA | 421 | 852 | 1171 | 5 |
| 84 | G | C | 418 | 866 | 1171 | 4 |
| 84 | G | O | 423 | 871 | 1161 | 2 |
| 85 | W | N | 410 | 873 | 1179 | 5 |
| 8S | W | CA | 406 | 887 | 1176 | 9 |
| 85 | W | CB | 391 | 888 | 1174 | 8 |
| 85 | W | CG | 385 | 880 | 1162 | 3 |
| 85 | W | CD2 | 377 | 868 | 1163 | 2 |
| 85 | W | CE2 | 372 | 865 | 1150 | 2 |
| 85 | W | CE3 | 373 | 859 | 1174 | 8 |
| 85 | W | CD1 | 385 | 884 | 1149 | 2 |
| 85 | W | NE1 | 377 | 875 | 1142 | 4 |
| 85 | W | CZ2 | 364 | 854 | 1147 | 2 |
| 85 | W | CZ3 | 365 | 848 | 1171 | 2 |
| 85 | W | CH2 | 361 | 846 | 1158 | 6 |
| 85 | W | C | 409 | 895 | 1188 | 10 |
| 85 | W | O | 410 | 889 | 1199 | 18 |
| 86 | Q | N | 412 | 908 | 1187 | 17 |
| 86 | Q | CA | 414 | 916 | 1199 | 15 |
| 86 | Q | CB | 419 | 930 | 1195 | 18 |
| 86 | Q | CG | 432 | 934 | 1202 | 36 |
| 86 | Q | CD | 440 | 945 | 1195 | 43 |
| 86 | Q | OE1 | 438 | 957 | 1197 | 45 |
| 86 | Q | NE2 | 449 | 941 | 1186 | 49 |
| 86 | Q | C | 401 | 917 | 1207 | 12 |
| 86 | Q | O | 391 | 921 | 1202 | 14 |
| 87 | A | N | 402 | 912 | 1219 | 11 |
| 87 | A | CA | 390 | 913 | 1228 | 13 |
| 87 | A | CB | 394 | 908 | 1242 | 7 |
| 87 | A | C | 384 | 927 | 1229 | 19 |
| 87 | A | O | 391 | 936 | 1234 | 23 |
| 88 | P | N | 371 | 928 | 1225 | 28 |
| 88 | P | CD | 363 | 918 | 1219 | 35 |
| 88 | P | CA | 364 | 941 | 1225 | 32 |
| 88 | P | CB | 351 | 938 | 1218 | 31 |
| 88 | P | CG | 350 | 924 | 1218 | 34 |
| 88 | P | C | 362 | 945 | 1240 | 36 |
| 88 | P | O | 363 | 938 | 1249 | 37 |
| 89 | P | N | 357 | 958 | 1242 | 42 |
| 89 | P | CD | 355 | 968 | 1231 | 43 |
| 89 | P | CA | 354 | 963 | 1255 | 42 |
| 89 | P | CB | 349 | 978 | 1252 | 45 |
| 89 | P | CG | 345 | 977 | 1238 | 45 |
| 89 | P | C | 344 | 955 | 1263 | 42 |
| 89 | P | O | 334 | 951 | 1258 | 41 |
| 90 | G | N | 347 | 954 | 1276 | 40 |
| 90 | G | CA | 338 | 946 | 1285 | 40 |
| 90 | G | C | 341 | 932 | 1284 | 40 |
| 90 | G | O | 334 | 923 | 1288 | 41 |
| 91 | A | N | 354 | 929 | 1280 | 40 |
| 91 | A | CA | 358 | 915 | 1278 | 34 |
| 91 | A | CB | 366 | 914 | 1265 | 34 |

TABLE 3-continued

| | | | | | | |
|---|---|---|---|---|---|---|
| 91 | A | C | 367 | 911 | 1290 | 30 |
| 91 | A | O | 378 | 915 | 1292 | 27 |
| 92 | R | N | 361 | 902 | 1298 | 30 |
| 92 | R | CA | 368 | 896 | 1309 | 26 |
| 92 | R | CB | 359 | 890 | 1319 | 30 |
| 92 | R | CG | 353 | 899 | 1330 | 47 |
| 92 | R | CD | 349 | 891 | 1343 | 59 |
| 92 | R | NE | 361 | 888 | 1351 | 71 |
| 92 | R | CZ | 364 | 894 | 1362 | 77 |
| 92 | R | NH1 | 356 | 904 | 1367 | 79 |
| 92 | R | NH2 | 374 | 891 | 1369 | 77 |
| 92 | R | C | 377 | 886 | 1302 | 17 |
| 92 | R | O | 373 | 881 | 1292 | 21 |
| 93 | S | N | 389 | 883 | 1308 | 17 |
| 93 | S | CA | 397 | 874 | 1301 | 13 |
| 93 | S | CB | 410 | 880 | 1295 | 17 |
| 93 | S | OG | 409 | 880 | 1281 | 19 |
| 93 | S | C | 401 | 863 | 1311 | 12 |
| 93 | S | O | 402 | 865 | 1323 | 19 |
| 94 | L | N | 404 | 851 | 1306 | 6 |
| 94 | L | CA | 409 | 840 | 1314 | 6 |
| 94 | L | CB | 405 | 827 | 1307 | 9 |
| 94 | L | CG | 397 | 816 | 1313 | 12 |
| 94 | L | CD1 | 389 | 821 | 1325 | 10 |
| 94 | L | CD2 | 387 | 811 | 1303 | 5 |
| 94 | L | C | 424 | 842 | 1313 | 13 |
| 94 | L | O | 429 | 850 | 1304 | 17 |
| 95 | T | N | 432 | 837 | 1322 | 11 |
| 95 | T | CA | 446 | 838 | 1321 | 13 |
| 95 | T | CB | 452 | 848 | 1332 | 19 |
| 95 | T | OG1 | 449 | 842 | 1345 | 20 |
| 95 | T | CG2 | 445 | 861 | 1331 | 21 |
| 95 | T | C | 452 | 824 | 1323 | 16 |
| 95 | T | O | 445 | 815 | 1329 | 17 |
| 96 | P | N | 464 | 822 | 1319 | 17 |
| 96 | P | CD | 472 | 832 | 1312 | 15 |
| 96 | P | CA | 471 | 809 | 1320 | 17 |
| 96 | P | CB | 485 | 812 | 1315 | 18 |
| 96 | P | CG | 483 | 824 | 1306 | 18 |
| 96 | P | C | 472 | 803 | 1334 | 17 |
| 96 | P | O | 471 | 810 | 1344 | 20 |
| 97 | C | N | 473 | 790 | 1335 | 23 |
| 97 | C | CA | 473 | 783 | 1348 | 26 |
| 97 | C | CB | 466 | 770 | 1347 | 25 |
| 97 | C | SG | 474 | 756 | 1354 | 46 |
| 97 | C | C | 488 | 781 | 1351 | 26 |
| 97 | C | O | 496 | 778 | 1342 | 28 |
| 98 | T | N | 491 | 782 | 1364 | 28 |
| 98 | T | CA | 505 | 780 | 1368 | 28 |
| 98 | T | CB | 510 | 793 | 1376 | 23 |
| 98 | T | OG1 | 502 | 796 | 1387 | 31 |
| 98 | T | CG2 | 510 | 805 | 1366 | 18 |
| 98 | T | C | 507 | 768 | 1378 | 31 |
| 98 | T | O | 518 | 766 | 1382 | 35 |
| 99 | C | N | 496 | 761 | 1380 | 36 |
| 99 | C | CA | 496 | 750 | 1389 | 40 |
| 99 | C | CB | 482 | 746 | 1395 | 39 |
| 99 | C | SG | 468 | 750 | 1383 | 51 |
| 99 | C | C | 502 | 737 | 1383 | 43 |
| 99 | C | O | 509 | 730 | 1389 | 44 |
| 100 | G | N | 500 | 735 | 1370 | 45 |
| 100 | G | CA | 505 | 724 | 1363 | 47 |
| 100 | G | C | 498 | 711 | 1367 | 48 |
| 100 | G | O | 504 | 700 | 1367 | 48 |
| 101 | S | N | 486 | 712 | 1371 | 45 |
| 101 | S | CA | 478 | 700 | 1376 | 40 |
| 101 | S | CB | 466 | 704 | 1384 | 41 |
| 101 | S | OG | 456 | 709 | 1375 | 46 |
| 101 | S | C | 474 | 692 | 1363 | 35 |
| 101 | S | O | 472 | 698 | 1352 | 35 |
| 102 | S | N | 471 | 679 | 1365 | 33 |
| 102 | S | CA | 466 | 671 | 1353 | 28 |
| 102 | S | CB | 474 | 658 | 1353 | 29 |
| 102 | S | OG | 486 | 659 | 1346 | 35 |
| 102 | S | C | 451 | 669 | 1354 | 25 |
| 102 | S | O | 446 | 663 | 1345 | 26 |
| 103 | D | N | 445 | 675 | 1364 | 20 |
| 103 | D | CA | 430 | 673 | 1365 | 21 |
| 103 | D | CB | 426 | 672 | 1380 | 26 |
| 103 | D | CG | 433 | 660 | 1387 | 31 |
| 103 | D | OD1 | 427 | 649 | 1385 | 34 |
| 103 | D | OD2 | 443 | 662 | 1393 | 41 |
| 103 | D | C | 424 | 685 | 1359 | 19 |
| 103 | D | O | 422 | 696 | 1365 | 16 |
| 104 | L | N | 419 | 684 | 1346 | 15 |
| 104 | L | CA | 413 | 695 | 1339 | 6 |
| 104 | L | CB | 418 | 695 | 1325 | 7 |
| 104 | L | CG | 432 | 691 | 1323 | 12 |
| 104 | L | CD1 | 436 | 691 | 1308 | 13 |
| 104 | L | CD2 | 441 | 702 | 1330 | 10 |
| 104 | L | C | 398 | 694 | 1339 | 5 |
| 104 | L | O | 392 | 684 | 1343 | 9 |
| 105 | Y | N | 391 | 704 | 1334 | 7 |
| 105 | Y | CA | 377 | 706 | 1334 | 9 |
| 105 | Y | CB | 371 | 714 | 1346 | 10 |
| 105 | Y | CG | 375 | 707 | 1359 | 8 |
| 105 | Y | CD1 | 366 | 696 | 1363 | 11 |
| 105 | Y | CE1 | 370 | 689 | 1374 | 22 |
| 105 | Y | CD2 | 386 | 709 | 1366 | 11 |
| 105 | Y | CE2 | 390 | 702 | 1377 | 17 |
| 105 | Y | CZ | 382 | 692 | 1381 | 24 |
| 105 | Y | OH | 386 | 684 | 1391 | 29 |
| 105 | Y | C | 373 | 713 | 1321 | 13 |
| 10S | Y | O | 378 | 724 | 1318 | 19 |
| 106 | L | N | 365 | 706 | 1313 | 13 |
| 106 | L | CA | 360 | 712 | 1300 | 10 |
| 106 | L | CB | 360 | 700 | 1289 | 8 |
| 106 | L | CG | 361 | 704 | 1275 | 7 |
| 106 | L | CD1 | 356 | 692 | 1267 | 7 |
| 106 | L | CD2 | 354 | 716 | 1271 | 12 |
| 106 | L | C | 347 | 718 | 1301 | 7 |
| 106 | L | O | 337 | 712 | 1306 | 8 |
| 107 | V | N | 346 | 731 | 1297 | 8 |
| 107 | V | CA | 333 | 738 | 1297 | 11 |
| 107 | V | CB | 335 | 753 | 1300 | 11 |
| 107 | V | CG1 | 321 | 759 | 1303 | 5 |
| 107 | V | CG2 | 344 | 755 | 1312 | 13 |
| 107 | V | C | 326 | 736 | 1283 | 9 |
| 107 | V | O | 333 | 739 | 1273 | 12 |
| 108 | T | N | 314 | 731 | 1283 | 10 |
| 108 | T | CA | 307 | 729 | 1271 | 8 |
| 108 | T | CB | 299 | 715 | 1271 | 7 |
| 108 | T | OG1 | 290 | 715 | 1282 | 14 |
| 108 | T | CG2 | 309 | 704 | 1272 | 2 |
| 108 | T | C | 297 | 740 | 1268 | 15 |
| 108 | T | O | 294 | 748 | 1277 | 16 |
| 109 | R | N | 292 | 741 | 1256 | 17 |
| 109 | R | CA | 282 | 751 | 1252 | 16 |
| 109 | R | CB | 278 | 750 | 1237 | 20 |
| 109 | R | CG | 269 | 738 | 1234 | 18 |
| 109 | R | CD | 267 | 738 | 1219 | 18 |
| 109 | R | NE | 259 | 749 | 1214 | 17 |
| 109 | R | CZ | 265 | 760 | 1209 | 20 |
| 109 | R | NH1 | 278 | 761 | 1207 | 15 |
| 109 | R | NH2 | 257 | 770 | 1205 | 22 |
| 109 | R | C | 269 | 750 | 1261 | 18 |
| 109 | R | O | 261 | 759 | 1262 | 14 |
| 110 | H | N | 267 | 738 | 1267 | 18 |
| 110 | H | CA | 255 | 735 | 1275 | 24 |
| 110 | H | CB | 251 | 721 | 1274 | 26 |
| 110 | H | CG | 248 | 717 | 1260 | 36 |
| 110 | H | CD2 | 238 | 721 | 1251 | 36 |
| 110 | H | ND1 | 255 | 708 | 1252 | 38 |
| 110 | H | CE1 | 250 | 707 | 1240 | 42 |
| 110 | H | NE2 | 239 | 715 | 1239 | 40 |
| 110 | H | C | 259 | 739 | 1289 | 25 |
| 110 | H | O | 251 | 735 | 1298 | 32 |
| 111 | A | N | 270 | 746 | 1292 | 22 |
| 111 | A | CA | 274 | 749 | 1305 | 15 |
| 111 | A | CB | 263 | 759 | 1311 | 9 |
| 111 | A | C | 276 | 737 | 1314 | 17 |
| 111 | A | O | 273 | 738 | 1326 | 20 |
| 112 | D | N | 281 | 727 | 1308 | 13 |
| 112 | D | CA | 284 | 715 | 1316 | 15 |
| 112 | D | CB | 281 | 702 | 1308 | 21 |
| 112 | D | CG | 266 | 700 | 1306 | 31 |
| 112 | D | OD1 | 258 | 702 | 1316 | 36 |
| 112 | D | OD2 | 262 | 696 | 1294 | 31 |

TABLE 3-continued

| | | | | | | |
|---|---|---|---|---|---|---|
| 112 | D | C | 299 | 715 | 1318 | 11 |
| 112 | D | O | 307 | 720 | 1310 | 9 |
| 113 | V | N | 304 | 711 | 1330 | 12 |
| 113 | V | CA | 318 | 711 | 1333 | 15 |
| 113 | V | CB | 321 | 719 | 1345 | 10 |
| 113 | V | CG1 | 336 | 721 | 1347 | 15 |
| 113 | V | CG2 | 315 | 733 | 1344 | 7 |
| 113 | V | C | 322 | 697 | 1335 | 19 |
| 113 | V | O | 320 | 691 | 1346 | 24 |
| 114 | I | N | 327 | 690 | 1325 | 23 |
| 114 | I | CA | 332 | 676 | 1326 | 16 |
| 114 | I | CB | 328 | 668 | 1314 | 18 |
| 114 | I | CG2 | 313 | 667 | 1313 | 26 |
| 114 | I | CG1 | 334 | 675 | 1301 | 17 |
| 114 | I | CD1 | 324 | 677 | 1290 | 27 |
| 114 | I | C | 347 | 676 | 1329 | 14 |
| 114 | I | O | 355 | 683 | 1323 | 13 |
| 115 | P | N | 351 | 667 | 1338 | 12 |
| 115 | P | CD | 342 | 657 | 1345 | 15 |
| 115 | P | CA | 365 | 664 | 1341 | 12 |
| 115 | P | CB | 364 | 656 | 1354 | 13 |
| 115 | P | CG | 351 | 648 | 1352 | 15 |
| 115 | P | C | 373 | 657 | 1331 | 13 |
| 115 | P | O | 368 | 647 | 1325 | 15 |
| 116 | V | N | 385 | 661 | 1329 | 13 |
| 116 | V | CA | 394 | 655 | 1319 | 13 |
| 116 | V | CB | 396 | 665 | 1307 | 11 |
| 116 | V | CG1 | 408 | 660 | 1299 | 6 |
| 116 | V | CG2 | 383 | 665 | 1299 | 2 |
| 116 | V | C | 407 | 653 | 1326 | 18 |
| 116 | V | O | 412 | 661 | 1334 | 25 |
| 117 | R | N | 414 | 642 | 1322 | 18 |
| 117 | R | CA | 427 | 639 | 1328 | 18 |
| 117 | R | CB | 428 | 625 | 1332 | 15 |
| 117 | R | CG | 442 | 621 | 1336 | 21 |
| 117 | R | CD | 448 | 631 | 1346 | 29 |
| 117 | R | NE | 461 | 627 | 1352 | 43 |
| 117 | R | CZ | 464 | 628 | 1364 | 49 |
| 117 | R | NH1 | 456 | 634 | 1373 | 51 |
| 117 | R | NH2 | 476 | 624 | 1369 | 54 |
| 117 | R | C | 437 | 642 | 1316 | 14 |
| 117 | R | O | 437 | 635 | 1306 | 10 |
| 118 | R | N | 445 | 652 | 1318 | 10 |
| 118 | R | CA | 455 | 656 | 1309 | 11 |
| 118 | R | CB | 464 | 667 | 1314 | 12 |
| 118 | R | CG | 473 | 673 | 1303 | 13 |
| 118 | R | CD | 479 | 686 | 1307 | 13 |
| 118 | R | NE | 485 | 693 | 1296 | 16 |
| 118 | R | CZ | 488 | 706 | 1295 | 21 |
| 118 | R | NH1 | 487 | 713 | 1306 | 26 |
| 118 | R | NH2 | 493 | 711 | 1284 | 17 |
| 118 | R | C | 464 | 644 | 1306 | 18 |
| 118 | R | O | 469 | 637 | 1315 | 18 |
| 119 | R | N | 467 | 641 | 1293 | 23 |
| 119 | R | CA | 475 | 630 | 1289 | 25 |
| 119 | R | CB | 467 | 620 | 1280 | 26 |
| 119 | R | CG | 456 | 613 | 1287 | 33 |
| 119 | R | CD | 462 | 604 | 1298 | 31 |
| 119 | R | NE | 451 | 600 | 1307 | 39 |
| 119 | R | CZ | 452 | 594 | 1319 | 41 |
| 119 | R | NH1 | 465 | 591 | 1323 | 45 |
| 119 | R | NH2 | 442 | 591 | 1326 | 42 |
| 119 | R | C | 487 | 635 | 1281 | 28 |
| 119 | R | O | 497 | 627 | 1280 | 37 |
| 120 | G | N | 487 | 647 | 1277 | 31 |
| 120 | G | CA | 498 | 653 | 1269 | 29 |
| 120 | G | C | 496 | 668 | 1269 | 30 |
| 120 | G | O | 488 | 673 | 1277 | 34 |
| 121 | D | N | 503 | 675 | 1261 | 30 |
| 121 | D | CA | 502 | 689 | 1260 | 28 |
| 121 | D | CB | 514 | 696 | 1252 | 38 |
| 121 | D | CG | 527 | 692 | 1258 | 51 |
| 121 | D | OD1 | 533 | 682 | 1252 | 60 |
| 121 | D | OD2 | 532 | 699 | 1267 | 55 |
| 121 | D | C | 489 | 693 | 1254 | 21 |
| 121 | D | O | 483 | 703 | 1258 | 19 |
| 122 | S | N | 485 | 685 | 1244 | 16 |
| 122 | S | CA | 473 | 687 | 1237 | 15 |
| 122 | S | CB | 477 | 690 | 1222 | 15 |

TABLE 3-continued

| | | | | | | |
|---|---|---|---|---|---|---|
| 122 | S | OG | 485 | 679 | 1218 | 21 |
| 122 | S | C | 462 | 676 | 1237 | 14 |
| 122 | S | O | 453 | 676 | 1229 | 15 |
| 123 | R | N | 464 | 667 | 1247 | 11 |
| 123 | R | CA | 454 | 656 | 1247 | 13 |
| 123 | R | CB | 461 | 643 | 1242 | 15 |
| 123 | R | CG | 452 | 635 | 1232 | 26 |
| 123 | R | CD | 443 | 644 | 1224 | 29 |
| 123 | R | NE | 445 | 643 | 1210 | 27 |
| 123 | R | CZ | 448 | 632 | 1203 | 22 |
| 123 | R | NH1 | 449 | 620 | 1210 | 18 |
| 123 | R | NH2 | 449 | 632 | 1190 | 17 |
| 123 | R | C | 449 | 653 | 1262 | 13 |
| 123 | R | O | 457 | 655 | 1271 | 14 |
| 124 | G | N | 437 | 650 | 1263 | 15 |
| 124 | G | CA | 431 | 647 | 1276 | 15 |
| 124 | G | C | 420 | 636 | 1276 | 16 |
| 124 | G | O | 413 | 635 | 1266 | 16 |
| 125 | S | N | 420 | 628 | 1286 | 15 |
| 125 | S | CA | 410 | 616 | 1287 | 12 |
| 125 | S | CB | 417 | 604 | 1294 | 11 |
| 125 | S | OG | 425 | 597 | 1284 | 20 |
| 125 | S | C | 398 | 620 | 1295 | 14 |
| 125 | S | O | 398 | 624 | 1306 | 17 |
| 126 | L | N | 386 | 617 | 1289 | 14 |
| 126 | L | CA | 374 | 619 | 1296 | 12 |
| 126 | L | CB | 362 | 618 | 1286 | 10 |
| 126 | L | CG | 360 | 629 | 1275 | 9 |
| 126 | L | CD1 | 346 | 627 | 1269 | 10 |
| 126 | L | CD2 | 361 | 643 | 1282 | 13 |
| 126 | L | C | 372 | 608 | 1306 | 17 |
| 126 | L | O | 373 | 596 | 1302 | 20 |
| 127 | L | N | 370 | 612 | 1319 | 21 |
| 127 | L | CA | 369 | 602 | 1329 | 19 |
| 127 | L | CB | 368 | 608 | 1343 | 19 |
| 127 | L | CG | 379 | 618 | 1347 | 23 |
| 127 | L | CD1 | 377 | 623 | 1361 | 20 |
| 127 | L | CD2 | 392 | 611 | 1345 | 23 |
| 127 | L | C | 356 | 593 | 1326 | 20 |
| 127 | L | O | 355 | 582 | 1331 | 25 |
| 128 | S | N | 347 | 599 | 1318 | 22 |
| 128 | S | CA | 335 | 591 | 1314 | 21 |
| 128 | S | CB | 324 | 595 | 1323 | 20 |
| 128 | S | OG | 327 | 606 | 1331 | 37 |
| 128 | S | C | 332 | 594 | 1299 | 21 |
| 128 | S | O | 327 | 605 | 1296 | 20 |
| 129 | P | N | 335 | 584 | 1290 | 19 |
| 129 | P | CD | 340 | 571 | 1294 | 23 |
| 129 | P | CA | 332 | 586 | 1276 | 19 |
| 129 | P | CB | 334 | 572 | 1271 | 18 |
| 129 | P | CG | 343 | 565 | 1280 | 24 |
| 129 | P | C | 318 | 591 | 1273 | 23 |
| 129 | P | O | 309 | 589 | 1280 | 25 |
| 130 | R | N | 317 | 599 | 1262 | 26 |
| 130 | R | CA | 305 | 605 | 1258 | 27 |
| 130 | R | CB | 304 | 619 | 1263 | 35 |
| 130 | R | CG | 298 | 621 | 1277 | 41 |
| 130 | R | CD | 309 | 627 | 1286 | 45 |
| 130 | R | NE | 303 | 631 | 1299 | 50 |
| 130 | R | CZ | 310 | 633 | 1310 | 51 |
| 130 | R | NH1 | 323 | 632 | 1310 | 52 |
| 130 | R | NH2 | 304 | 637 | 1321 | 52 |
| 130 | R | C | 303 | 605 | 1243 | 24 |
| 130 | R | O | 313 | 606 | 1236 | 24 |
| 131 | P | N | 291 | 603 | 1238 | 21 |
| 131 | P | CD | 279 | 602 | 1247 | 16 |
| 131 | P | CA | 287 | 603 | 1224 | 24 |
| 131 | P | CB | 272 | 601 | 1224 | 22 |
| 131 | P | CG | 269 | 596 | 1237 | 17 |
| 131 | P | C | 291 | 617 | 1218 | 27 |
| 131 | P | O | 286 | 627 | 1223 | 32 |
| 132 | V | N | 300 | 617 | 1209 | 28 |
| 132 | V | CA | 305 | 629 | 1203 | 25 |
| 132 | V | CB | 312 | 627 | 1189 | 25 |
| 132 | V | CG1 | 315 | 612 | 1187 | 27 |
| 132 | V | CG2 | 302 | 631 | 1178 | 31 |
| 132 | V | C | 294 | 640 | 1201 | 23 |
| 132 | V | O | 297 | 652 | 1204 | 25 |
| 133 | S | N | 282 | 636 | 1198 | 15 |

TABLE 3-continued

| | | | | | | |
|---|---|---|---|---|---|---|
| 133 | S | CA | 271 | 646 | 1196 | 17 |
| 133 | S | CB | 258 | 638 | 1195 | 22 |
| 133 | S | OG | 254 | 634 | 1208 | 27 |
| 133 | S | C | 270 | 655 | 1208 | 16 |
| 133 | S | O | 266 | 666 | 1207 | 23 |
| 134 | Y | N | 275 | 650 | 1220 | 15 |
| 134 | Y | CA | 274 | 658 | 1232 | 15 |
| 134 | Y | CB | 276 | 649 | 1244 | 24 |
| 134 | Y | CG | 279 | 656 | 1257 | 37 |
| 134 | Y | CD1 | 270 | 666 | 1261 | 42 |
| 134 | Y | CE1 | 272 | 673 | 1273 | 47 |
| 134 | Y | CD2 | 290 | 654 | 1264 | 41 |
| 134 | Y | CE2 | 293 | 662 | 1276 | 46 |
| 134 | Y | CZ | 283 | 671 | 1280 | 49 |
| 134 | Y | OH | 286 | 679 | 1291 | 55 |
| 134 | Y | C | 285 | 669 | 1232 | 15 |
| 134 | Y | O | 282 | 680 | 1238 | 12 |
| 135 | L | N | 296 | 667 | 1226 | 14 |
| 135 | L | CA | 307 | 677 | 1226 | 11 |
| 135 | L | CB | 320 | 669 | 1226 | 15 |
| 135 | L | CG | 327 | 666 | 1239 | 10 |
| 135 | L | CD1 | 322 | 674 | 1250 | 13 |
| 135 | L | CD2 | 326 | 651 | 1242 | 25 |
| 135 | L | C | 306 | 686 | 1214 | 12 |
| 135 | L | O | 313 | 696 | 1213 | 8 |
| 136 | K | N | 298 | 682 | 1204 | 9 |
| 136 | K | CA | 297 | 690 | 1192 | 10 |
| 136 | K | CB | 288 | 683 | 1182 | 17 |
| 136 | K | CG | 294 | 671 | 1176 | 28 |
| 136 | K | CD | 296 | 671 | 1161 | 37 |
| 136 | K | CE | 310 | 671 | 1156 | 45 |
| 136 | K | NZ | 313 | 660 | 1147 | 45 |
| 136 | K | C | 291 | 704 | 1195 | 9 |
| 136 | K | O | 281 | 705 | 1202 | 14 |
| 137 | G | N | 297 | 714 | 1190 | 11 |
| 137 | G | CA | 293 | 728 | 1193 | 6 |
| 137 | G | C | 300 | 734 | 1205 | 4 |
| 137 | G | O | 297 | 745 | 1209 | 8 |
| 138 | S | N | 311 | 727 | 1209 | 2 |
| 138 | S | CA | 319 | 732 | 1220 | 7 |
| 138 | S | CB | 319 | 721 | 1231 | 7 |
| 138 | S | OG | 306 | 720 | 1237 | 11 |
| 138 | S | C | 333 | 735 | 1216 | 8 |
| 138 | S | O | 341 | 740 | 1225 | 14 |
| 139 | A | N | 336 | 734 | 1204 | 9 |
| 139 | A | CA | 350 | 737 | 1199 | 7 |
| 139 | A | CB | 351 | 735 | 1184 | 8 |
| 139 | A | C | 351 | 752 | 1202 | 6 |
| 139 | A | O | 341 | 760 | 1200 | 3 |
| 140 | G | N | 362 | 756 | 1208 | 4 |
| 140 | G | CA | 364 | 770 | 1212 | 4 |
| 140 | G | C | 363 | 771 | 1227 | 5 |
| 140 | G | O | 369 | 781 | 1232 | 8 |
| 141 | G | N | 357 | 762 | 1233 | 6 |
| 141 | G | CA | 355 | 763 | 1248 | 5 |
| 141 | G | C | 369 | 761 | 1255 | 11 |
| 141 | G | O | 378 | 755 | 1249 | 9 |
| 142 | P | N | 370 | 764 | 1268 | 9 |
| 142 | P | CD | 360 | 771 | 1276 | 8 |
| 142 | P | CA | 382 | 762 | 1275 | 11 |
| 142 | P | CB | 382 | 774 | 1285 | 11 |
| 142 | P | CG | 368 | 776 | 1288 | 5 |
| 142 | P | C | 384 | 749 | 1283 | 13 |
| 142 | P | O | 374 | 743 | 1287 | 15 |
| 143 | L | N | 396 | 745 | 1285 | 15 |
| 143 | L | CA | 400 | 734 | 1293 | 13 |
| 143 | L | CB | 411 | 726 | 1287 | 16 |
| 143 | L | CG | 408 | 714 | 1278 | 15 |
| 143 | L | CD1 | 401 | 703 | 1286 | 12 |
| 143 | L | CD2 | 399 | 718 | 1266 | 21 |
| 143 | L | C | 405 | 741 | 1305 | 11 |
| 143 | L | O | 414 | 749 | 1304 | 13 |
| 144 | L | N | 398 | 739 | 1317 | 10 |
| 144 | L | CA | 402 | 747 | 1329 | 10 |
| 144 | L | CB | 390 | 752 | 1336 | 9 |
| 144 | L | CG | 384 | 766 | 1332 | 7 |
| 144 | L | CD1 | 390 | 771 | 1319 | 6 |
| 144 | L | CD2 | 369 | 764 | 1331 | 7 |
| 144 | L | C | 410 | 738 | 1338 | 11 |
| 144 | L | O | 410 | 726 | 1338 | 14 |
| 145 | C | N | 418 | 745 | 1347 | 15 |
| 145 | C | CA | 426 | 738 | 1357 | 18 |
| 145 | C | CB | 440 | 745 | 1359 | 20 |
| 145 | C | SG | 440 | 760 | 1369 | 29 |
| 145 | C | C | 417 | 739 | 1370 | 16 |
| 145 | C | O | 408 | 748 | 1370 | 15 |
| 146 | P | N | 420 | 731 | 1380 | 17 |
| 146 | P | CD | 431 | 721 | 1382 | 18 |
| 146 | P | CA | 412 | 732 | 1392 | 18 |
| 146 | P | CB | 419 | 723 | 1402 | 14 |
| 146 | P | CG | 427 | 714 | 1394 | 17 |
| 146 | P | C | 411 | 747 | 1398 | 21 |
| 146 | P | O | 401 | 750 | 1404 | 20 |
| 147 | S | N | 420 | 755 | 1394 | 26 |
| 147 | S | CA | 421 | 769 | 1399 | 25 |
| 147 | S | CB | 435 | 775 | 1398 | 29 |
| 147 | S | OG | 444 | 765 | 1400 | 44 |
| 147 | S | C | 412 | 778 | 1390 | 19 |
| 147 | S | O | 409 | 789 | 1393 | 22 |
| 148 | G | N | 407 | 772 | 1379 | 13 |
| 148 | G | CA | 398 | 780 | 1370 | 12 |
| 148 | G | C | 406 | 788 | 1359 | 13 |
| 148 | G | O | 401 | 797 | 1353 | 15 |
| 149 | H | N | 419 | 784 | 1358 | 12 |
| 149 | H | CA | 427 | 791 | 1348 | 10 |
| 149 | H | CB | 441 | 794 | 1354 | 13 |
| 149 | H | CG | 441 | 805 | 1364 | 18 |
| 149 | H | CD2 | 444 | 805 | 1377 | 21 |
| 149 | H | ND1 | 437 | 818 | 1361 | 22 |
| 149 | H | CE1 | 438 | 825 | 1371 | 22 |
| 149 | H | NE2 | 442 | 818 | 1382 | 25 |
| 149 | H | C | 428 | 783 | 1336 | 8 |
| 149 | H | O | 426 | 771 | 1336 | 7 |
| 150 | A | N | 431 | 789 | 1324 | 8 |
| 150 | A | CA | 431 | 783 | 1312 | 8 |
| 150 | A | CB | 430 | 793 | 1300 | 2 |
| 150 | A | C | 443 | 774 | 1309 | 11 |
| 150 | A | O | 454 | 777 | 1311 | 15 |
| 151 | V | N | 440 | 762 | 1304 | 10 |
| 151 | V | CA | 450 | 752 | 1300 | 11 |
| 151 | V | CB | 447 | 738 | 1306 | 11 |
| 151 | V | CG1 | 456 | 728 | 1301 | 9 |
| 151 | V | CG2 | 447 | 739 | 1321 | 9 |
| 151 | V | C | 451 | 751 | 1285 | 11 |
| 151 | V | O | 461 | 748 | 1279 | 9 |
| 152 | G | N | 440 | 754 | 1278 | 6 |
| 152 | G | CA | 439 | 754 | 1264 | 6 |
| 152 | G | C | 425 | 755 | 1259 | 8 |
| 152 | G | O | 415 | 755 | 1266 | 9 |
| 153 | I | N | 423 | 756 | 1245 | 9 |
| 153 | I | CA | 410 | 756 | 1239 | 6 |
| 153 | I | CB | 409 | 769 | 1230 | 8 |
| 153 | I | CG2 | 417 | 781 | 1235 | 5 |
| 153 | I | CG1 | 413 | 765 | 1216 | 13 |
| 153 | I | CD1 | 410 | 775 | 1205 | 25 |
| 153 | I | C | 407 | 743 | 1232 | 7 |
| 153 | I | O | 414 | 738 | 1224 | 9 |
| 154 | F | N | 395 | 738 | 1236 | 8 |
| 154 | F | CA | 390 | 726 | 1230 | 6 |
| 154 | F | CB | 376 | 723 | 1236 | 5 |
| 154 | F | CG | 369 | 711 | 1231 | 3 |
| 154 | F | CD1 | 376 | 699 | 1230 | 2 |
| 154 | F | CD2 | 356 | 711 | 1226 | 4 |
| 154 | F | CE1 | 370 | 688 | 1225 | 7 |
| 154 | F | CE2 | 350 | 700 | 1222 | 5 |
| 154 | F | CZ | 357 | 688 | 1221 | 10 |
| 154 | F | C | 389 | 727 | 1215 | 6 |
| 154 | F | O | 385 | 738 | 1210 | 6 |
| 155 | R | N | 393 | 717 | 1208 | 9 |
| 155 | R | CA | 393 | 718 | 1194 | 10 |
| 155 | R | CB | 407 | 721 | 1189 | 9 |
| 155 | R | CG | 411 | 717 | 1176 | 9 |
| 155 | R | CD | 426 | 715 | 1175 | 11 |
| 155 | R | NE | 428 | 701 | 1169 | 17 |
| 155 | R | CZ | 422 | 697 | 1158 | 23 |
| 155 | R | NH1 | 414 | 705 | 1151 | 27 |
| 155 | R | NH2 | 425 | 685 | 1153 | 22 |
| 155 | R | C | 388 | 705 | 1186 | 14 |

TABLE 3-continued

| | | | | | | |
|---|---|---|---|---|---|---|
| 155 | R | O | 384 | 706 | 1174 | 17 |
| 156 | A | N | 388 | 694 | 1193 | 11 |
| 156 | A | CA | 384 | 681 | 1186 | 11 |
| 156 | A | CB | 394 | 677 | 1175 | 7 |
| 156 | A | C | 382 | 670 | 1197 | 12 |
| 156 | A | O | 388 | 670 | 1208 | 12 |
| 157 | A | N | 374 | 660 | 1193 | 10 |
| 157 | A | CA | 371 | 648 | 1202 | 8 |
| 157 | A | CB | 356 | 646 | 1201 | 2 |
| 157 | A | C | 378 | 635 | 1202 | 10 |
| 157 | A | O | 379 | 629 | 1213 | 16 |
| 158 | V | N | 384 | 630 | 1191 | 12 |
| 158 | V | CA | 390 | 617 | 1192 | 10 |
| 158 | V | CB | 402 | 617 | 1202 | 6 |
| 158 | V | CG1 | 409 | 603 | 1202 | 7 |
| 158 | V | CG2 | 412 | 628 | 1199 | 12 |
| 158 | V | C | 381 | 606 | 1197 | 13 |
| 158 | V | O | 379 | 604 | 1209 | 18 |
| 159 | C | N | 374 | 599 | 1188 | 17 |
| 159 | C | CA | 365 | 589 | 1191 | 16 |
| 159 | C | CB | 352 | 592 | 1183 | 16 |
| 159 | C | SG | 346 | 608 | 1186 | 24 |
| 159 | C | C | 369 | 574 | 1188 | 18 |
| 159 | C | O | 379 | 571 | 1183 | 21 |
| 160 | T | N | 360 | 566 | 1192 | 17 |
| 160 | T | CA | 361 | 551 | 1190 | 20 |
| 160 | T | CB | 367 | 545 | 1203 | 18 |
| 160 | T | OG1 | 381 | 549 | 1205 | 22 |
| 160 | T | CG2 | 367 | 530 | 1202 | 18 |
| 160 | T | C | 347 | 546 | 1188 | 21 |
| 160 | T | O | 339 | 545 | 1197 | 23 |
| 161 | R | N | 344 | 544 | 1175 | 19 |
| 161 | R | CA | 331 | 539 | 1172 | 21 |
| 161 | R | CB | 330 | 525 | 1178 | 23 |
| 161 | R | CG | 333 | 513 | 1168 | 24 |
| 161 | R | CD | 334 | 500 | 1175 | 27 |
| 161 | R | NE | 344 | 500 | 1185 | 23 |
| 161 | R | CZ | 342 | 497 | 1198 | 21 |
| 161 | R | NH1 | 330 | 494 | 1203 | 32 |
| 161 | R | NH2 | 352 | 497 | 1207 | 18 |
| 161 | R | C | 320 | 548 | 1176 | 20 |
| 161 | R | O | 309 | 543 | 1180 | 22 |
| 162 | G | N | 323 | 561 | 1176 | 19 |
| 162 | G | CA | 312 | 570 | 1179 | 18 |
| 162 | G | C | 312 | 576 | 1193 | 16 |
| 162 | G | O | 305 | 586 | 1195 | 17 |
| 163 | V | N | 319 | 570 | 1203 | 11 |
| 163 | V | CA | 319 | 576 | 1216 | 12 |
| 163 | V | CB | 316 | 566 | 1228 | 13 |
| 163 | V | CG1 | 308 | 555 | 1222 | 9 |
| 163 | V | CG2 | 329 | 561 | 1234 | 18 |
| 163 | V | C | 333 | 583 | 1218 | 14 |
| 163 | V | O | 343 | 578 | 1214 | 13 |
| 164 | A | N | 332 | 595 | 1224 | 12 |
| 164 | A | CA | 345 | 602 | 1227 | 13 |
| 164 | A | CB | 342 | 617 | 1228 | 4 |
| 164 | A | C | 351 | 597 | 1240 | 17 |
| 164 | A | O | 344 | 596 | 1250 | 19 |
| 165 | K | N | 364 | 594 | 1239 | 16 |
| 165 | K | CA | 371 | 589 | 1251 | 14 |
| 165 | K | CB | 376 | 575 | 1248 | 25 |
| 165 | K | CG | 390 | 575 | 1242 | 29 |
| 165 | K | CD | 390 | 577 | 1227 | 35 |
| 165 | K | CE | 397 | 565 | 1221 | 44 |
| 165 | K | NZ | 405 | 557 | 1231 | 45 |
| 165 | K | C | 382 | 598 | 1255 | 13 |
| 165 | K | O | 387 | 597 | 1266 | 16 |
| 166 | A | N | 385 | 608 | 1246 | 10 |
| 166 | A | CA | 395 | 618 | 1249 | 4 |
| 166 | A | CB | 409 | 613 | 1245 | 2 |
| 166 | A | C | 392 | 630 | 1242 | 7 |
| 166 | A | O | 383 | 631 | 1234 | 8 |
| 167 | V | N | 400 | 641 | 1244 | 9 |
| 167 | V | CA | 398 | 654 | 1237 | 7 |
| 167 | V | CB | 390 | 664 | 1246 | 11 |
| 167 | V | CG1 | 376 | 659 | 1249 | 2 |
| 167 | V | CG2 | 398 | 666 | 1259 | 3 |
| 167 | V | C | 411 | 659 | 1233 | 7 |
| 167 | V | O | 421 | 657 | 1239 | 6 |
| 168 | D | N | 411 | 667 | 1222 | 11 |
| 168 | D | CA | 423 | 673 | 1217 | 14 |
| 168 | D | CB | 424 | 670 | 1202 | 22 |
| 168 | D | CG | 437 | 675 | 1197 | 34 |
| 168 | D | OD1 | 448 | 669 | 1199 | 36 |
| 168 | D | OD2 | 437 | 686 | 1190 | 41 |
| 168 | D | C | 421 | 689 | 1219 | 12 |
| 168 | D | O | 410 | 694 | 1214 | 15 |
| 169 | F | N | 430 | 695 | 1225 | 10 |
| 169 | F | CA | 429 | 710 | 1227 | 4 |
| 169 | F | CB | 426 | 712 | 1242 | 7 |
| 169 | F | CG | 435 | 706 | 1252 | 3 |
| 169 | F | CD1 | 447 | 713 | 1256 | 4 |
| 169 | F | CD2 | 433 | 694 | 1257 | 2 |
| 169 | F | CE1 | 456 | 708 | 1265 | 2 |
| 169 | F | CE2 | 442 | 688 | 1267 | 4 |
| 169 | F | CZ | 453 | 695 | 1271 | 2 |
| 169 | F | C | 442 | 717 | 1223 | 5 |
| 169 | F | O | 453 | 711 | 1222 | 3 |
| 170 | V | N | 441 | 730 | 1221 | 7 |
| 170 | V | CA | 453 | 738 | 1218 | 7 |
| 170 | V | CB | 449 | 750 | 1209 | 10 |
| 170 | V | CG1 | 462 | 758 | 1205 | 5 |
| 170 | V | CG2 | 441 | 746 | 1197 | 15 |
| 170 | V | C | 459 | 743 | 1231 | 11 |
| 170 | V | O | 453 | 751 | 1238 | 11 |
| 171 | P | N | 471 | 739 | 1234 | 10 |
| 171 | P | CD | 480 | 730 | 1226 | 7 |
| 171 | P | CA | 478 | 743 | 1246 | 5 |
| 171 | P | CB | 491 | 736 | 1246 | 3 |
| 171 | P | CG | 494 | 732 | 1232 | 5 |
| 171 | P | C | 479 | 759 | 1248 | 7 |
| 171 | P | O | 483 | 765 | 1238 | 12 |
| 172 | V | N | 477 | 764 | 1260 | 10 |
| 172 | V | CA | 478 | 778 | 1262 | 11 |
| 172 | V | CB | 474 | 781 | 1277 | 10 |
| 172 | V | CG1 | 485 | 778 | 1286 | 8 |
| 172 | V | CG2 | 469 | 795 | 1278 | 2 |
| 172 | V | C | 492 | 784 | 1259 | 16 |
| 172 | V | O | 493 | 795 | 1255 | 19 |
| 173 | E | N | 502 | 776 | 1261 | 15 |
| 173 | E | CA | 515 | 781 | 1258 | 17 |
| 173 | E | CB | 526 | 770 | 1261 | 20 |
| 173 | E | CG | 520 | 756 | 1263 | 40 |
| 173 | E | CD | 512 | 755 | 1276 | 41 |
| 173 | E | OE1 | 500 | 753 | 1275 | 43 |
| 173 | E | OE2 | 518 | 756 | 1287 | 45 |
| 173 | E | C | 516 | 784 | 1243 | 17 |
| 173 | E | O | 523 | 794 | 1240 | 24 |
| 174 | S | N | 510 | 777 | 1234 | 17 |
| 174 | S | CA | 510 | 779 | 1220 | 14 |
| 174 | S | CB | 502 | 769 | 1213 | 9 |
| 174 | S | OG | 509 | 757 | 1210 | 10 |
| 174 | S | C | 505 | 793 | 1217 | 19 |
| 174 | S | O | 510 | 801 | 1209 | 19 |
| 175 | M | N | 494 | 797 | 1224 | 17 |
| 175 | M | CA | 488 | 810 | 1222 | 14 |
| 175 | M | CB | 474 | 810 | 1229 | 9 |
| 175 | M | CG | 465 | 798 | 1226 | 11 |
| 175 | M | SD | 450 | 797 | 1236 | 17 |
| 175 | M | CE | 451 | 781 | 1242 | 19 |
| 175 | M | C | 496 | 820 | 1228 | 14 |
| 175 | M | O | 497 | 832 | 1222 | 14 |
| 176 | E | N | 504 | 817 | 1239 | 17 |
| 176 | E | CA | 513 | 827 | 1245 | 21 |
| 176 | E | CB | 519 | 821 | 1258 | 22 |
| 176 | E | CG | 509 | 822 | 1269 | 35 |
| 176 | E | CD | 515 | 818 | 1283 | 42 |
| 176 | E | OE1 | 525 | 809 | 1282 | 47 |
| 176 | E | OE2 | 511 | 823 | 1293 | 41 |
| 176 | E | C | 524 | 830 | 1235 | 22 |
| 176 | E | O | 527 | 842 | 1233 | 25 |
| 177 | T | N | 529 | 820 | 1228 | 22 |
| 177 | T | CA | 539 | 822 | 1218 | 21 |
| 177 | T | CB | 543 | 809 | 1212 | 18 |
| 177 | T | OG1 | 549 | 800 | 1222 | 24 |
| 177 | T | CG2 | 553 | 811 | 1201 | 20 |
| 177 | T | C | 534 | 831 | 1207 | 23 |
| 177 | T | O | 540 | 842 | 1204 | 24 |

TABLE 3-continued

| | | | | | | |
|---|---|---|---|---|---|---|
| 178 | T | N | 523 | 827 | 1201 | 24 |
| 178 | T | CA | 516 | 834 | 1190 | 20 |
| 178 | T | CB | 502 | 829 | 1188 | 20 |
| 178 | T | OG1 | 503 | 816 | 1182 | 21 |
| 178 | T | CG2 | 494 | 838 | 1179 | 21 |
| 178 | T | C | 515 | 849 | 1194 | 19 |
| 178 | T | O | 518 | 858 | 1186 | 21 |
| 179 | M | N | 511 | 852 | 1206 | 15 |
| 179 | M | CA | 509 | 865 | 1210 | 14 |
| 179 | M | CB | 502 | 866 | 1224 | 13 |
| 179 | M | CG | 487 | 863 | 1223 | 12 |
| 179 | M | SD | 479 | 866 | 1238 | 12 |
| 179 | M | CE | 477 | 884 | 1239 | 17 |
| 179 | M | C | 522 | 874 | 1211 | 19 |
| 179 | M | O | 521 | 886 | 1211 | 18 |
| 180 | R | N | 533 | 867 | 1212 | 20 |
| 180 | R | CA | 545 | 874 | 1212 | 22 |
| 180 | R | CB | 554 | 869 | 1224 | 23 |
| 180 | R | CG | 562 | 856 | 1220 | 37 |
| 180 | R | CD | 571 | 852 | 1232 | 45 |
| 180 | R | NE | 564 | 852 | 1245 | 51 |
| 180 | R | CZ | 562 | 841 | 1252 | 57 |
| 180 | R | NH1 | 567 | 829 | 1248 | 57 |
| 180 | R | NH2 | 555 | 841 | 1263 | 59 |
| 180 | R | C | 553 | 874 | 1199 | 20 |
| 180 | R | O | 562 | 882 | 1197 | 24 |
| 181 | S | N | 548 | 866 | 1190 | 19 |
| 181 | S | CA | 554 | 866 | 1176 | 16 |
| 181 | S | CB | 552 | 852 | 1170 | 18 |
| 181 | S | OG | 554 | 842 | 1180 | 25 |
| 181 | S | C | 548 | 876 | 1167 | 14 |
| 181 | S | O | 538 | 882 | 1170 | 15 |
| 182 | P | N | 554 | 878 | 1155 | 14 |
| 182 | P | CD | 566 | 871 | 1150 | 12 |
| 182 | P | CA | 550 | 888 | 1145 | 15 |
| 182 | P | CB | 560 | 887 | 1134 | 10 |
| 182 | P | CG | 571 | 880 | 1139 | 18 |
| 182 | P | C | 535 | 885 | 1140 | 14 |
| 182 | P | O | 531 | 874 | 1139 | 20 |
| 183 | V | N | 528 | 896 | 1138 | 12 |
| 183 | V | CA | 514 | 895 | 1133 | 9 |
| 183 | V | CB | 506 | 908 | 1138 | 8 |
| 183 | V | CG1 | 493 | 909 | 1131 | 2 |
| 183 | V | CG2 | 503 | 906 | 1153 | 4 |
| 183 | V | C | 514 | 895 | 1118 | 14 |
| 183 | V | O | 505 | 889 | 1112 | 19 |
| 184 | F | N | 524 | 901 | 1112 | 13 |
| 184 | F | CA | 526 | 901 | 1097 | 11 |
| 184 | F | CB | 526 | 915 | 1092 | 7 |
| 184 | F | CG | 514 | 924 | 1097 | 8 |
| 184 | F | CD1 | 502 | 923 | 1090 | 12 |
| 184 | F | CD2 | 514 | 932 | 1108 | 2 |
| 184 | F | CE1 | 491 | 931 | 1094 | 7 |
| 184 | F | CE2 | 503 | 939 | 1112 | 4 |
| 184 | F | CZ | 492 | 939 | 1105 | 5 |
| 184 | F | C | 539 | 894 | 1094 | 17 |
| 184 | F | O | 549 | 896 | 1100 | 19 |
| 185 | T | N | 539 | 886 | 1083 | 21 |
| 185 | T | CA | 551 | 880 | 1079 | 26 |
| 185 | T | CB | 551 | 865 | 1083 | 30 |
| 185 | T | OG1 | 552 | 865 | 1098 | 38 |
| 185 | T | CG2 | 562 | 857 | 1077 | 32 |
| 185 | T | C | 552 | 880 | 1064 | 26 |
| 185 | T | O | 542 | 880 | 1056 | 27 |
| 186 | D | N | 565 | 881 | 1059 | 29 |
| 186 | D | CA | 568 | 882 | 1045 | 30 |
| 186 | D | CB | 579 | 892 | 1043 | 30 |
| 186 | D | CG | 581 | 896 | 1028 | 34 |
| 186 | D | OD1 | 571 | 899 | 1022 | 34 |
| 186 | D | OD2 | 592 | 896 | 1024 | 41 |
| 186 | D | C | 572 | 868 | 1039 | 30 |
| 186 | D | O | 582 | 862 | 1044 | 32 |
| 187 | N | N | 565 | 864 | 1028 | 29 |
| 187 | N | CA | 568 | 852 | 1021 | 26 |
| 187 | N | CB | 557 | 841 | 1024 | 29 |
| 187 | N | CG | 556 | 838 | 1039 | 30 |
| 187 | N | OD1 | 545 | 840 | 1045 | 29 |
| 187 | N | ND2 | 566 | 832 | 1044 | 30 |
| 187 | N | C | 568 | 854 | 1006 | 25 |
| 187 | N | O | 573 | 846 | 999 | 28 |
| 188 | S | N | 563 | 866 | 1003 | 26 |
| 188 | S | CA | 563 | 871 | 989 | 28 |
| 188 | S | CB | 558 | 886 | 989 | 30 |
| 188 | S | OG | 565 | 893 | 998 | 32 |
| 188 | S | C | 575 | 870 | 980 | 31 |
| 188 | S | O | 574 | 869 | 968 | 31 |
| 189 | S | N | 587 | 869 | 986 | 32 |
| 189 | S | CA | 599 | 868 | 978 | 32 |
| 189 | S | CB | 609 | 878 | 983 | 34 |
| 189 | S | OG | 606 | 891 | 978 | 37 |
| 189 | S | C | 605 | 854 | 978 | 33 |
| 189 | S | O | 606 | 848 | 988 | 33 |
| 190 | P | N | 609 | 849 | 966 | 33 |
| 190 | P | CD | 609 | 856 | 953 | 36 |
| 190 | P | CA | 615 | 836 | 965 | 32 |
| 190 | P | CB | 618 | 835 | 950 | 33 |
| 190 | P | CG | 618 | 849 | 945 | 37 |
| 190 | P | C | 628 | 835 | 974 | 79 |
| 190 | P | O | 636 | 844 | 974 | 29 |
| 191 | P | N | 629 | 824 | 981 | 25 |
| 191 | P | CD | 620 | 813 | 982 | 24 |
| 191 | P | CA | 641 | 823 | 989 | 25 |
| 191 | P | CB | 638 | 810 | 998 | 23 |
| 191 | P | CG | 629 | 802 | 989 | 25 |
| 191 | P | C | 654 | 820 | 982 | 26 |
| 191 | P | O | 654 | 815 | 970 | 24 |
| 192 | A | N | 665 | 825 | 987 | 27 |
| 192 | A | CA | 678 | 823 | 981 | 24 |
| 192 | A | CB | 688 | 833 | 986 | 28 |
| 192 | A | C | 681 | 809 | 985 | 24 |
| 192 | A | O | 678 | 805 | 996 | 24 |
| 193 | V | N | 688 | 801 | 977 | 24 |
| 193 | V | CA | 692 | 787 | 980 | 21 |
| 193 | V | CB | 699 | 781 | 968 | 19 |
| 193 | V | CG1 | 699 | 766 | 969 | 12 |
| 193 | V | CG2 | 692 | 785 | 955 | 19 |
| 193 | V | C | 700 | 787 | 992 | 23 |
| 193 | V | O | 711 | 793 | 993 | 27 |
| 194 | P | N | 695 | 779 | 1002 | 23 |
| 194 | P | CD | 682 | 772 | 1003 | 17 |
| 194 | P | CA | 703 | 778 | 1015 | 24 |
| 194 | P | CB | 692 | 773 | 1025 | 20 |
| 194 | P | CG | 683 | 766 | 1016 | 16 |
| 194 | P | C | 714 | 768 | 1013 | 25 |
| 194 | P | O | 715 | 761 | 1003 | 29 |
| 195 | Q | N | 723 | 768 | 1023 | 24 |
| 195 | Q | CA | 735 | 759 | 1022 | 26 |
| 195 | Q | CB | 746 | 763 | 1032 | 33 |
| 195 | Q | CG | 746 | 754 | 1045 | 45 |
| 195 | Q | CD | 759 | 747 | 1046 | 49 |
| 195 | Q | OE1 | 760 | 734 | 1046 | 53 |
| 195 | Q | NE2 | 770 | 754 | 1047 | 53 |
| 195 | Q | C | 730 | 744 | 1025 | 24 |
| 195 | Q | O | 736 | 735 | 1020 | 25 |
| 196 | S | N | 720 | 743 | 1033 | 22 |
| 196 | S | CA | 715 | 730 | 1037 | 21 |
| 196 | S | CB | 718 | 727 | 1051 | 24 |
| 196 | S | OG | 706 | 723 | 1059 | 35 |
| 196 | S | C | 700 | 729 | 1034 | 16 |
| 196 | S | O | 693 | 739 | 1035 | 17 |
| 197 | F | N | 694 | 717 | 1031 | 14 |
| 197 | F | CA | 680 | 715 | 1028 | 13 |
| 197 | F | CB | 676 | 701 | 1030 | 10 |
| 197 | F | CG | 662 | 698 | 1027 | 12 |
| 197 | F | CD1 | 658 | 696 | 1014 | 7 |
| 197 | F | CD2 | 652 | 698 | 1038 | 8 |
| 197 | F | CE1 | 644 | 694 | 1012 | 11 |
| 197 | F | CE2 | 639 | 695 | 1035 | 5 |
| 197 | F | CZ | 635 | 694 | 1022 | 13 |
| 197 | F | C | 671 | 724 | 1036 | 14 |
| 197 | F | O | 671 | 724 | 1048 | 20 |
| 198 | Q | N | 662 | 731 | 1029 | 15 |
| 198 | Q | CA | 652 | 740 | 1035 | 15 |
| 198 | Q | CB | 658 | 754 | 1036 | 24 |
| 198 | Q | CG | 656 | 761 | 1049 | 40 |
| 198 | Q | CD | 665 | 754 | 1060 | 46 |
| 198 | Q | OE1 | 660 | 747 | 1069 | 50 |
| 198 | Q | NE2 | 678 | 758 | 1059 | 51 |

TABLE 3-continued

| | | | | | | |
|---|---|---|---|---|---|---|
| 198 | Q | C | 639 | 740 | 1028 | 15 |
| 198 | Q | O | 639 | 738 | 1016 | 17 |
| 199 | V | N | 628 | 741 | 1035 | 14 |
| 199 | V | CA | 615 | 741 | 1030 | 15 |
| 199 | V | CB | 605 | 732 | 1037 | 12 |
| 199 | V | CG1 | 592 | 730 | 1029 | 11 |
| 199 | V | CG2 | 611 | 719 | 1040 | 15 |
| 199 | V | C | 610 | 755 | 1031 | 16 |
| 199 | V | O | 610 | 761 | 1042 | 20 |
| 200 | A | N | 607 | 762 | 1020 | 13 |
| 200 | A | CA | 603 | 776 | 1020 | 12 |
| 200 | A | CB | 613 | 784 | 1012 | 12 |
| 200 | A | C | 589 | 778 | 1014 | 10 |
| 200 | A | O | 585 | 770 | 1005 | 11 |
| 201 | H | N | 582 | 788 | 1018 | 14 |
| 201 | H | CA | 569 | 791 | 1013 | 13 |
| 201 | H | CB | 560 | 794 | 1025 | 12 |
| 201 | H | CG | 557 | 782 | 1033 | 12 |
| 201 | H | CD2 | 564 | 775 | 1042 | 11 |
| 201 | H | ND1 | 545 | 774 | 1031 | 14 |
| 201 | H | CE1 | 546 | 764 | 1038 | 15 |
| 201 | H | NE2 | 557 | 764 | 1046 | 11 |
| 201 | H | C | 570 | 804 | 1004 | 11 |
| 201 | H | O | 576 | 814 | 1008 | 12 |
| 202 | L | N | 564 | 803 | 993 | 14 |
| 202 | L | CA | 563 | 814 | 983 | 11 |
| 202 | L | CB | 570 | 811 | 970 | 12 |
| 202 | L | CG | 569 | 821 | 959 | 5 |
| 202 | L | CD1 | 573 | 835 | 964 | 11 |
| 202 | L | CD2 | 578 | 817 | 947 | 2 |
| 202 | L | C | 549 | 818 | 980 | 14 |
| 202 | L | O | 542 | 810 | 974 | 17 |
| 203 | H | N | 544 | 829 | 986 | 13 |
| 203 | H | CA | 531 | 834 | 984 | 15 |
| 203 | H | CB | 524 | 836 | 997 | 17 |
| 203 | H | CG | 525 | 825 | 1007 | 17 |
| 203 | H | CD2 | 526 | 812 | 1005 | 17 |
| 203 | H | ND1 | 525 | 827 | 1021 | 19 |
| 203 | H | CE1 | 525 | 815 | 1027 | 14 |
| 203 | H | NE2 | 526 | 806 | 1017 | 18 |
| 203 | H | C | 531 | 846 | 975 | 20 |
| 203 | H | O | 535 | 857 | 980 | 27 |
| 204 | A | N | 528 | 845 | 963 | 18 |
| 204 | A | CA | 528 | 856 | 954 | 20 |
| 204 | A | CB | 541 | 856 | 946 | 24 |
| 204 | A | C | 516 | 856 | 945 | 19 |
| 204 | A | O | 512 | 845 | 940 | 19 |
| 205 | P | N | 511 | 868 | 941 | 20 |
| 205 | P | CD | 516 | 881 | 945 | 17 |
| 205 | P | CA | 499 | 869 | 932 | 21 |
| 205 | P | CB | 498 | 883 | 929 | 17 |
| 205 | P | CG | 505 | 890 | 941 | 17 |
| 205 | P | C | 501 | 860 | 920 | 24 |
| 205 | P | O | 512 | 856 | 917 | 27 |
| 206 | T | N | 490 | 858 | 913 | 27 |
| 206 | T | CA | 491 | 850 | 900 | 30 |
| 206 | T | CB | 477 | 846 | 895 | 31 |
| 206 | T | OG1 | 470 | 839 | 905 | 32 |
| 206 | T | CG2 | 478 | 838 | 883 | 27 |
| 206 | T | C | 499 | 858 | 890 | 32 |
| 206 | T | O | 499 | 870 | 890 | 32 |
| 207 | G | N | 505 | 851 | 880 | 33 |
| 207 | G | CA | 513 | 858 | 870 | 34 |
| 207 | G | C | 525 | 864 | 876 | 34 |
| 207 | G | O | 531 | 872 | 868 | 41 |
| 208 | S | N | 528 | 862 | 888 | 31 |
| 208 | S | CA | 540 | 868 | 894 | 28 |
| 208 | S | CB | 539 | 867 | 909 | 30 |
| 208 | S | OG | 545 | 855 | 914 | 45 |
| 208 | S | C | 553 | 860 | 889 | 23 |
| 208 | S | O | 564 | 865 | 892 | 20 |
| 209 | G | N | 551 | 849 | 882 | 23 |
| 209 | G | CA | 562 | 842 | 877 | 23 |
| 209 | G | C | 568 | 831 | 886 | 22 |
| 209 | G | O | 580 | 829 | 886 | 23 |
| 210 | K | N | 560 | 825 | 895 | 23 |
| 210 | K | CA | 565 | 815 | 904 | 23 |
| 210 | K | CB | 554 | 812 | 915 | 20 |
| 210 | K | CG | 548 | 824 | 921 | 11 |
| 210 | K | CD | 539 | 819 | 933 | 8 |
| 210 | K | CE | 526 | 814 | 928 | 9 |
| 210 | K | NZ | 517 | 825 | 923 | 8 |
| 210 | K | C | 568 | 802 | 897 | 24 |
| 210 | K | O | 577 | 795 | 900 | 26 |
| 211 | S | N | 561 | 800 | 886 | 25 |
| 211 | S | CA | 563 | 788 | 878 | 26 |
| 211 | S | CB | 550 | 782 | 873 | 21 |
| 211 | S | OG | 540 | 791 | 871 | 31 |
| 211 | S | C | 572 | 791 | 866 | 25 |
| 211 | S | O | 575 | 782 | 858 | 25 |
| 212 | T | N | 576 | 803 | 864 | 26 |
| 212 | T | CA | 584 | 807 | 853 | 21 |
| 212 | T | CB | 576 | 815 | 842 | 20 |
| 212 | T | OG1 | 569 | 826 | 848 | 26 |
| 212 | T | CG2 | 566 | 805 | 836 | 18 |
| 212 | T | C | 596 | 816 | 856 | 19 |
| 212 | T | O | 607 | 812 | 855 | 22 |
| 213 | K | N | 593 | 828 | 861 | 20 |
| 213 | K | CA | 604 | 837 | 865 | 21 |
| 213 | K | CB | 598 | 851 | 869 | 23 |
| 213 | K | CG | 605 | 862 | 862 | 21 |
| 213 | K | CD | 596 | 875 | 862 | 30 |
| 213 | K | CE | 597 | 882 | 878 | 38 |
| 213 | K | NZ | 610 | 890 | 876 | 42 |
| 213 | K | C | 613 | 831 | 876 | 21 |
| 213 | K | O | 625 | 831 | 874 | 27 |
| 214 | V | N | 607 | 826 | 886 | 21 |
| 214 | V | CA | 615 | 821 | 897 | 19 |
| 214 | V | CB | 605 | 816 | 909 | 16 |
| 214 | V | CG1 | 613 | 811 | 920 | 12 |
| 214 | V | CG2 | 597 | 828 | 913 | 9 |
| 214 | V | C | 624 | 809 | 894 | 20 |
| 214 | V | O | 636 | 809 | 898 | 21 |
| 215 | P | N | 619 | 799 | 886 | 17 |
| 215 | P | CD | 605 | 798 | 881 | 19 |
| 215 | P | CA | 627 | 788 | 882 | 14 |
| 215 | P | CB | 617 | 778 | 875 | 12 |
| 215 | P | CG | 604 | 784 | 878 | 18 |
| 215 | P | C | 638 | 792 | 873 | 18 |
| 215 | P | O | 650 | 788 | 874 | 19 |
| 216 | A | N | 635 | 801 | 863 | 20 |
| 216 | A | CA | 645 | 806 | 853 | 21 |
| 216 | A | CB | 638 | 816 | 844 | 17 |
| 216 | A | C | 657 | 812 | 861 | 23 |
| 216 | A | O | 668 | 810 | 857 | 25 |
| 217 | A | N | 654 | 820 | 871 | 23 |
| 217 | A | CA | 664 | 827 | 878 | 18 |
| 217 | A | CB | 658 | 836 | 888 | 22 |
| 217 | A | C | 673 | 817 | 885 | 16 |
| 217 | A | O | 685 | 818 | 884 | 23 |
| 218 | Y | N | 667 | 808 | 892 | 16 |
| 218 | Y | CA | 675 | 798 | 899 | 15 |
| 218 | Y | CB | 666 | 788 | 906 | 18 |
| 218 | Y | CG | 660 | 793 | 919 | 23 |
| 218 | Y | CD1 | 667 | 798 | 929 | 16 |
| 218 | Y | CE1 | 661 | 802 | 941 | 22 |
| 218 | Y | CD2 | 646 | 792 | 920 | 29 |
| 218 | Y | CE2 | 640 | 796 | 932 | 25 |
| 218 | Y | CZ | 647 | 801 | 943 | 24 |
| 218 | Y | OH | 641 | 805 | 954 | 27 |
| 218 | Y | C | 684 | 791 | 890 | 20 |
| 218 | Y | O | 696 | 788 | 892 | 23 |
| 219 | A | N | 679 | 787 | 878 | 21 |
| 219 | A | CA | 686 | 780 | 868 | 19 |
| 219 | A | CB | 677 | 777 | 856 | 9 |
| 219 | A | C | 698 | 789 | 863 | 23 |
| 219 | A | O | 709 | 784 | 862 | 28 |
| 220 | A | N | 695 | 801 | 861 | 21 |
| 220 | A | CA | 705 | 811 | 857 | 23 |
| 220 | A | CB | 698 | 825 | 855 | 19 |
| 220 | A | C | 716 | 812 | 867 | 25 |
| 220 | A | O | 725 | 820 | 865 | 28 |
| 221 | Q | N | 715 | 805 | 878 | 29 |
| 221 | Q | CA | 726 | 805 | 889 | 28 |
| 221 | Q | CB | 720 | 809 | 902 | 32 |
| 221 | Q | CG | 710 | 820 | 902 | 37 |
| 221 | Q | CD | 703 | 822 | 916 | 40 |
| 221 | Q | OE1 | 709 | 817 | 926 | 42 |

TABLE 3-continued

| | | | | | | |
|---|---|---|---|---|---|---|
| 221 | Q | NE2 | 692 | 829 | 917 | 45 |
| 221 | Q | C | 732 | 792 | 889 | 28 |
| 221 | Q | O | 740 | 789 | 899 | 32 |
| 222 | G | N | 729 | 783 | 880 | 27 |
| 222 | G | CA | 735 | 770 | 879 | 27 |
| 222 | G | C | 729 | 760 | 888 | 25 |
| 222 | G | O | 735 | 750 | 892 | 29 |
| 223 | Y | N | 716 | 761 | 890 | 24 |
| 223 | Y | CA | 708 | 752 | 898 | 22 |
| 223 | Y | CB | 700 | 759 | 909 | 24 |
| 223 | Y | CG | 708 | 764 | 920 | 23 |
| 223 | Y | CD1 | 714 | 755 | 929 | 26 |
| 223 | Y | CE1 | 722 | 759 | 940 | 29 |
| 223 | Y | CD2 | 710 | 778 | 923 | 22 |
| 223 | Y | CE2 | 717 | 782 | 934 | 25 |
| 223 | Y | CZ | 723 | 773 | 942 | 29 |
| 223 | Y | OH | 731 | 777 | 953 | 33 |
| 223 | Y | C | 699 | 743 | 889 | 17 |
| 223 | Y | O | 693 | 748 | 880 | 12 |
| 224 | K | N | 698 | 731 | 893 | 17 |
| 224 | K | CA | 689 | 721 | 886 | 17 |
| 224 | K | CB | 695 | 707 | 886 | 13 |
| 224 | K | CG | 708 | 706 | 879 | 13 |
| 224 | K | CD | 714 | 692 | 882 | 29 |
| 224 | K | CE | 719 | 691 | 896 | 32 |
| 224 | K | NZ | 718 | 678 | 902 | 38 |
| 224 | K | C | 675 | 721 | 893 | 17 |
| 224 | K | O | 674 | 716 | 904 | 19 |
| 225 | V | N | 666 | 728 | 886 | 18 |
| 225 | V | CA | 652 | 729 | 892 | 10 |
| 225 | V | CB | 648 | 743 | 891 | 8 |
| 225 | V | CG1 | 636 | 746 | 900 | 2 |
| 225 | V | CG2 | 659 | 753 | 894 | 9 |
| 225 | V | C | 641 | 721 | 886 | 10 |
| 225 | V | O | 640 | 719 | 874 | 14 |
| 226 | L | N | 633 | 715 | 895 | 8 |
| 226 | L | CA | 622 | 707 | 891 | 3 |
| 226 | L | CB | 622 | 693 | 898 | 3 |
| 226 | L | CG | 608 | 686 | 896 | 2 |
| 226 | L | CD1 | 606 | 681 | 882 | 2 |
| 226 | L | CD2 | 608 | 675 | 906 | 2 |
| 226 | L | C | 609 | 714 | 895 | 9 |
| 226 | L | O | 607 | 717 | 907 | 8 |
| 227 | V | N | 600 | 718 | 886 | 6 |
| 227 | V | CA | 588 | 725 | 889 | 6 |
| 227 | V | CB | 586 | 737 | 881 | 5 |
| 227 | V | CG1 | 573 | 744 | 885 | 2 |
| 227 | V | CG2 | 598 | 746 | 882 | 3 |
| 227 | V | C | 576 | 715 | 887 | 11 |
| 227 | V | O | 574 | 710 | 876 | 13 |
| 228 | L | N | 569 | 713 | 898 | 7 |
| 228 | L | CA | 557 | 704 | 897 | 8 |
| 228 | L | CB | 556 | 695 | 909 | 2 |
| 228 | L | CG | 569 | 686 | 911 | 2 |
| 228 | L | CD1 | 569 | 680 | 925 | 6 |
| 228 | L | CD2 | 569 | 676 | 900 | 2 |
| 228 | L | C | 544 | 713 | 897 | 11 |
| 228 | L | O | 543 | 723 | 904 | 12 |
| 229 | N | N | 535 | 708 | 889 | 9 |
| 229 | N | CA | 522 | 715 | 887 | 11 |
| 229 | N | CB | 522 | 724 | 875 | 15 |
| 229 | N | CG | 512 | 735 | 876 | 20 |
| 229 | N | OD1 | 514 | 745 | 882 | 21 |
| 229 | N | ND2 | 500 | 733 | 870 | 18 |
| 229 | N | C | 511 | 705 | 886 | 12 |
| 229 | N | O | 513 | 694 | 880 | 17 |
| 230 | P | N | 499 | 707 | 892 | 11 |
| 230 | P | CD | 496 | 720 | 899 | 6 |
| 230 | P | CA | 487 | 698 | 891 | 11 |
| 230 | P | CB | 478 | 703 | 902 | 5 |
| 230 | P | CG | 482 | 717 | 904 | 6 |
| 230 | P | C | 480 | 697 | 878 | 13 |
| 230 | P | O | 472 | 688 | 876 | 19 |
| 231 | S | N | 482 | 707 | 869 | 15 |
| 231 | S | CA | 476 | 707 | 856 | 12 |
| 231 | S | CB | 470 | 721 | 853 | 16 |
| 231 | S | OG | 465 | 722 | 840 | 16 |
| 231 | S | C | 485 | 702 | 844 | 17 |
| 231 | S | O | 496 | 708 | 842 | 25 |
| 232 | V | N | 480 | 693 | 836 | 17 |
| 232 | V | CA | 487 | 688 | 825 | 19 |
| 232 | V | CB | 481 | 676 | 818 | 19 |
| 232 | V | CG1 | 466 | 677 | 817 | 31 |
| 232 | V | CG2 | 487 | 673 | 805 | 17 |
| 232 | V | C | 488 | 699 | 814 | 16 |
| 232 | V | O | 498 | 701 | 807 | 19 |
| 233 | A | N | 477 | 707 | 813 | 17 |
| 233 | A | CA | 476 | 718 | 804 | 14 |
| 233 | A | CB | 462 | 724 | 803 | 10 |
| 233 | A | C | 486 | 729 | 807 | 15 |
| 233 | A | O | 494 | 734 | 799 | 22 |
| 234 | A | N | 486 | 733 | 820 | 12 |
| 234 | A | CA | 495 | 743 | 825 | 12 |
| 234 | A | CB | 493 | 746 | 840 | 11 |
| 234 | A | C | 510 | 738 | 823 | 16 |
| 234 | A | O | 518 | 745 | 818 | 22 |
| 235 | T | N | 513 | 726 | 828 | 16 |
| 235 | T | CA | 526 | 720 | 826 | 17 |
| 235 | T | CB | 526 | 706 | 831 | 12 |
| 235 | T | OG1 | 524 | 705 | 845 | 18 |
| 235 | T | CG2 | 539 | 699 | 827 | 13 |
| 235 | T | C | 531 | 721 | 812 | 19 |
| 235 | T | O | 542 | 726 | 810 | 22 |
| 236 | L | N | 523 | 716 | 803 | 19 |
| 236 | L | CA | 527 | 716 | 789 | 17 |
| 236 | L | CB | 516 | 709 | 780 | 18 |
| 236 | L | CG | 514 | 694 | 781 | 17 |
| 236 | L | CD1 | 503 | 690 | 771 | 23 |
| 236 | L | CD2 | 526 | 687 | 779 | 24 |
| 236 | L | C | 529 | 730 | 783 | 14 |
| 236 | L | O | 538 | 732 | 775 | 19 |
| 237 | G | N | 522 | 740 | 789 | 15 |
| 237 | G | CA | 523 | 754 | 785 | 20 |
| 237 | G | C | 537 | 760 | 788 | 25 |
| 237 | G | O | 543 | 766 | 779 | 28 |
| 238 | F | N | 541 | 759 | 801 | 28 |
| 238 | F | CA | 554 | 765 | 805 | 27 |
| 238 | F | CB | 558 | 760 | 819 | 27 |
| 238 | F | CG | 547 | 762 | 829 | 33 |
| 238 | F | CD1 | 540 | 774 | 829 | 35 |
| 238 | F | CD2 | 544 | 752 | 838 | 34 |
| 238 | F | CE1 | 529 | 776 | 838 | 40 |
| 238 | F | CE2 | 533 | 754 | 847 | 35 |
| 238 | F | CZ | 526 | 766 | 848 | 37 |
| 238 | F | C | 565 | 761 | 795 | 29 |
| 238 | F | O | 573 | 769 | 791 | 34 |
| 239 | G | N | 565 | 748 | 791 | 32 |
| 239 | G | CA | 575 | 743 | 781 | 35 |
| 239 | G | C | 577 | 753 | 770 | 35 |
| 239 | G | O | 588 | 756 | 766 | 35 |
| 240 | A | N | 566 | 758 | 764 | 33 |
| 240 | A | CA | 567 | 767 | 753 | 35 |
| 240 | A | CB | 554 | 767 | 745 | 33 |
| 240 | A | C | 570 | 782 | 757 | 37 |
| 240 | A | O | 577 | 789 | 750 | 40 |
| 241 | Y | N | 565 | 786 | 768 | 34 |
| 241 | Y | CA | 567 | 799 | 773 | 32 |
| 241 | Y | CB | 557 | 803 | 784 | 35 |
| 241 | Y | CG | 560 | 815 | 791 | 41 |
| 241 | Y | CD1 | 568 | 815 | 803 | 41 |
| 241 | Y | CE1 | 571 | 827 | 809 | 44 |
| 241 | Y | CD2 | 555 | 828 | 787 | 40 |
| 241 | Y | CE2 | 558 | 839 | 794 | 42 |
| 241 | Y | CZ | 566 | 839 | 805 | 42 |
| 241 | Y | OH | 569 | 850 | 812 | 43 |
| 241 | Y | C | 581 | 801 | 779 | 31 |
| 241 | Y | O | 586 | 812 | 779 | 29 |
| 242 | M | N | 586 | 790 | 783 | 33 |
| 242 | M | CA | 600 | 791 | 789 | 32 |
| 242 | M | CB | 602 | 779 | 798 | 37 |
| 242 | M | CG | 593 | 779 | 810 | 38 |
| 242 | M | SD | 592 | 795 | 818 | 37 |
| 242 | M | CE | 608 | 795 | 826 | 30 |
| 242 | M | C | 611 | 792 | 779 | 30 |
| 242 | M | O | 620 | 799 | 781 | 29 |
| 243 | S | N | 609 | 785 | 768 | 33 |
| 243 | S | CA | 620 | 786 | 757 | 40 |
| 243 | S | CB | 618 | 775 | 747 | 40 |

TABLE 3-continued

| | | | | | | |
|---|---|---|---|---|---|---|
| 243 | S | OG | 606 | 775 | 741 | 47 |
| 243 | S | C | 619 | 799 | 750 | 42 |
| 243 | S | O | 629 | 805 | 746 | 47 |
| 244 | K | N | 607 | 804 | 747 | 39 |
| 244 | K | CA | 605 | 817 | 740 | 41 |
| 244 | K | CB | 591 | 817 | 733 | 47 |
| 244 | K | CG | 581 | 826 | 739 | 58 |
| 244 | K | CD | 567 | 824 | 732 | 64 |
| 244 | K | CE | 556 | 819 | 741 | 65 |
| 244 | K | NZ | 548 | 808 | 735 | 66 |
| 244 | K | C | 606 | 829 | 749 | 40 |
| 244 | K | O | 609 | 840 | 744 | 40 |
| 245 | A | N | 604 | 828 | 762 | 38 |
| 245 | A | CA | 604 | 839 | 771 | 33 |
| 245 | A | CB | 591 | 840 | 779 | 37 |
| 245 | A | C | 616 | 839 | 781 | 32 |
| 245 | A | O | 621 | 850 | 785 | 35 |
| 246 | H | N | 622 | 828 | 784 | 29 |
| 246 | H | CA | 633 | 827 | 793 | 26 |
| 246 | H | CB | 630 | 820 | 805 | 26 |
| 246 | H | CG | 620 | 827 | 814 | 28 |
| 246 | H | CD2 | 606 | 826 | 815 | 31 |
| 246 | H | ND1 | 624 | 837 | 823 | 29 |
| 246 | H | CE1 | 613 | 842 | 829 | 30 |
| 246 | H | NE2 | 602 | 836 | 824 | 26 |
| 246 | H | C | 645 | 821 | 786 | 27 |
| 246 | H | O | 655 | 818 | 792 | 32 |
| 247 | G | N | 644 | 818 | 773 | 29 |
| 247 | G | CA | 654 | 812 | 765 | 32 |
| 247 | G | C | 659 | 798 | 770 | 35 |
| 247 | G | O | 671 | 795 | 770 | 38 |
| 248 | I | N | 649 | 790 | 773 | 37 |
| 248 | I | CA | 653 | 776 | 778 | 36 |
| 248 | I | CB | 655 | 776 | 793 | 42 |
| 248 | I | CG2 | 644 | 784 | 801 | 39 |
| 248 | I | CG1 | 655 | 762 | 798 | 45 |
| 248 | I | CD1 | 667 | 753 | 793 | 53 |
| 248 | I | C | 642 | 766 | 775 | 35 |
| 248 | I | O | 630 | 768 | 779 | 38 |
| 249 | D | N | 646 | 756 | 768 | 29 |
| 249 | D | CA | 637 | 745 | 764 | 28 |
| 249 | D | CB | 640 | 739 | 751 | 36 |
| 249 | D | CG | 628 | 737 | 742 | 46 |
| 249 | D | OD1 | 628 | 726 | 735 | 52 |
| 249 | D | OD2 | 619 | 745 | 742 | 49 |
| 249 | D | C | 639 | 735 | 775 | 25 |
| 249 | D | O | 649 | 728 | 775 | 22 |
| 250 | P | N | 630 | 734 | 785 | 20 |
| 250 | P | CD | 617 | 742 | 785 | 16 |
| 250 | P | CA | 631 | 725 | 797 | 18 |
| 250 | P | CB | 622 | 732 | 807 | 18 |
| 250 | P | CG | 611 | 738 | 798 | 18 |
| 250 | P | C | 626 | 711 | 793 | 19 |
| 250 | P | O | 620 | 709 | 783 | 18 |
| 251 | N | N | 628 | 702 | 803 | 17 |
| 251 | N | CA | 623 | 689 | 801 | 12 |
| 251 | N | CB | 630 | 679 | 811 | 15 |
| 251 | N | CG | 646 | 681 | 810 | 8 |
| 251 | N | OD1 | 652 | 678 | 799 | 14 |
| 251 | N | ND2 | 652 | 686 | 820 | 10 |
| 251 | N | C | 608 | 689 | 805 | 10 |
| 251 | N | O | 604 | 696 | 814 | 11 |
| 252 | I | N | 600 | 682 | 797 | 10 |
| 252 | I | CA | 586 | 681 | 800 | 7 |
| 252 | I | CB | 578 | 686 | 787 | 6 |
| 252 | I | CG2 | 563 | 685 | 790 | 10 |
| 252 | I | CG1 | 582 | 700 | 783 | 7 |
| 252 | I | CD1 | 579 | 710 | 794 | 4 |
| 252 | I | C | 582 | 667 | 803 | 7 |
| 252 | I | O | 585 | 658 | 796 | 16 |
| 253 | R | N | 574 | 665 | 814 | 9 |
| 253 | R | CA | 570 | 652 | 818 | 6 |
| 253 | R | CB | 579 | 647 | 829 | 11 |
| 253 | R | CG | 593 | 646 | 826 | 10 |
| 253 | R | CD | 600 | 638 | 837 | 12 |
| 253 | R | NE | 598 | 624 | 837 | 12 |
| 253 | R | CZ | 603 | 616 | 828 | 18 |
| 253 | R | NH1 | 611 | 620 | 819 | 21 |
| 253 | R | NH2 | 600 | 603 | 828 | 20 |
| 253 | R | C | 555 | 651 | 821 | 6 |
| 253 | R | O | 551 | 656 | 832 | 9 |
| 254 | T | N | 547 | 645 | 813 | 6 |
| 254 | T | CA | 533 | 644 | 815 | 6 |
| 254 | T | CB | 525 | 654 | 808 | 5 |
| 254 | T | OG1 | 528 | 653 | 794 | 17 |
| 254 | T | CG2 | 529 | 668 | 813 | 10 |
| 254 | T | C | 530 | 630 | 809 | 9 |
| 254 | T | O | 538 | 625 | 801 | 15 |
| 255 | G | N | 519 | 624 | 812 | 12 |
| 255 | G | CA | 515 | 611 | 806 | 15 |
| 255 | G | C | 515 | 612 | 791 | 20 |
| 255 | G | O | 521 | 604 | 784 | 21 |
| 256 | V | N | 508 | 623 | 786 | 20 |
| 256 | V | CA | 507 | 624 | 771 | 16 |
| 256 | V | CB | 495 | 634 | 768 | 11 |
| 256 | V | CG1 | 483 | 628 | 774 | 13 |
| 256 | V | CG2 | 498 | 648 | 773 | 14 |
| 256 | V | C | 520 | 630 | 764 | 17 |
| 256 | V | O | 522 | 627 | 752 | 20 |
| 257 | R | N | 528 | 638 | 771 | 17 |
| 257 | R | CA | 540 | 643 | 764 | 13 |
| 257 | R | CB | 537 | 657 | 759 | 16 |
| 257 | R | CG | 550 | 664 | 755 | 16 |
| 257 | R | CD | 548 | 679 | 751 | 24 |
| 257 | R | NE | 534 | 680 | 745 | 34 |
| 257 | R | CZ | 530 | 692 | 739 | 43 |
| 257 | R | NH1 | 538 | 702 | 738 | 47 |
| 257 | R | NH2 | 518 | 692 | 735 | 44 |
| 257 | R | C | 552 | 643 | 773 | 14 |
| 257 | R | O | 552 | 650 | 783 | 15 |
| 258 | T | N | 562 | 636 | 770 | 12 |
| 258 | T | CA | 574 | 635 | 777 | 11 |
| 258 | T | CB | 577 | 621 | 783 | 12 |
| 258 | T | OG1 | 568 | 618 | 793 | 16 |
| 258 | T | CG2 | 591 | 620 | 789 | 8 |
| 258 | T | C | 586 | 639 | 768 | 13 |
| 258 | T | O | 587 | 634 | 757 | 16 |
| 259 | I | N | 593 | 649 | 773 | 15 |
| 259 | I | CA | 605 | 654 | 765 | 14 |
| 259 | I | CB | 601 | 667 | 758 | 12 |
| 259 | I | CG2 | 613 | 672 | 750 | 9 |
| 259 | I | CG1 | 589 | 665 | 749 | 17 |
| 259 | I | CD1 | 583 | 678 | 744 | 16 |
| 259 | I | C | 617 | 656 | 774 | 14 |
| 259 | I | O | 616 | 663 | 784 | 16 |
| 260 | T | N | 628 | 651 | 769 | 16 |
| 260 | T | CA | 641 | 653 | 777 | 18 |
| 260 | T | CB | 647 | 639 | 780 | 22 |
| 260 | T | OG1 | 638 | 632 | 788 | 25 |
| 260 | T | CG2 | 660 | 641 | 787 | 19 |
| 260 | T | C | 650 | 661 | 768 | 21 |
| 260 | T | O | 654 | 656 | 757 | 21 |
| 261 | T | N | 653 | 673 | 772 | 21 |
| 261 | T | CA | 661 | 682 | 764 | 24 |
| 261 | T | CB | 655 | 696 | 762 | 22 |
| 261 | T | OG1 | 656 | 703 | 774 | 27 |
| 261 | T | CG2 | 640 | 694 | 759 | 22 |
| 261 | T | C | 675 | 684 | 769 | 27 |
| 261 | T | O | 684 | 688 | 762 | 31 |
| 262 | G | N | 677 | 680 | 782 | 29 |
| 262 | G | CA | 690 | 681 | 788 | 28 |
| 262 | G | C | 691 | 694 | 796 | 28 |
| 262 | G | O | 702 | 698 | 801 | 27 |
| 263 | A | N | 680 | 702 | 796 | 25 |
| 263 | A | CA | 680 | 715 | 803 | 26 |
| 263 | A | CB | 667 | 722 | 799 | 28 |
| 263 | A | C | 681 | 713 | 818 | 26 |
| 263 | A | O | 678 | 702 | 824 | 24 |
| 264 | P | N | 685 | 723 | 825 | 28 |
| 264 | P | CD | 688 | 737 | 820 | 27 |
| 264 | P | CA | 686 | 723 | 840 | 26 |
| 264 | P | CB | 696 | 734 | 843 | 22 |
| 264 | P | CG | 693 | 744 | 833 | 25 |
| 264 | P | C | 672 | 725 | 847 | 25 |
| 264 | P | O | 611 | 725 | 859 | 28 |
| 265 | V | N | 662 | 727 | 839 | 23 |
| 265 | V | CA | 648 | 729 | 844 | 20 |
| 265 | V | CB | 643 | 743 | 840 | 25 |

TABLE 3-continued

| | | | | | | |
|---|---|---|---|---|---|---|
| 265 | V | CG1 | 630 | 746 | 847 | 22 |
| 265 | V | CG2 | 653 | 754 | 844 | 21 |
| 265 | V | C | 639 | 719 | 838 | 18 |
| 265 | V | O | 639 | 717 | 826 | 19 |
| 266 | T | N | 631 | 713 | 847 | 17 |
| 266 | T | CA | 621 | 703 | 843 | 13 |
| 266 | T | CB | 625 | 689 | 848 | 14 |
| 266 | T | OG1 | 638 | 686 | 843 | 18 |
| 266 | T | CG2 | 616 | 678 | 843 | 14 |
| 266 | T | C | 607 | 706 | 848 | 10 |
| 266 | T | O | 606 | 710 | 860 | 9 |
| 267 | Y | N | 597 | 705 | 840 | 9 |
| 267 | Y | CA | 583 | 707 | 844 | 7 |
| 267 | Y | CB | 577 | 717 | 834 | 6 |
| 267 | Y | CG | 580 | 731 | 836 | 5 |
| 267 | Y | CD1 | 573 | 739 | 844 | 12 |
| 267 | Y | CE1 | 577 | 752 | 847 | 19 |
| 267 | Y | CD2 | 592 | 736 | 830 | 9 |
| 267 | Y | CE2 | 596 | 749 | 833 | 17 |
| 267 | Y | CZ | 588 | 757 | 841 | 19 |
| 267 | Y | OH | 593 | 770 | 845 | 23 |
| 267 | Y | C | 576 | 694 | 843 | 9 |
| 267 | Y | O | 577 | 687 | 833 | 9 |
| 268 | S | N | 570 | 691 | 854 | 13 |
| 268 | S | CA | 562 | 678 | 855 | 8 |
| 268 | S | CB | 571 | 668 | 862 | 7 |
| 268 | S | OG | 564 | 657 | 867 | 12 |
| 268 | S | C | 550 | 680 | 864 | 9 |
| 268 | S | O | 548 | 690 | 871 | 9 |
| 269 | T | N | 540 | 671 | 862 | 10 |
| 269 | T | CA | 528 | 671 | 870 | 10 |
| 269 | T | CB | 515 | 666 | 862 | 9 |
| 269 | T | OG1 | 519 | 653 | 857 | 7 |
| 269 | T | CG2 | 511 | 675 | 851 | 3 |
| 269 | T | C | 530 | 662 | 882 | 11 |
| 269 | T | O | 538 | 653 | 880 | 15 |
| 270 | Y | N | 524 | 665 | 893 | 9 |
| 270 | Y | CA | 526 | 656 | 905 | 5 |
| 270 | Y | CB | 517 | 660 | 916 | 2 |
| 270 | Y | CG | 520 | 674 | 922 | 2 |
| 270 | Y | CD1 | 531 | 676 | 930 | 2 |
| 270 | Y | CE1 | 534 | 688 | 935 | 2 |
| 270 | Y | CD2 | 512 | 685 | 918 | 2 |
| 270 | Y | CE2 | 515 | 698 | 923 | 2 |
| 270 | Y | CZ | 526 | 699 | 932 | 2 |
| 270 | Y | OH | 530 | 712 | 936 | 2 |
| 270 | Y | C | 523 | 642 | 901 | 2 |
| 270 | Y | O | 529 | 632 | 906 | 8 |
| 271 | G | N | 513 | 640 | 892 | 3 |
| 271 | G | CA | 510 | 626 | 888 | 5 |
| 271 | G | C | 521 | 619 | 881 | 8 |
| 271 | G | O | 524 | 607 | 885 | 9 |
| 272 | K | N | 528 | 625 | 872 | 10 |
| 272 | K | CA | 539 | 619 | 864 | 6 |
| 272 | K | CB | 544 | 628 | 853 | 4 |
| 272 | K | CG | 552 | 621 | 842 | 7 |
| 272 | K | CD | 545 | 608 | 838 | 11 |
| 272 | K | CE | 553 | 600 | 828 | 13 |
| 272 | K | NZ | 567 | 600 | 833 | 21 |
| 272 | K | C | 551 | 617 | 874 | 9 |
| 272 | K | O | 557 | 607 | 874 | 13 |
| 273 | F | N | 553 | 627 | 882 | 8 |
| 273 | F | CA | 564 | 627 | 892 | 6 |
| 273 | F | CB | 563 | 639 | 901 | 4 |
| 273 | F | CG | 573 | 639 | 913 | 3 |
| 273 | F | CD1 | 586 | 641 | 911 | 3 |
| 273 | F | CD2 | 568 | 637 | 926 | 2 |
| 273 | F | CE1 | 595 | 641 | 922 | 5 |
| 273 | F | CE2 | 577 | 637 | 937 | 6 |
| 273 | F | CZ | 590 | 639 | 935 | 5 |
| 273 | F | C | 562 | 614 | 900 | 5 |
| 273 | F | O | 572 | 606 | 902 | 12 |
| 274 | L | N | 550 | 611 | 905 | 11 |
| 274 | L | CA | 547 | 599 | 912 | 8 |
| 274 | L | CB | 533 | 600 | 917 | 5 |
| 274 | L | CG | 530 | 610 | 928 | 2 |
| 274 | L | CD1 | 515 | 613 | 930 | 3 |
| 274 | L | CD2 | 537 | 606 | 941 | 2 |
| 274 | L | C | 548 | 587 | 904 | 8 |
| 274 | L | O | 553 | 576 | 908 | 11 |
| 275 | A | N | 545 | 588 | 891 | 12 |
| 275 | A | CA | 546 | 576 | 882 | 12 |
| 275 | A | CB | 539 | 579 | 869 | 4 |
| 275 | A | C | 560 | 573 | 880 | 14 |
| 275 | A | O | 564 | 561 | 878 | 22 |
| 276 | D | N | 569 | 583 | 880 | 15 |
| 276 | D | CA | 583 | 582 | 879 | 15 |
| 276 | D | CB | 590 | 595 | 874 | 19 |
| 276 | D | CG | 586 | 598 | 860 | 16 |
| 276 | D | OD1 | 585 | 589 | 852 | 17 |
| 276 | D | OD2 | 585 | 610 | 857 | 15 |
| 276 | D | C | 590 | 577 | 891 | 16 |
| 276 | D | O | 602 | 576 | 892 | 18 |
| 277 | G | N | 582 | 574 | 901 | 18 |
| 277 | G | CA | 588 | 569 | 914 | 26 |
| 277 | G | C | 591 | 580 | 924 | 28 |
| 277 | G | O | 593 | 578 | 936 | 33 |
| 278 | G | N | 591 | 592 | 919 | 26 |
| 278 | G | CA | 594 | 604 | 927 | 25 |
| 278 | G | C | 607 | 610 | 925 | 25 |
| 278 | G | O | 611 | 613 | 913 | 23 |
| 279 | C | N | 614 | 613 | 936 | 25 |
| 279 | C | CA | 627 | 619 | 935 | 26 |
| 279 | C | CB | 632 | 625 | 948 | 22 |
| 279 | C | SG | 622 | 639 | 954 | 23 |
| 279 | C | C | 638 | 610 | 929 | 32 |
| 279 | C | O | 641 | 599 | 934 | 32 |
| 280 | S | N | 645 | 615 | 918 | 40 |
| 280 | S | CA | 655 | 608 | 912 | 46 |
| 280 | S | CB | 655 | 611 | 897 | 52 |
| 280 | S | OG | 652 | 624 | 894 | 51 |
| 280 | S | C | 669 | 612 | 917 | 48 |
| 280 | S | O | 675 | 621 | 912 | 51 |
| 281 | G | N | 673 | 604 | 928 | 45 |
| 281 | G | CA | 686 | 607 | 934 | 45 |
| 281 | G | C | 690 | 622 | 934 | 45 |
| 281 | G | O | 682 | 630 | 935 | 50 |
| 282 | G | N | 703 | 624 | 932 | 38 |
| 282 | G | CA | 708 | 638 | 932 | 34 |
| 282 | G | C | 705 | 645 | 919 | 30 |
| 282 | G | O | 715 | 649 | 912 | 25 |
| 283 | A | N | 693 | 646 | 915 | 24 |
| 283 | A | CA | 689 | 651 | 902 | 17 |
| 283 | A | CB | 677 | 644 | 896 | 21 |
| 283 | A | C | 686 | 666 | 902 | 16 |
| 283 | A | O | 688 | 673 | 893 | 23 |
| 284 | Y | N | 680 | 671 | 913 | 15 |
| 284 | Y | CA | 676 | 685 | 914 | 16 |
| 284 | Y | CB | 661 | 686 | 913 | 11 |
| 284 | Y | CG | 656 | 681 | 900 | 14 |
| 284 | Y | CD1 | 655 | 688 | 889 | 12 |
| 284 | Y | CE1 | 650 | 683 | 877 | 11 |
| 284 | Y | CD2 | 651 | 668 | 900 | 15 |
| 284 | Y | CE2 | 646 | 662 | 888 | 12 |
| 284 | Y | CZ | 645 | 670 | 877 | 11 |
| 284 | Y | OH | 640 | 665 | 865 | 27 |
| 284 | Y | C | 681 | 691 | 927 | 17 |
| 284 | Y | O | 681 | 684 | 938 | 21 |
| 285 | D | N | 684 | 704 | 927 | 14 |
| 285 | D | CA | 688 | 711 | 939 | 19 |
| 285 | D | CB | 699 | 722 | 935 | 23 |
| 285 | D | CG | 710 | 716 | 926 | 22 |
| 285 | D | OD1 | 716 | 705 | 930 | 29 |
| 285 | D | OD2 | 712 | 722 | 915 | 25 |
| 285 | D | C | 676 | 719 | 944 | 19 |
| 285 | D | O | 675 | 721 | 957 | 24 |
| 286 | I | N | 667 | 723 | 936 | 16 |
| 286 | I | CA | 655 | 730 | 940 | 13 |
| 286 | I | CB | 655 | 744 | 934 | 16 |
| 286 | I | CG2 | 644 | 752 | 941 | 8 |
| 286 | I | CG1 | 668 | 751 | 936 | 16 |
| 286 | I | CD1 | 674 | 750 | 950 | 23 |
| 286 | I | C | 642 | 723 | 934 | 14 |
| 286 | I | O | 642 | 719 | 922 | 19 |
| 287 | I | N | 632 | 722 | 942 | 11 |
| 287 | I | CA | 619 | 716 | 938 | 6 |
| 287 | I | CB | 617 | 702 | 945 | 2 |
| 287 | I | CG2 | 604 | 696 | 939 | 2 |

TABLE 3-continued

| | | | | | | |
|---|---|---|---|---|---|---|
| 287 | I | CG1 | 629 | 693 | 942 | 2 |
| 287 | I | CD1 | 626 | 679 | 944 | 9 |
| 287 | I | C | 608 | 725 | 942 | 6 |
| 287 | I | O | 605 | 727 | 953 | 9 |
| 288 | I | N | 602 | 731 | 932 | 3 |
| 288 | I | CA | 591 | 740 | 934 | 3 |
| 288 | I | CB | 591 | 752 | 923 | 3 |
| 288 | I | CG2 | 579 | 761 | 925 | 4 |
| 288 | I | CG1 | 604 | 760 | 925 | 6 |
| 288 | I | CD1 | 606 | 771 | 915 | 9 |
| 288 | I | C | 577 | 733 | 932 | 7 |
| 288 | I | O | 574 | 728 | 921 | 5 |
| 289 | C | N | 569 | 733 | 943 | 6 |
| 289 | C | CA | 556 | 727 | 943 | 5 |
| 289 | C | CB | 554 | 720 | 956 | 7 |
| 289 | C | SG | 565 | 706 | 960 | 8 |
| 289 | C | C | 546 | 738 | 941 | 5 |
| 289 | C | O | 540 | 743 | 950 | 13 |
| 290 | D | N | 543 | 741 | 928 | 9 |
| 290 | D | CA | 533 | 751 | 924 | 14 |
| 290 | D | CB | 534 | 754 | 909 | 22 |
| 290 | D | CG | 529 | 769 | 906 | 29 |
| 290 | D | OD1 | 533 | 773 | 895 | 37 |
| 290 | D | OD2 | 523 | 775 | 914 | 27 |
| 290 | D | C | 519 | 747 | 928 | 15 |
| 290 | D | O | 516 | 735 | 929 | 16 |
| 291 | E | N | 510 | 757 | 930 | 13 |
| 291 | E | CA | 497 | 754 | 934 | 12 |
| 291 | E | CB | 489 | 750 | 922 | 16 |
| 291 | E | CG | 488 | 760 | 911 | 36 |
| 291 | E | CD | 476 | 759 | 901 | 50 |
| 291 | E | OE1 | 472 | 747 | 898 | 57 |
| 291 | E | OE2 | 471 | 769 | 898 | 58 |
| 291 | E | C | 496 | 744 | 945 | 11 |
| 291 | E | O | 488 | 735 | 944 | 9 |
| 292 | C | N | 504 | 746 | 955 | 8 |
| 292 | C | CA | 505 | 737 | 967 | 10 |
| 292 | C | CB | 518 | 740 | 974 | 8 |
| 292 | C | SG | 519 | 756 | 983 | 19 |
| 292 | C | C | 493 | 738 | 976 | 12 |
| 292 | C | O | 492 | 732 | 986 | 19 |
| 293 | H | N | 483 | 747 | 972 | 15 |
| 293 | H | CA | 471 | 748 | 979 | 15 |
| 293 | H | CB | 465 | 762 | 977 | 12 |
| 293 | H | CG | 461 | 764 | 962 | 11 |
| 293 | H | CD2 | 451 | 758 | 955 | 7 |
| 293 | H | ND1 | 468 | 772 | 954 | 10 |
| 293 | H | CE1 | 463 | 771 | 942 | 12 |
| 293 | H | NE2 | 452 | 763 | 942 | 16 |
| 293 | H | C | 461 | 738 | 975 | 15 |
| 293 | H | O | 451 | 736 | 982 | 15 |
| 294 | S | N | 463 | 731 | 964 | 16 |
| 294 | S | CA | 454 | 721 | 959 | 13 |
| 294 | S | CB | 459 | 715 | 945 | 13 |
| 294 | S | OG | 463 | 726 | 937 | 22 |
| 294 | S | C | 453 | 709 | 969 | 12 |
| 294 | S | O | 462 | 705 | 974 | 13 |
| 295 | T | N | 440 | 705 | 970 | 13 |
| 295 | T | CA | 437 | 694 | 979 | 12 |
| 295 | T | CB | 426 | 699 | 989 | 13 |
| 295 | T | OG1 | 415 | 704 | 982 | 25 |
| 295 | T | CG2 | 431 | 709 | 999 | 14 |
| 295 | T | C | 433 | 682 | 972 | 11 |
| 295 | T | O | 426 | 673 | 978 | 12 |
| 296 | D | N | 437 | 680 | 960 | 13 |
| 296 | D | CA | 434 | 668 | 953 | 15 |
| 296 | D | CB | 435 | 670 | 938 | 14 |
| 296 | D | CG | 449 | 674 | 934 | 26 |
| 296 | D | OD1 | 452 | 686 | 933 | 33 |
| 296 | D | OD2 | 457 | 664 | 931 | 37 |
| 296 | D | C | 444 | 657 | 957 | 12 |
| 296 | D | O | 456 | 660 | 959 | 15 |
| 297 | S | N | 440 | 645 | 958 | 14 |
| 297 | S | CA | 449 | 634 | 962 | 15 |
| 297 | S | CB | 442 | 621 | 959 | 16 |
| 297 | S | OG | 435 | 621 | 947 | 27 |
| 297 | S | C | 463 | 634 | 956 | 19 |
| 297 | S | O | 473 | 633 | 963 | 26 |
| 298 | T | N | 463 | 636 | 943 | 18 |
| 298 | T | CA | 476 | 636 | 936 | 15 |
| 298 | T | CB | 473 | 637 | 921 | 13 |
| 298 | T | OG1 | 463 | 628 | 916 | 18 |
| 298 | T | CG2 | 486 | 634 | 913 | 10 |
| 298 | T | C | 485 | 647 | 940 | 10 |
| 298 | T | O | 497 | 644 | 942 | 14 |
| 299 | T | N | 480 | 659 | 943 | 4 |
| 299 | T | CA | 489 | 669 | 947 | 3 |
| 299 | T | CB | 482 | 683 | 947 | 2 |
| 299 | T | OG1 | 479 | 686 | 934 | 4 |
| 299 | T | CG2 | 491 | 693 | 953 | 2 |
| 299 | T | C | 494 | 666 | 962 | 6 |
| 299 | T | O | 506 | 667 | 964 | 5 |
| 300 | I | N | 485 | 662 | 970 | 9 |
| 300 | I | CA | 488 | 659 | 984 | 5 |
| 300 | I | CB | 476 | 654 | 992 | 8 |
| 300 | I | CG2 | 480 | 650 | 1006 | 6 |
| 300 | I | CG1 | 465 | 664 | 992 | 7 |
| 300 | I | CD1 | 469 | 678 | 995 | 12 |
| 300 | I | C | 499 | 649 | 985 | 4 |
| 300 | I | O | 510 | 650 | 991 | 7 |
| 301 | L | N | 497 | 638 | 978 | 2 |
| 301 | L | CA | 506 | 627 | 977 | 4 |
| 301 | L | CB | 500 | 615 | 970 | 3 |
| 301 | L | CG | 507 | 601 | 970 | 4 |
| 301 | L | CD1 | 512 | 598 | 984 | 2 |
| 301 | L | CD2 | 497 | 590 | 966 | 2 |
| 301 | L | C | 519 | 631 | 971 | 7 |
| 301 | L | O | 530 | 627 | 975 | 6 |
| 302 | G | N | 518 | 638 | 960 | 3 |
| 302 | G | CA | 530 | 642 | 953 | 2 |
| 302 | G | C | 539 | 651 | 961 | 4 |
| 302 | G | O | 551 | 650 | 962 | 9 |
| 303 | I | N | 532 | 661 | 968 | 5 |
| 303 | I | CA | 540 | 670 | 977 | 7 |
| 303 | I | CB | 531 | 681 | 982 | 6 |
| 303 | I | CG2 | 539 | 690 | 991 | 8 |
| 303 | I | CG1 | 526 | 690 | 970 | 6 |
| 303 | I | CD1 | 519 | 703 | 974 | 2 |
| 303 | I | C | 545 | 662 | 989 | 11 |
| 303 | I | O | 556 | 665 | 994 | 15 |
| 304 | G | N | 537 | 652 | 994 | 11 |
| 304 | G | CA | 542 | 644 | 1005 | 11 |
| 304 | G | C | 554 | 637 | 1002 | 10 |
| 304 | G | O | 563 | 635 | 1010 | 8 |
| 305 | T | N | 555 | 632 | 989 | 8 |
| 305 | T | CA | 567 | 624 | 984 | 8 |
| 305 | T | CB | 564 | 619 | 970 | 9 |
| 305 | T | OG1 | 553 | 609 | 971 | 6 |
| 305 | T | CG2 | 576 | 612 | 965 | 6 |
| 305 | T | C | 579 | 633 | 984 | 10 |
| 305 | T | O | 590 | 629 | 988 | 14 |
| 306 | V | N | 577 | 645 | 978 | 9 |
| 306 | V | CA | 588 | 655 | 977 | 8 |
| 306 | V | CB | 584 | 668 | 971 | 2 |
| 306 | V | CG1 | 594 | 679 | 973 | 2 |
| 306 | V | CG2 | 581 | 666 | 956 | 2 |
| 306 | V | C | 594 | 657 | 991 | 14 |
| 306 | V | O | 606 | 656 | 994 | 20 |
| 307 | L | N | 585 | 661 | 1000 | 18 |
| 307 | L | CA | 588 | 664 | 1014 | 13 |
| 307 | L | CB | 576 | 668 | 1022 | 11 |
| 307 | L | CG | 569 | 681 | 1017 | 12 |
| 307 | L | CD1 | 556 | 683 | 1023 | 6 |
| 307 | L | CD2 | 579 | 693 | 1021 | 11 |
| 307 | L | C | 595 | 653 | 1021 | 12 |
| 307 | L | O | 604 | 654 | 1029 | 18 |
| 308 | D | N | 591 | 641 | 1017 | 12 |
| 308 | D | CA | 597 | 629 | 1023 | 14 |
| 308 | D | CB | 587 | 617 | 1023 | 18 |
| 308 | D | CG | 593 | 605 | 1028 | 26 |
| 308 | D | OD1 | 595 | 604 | 1041 | 34 |
| 308 | D | OD2 | 596 | 596 | 1020 | 30 |
| 308 | D | C | 610 | 625 | 1016 | 15 |
| 308 | D | O | 618 | 617 | 1022 | 17 |
| 309 | Q | N | 613 | 630 | 1005 | 9 |
| 309 | Q | CA | 625 | 625 | 998 | 8 |
| 309 | Q | CB | 621 | 617 | 985 | 9 |
| 309 | Q | CG | 611 | 605 | 988 | 3 |

TABLE 3-continued

| | | | | | | |
|---|---|---|---|---|---|---|
| 309 | Q | CD | 606 | 599 | 976 | 10 |
| 309 | Q | OE1 | 609 | 603 | 965 | 9 |
| 309 | Q | NE2 | 600 | 587 | 977 | 11 |
| 309 | Q | C | 635 | 636 | 993 | 7 |
| 309 | Q | O | 646 | 633 | 991 | 10 |
| 310 | A | N | 630 | 648 | 992 | 9 |
| 310 | A | CA | 639 | 659 | 987 | 6 |
| 310 | A | CB | 632 | 672 | 988 | 3 |
| 310 | A | C | 653 | 659 | 993 | 14 |
| 310 | A | O | 663 | 660 | 986 | 17 |
| 311 | E | N | 653 | 659 | 1007 | 18 |
| 311 | E | CA | 666 | 660 | 1013 | 19 |
| 311 | E | CB | 664 | 661 | 1028 | 22 |
| 311 | E | CG | 676 | 669 | 1035 | 29 |
| 311 | E | CD | 676 | 667 | 10S0 | 28 |
| 311 | E | OE1 | 687 | 670 | 1056 | 32 |
| 311 | E | OE2 | 666 | 664 | 1056 | 33 |
| 311 | E | C | 676 | 648 | 1011 | 19 |
| 311 | E | O | 687 | 650 | 1008 | 22 |
| 312 | T | N | 671 | 636 | 1012 | 23 |
| 312 | T | CA | 679 | 624 | 1009 | 24 |
| 312 | T | CB | 672 | 611 | 1012 | 31 |
| 312 | T | OG1 | 665 | 613 | 1025 | 37 |
| 312 | T | CG2 | 682 | 600 | 1013 | 32 |
| 312 | T | C | 684 | 624 | 994 | 23 |
| 312 | T | O | 695 | 619 | 991 | 29 |
| 313 | A | N | 675 | 629 | 986 | 22 |
| 313 | A | CA | 678 | 629 | 971 | 15 |
| 313 | A | CB | 665 | 632 | 963 | 10 |
| 313 | A | C | 688 | 640 | 968 | 19 |
| 313 | A | O | 691 | 643 | 957 | 19 |
| 314 | G | N | 693 | 647 | 979 | 22 |
| 314 | G | CA | 703 | 657 | 978 | 17 |
| 314 | G | C | 698 | 671 | 974 | 16 |
| 314 | G | O | 706 | 679 | 970 | 19 |
| 315 | A | N | 685 | 673 | 975 | 14 |
| 315 | A | CA | 680 | 687 | 972 | 13 |
| 315 | A | CB | 664 | 686 | 971 | 14 |
| 315 | A | C | 684 | 696 | 982 | 12 |
| 315 | A | O | 690 | 691 | 993 | 17 |
| 316 | R | N | 683 | 709 | 981 | 6 |
| 316 | R | CA | 687 | 718 | 991 | 14 |
| 316 | R | CB | 699 | 727 | 986 | 19 |
| 316 | R | CG | 712 | 720 | 989 | 31 |
| 316 | R | CD | 722 | 725 | 978 | 38 |
| 316 | R | NE | 725 | 739 | 980 | 43 |
| 316 | R | CZ | 737 | 744 | 983 | 56 |
| 316 | R | NH1 | 747 | 736 | 985 | 61 |
| 316 | R | NH2 | 739 | 157 | 984 | 58 |
| 316 | R | C | 676 | 728 | 994 | 17 |
| 316 | R | O | 676 | 734 | 1004 | 18 |
| 317 | L | N | 666 | 728 | 985 | 17 |
| 317 | L | CA | 654 | 737 | 988 | 15 |
| 317 | L | CB | 658 | 751 | 982 | 2 |
| 317 | L | CG | 647 | 761 | 983 | 2 |
| 317 | L | CD1 | 646 | 765 | 998 | 2 |
| 317 | L | CD2 | 650 | 773 | 974 | 2 |
| 317 | L | C | 641 | 732 | 981 | 15 |
| 317 | L | O | 641 | 727 | 970 | 12 |
| 318 | V | N | 631 | 732 | 989 | 14 |
| 318 | V | CA | 617 | 728 | 984 | 6 |
| 318 | V | CB | 611 | 717 | 993 | 5 |
| 318 | V | CG1 | 596 | 717 | 991 | 2 |
| 318 | V | CG2 | 616 | 703 | 988 | 3 |
| 318 | V | C | 609 | 741 | 986 | 7 |
| 318 | V | O | 607 | 746 | 997 | 7 |
| 319 | V | N | 604 | 746 | 975 | 3 |
| 319 | V | CA | 596 | 758 | 976 | 6 |
| 319 | V | CB | 600 | 768 | 966 | 4 |
| 319 | V | CG1 | 593 | 781 | 968 | 2 |
| 319 | V | CG2 | 615 | 770 | 966 | 2 |
| 319 | V | C | 581 | 754 | 974 | 9 |
| 319 | V | O | 577 | 747 | 965 | 10 |
| 320 | L | N | 573 | 758 | 984 | 12 |
| 320 | L | CA | 558 | 755 | 983 | 8 |
| 320 | L | CB | 554 | 751 | 997 | 8 |
| 320 | L | CG | 560 | 738 | 1003 | 6 |
| 320 | L | CD1 | 558 | 737 | 1018 | 2 |
| 320 | L | CD2 | 553 | 726 | 996 | 5 |
| 320 | L | C | 551 | 768 | 979 | 6 |
| 320 | L | O | 548 | 776 | 987 | 7 |
| 321 | A | N | 549 | 769 | 966 | 6 |
| 321 | A | CA | 543 | 781 | 960 | 6 |
| 321 | A | CB | 550 | 785 | 947 | 3 |
| 321 | A | C | 528 | 780 | 958 | 9 |
| 321 | A | O | 522 | 770 | 955 | 13 |
| 322 | T | N | 522 | 792 | 959 | 14 |
| 322 | T | CA | 507 | 793 | 957 | 10 |
| 322 | T | CB | 499 | 785 | 967 | 11 |
| 322 | T | OG1 | 485 | 788 | 966 | 11 |
| 322 | T | CG2 | 503 | 788 | 981 | 12 |
| 322 | T | C | 503 | 808 | 959 | 13 |
| 322 | T | O | 510 | 815 | 966 | 13 |
| 323 | A | N | 492 | 812 | 953 | 14 |
| 323 | A | CA | 487 | 825 | 955 | 15 |
| 323 | A | CB | 481 | 830 | 942 | 12 |
| 323 | A | C | 478 | 826 | 967 | 16 |
| 323 | A | O | 477 | 836 | 974 | 20 |
| 324 | T | N | 470 | 815 | 969 | 16 |
| 324 | T | CA | 461 | 814 | 980 | 13 |
| 324 | T | CB | 446 | 811 | 974 | 14 |
| 324 | T | OG1 | 447 | 799 | 967 | 14 |
| 324 | T | CG2 | 442 | 823 | 965 | 8 |
| 324 | T | C | 464 | 804 | 990 | 11 |
| 324 | T | O | 459 | 793 | 990 | 20 |
| 325 | P | N | 473 | 807 | 999 | 12 |
| 325 | P | CD | 480 | 820 | 1001 | 10 |
| 325 | P | CA | 477 | 798 | 1010 | 11 |
| 325 | P | CB | 489 | 804 | 1017 | 10 |
| 325 | P | CG | 486 | 819 | 1015 | 9 |
| 325 | P | C | 465 | 795 | 1020 | 14 |
| 325 | P | O | 455 | 803 | 1019 | 16 |
| 326 | P | N | 466 | 785 | 1028 | 15 |
| 326 | P | CD | 477 | 776 | 1030 | 16 |
| 326 | P | CA | 455 | 783 | 1038 | 17 |
| 326 | P | CB | 460 | 771 | 1047 | 14 |
| 326 | P | CG | 471 | 765 | 1039 | 16 |
| 326 | P | C | 452 | 795 | 1046 | 20 |
| 326 | P | O | 460 | 802 | 1051 | 20 |
| 327 | G | N | 439 | 798 | 1048 | 19 |
| 327 | G | CA | 434 | 809 | 1055 | 14 |
| 327 | G | C | 433 | 822 | 1047 | 12 |
| 327 | G | O | 430 | 833 | 1052 | 10 |
| 328 | S | N | 437 | 821 | 1034 | 16 |
| 328 | S | CA | 436 | 833 | 1026 | 22 |
| 328 | S | CB | 444 | 830 | 1013 | 20 |
| 328 | S | OG | 439 | 819 | 1006 | 16 |
| 328 | S | C | 422 | 836 | 1023 | 24 |
| 328 | S | O | 413 | 827 | 1025 | 29 |
| 329 | V | N | 419 | 848 | 1019 | 26 |
| 329 | V | CA | 405 | 852 | 1015 | 28 |
| 329 | V | CB | 399 | 861 | 1027 | 31 |
| 329 | V | CG1 | 398 | 853 | 1039 | 35 |
| 329 | V | CG2 | 408 | 873 | 1029 | 26 |
| 329 | V | C | 404 | 859 | 1002 | 27 |
| 329 | V | O | 413 | 868 | 1000 | 30 |
| 330 | T | N | 394 | 857 | 994 | 29 |
| 330 | T | CA | 393 | 864 | 982 | 31 |
| 330 | T | CB | 380 | 858 | 974 | 28 |
| 330 | T | OG1 | 385 | 848 | 964 | 28 |
| 330 | T | CG2 | 373 | 869 | 967 | 34 |
| 330 | T | C | 391 | 879 | 984 | 30 |
| 330 | T | O | 383 | 883 | 993 | 35 |
| 331 | V | N | 397 | 887 | 976 | 32 |
| 331 | V | CA | 396 | 901 | 977 | 34 |
| 331 | V | CB | 408 | 908 | 984 | 31 |
| 331 | V | CG1 | 408 | 903 | 999 | 30 |
| 331 | V | CG2 | 421 | 904 | 977 | 34 |
| 331 | V | C | 395 | 968 | 963 | 37 |
| 331 | V | O | 399 | 901 | 953 | 35 |
| 332 | P | N | 391 | 920 | 962 | 39 |
| 332 | P | CD | 386 | 928 | 973 | 39 |
| 332 | P | CA | 389 | 927 | 949 | 39 |
| 332 | P | CB | 387 | 942 | 954 | 39 |
| 332 | P | CG | 381 | 941 | 967 | 40 |
| 332 | P | C | 401 | 926 | 939 | 38 |
| 332 | P | O | 413 | 927 | 943 | 36 |
| 333 | H | N | 397 | 925 | 927 | 39 |

TABLE 3-continued

| | | | | | | |
|---|---|---|---|---|---|---|
| 333 | H | CA | 407 | 924 | 915 | 39 |
| 333 | H | CB | 404 | 911 | 907 | 41 |
| 333 | H | CG | 414 | 908 | 897 | 48 |
| 333 | H | CD2 | 422 | 917 | 889 | 49 |
| 333 | H | ND1 | 417 | 896 | 893 | 52 |
| 333 | H | CE1 | 427 | 896 | 883 | 49 |
| 333 | H | NE2 | 430 | 909 | 881 | 51 |
| 333 | H | C | 404 | 936 | 907 | 39 |
| 333 | H | O | 394 | 938 | 900 | 35 |
| 334 | P | N | 414 | 945 | 907 | 41 |
| 334 | P | CD | 427 | 944 | 914 | 40 |
| 334 | P | CA | 413 | 958 | 899 | 40 |
| 334 | P | CB | 427 | 964 | 900 | 42 |
| 334 | P | CG | 436 | 953 | 905 | 42 |
| 334 | P | C | 409 | 956 | 884 | 41 |
| 334 | P | O | 404 | 966 | 878 | 43 |
| 335 | N | N | 411 | 944 | 879 | 38 |
| 335 | N | CA | 407 | 942 | 865 | 32 |
| 335 | N | CB | 418 | 932 | 859 | 31 |
| 335 | N | CG | 428 | 940 | 851 | 31 |
| 335 | N | OD1 | 440 | 935 | 850 | 35 |
| 335 | N | ND2 | 425 | 951 | 846 | 39 |
| 335 | N | C | 394 | 936 | 863 | 31 |
| 335 | N | O | 389 | 934 | 852 | 30 |
| 336 | I | N | 388 | 932 | 874 | 30 |
| 336 | I | CA | 375 | 925 | 874 | 29 |
| 336 | I | CB | 376 | 911 | 879 | 26 |
| 336 | I | CG2 | 363 | 903 | 876 | 22 |
| 336 | I | CG1 | 388 | 904 | 872 | 26 |
| 336 | I | CD1 | 391 | 890 | 878 | 31 |
| 336 | I | C | 363 | 932 | 881 | 32 |
| 336 | I | O | 364 | 936 | 892 | 28 |
| 337 | E | N | 352 | 933 | 873 | 33 |
| 337 | E | CA | 340 | 939 | 878 | 32 |
| 337 | E | CB | 333 | 947 | 867 | 38 |
| 337 | E | CG | 322 | 957 | 872 | 48 |
| 337 | E | CD | 327 | 967 | 882 | 54 |
| 337 | E | OE1 | 322 | 969 | 893 | 57 |
| 337 | E | OE2 | 337 | 974 | 878 | 54 |
| 337 | E | C | 331 | 928 | 883 | 31 |
| 337 | E | O | 327 | 919 | 875 | 31 |
| 338 | E | N | 327 | 928 | 895 | 31 |
| 338 | E | CA | 319 | 917 | 901 | 30 |
| 338 | E | CB | 324 | 913 | 915 | 30 |
| 338 | E | CG | 338 | 908 | 915 | 35 |
| 338 | E | CD | 342 | 902 | 928 | 43 |
| 338 | E | OE1 | 333 | 896 | 935 | 48 |
| 338 | E | OE2 | 354 | 903 | 932 | 45 |
| 338 | E | C | 304 | 922 | 901 | 29 |
| 338 | E | O | 301 | 931 | 908 | 30 |
| 339 | V | N | 296 | 916 | 893 | 30 |
| 339 | V | CA | 282 | 919 | 892 | 29 |
| 339 | V | CB | 278 | 922 | 877 | 33 |
| 339 | V | CG1 | 264 | 928 | 877 | 35 |
| 339 | V | CG2 | 288 | 932 | 871 | 37 |
| 339 | V | C | 273 | 908 | 897 | 28 |
| 339 | V | O | 273 | 897 | 891 | 23 |
| 340 | A | N | 266 | 910 | 907 | 27 |
| 340 | A | CA | 257 | 900 | 913 | 27 |
| 340 | A | CB | 252 | 904 | 927 | 29 |
| 340 | A | C | 245 | 897 | 904 | 27 |
| 340 | A | O | 238 | 906 | 900 | 29 |
| 341 | L | N | 244 | 885 | 900 | 27 |
| 341 | L | CA | 233 | 880 | 891 | 23 |
| 341 | L | CB | 233 | 865 | 889 | 22 |
| 341 | L | CG | 234 | 860 | 874 | 26 |
| 341 | L | CD1 | 242 | 870 | 865 | 21 |
| 341 | L | CD2 | 240 | 846 | 874 | 14 |
| 341 | L | C | 220 | 884 | 899 | 26 |
| 341 | L | O | 220 | 888 | 910 | 31 |
| 342 | S | N | 209 | 882 | 892 | 29 |
| 342 | S | CA | 196 | 885 | 899 | 30 |
| 342 | S | CB | 192 | 899 | 896 | 31 |
| 342 | S | OG | 183 | 900 | 885 | 45 |
| 342 | S | C | 185 | 876 | 893 | 30 |
| 342 | S | O | 188 | 865 | 887 | 33 |
| 343 | N | N | 173 | 879 | 895 | 33 |
| 343 | N | CA | 162 | 871 | 889 | 38 |
| 343 | N | CB | 150 | 871 | 899 | 41 |
| 343 | N | CG | 153 | 864 | 912 | 39 |
| 343 | N | OD1 | 158 | 869 | 922 | 42 |
| 343 | N | ND2 | 151 | 851 | 911 | 38 |
| 343 | N | C | 158 | 877 | 876 | 41 |
| 343 | N | O | 151 | 870 | 868 | 42 |
| 344 | T | N | 161 | 889 | 873 | 41 |
| 344 | T | CA | 158 | 895 | 860 | 43 |
| 344 | T | CB | 160 | 911 | 861 | 48 |
| 344 | T | OG1 | 164 | 915 | 874 | 57 |
| 344 | T | CG2 | 147 | 918 | 857 | 52 |
| 344 | T | C | 168 | 890 | 850 | 36 |
| 344 | T | O | 180 | 893 | 849 | 39 |
| 345 | G | N | 163 | 880 | 842 | 30 |
| 345 | G | CA | 171 | 874 | 832 | 27 |
| 345 | G | C | 164 | 864 | 824 | 30 |
| 345 | G | O | 154 | 858 | 830 | 36 |
| 346 | E | N | 168 | 861 | 812 | 26 |
| 346 | E | CA | 161 | 851 | 804 | 30 |
| 346 | E | CB | 162 | 855 | 789 | 37 |
| 346 | E | CG | 174 | 863 | 785 | 42 |
| 346 | E | CD | 172 | 878 | 788 | 49 |
| 346 | E | OE1 | 173 | 882 | 800 | 55 |
| 346 | E | OE2 | 169 | 886 | 779 | 55 |
| 346 | E | C | 167 | 836 | 805 | 31 |
| 346 | E | O | 160 | 827 | 802 | 31 |
| 347 | I | N | 179 | 835 | 811 | 31 |
| 347 | I | CA | 185 | 822 | 812 | 28 |
| 347 | I | CB | 199 | 822 | 807 | 28 |
| 347 | I | CG2 | 205 | 808 | 810 | 24 |
| 347 | I | CG1 | 200 | 825 | 792 | 24 |
| 347 | I | CD1 | 211 | 834 | 788 | 28 |
| 347 | I | C | 184 | 817 | 827 | 28 |
| 347 | I | O | 191 | 823 | 835 | 25 |
| 348 | P | N | 177 | 807 | 830 | 28 |
| 348 | P | CD | 168 | 799 | 821 | 28 |
| 348 | P | CA | 176 | 802 | 844 | 28 |
| 348 | P | CB | 166 | 791 | 843 | 31 |
| 348 | P | CG | 158 | 793 | 830 | 25 |
| 348 | P | C | 190 | 797 | 849 | 27 |
| 348 | P | O | 196 | 790 | 842 | 28 |
| 349 | F | N | 194 | 802 | 860 | 22 |
| 349 | F | CA | 207 | 798 | 865 | 21 |
| 349 | F | CB | 218 | 807 | 860 | 15 |
| 349 | F | CG | 231 | 802 | 861 | 10 |
| 349 | F | CD1 | 236 | 791 | 854 | 10 |
| 349 | F | CD2 | 240 | 808 | 870 | 11 |
| 349 | F | CE1 | 249 | 786 | 855 | 12 |
| 349 | F | CE2 | 253 | 803 | 871 | 17 |
| 349 | F | CZ | 257 | 792 | 863 | 12 |
| 349 | F | C | 208 | 797 | 881 | 21 |
| 349 | F | O | 209 | 808 | 887 | 20 |
| 350 | Y | N | 208 | 785 | 886 | 18 |
| 350 | Y | CA | 209 | 783 | 901 | 16 |
| 350 | Y | CB | 224 | 785 | 905 | 17 |
| 350 | Y | CG | 233 | 774 | 900 | 15 |
| 350 | Y | CD1 | 237 | 774 | 886 | 14 |
| 350 | Y | CE1 | 244 | 763 | 881 | 19 |
| 350 | Y | CD2 | 236 | 763 | 908 | 16 |
| 350 | Y | CE2 | 243 | 752 | 903 | 18 |
| 350 | Y | CZ | 247 | 752 | 889 | 18 |
| 350 | Y | OH | 254 | 741 | 884 | 11 |
| 350 | Y | C | 200 | 792 | 909 | 18 |
| 350 | Y | O | 205 | 799 | 918 | 20 |
| 351 | G | N | 188 | 793 | 906 | 21 |
| 351 | G | CA | 178 | 801 | 913 | 21 |
| 351 | G | C | 178 | 815 | 909 | 22 |
| 351 | G | O | 169 | 823 | 911 | 20 |
| 352 | K | N | 188 | 819 | 901 | 20 |
| 352 | K | CA | 189 | 833 | 896 | 18 |
| 352 | K | CB | 203 | 839 | 899 | 14 |
| 352 | K | CG | 205 | 842 | 914 | 17 |
| 352 | K | CD | 196 | 853 | 918 | 25 |
| 352 | K | CE | 196 | 854 | 933 | 33 |
| 352 | K | NZ | 182 | 856 | 939 | 33 |
| 352 | K | C | 188 | 832 | 881 | 18 |
| 352 | K | O | 183 | 822 | 875 | 13 |
| 353 | A | N | 191 | 843 | 874 | 22 |
| 353 | A | CA | 190 | 844 | 859 | 23 |
| 353 | A | CB | 177 | 851 | 855 | 20 |

TABLE 3-continued

| | | | | | | |
|---|---|---|---|---|---|---|
| 353 | A | C | 201 | 851 | 852 | 21 |
| 353 | A | O | 208 | 859 | 858 | 20 |
| 354 | I | N | 204 | 847 | 840 | 23 |
| 354 | I | CA | 215 | 852 | 832 | 25 |
| 354 | I | CB | 225 | 842 | 827 | 23 |
| 354 | I | CG2 | 236 | 849 | 819 | 20 |
| 354 | I | CG1 | 231 | 834 | 839 | 15 |
| 354 | I | CD1 | 239 | 822 | 834 | 21 |
| 354 | I | C | 209 | 859 | 820 | 28 |
| 354 | I | O | 203 | 852 | 811 | 29 |
| 355 | P | N | 211 | 872 | 818 | 30 |
| 355 | P | CD | 217 | 881 | 827 | 34 |
| 355 | P | CA | 205 | 879 | 806 | 34 |
| 355 | P | CB | 206 | 894 | 810 | 34 |
| 355 | P | CG | 210 | 894 | 825 | 36 |
| 355 | P | C | 215 | 876 | 794 | 35 |
| 355 | P | O | 227 | 879 | 795 | 40 |
| 356 | I | N | 209 | 871 | 783 | 33 |
| 356 | I | CA | 217 | 868 | 771 | 39 |
| 356 | I | CB | 208 | 864 | 759 | 44 |
| 356 | I | CG2 | 217 | 859 | 748 | 42 |
| 356 | I | CG1 | 198 | 854 | 763 | 50 |
| 356 | I | CD1 | 185 | 854 | 755 | 51 |
| 356 | I | C | 226 | 880 | 767 | 40 |
| 356 | I | O | 237 | 878 | 762 | 40 |
| 357 | E | N | 220 | 892 | 769 | 40 |
| 357 | E | CA | 228 | 904 | 765 | 40 |
| 357 | E | CB | 219 | 916 | 767 | 49 |
| 357 | E | CG | 210 | 916 | 780 | 59 |
| 357 | E | CD | 197 | 909 | 778 | 65 |
| 357 | E | OE1 | 197 | 896 | 781 | 67 |
| 357 | E | OE2 | 187 | 915 | 775 | 65 |
| 357 | E | C | 240 | 906 | 774 | 39 |
| 357 | E | O | 245 | 917 | 775 | 43 |
| 358 | A | N | 246 | 895 | 779 | 36 |
| 358 | A | CA | 258 | 896 | 787 | 36 |
| 358 | A | CB | 254 | 893 | 801 | 37 |
| 358 | A | C | 267 | 885 | 782 | 37 |
| 358 | A | O | 279 | 885 | 786 | 36 |
| 359 | I | N | 263 | 876 | 773 | 36 |
| 359 | I | CA | 271 | 866 | 768 | 34 |
| 359 | I | CB | 268 | 853 | 776 | 31 |
| 359 | I | CG2 | 272 | 855 | 790 | 26 |
| 359 | I | CG1 | 253 | 849 | 775 | 28 |
| 359 | I | CD1 | 250 | 835 | 781 | 21 |
| 359 | I | C | 268 | 863 | 753 | 37 |
| 359 | I | O | 274 | 854 | 747 | 35 |
| 360 | R | N | 260 | 871 | 747 | 42 |
| 360 | R | CA | 257 | 869 | 733 | 49 |
| 360 | R | CB | 245 | 878 | 729 | 52 |
| 360 | R | CG | 245 | 892 | 735 | 57 |
| 360 | R | CD | 254 | 901 | 728 | 62 |
| 360 | R | NE | 258 | 913 | 736 | 66 |
| 360 | R | CZ | 266 | 913 | 746 | 67 |
| 360 | R | NH1 | 272 | 902 | 750 | 69 |
| 360 | R | NH2 | 268 | 924 | 753 | 65 |
| 360 | R | C | 269 | 873 | 724 | 49 |
| 360 | R | O | 271 | 866 | 714 | 52 |
| 361 | G | N | 276 | 883 | 729 | 49 |
| 361 | G | CA | 288 | 887 | 721 | 47 |
| 361 | G | C | 301 | 884 | 729 | 47 |
| 361 | G | O | 302 | 888 | 741 | 48 |
| 362 | G | N | 311 | 878 | 722 | 42 |
| 362 | G | CA | 324 | 876 | 729 | 34 |
| 362 | G | C | 325 | 861 | 734 | 29 |
| 362 | G | O | 318 | 852 | 729 | 27 |
| 363 | R | N | 335 | 859 | 742 | 26 |
| 363 | R | CA | 338 | 846 | 748 | 23 |
| 363 | R | CB | 352 | 842 | 745 | 23 |
| 363 | R | CG | 359 | 850 | 733 | 22 |
| 363 | R | CD | 373 | 845 | 731 | 21 |
| 363 | R | NE | 373 | 832 | 725 | 22 |
| 363 | R | CZ | 379 | 821 | 731 | 24 |
| 363 | R | NH1 | 386 | 823 | 742 | 34 |
| 363 | R | NH2 | 379 | 810 | 725 | 17 |
| 363 | R | C | 336 | 846 | 763 | 19 |
| 363 | R | O | 341 | 855 | 770 | 19 |
| 364 | H | N | 328 | 837 | 768 | 16 |
| 364 | H | CA | 325 | 836 | 782 | 15 |

TABLE 3-continued

| | | | | | | |
|---|---|---|---|---|---|---|
| 364 | H | CB | 311 | 842 | 784 | 15 |
| 364 | H | CG | 309 | 855 | 777 | 22 |
| 364 | H | CD2 | 304 | 857 | 764 | 20 |
| 364 | H | ND1 | 311 | 867 | 782 | 19 |
| 364 | H | CE1 | 308 | 876 | 773 | 23 |
| 364 | H | NE2 | 304 | 871 | 763 | 22 |
| 364 | H | C | 326 | 822 | 788 | 20 |
| 364 | H | O | 324 | 812 | 781 | 19 |
| 365 | L | N | 329 | 822 | 801 | 21 |
| 365 | L | CA | 330 | 810 | 809 | 23 |
| 365 | L | CB | 344 | 808 | 815 | 21 |
| 365 | L | CG | 349 | 794 | 816 | 23 |
| 365 | L | CD1 | 359 | 794 | 827 | 23 |
| 365 | L | CD2 | 338 | 784 | 818 | 15 |
| 365 | L | C | 319 | 809 | 820 | 25 |
| 365 | L | O | 319 | 817 | 829 | 25 |
| 366 | I | N | 310 | 800 | 818 | 25 |
| 366 | I | CA | 300 | 798 | 828 | 19 |
| 366 | I | CB | 286 | 795 | 822 | 16 |
| 366 | I | CG2 | 277 | 790 | 832 | 12 |
| 366 | I | CG1 | 281 | 808 | 815 | 20 |
| 366 | I | CD1 | 271 | 806 | 805 | 17 |
| 366 | I | C | 305 | 785 | 836 | 21 |
| 366 | I | O | 308 | 775 | 829 | 20 |
| 367 | F | N | 305 | 786 | 849 | 20 |
| 367 | F | CA | 309 | 775 | 857 | 15 |
| 367 | F | CB | 318 | 779 | 868 | 13 |
| 367 | F | CG | 333 | 779 | 864 | 14 |
| 367 | F | CD1 | 340 | 767 | 862 | 12 |
| 367 | F | CD2 | 340 | 791 | 862 | 11 |
| 367 | F | CE1 | 353 | 767 | 859 | 6 |
| 367 | F | CE2 | 353 | 791 | 859 | 12 |
| 367 | F | CZ | 360 | 779 | 857 | 12 |
| 367 | F | C | 297 | 768 | 863 | 17 |
| 367 | F | O | 289 | 774 | 870 | 17 |
| 368 | C | N | 296 | 755 | 860 | 17 |
| 368 | C | CA | 285 | 747 | 866 | 21 |
| 368 | C | CB | 277 | 740 | 854 | 23 |
| 368 | C | SG | 268 | 753 | 844 | 27 |
| 368 | C | C | 290 | 736 | 875 | 22 |
| 368 | C | O | 301 | 731 | 874 | 22 |
| 369 | H | N | 282 | 732 | 885 | 23 |
| 369 | H | CA | 286 | 723 | 895 | 26 |
| 369 | H | CB | 277 | 722 | 907 | 24 |
| 369 | H | CG | 265 | 714 | 905 | 26 |
| 369 | H | CD2 | 254 | 716 | 896 | 24 |
| 369 | H | ND1 | 262 | 703 | 912 | 34 |
| 369 | H | CE1 | 251 | 697 | 908 | 33 |
| 369 | H | NE2 | 246 | 705 | 898 | 23 |
| 369 | H | C | 288 | 708 | 889 | 29 |
| 369 | H | O | 296 | 701 | 894 | 33 |
| 370 | S | N | 279 | 705 | 880 | 31 |
| 370 | S | CA | 279 | 691 | 874 | 33 |
| 370 | S | CB | 267 | 684 | 879 | 34 |
| 370 | S | OG | 255 | 688 | 873 | 42 |
| 370 | S | C | 280 | 690 | 859 | 32 |
| 370 | S | O | 278 | 700 | 852 | 30 |
| 371 | K | N | 283 | 678 | 854 | 32 |
| 371 | K | CA | 284 | 676 | 840 | 34 |
| 371 | K | CB | 289 | 661 | 838 | 32 |
| 371 | K | CG | 285 | 655 | 825 | 35 |
| 371 | K | CD | 287 | 640 | 825 | 34 |
| 371 | K | CE | 292 | 634 | 812 | 34 |
| 371 | K | NZ | 282 | 636 | 801 | 38 |
| 371 | K | C | 270 | 677 | 834 | 36 |
| 371 | K | O | 268 | 682 | 823 | 36 |
| 372 | K | N | 260 | 673 | 841 | 34 |
| 372 | K | CA | 246 | 673 | 837 | 32 |
| 372 | K | CB | 237 | 668 | 848 | 33 |
| 372 | K | CG | 226 | 659 | 842 | 38 |
| 372 | K | CD | 212 | 663 | 847 | 45 |
| 372 | K | CE | 207 | 656 | 860 | 46 |
| 372 | K | NZ | 197 | 663 | 868 | 43 |
| 372 | K | C | 242 | 688 | 833 | 31 |
| 372 | K | O | 237 | 690 | 822 | 35 |
| 373 | K | N | 243 | 697 | 843 | 32 |
| 373 | K | CA | 239 | 711 | 841 | 32 |
| 373 | K | CB | 241 | 718 | 854 | 38 |
| 373 | K | CG | 229 | 717 | 864 | 52 |

TABLE 3-continued

| | | | | | | |
|---|---|---|---|---|---|---|
| 373 | K | CD | 227 | 703 | 868 | 59 |
| 373 | K | CE | 213 | 700 | 873 | 64 |
| 373 | K | NZ | 211 | 687 | 879 | 70 |
| 373 | K | C | 247 | 718 | 830 | 32 |
| 373 | K | O | 243 | 728 | 825 | 33 |
| 374 | C | N | 259 | 712 | 827 | 34 |
| 374 | C | CA | 267 | 718 | 816 | 35 |
| 374 | C | CB | 281 | 711 | 816 | 34 |
| 374 | C | SG | 292 | 717 | 830 | 31 |
| 374 | C | C | 260 | 715 | 803 | 37 |
| 374 | C | O | 259 | 723 | 794 | 38 |
| 375 | D | N | 255 | 702 | 802 | 37 |
| 375 | D | CA | 248 | 698 | 790 | 37 |
| 375 | D | CB | 246 | 683 | 791 | 37 |
| 375 | D | CG | 258 | 674 | 788 | 40 |
| 375 | D | OD1 | 268 | 680 | 784 | 43 |
| 375 | D | OD2 | 258 | 662 | 791 | 38 |
| 375 | D | C | 235 | 705 | 789 | 39 |
| 375 | D | O | 231 | 709 | 777 | 43 |
| 376 | E | N | 228 | 707 | 800 | 38 |
| 376 | E | CA | 215 | 714 | 799 | 38 |
| 376 | E | CB | 209 | 714 | 813 | 40 |
| 376 | E | CG | 207 | 700 | 819 | 49 |
| 376 | E | CD | 201 | 700 | 833 | 54 |
| 376 | E | OE1 | 194 | 710 | 836 | 56 |
| 376 | E | OE2 | 202 | 690 | 840 | 54 |
| 376 | E | C | 217 | 728 | 795 | 37 |
| 376 | E | O | 209 | 733 | 787 | 38 |
| 377 | L | N | 226 | 735 | 801 | 38 |
| 377 | L | CA | 229 | 749 | 798 | 34 |
| 377 | L | CB | 240 | 755 | 807 | 30 |
| 377 | L | CG | 237 | 768 | 814 | 25 |
| 377 | L | CD1 | 247 | 778 | 810 | 34 |
| 377 | L | CD2 | 223 | 773 | 810 | 31 |
| 377 | L | C | 233 | 751 | 784 | 36 |
| 377 | L | O | 228 | 759 | 776 | 35 |
| 378 | A | N | 243 | 743 | 780 | 38 |
| 378 | A | CA | 248 | 743 | 766 | 34 |
| 378 | A | CB | 257 | 731 | 764 | 28 |
| 378 | A | C | 236 | 742 | 757 | 32 |
| 378 | A | O | 235 | 751 | 748 | 33 |
| 379 | A | N | 228 | 732 | 759 | 32 |
| 379 | A | CA | 216 | 730 | 751 | 34 |
| 379 | A | CB | 207 | 719 | 757 | 33 |
| 379 | A | C | 207 | 743 | 750 | 36 |
| 379 | A | O | 204 | 747 | 739 | 39 |
| 380 | K | N | 203 | 748 | 761 | 38 |
| 380 | K | CA | 195 | 760 | 761 | 39 |
| 380 | K | CB | 192 | 764 | 776 | 40 |
| 380 | K | CG | 184 | 777 | 777 | 42 |
| 380 | K | CD | 170 | 775 | 782 | 42 |
| 380 | K | CE | 163 | 788 | 787 | 44 |
| 380 | K | NZ | 150 | 791 | 781 | 47 |
| 380 | K | C | 202 | 772 | 754 | 38 |
| 380 | K | O | 195 | 779 | 747 | 38 |
| 381 | L | N | 215 | 774 | 757 | 39 |
| 381 | L | CA | 222 | 785 | 750 | 41 |
| 381 | L | CB | 236 | 786 | 756 | 39 |
| 381 | L | CG | 237 | 789 | 770 | 35 |
| 381 | L | CD1 | 251 | 784 | 776 | 36 |
| 381 | L | CD2 | 235 | 804 | 773 | 37 |
| 381 | L | C | 222 | 784 | 735 | 44 |
| 381 | L | O | 219 | 794 | 728 | 46 |
| 382 | S | N | 224 | 772 | 730 | 46 |
| 382 | S | CA | 224 | 769 | 716 | 52 |
| 382 | S | CB | 228 | 755 | 713 | 52 |
| 382 | S | OG | 242 | 754 | 709 | 52 |
| 382 | S | C | 211 | 772 | 710 | 54 |
| 382 | S | O | 210 | 780 | 700 | 55 |
| 383 | G | N | 200 | 767 | 716 | 54 |
| 383 | G | CA | 187 | 770 | 712 | 53 |
| 383 | G | C | 183 | 785 | 712 | 48 |
| 383 | G | O | 174 | 790 | 706 | 48 |
| 384 | L | N | 191 | 792 | 721 | 45 |
| 384 | L | CA | 189 | 806 | 723 | 41 |
| 384 | L | CB | 194 | 811 | 737 | 42 |
| 384 | L | CG | 183 | 812 | 747 | 40 |
| 384 | L | CD1 | 188 | 821 | 759 | 33 |
| 384 | L | CD2 | 171 | 819 | 741 | 41 |
| 384 | L | C | 197 | 814 | 712 | 40 |
| 384 | L | O | 197 | 826 | 712 | 35 |
| 385 | G | N | 204 | 806 | 734 | 44 |
| 385 | G | CA | 212 | 812 | 693 | 47 |
| 385 | G | C | 226 | 816 | 698 | 51 |
| 385 | G | O | 231 | 827 | 693 | 53 |
| 386 | I | N | 232 | 808 | 706 | 51 |
| 386 | I | CA | 245 | 811 | 711 | 50 |
| 386 | I | CB | 245 | 813 | 727 | 52 |
| 386 | I | CG2 | 258 | 810 | 733 | 52 |
| 386 | I | CG1 | 240 | 828 | 730 | 52 |
| 386 | I | CD1 | 229 | 829 | 739 | 57 |
| 386 | I | C | 255 | 799 | 708 | 49 |
| 386 | I | O | 251 | 788 | 709 | 48 |
| 387 | N | N | 267 | 803 | 705 | 49 |
| 387 | N | CA | 277 | 793 | 702 | 49 |
| 387 | N | CB | 288 | 798 | 694 | 52 |
| 387 | N | CG | 299 | 787 | 690 | 49 |
| 387 | N | OD1 | 295 | 775 | 688 | 44 |
| 387 | N | ND2 | 311 | 791 | 690 | 50 |
| 387 | N | C | 282 | 789 | 716 | 46 |
| 387 | N | O | 291 | 795 | 721 | 45 |
| 388 | A | N | 276 | 779 | 722 | 44 |
| 388 | A | CA | 280 | 774 | 735 | 42 |
| 388 | A | CB | 267 | 773 | 744 | 36 |
| 388 | A | C | 286 | 761 | 733 | 44 |
| 388 | A | O | 284 | 754 | 723 | 48 |
| 389 | V | N | 294 | 757 | 743 | 42 |
| 389 | V | CA | 301 | 744 | 743 | 39 |
| 389 | V | CB | 315 | 745 | 735 | 38 |
| 389 | V | CG1 | 323 | 733 | 738 | 36 |
| 389 | V | CG2 | 312 | 747 | 720 | 37 |
| 389 | V | C | 303 | 740 | 757 | 40 |
| 389 | V | O | 308 | 747 | 765 | 43 |
| 390 | A | N | 300 | 727 | 760 | 37 |
| 390 | A | CA | 301 | 722 | 773 | 36 |
| 390 | A | CB | 290 | 712 | 776 | 32 |
| 390 | A | C | 315 | 715 | 775 | 35 |
| 390 | A | O | 320 | 710 | 765 | 33 |
| 391 | Y | N | 320 | 716 | 787 | 36 |
| 391 | Y | CA | 333 | 709 | 789 | 36 |
| 391 | Y | CB | 345 | 719 | 787 | 32 |
| 391 | Y | CG | 358 | 712 | 789 | 36 |
| 391 | Y | CD1 | 364 | 704 | 779 | 34 |
| 391 | Y | CE1 | 375 | 696 | 782 | 33 |
| 391 | Y | CD2 | 365 | 712 | 801 | 39 |
| 391 | Y | CE2 | 376 | 705 | 804 | 37 |
| 391 | Y | CZ | 382 | 697 | 794 | 35 |
| 391 | Y | OH | 393 | 690 | 797 | 38 |
| 391 | Y | C | 334 | 704 | 803 | 36 |
| 391 | Y | O | 329 | 710 | 813 | 38 |
| 392 | Y | N | 340 | 692 | 804 | 35 |
| 392 | Y | CA | 342 | 685 | 817 | 36 |
| 392 | Y | CB | 328 | 681 | 823 | 33 |
| 392 | Y | CG | 319 | 676 | 813 | 32 |
| 392 | Y | CD1 | 320 | 664 | 806 | 32 |
| 392 | Y | CE1 | 311 | 659 | 797 | 32 |
| 392 | Y | CD2 | 308 | 684 | 809 | 29 |
| 392 | Y | CE2 | 298 | 680 | 800 | 29 |
| 392 | Y | CZ | 300 | 667 | 794 | 31 |
| 392 | Y | OH | 291 | 663 | 785 | 30 |
| 392 | Y | C | 350 | 673 | 815 | 40 |
| 392 | Y | O | 355 | 670 | 804 | 44 |
| 393 | R | N | 353 | 666 | 826 | 43 |
| 393 | R | CA | 361 | 654 | 825 | 44 |
| 393 | R | CB | 362 | 647 | 839 | 49 |
| 393 | R | CG | 370 | 634 | 839 | 53 |
| 393 | R | CD | 373 | 629 | 853 | 55 |
| 393 | R | NE | 361 | 621 | 858 | 59 |
| 393 | R | CZ | 358 | 609 | 853 | 62 |
| 393 | R | NH1 | 365 | 603 | 843 | 61 |
| 393 | R | NH2 | 347 | 603 | 858 | 66 |
| 393 | R | C | 356 | 644 | 815 | 41 |
| 393 | R | O | 344 | 640 | 815 | 39 |
| 394 | G | N | 365 | 639 | 806 | 39 |
| 394 | G | CA | 361 | 629 | 796 | 41 |
| 394 | G | C | 363 | 635 | 782 | 41 |
| 394 | G | O | 368 | 628 | 773 | 42 |
| 395 | L | N | 359 | 647 | 781 | 39 |

TABLE 3-continued

| | | | | | | |
|---|---|---|---|---|---|---|
| 395 | L | CA | 361 | 654 | 768 | 38 |
| 395 | L | CB | 352 | 667 | 768 | 35 |
| 395 | L | CG | 337 | 665 | 766 | 34 |
| 395 | L | CD1 | 332 | 653 | 773 | 33 |
| 395 | L | CD2 | 330 | 677 | 771 | 31 |
| 395 | L | C | 375 | 659 | 766 | 43 |
| 395 | L | O | 382 | 661 | 775 | 42 |
| 396 | D | N | 378 | 660 | 753 | 51 |
| 396 | D | CA | 392 | 664 | 749 | 60 |
| 396 | D | CB | 397 | 657 | 737 | 69 |
| 396 | D | CG | 394 | 664 | 724 | 78 |
| 396 | D | OD1 | 384 | 662 | 717 | 82 |
| 396 | D | OD2 | 402 | 673 | 720 | 77 |
| 396 | D | C | 389 | 679 | 746 | 61 |
| 396 | D | O | 379 | 682 | 740 | 65 |
| 397 | V | N | 398 | 687 | 750 | 61 |
| 397 | V | CA | 397 | 702 | 747 | 63 |
| 397 | V | CB | 410 | 709 | 748 | 59 |
| 397 | V | CG1 | 408 | 724 | 747 | 59 |
| 397 | V | CG2 | 417 | 706 | 762 | 62 |
| 397 | V | C | 391 | 705 | 734 | 65 |
| 397 | V | O | 397 | 706 | 723 | 69 |
| 398 | S | N | 377 | 706 | 734 | 61 |
| 398 | S | CA | 370 | 709 | 722 | 55 |
| 398 | S | CB | 357 | 700 | 721 | 53 |
| 398 | S | OG | 353 | 696 | 734 | 52 |
| 398 | S | C | 365 | 723 | 723 | 52 |
| 398 | S | O | 356 | 728 | 716 | 47 |
| 399 | V | N | 371 | 731 | 732 | 49 |
| 399 | V | CA | 368 | 745 | 734 | 49 |
| 399 | V | CB | 374 | 750 | 747 | 48 |
| 399 | V | CG1 | 371 | 765 | 749 | 41 |
| 399 | V | CG2 | 370 | 742 | 759 | 42 |
| 399 | V | C | 374 | 753 | 722 | 53 |
| 399 | V | O | 386 | 751 | 719 | 54 |
| 400 | I | N | 366 | 761 | 716 | 56 |
| 400 | I | CA | 370 | 769 | 705 | 59 |
| 400 | I | CB | 359 | 779 | 701 | 59 |
| 400 | I | CG2 | 362 | 784 | 687 | 59 |
| 400 | I | CG1 | 345 | 772 | 702 | 64 |
| 400 | I | CD1 | 344 | 759 | 695 | 72 |
| 400 | I | C | 382 | 778 | 710 | 65 |
| 400 | I | O | 380 | 786 | 718 | 68 |
| 401 | P | N | 394 | 775 | 705 | 70 |
| 401 | P | CD | 397 | 765 | 695 | 75 |
| 401 | P | CA | 406 | 783 | 709 | 73 |
| 401 | P | CB | 417 | 773 | 705 | 74 |
| 401 | P | CG | 412 | 766 | 693 | 77 |
| 401 | P | C | 407 | 796 | 701 | 73 |
| 401 | P | O | 410 | 806 | 707 | 71 |
| 402 | T | N | 403 | 795 | 688 | 76 |
| 402 | T | CA | 404 | 807 | 680 | 78 |
| 402 | T | CB | 399 | 804 | 666 | 80 |
| 402 | T | OG1 | 408 | 794 | 660 | 83 |
| 402 | T | CG2 | 400 | 817 | 657 | 81 |
| 402 | T | C | 395 | 818 | 686 | 77 |
| 402 | T | O | 382 | 817 | 684 | 76 |
| 403 | I | N | 401 | 827 | 693 | 79 |
| 403 | I | CA | 394 | 838 | 700 | 80 |
| 403 | I | CB | 404 | 849 | 703 | 80 |
| 403 | I | CG2 | 407 | 857 | 691 | 80 |
| 403 | I | CG1 | 399 | 858 | 715 | 80 |
| 403 | I | CD1 | 406 | 856 | 728 | 79 |
| 403 | I | C | 381 | 843 | 693 | 80 |
| 403 | I | O | 381 | 854 | 688 | 82 |
| 404 | G | N | 371 | 835 | 692 | 79 |
| 404 | G | CA | 359 | 839 | 685 | 75 |
| 404 | G | C | 347 | 836 | 694 | 72 |
| 404 | G | O | 346 | 827 | 702 | 73 |
| 405 | D | N | 336 | 845 | 692 | 67 |
| 405 | D | CA | 324 | 843 | 700 | 58 |
| 405 | D | CB | 312 | 849 | 692 | 58 |
| 405 | D | CG | 310 | 864 | 694 | 61 |
| 405 | D | OD1 | 299 | 869 | 691 | 66 |
| 405 | D | OD2 | 319 | 871 | 698 | 60 |
| 405 | D | C | 321 | 829 | 704 | 52 |
| 405 | D | O | 320 | 820 | 696 | 49 |
| 406 | V | N | 319 | 827 | 717 | 47 |
| 406 | V | CA | 316 | 814 | 723 | 39 |
| 406 | V | CB | 327 | 804 | 720 | 36 |
| 406 | V | CG1 | 339 | 807 | 730 | 29 |
| 406 | V | CG2 | 322 | 790 | 723 | 24 |
| 406 | V | C | 313 | 815 | 738 | 38 |
| 406 | V | O | 318 | 825 | 744 | 32 |
| 407 | V | N | 306 | 806 | 743 | 34 |
| 407 | V | CA | 303 | 805 | 757 | 30 |
| 407 | V | CB | 288 | 807 | 759 | 29 |
| 407 | V | CG1 | 285 | 806 | 774 | 34 |
| 407 | V | CG2 | 284 | 820 | 753 | 26 |
| 407 | V | C | 307 | 791 | 761 | 31 |
| 407 | V | O | 301 | 781 | 756 | 35 |
| 408 | V | N | 316 | 790 | 770 | 26 |
| 408 | V | CA | 321 | 777 | 775 | 20 |
| 408 | V | CB | 336 | 776 | 777 | 21 |
| 408 | V | CG1 | 340 | 762 | 780 | 23 |
| 408 | V | CG2 | 343 | 781 | 764 | 26 |
| 408 | V | C | 314 | 774 | 788 | 19 |
| 408 | V | O | 316 | 782 | 798 | 22 |
| 409 | V | N | 306 | 763 | 789 | 18 |
| 409 | V | CA | 300 | 760 | 802 | 14 |
| 409 | V | CB | 285 | 755 | 799 | 13 |
| 409 | V | CG1 | 278 | 755 | 813 | 13 |
| 409 | V | CG2 | 279 | 765 | 790 | 17 |
| 409 | V | C | 308 | 748 | 806 | 18 |
| 409 | V | O | 308 | 737 | 800 | 13 |
| 410 | A | N | 316 | 750 | 817 | 20 |
| 410 | A | CA | 325 | 739 | 822 | 22 |
| 410 | A | CB | 339 | 742 | 818 | 24 |
| 410 | A | C | 324 | 737 | 836 | 25 |
| 410 | A | O | 317 | 744 | 844 | 26 |
| 411 | T | N | 331 | 726 | 841 | 25 |
| 411 | T | CA | 331 | 722 | 855 | 24 |
| 411 | T | CB | 330 | 707 | 857 | 21 |
| 411 | T | OG1 | 338 | 700 | 847 | 27 |
| 411 | T | CG2 | 315 | 704 | 855 | 23 |
| 411 | T | C | 346 | 726 | 858 | 24 |
| 411 | T | O | 353 | 731 | 850 | 21 |
| 412 | D | N | 350 | 723 | 871 | 26 |
| 412 | D | CA | 363 | 727 | 875 | 31 |
| 412 | D | CB | 365 | 724 | 890 | 36 |
| 412 | D | CG | 358 | 734 | 898 | 39 |
| 412 | D | OD1 | 359 | 746 | 896 | 48 |
| 412 | D | OD2 | 351 | 729 | 908 | 44 |
| 412 | D | C | 374 | 720 | 867 | 31 |
| 412 | D | O | 386 | 723 | 867 | 30 |
| 413 | A | N | 370 | 710 | 859 | 29 |
| 413 | A | CA | 379 | 703 | 850 | 27 |
| 413 | A | CB | 372 | 692 | 842 | 27 |
| 413 | A | C | 386 | 712 | 840 | 27 |
| 413 | A | O | 397 | 709 | 835 | 30 |
| 414 | L | N | 380 | 724 | 839 | 27 |
| 414 | L | CA | 386 | 735 | 830 | 26 |
| 414 | L | CB | 378 | 747 | 832 | 20 |
| 414 | L | CG | 375 | 756 | 820 | 19 |
| 414 | L | CD1 | 381 | 769 | 822 | 14 |
| 414 | L | CD2 | 379 | 750 | 807 | 16 |
| 414 | L | C | 400 | 737 | 834 | 31 |
| 414 | L | O | 409 | 739 | 826 | 33 |
| 415 | M | N | 403 | 738 | 847 | 35 |
| 415 | M | CA | 416 | 740 | 853 | 38 |
| 415 | M | CB | 416 | 738 | 868 | 46 |
| 415 | M | CG | 430 | 739 | 875 | 58 |
| 415 | M | SD | 438 | 724 | 876 | 66 |
| 415 | M | CE | 450 | 727 | 889 | 59 |
| 415 | M | C | 427 | 732 | 847 | 37 |
| 415 | M | O | 436 | 737 | 841 | 43 |
| 416 | T | N | 426 | 719 | 849 | 36 |
| 416 | T | CA | 436 | 709 | 844 | 35 |
| 416 | T | CB | 434 | 695 | 849 | 36 |
| 416 | T | OG1 | 420 | 692 | 850 | 34 |
| 416 | T | CG2 | 441 | 694 | 863 | 38 |
| 416 | T | C | 436 | 708 | 828 | 35 |
| 416 | T | O | 447 | 706 | 822 | 37 |
| 417 | G | N | 424 | 709 | 822 | 32 |
| 417 | G | CA | 423 | 707 | 808 | 32 |
| 417 | G | C | 424 | 719 | 799 | 33 |
| 417 | G | O | 426 | 718 | 787 | 35 |
| 418 | Y | N | 423 | 732 | 804 | 32 |

TABLE 3-continued

| | | | | | |
|---|---|---|---|---|---|
| 418 | Y | CA | 424 | 743 | 795 | 30 |
| 418 | Y | CB | 410 | 748 | 792 | 26 |
| 418 | Y | CG | 409 | 759 | 781 | 20 |
| 418 | Y | CD1 | 411 | 756 | 768 | 19 |
| 418 | Y | CE1 | 410 | 766 | 758 | 21 |
| 418 | Y | CD2 | 406 | 772 | 785 | 17 |
| 418 | Y | CE2 | 405 | 782 | 776 | 22 |
| 418 | Y | CZ | 407 | 779 | 762 | 28 |
| 418 | Y | OH | 406 | 789 | 753 | 36 |
| 418 | Y | C | 431 | 755 | 802 | 32 |
| 418 | Y | O | 430 | 758 | 813 | 36 |
| 419 | T | N | 439 | 762 | 793 | 33 |
| 419 | T | CA | 447 | 773 | 798 | 35 |
| 419 | T | CB | 462 | 772 | 795 | 36 |
| 419 | T | OG1 | 464 | 765 | 783 | 38 |
| 419 | T | CG2 | 468 | 763 | 806 | 37 |
| 419 | T | C | 442 | 785 | 789 | 36 |
| 419 | T | O | 445 | 785 | 777 | 38 |
| 420 | G | N | 434 | 794 | 794 | 31 |
| 420 | G | CA | 429 | 805 | 787 | 32 |
| 420 | G | C | 419 | 813 | 795 | 35 |
| 420 | G | O | 412 | 808 | 803 | 37 |
| 421 | D | N | 419 | 826 | 792 | 38 |
| 421 | D | CA | 410 | 835 | 799 | 42 |
| 421 | D | CB | 418 | 848 | 803 | 49 |
| 421 | D | CG | 424 | 855 | 791 | 57 |
| 421 | D | OD1 | 435 | 849 | 787 | 63 |
| 421 | D | OD2 | 420 | 865 | 787 | 61 |
| 421 | D | C | 398 | 839 | 791 | 39 |
| 421 | D | O | 397 | 834 | 779 | 39 |
| 422 | F | N | 389 | 847 | 796 | 37 |
| 422 | F | CA | 377 | 851 | 789 | 32 |
| 422 | F | CB | 366 | 841 | 792 | 24 |
| 422 | F | CG | 369 | 827 | 789 | 20 |
| 422 | F | CD1 | 376 | 819 | 797 | 22 |
| 422 | F | CD2 | 364 | 822 | 777 | 23 |
| 422 | F | CE1 | 379 | 806 | 794 | 20 |
| 422 | F | CE2 | 367 | 808 | 773 | 23 |
| 422 | F | CZ | 374 | 800 | 782 | 25 |
| 422 | F | C | 373 | 865 | 792 | 31 |
| 422 | F | O | 379 | 872 | 800 | 30 |
| 423 | D | N | 363 | 870 | 785 | 31 |
| 423 | D | CA | 358 | 884 | 787 | 34 |
| 423 | D | CB | 349 | 888 | 775 | 34 |
| 423 | D | CG | 355 | 886 | 762 | 36 |
| 423 | D | OD1 | 348 | 883 | 752 | 31 |
| 423 | D | OD2 | 368 | 887 | 761 | 36 |
| 423 | D | C | 351 | 885 | 800 | 34 |
| 423 | D | O | 352 | 895 | 807 | 33 |
| 424 | S | N | 343 | 875 | 804 | 33 |
| 424 | S | CA | 336 | 875 | 816 | 31 |
| 424 | S | CB | 322 | 882 | 814 | 36 |
| 424 | S | OG | 312 | 872 | 810 | 36 |
| 424 | S | C | 334 | 861 | 821 | 27 |
| 424 | S | O | 334 | 851 | 813 | 22 |
| 425 | V | N | 332 | 859 | 834 | 24 |
| 425 | V | CA | 330 | 846 | 840 | 23 |
| 425 | V | CB | 343 | 843 | 849 | 21 |
| 425 | V | CG1 | 340 | 830 | 857 | 15 |
| 425 | V | CG2 | 355 | 841 | 841 | 22 |
| 425 | V | C | 318 | 846 | 849 | 20 |
| 425 | V | O | 316 | 855 | 857 | 23 |
| 426 | I | N | 309 | 836 | 847 | 18 |
| 426 | I | CA | 297 | 834 | 855 | 17 |
| 426 | I | CB | 285 | 833 | 846 | 15 |
| 426 | I | CG2 | 272 | 830 | 854 | 13 |
| 426 | I | CG1 | 283 | 846 | 838 | 6 |
| 426 | I | CD1 | 271 | 846 | 828 | 15 |
| 426 | I | C | 299 | 822 | 864 | 15 |
| 426 | I | O | 300 | 811 | 859 | 16 |
| 427 | D | N | 299 | 825 | 877 | 17 |
| 427 | D | CA | 300 | 814 | 887 | 14 |
| 427 | D | CB | 310 | 819 | 898 | 13 |
| 427 | D | CG | 317 | 808 | 905 | 18 |
| 427 | D | OD1 | 312 | 796 | 905 | 25 |
| 427 | D | OD2 | 327 | 811 | 912 | 17 |
| 427 | D | C | 287 | 810 | 894 | 17 |
| 427 | D | O | 279 | 818 | 897 | 15 |
| 428 | C | N | 285 | 797 | 895 | 15 |
| 428 | C | CA | 273 | 792 | 901 | 12 |
| 428 | C | CB | 271 | 777 | 897 | 12 |
| 428 | C | SG | 283 | 765 | 902 | 19 |
| 428 | C | C | 277 | 792 | 916 | 20 |
| 428 | C | O | 268 | 791 | 925 | 23 |
| 429 | N | N | 290 | 793 | 919 | 19 |
| 429 | N | CA | 295 | 794 | 933 | 17 |
| 429 | N | CB | 288 | 805 | 940 | 16 |
| 429 | N | CG | 291 | 819 | 934 | 15 |
| 429 | N | OD1 | 282 | 827 | 931 | 15 |
| 429 | N | ND2 | 304 | 822 | 931 | 16 |
| 429 | N | C | 294 | 781 | 941 | 14 |
| 429 | N | O | 295 | 782 | 954 | 15 |
| 430 | T | N | 291 | 770 | 935 | 16 |
| 430 | T | CA | 291 | 757 | 943 | 16 |
| 430 | T | CB | 277 | 751 | 944 | 13 |
| 430 | T | OG1 | 271 | 749 | 931 | 16 |
| 430 | T | CG2 | 268 | 760 | 952 | 18 |
| 430 | T | C | 300 | 747 | 936 | 19 |
| 430 | T | O | 304 | 749 | 924 | 22 |
| 431 | C | N | 303 | 736 | 943 | 22 |
| 431 | C | CA | 312 | 726 | 937 | 25 |
| 431 | C | CB | 327 | 730 | 939 | 31 |
| 431 | C | SG | 331 | 736 | 955 | 47 |
| 431 | C | C | 309 | 713 | 944 | 22 |
| 431 | C | O | 306 | 713 | 956 | 29 |
| 432 | V | N | 311 | 702 | 937 | 20 |
| 432 | V | CA | 309 | 689 | 943 | 21 |
| 432 | V | CB | 304 | 679 | 933 | 17 |
| 432 | V | CG1 | 307 | 664 | 937 | 17 |
| 432 | V | CG2 | 290 | 680 | 929 | 13 |
| 432 | V | C | 321 | 684 | 950 | 19 |
| 432 | V | O | 332 | 684 | 945 | 23 |
| 433 | T | N | 319 | 679 | 963 | 16 |
| 433 | T | CA | 331 | 674 | 970 | 19 |
| 433 | T | CB | 336 | 683 | 981 | 22 |
| 433 | T | OG1 | 325 | 685 | 991 | 26 |
| 433 | T | CG2 | 339 | 697 | 975 | 36 |
| 433 | T | C | 326 | 661 | 977 | 18 |
| 433 | T | O | 314 | 659 | 979 | 16 |
| 434 | Q | N | 336 | 653 | 981 | 18 |
| 434 | Q | CA | 332 | 640 | 988 | 13 |
| 434 | Q | CB | 340 | 629 | 981 | 16 |
| 434 | Q | CG | 341 | 630 | 966 | 28 |
| 434 | Q | CD | 348 | 618 | 960 | 29 |
| 434 | Q | OE1 | 359 | 616 | 962 | 38 |
| 434 | Q | NE2 | 340 | 610 | 952 | 35 |
| 434 | Q | C | 336 | 641 | 1002 | 13 |
| 434 | Q | O | 345 | 648 | 1007 | 11 |
| 435 | T | N | 328 | 633 | 1010 | 13 |
| 435 | T | CA | 330 | 633 | 1025 | 18 |
| 435 | T | CB | 319 | 641 | 1032 | 21 |
| 435 | T | OG1 | 312 | 649 | 1022 | 30 |
| 435 | T | CG2 | 325 | 651 | 1042 | 31 |
| 435 | T | C | 330 | 619 | 1030 | 18 |
| 435 | T | O | 323 | 610 | 1024 | 20 |
| 436 | V | N | 337 | 616 | 1041 | 15 |
| 436 | V | CA | 337 | 603 | 1046 | 14 |
| 436 | V | CB | 351 | 598 | 1050 | 16 |
| 436 | V | CG1 | 357 | 607 | 1061 | 15 |
| 436 | V | CG2 | 350 | 584 | 1055 | 17 |
| 436 | V | C | 328 | 604 | 1058 | 11 |
| 436 | V | O | 328 | 613 | 1066 | 12 |
| 437 | D | N | 320 | 593 | 1061 | 10 |
| 437 | D | CA | 312 | 592 | 1072 | 10 |
| 437 | D | CB | 297 | 594 | 1068 | 12 |
| 437 | D | CG | 288 | 594 | 1080 | 25 |
| 437 | D | OD1 | 291 | 600 | 1090 | 34 |
| 437 | D | OD2 | 276 | 589 | 1079 | 33 |
| 437 | D | C | 314 | 579 | 1078 | 10 |
| 437 | D | O | 313 | 569 | 1072 | 12 |
| 438 | F | N | 318 | 579 | 1091 | 10 |
| 438 | F | CA | 321 | 566 | 1097 | 10 |
| 438 | F | CB | 332 | 569 | 1108 | 11 |
| 438 | F | CG | 344 | 576 | 1103 | 13 |
| 438 | F | CD1 | 347 | 589 | 1107 | 10 |
| 438 | F | CD2 | 353 | 569 | 1095 | 14 |
| 438 | F | CE1 | 358 | 595 | 1102 | 8 |
| 438 | F | CE2 | 364 | 575 | 1090 | 10 |

TABLE 3-continued

| | | | | | | |
|---|---|---|---|---|---|---|
| 438 | F | CZ | 367 | 588 | 1093 | 8 |
| 438 | F | C | 308 | 561 | 1103 | 14 |
| 438 | F | O | 306 | 560 | 1115 | 20 |
| 439 | S | N | 299 | 558 | 1094 | 11 |
| 439 | S | CA | 286 | 553 | 1097 | 9 |
| 439 | S | CB | 277 | 554 | 1084 | 6 |
| 439 | S | OG | 285 | 553 | 1073 | 8 |
| 439 | S | C | 284 | 540 | 1104 | 12 |
| 439 | S | O | 273 | 537 | 1109 | 19 |
| 440 | L | N | 293 | 531 | 1103 | 11 |
| 440 | L | CA | 292 | 518 | 1110 | 12 |
| 440 | L | CB | 290 | 520 | 1125 | 11 |
| 440 | L | CG | 301 | 529 | 1131 | 14 |
| 440 | L | CD1 | 299 | 531 | 1145 | 6 |
| 440 | L | CD2 | 315 | 522 | 1128 | 5 |
| 440 | L | C | 280 | 510 | 1105 | 15 |
| 440 | L | O | 273 | 504 | 1113 | 13 |
| 441 | D | N | 277 | 511 | 1092 | 17 |
| 441 | D | CA | 266 | 504 | 1086 | 16 |
| 441 | D | CB | 255 | 514 | 1083 | 17 |
| 441 | D | CG | 259 | 525 | 1074 | 29 |
| 441 | D | OD1 | 271 | 527 | 1072 | 28 |
| 441 | D | OD2 | 250 | 531 | 1068 | 33 |
| 441 | D | C | 270 | 497 | 1072 | 17 |
| 441 | D | O | 264 | 501 | 1062 | 22 |
| 442 | P | N | 279 | 488 | 1073 | 14 |
| 442 | P | CD | 283 | 481 | 1060 | 5 |
| 442 | P | CA | 287 | 482 | 1084 | 10 |
| 442 | P | CB | 289 | 468 | 1080 | 6 |
| 442 | P | CG | 292 | 469 | 1065 | 6 |
| 442 | P | C | 300 | 489 | 1087 | 14 |
| 442 | P | O | 306 | 486 | 1098 | 14 |
| 443 | T | N | 305 | 497 | 1078 | 12 |
| 443 | T | CA | 318 | 503 | 1080 | 9 |
| 443 | T | CB | 328 | 497 | 1071 | 9 |
| 443 | T | OG1 | 324 | 497 | 1058 | 7 |
| 443 | T | CG2 | 331 | 483 | 1075 | 7 |
| 443 | T | C | 318 | 518 | 1079 | 9 |
| 443 | T | O | 315 | 526 | 1088 | 9 |
| 444 | F | N | 321 | 523 | 1066 | 9 |
| 444 | F | CA | 321 | 537 | 1064 | 4 |
| 444 | F | CB | 335 | 543 | 1063 | 2 |
| 444 | F | CG | 344 | 537 | 1053 | 4 |
| 444 | F | CD1 | 352 | 526 | 1055 | 6 |
| 444 | F | CD2 | 344 | 543 | 1040 | 3 |
| 444 | F | CE1 | 360 | 521 | 1045 | 7 |
| 444 | F | CE2 | 352 | 538 | 1030 | 2 |
| 444 | F | CZ | 360 | 527 | 1032 | 6 |
| 444 | F | C | 314 | 540 | 1051 | 5 |
| 444 | F | O | 310 | 531 | 1043 | 3 |
| 445 | T | N | 312 | 553 | 1048 | 4 |
| 445 | T | CA | 305 | 557 | 1036 | 3 |
| 445 | T | CB | 290 | 562 | 1039 | 9 |
| 445 | T | OG1 | 283 | 551 | 1046 | 12 |
| 445 | T | CG2 | 283 | 566 | 1026 | 6 |
| 445 | T | C | 312 | S69 | 1030 | 3 |
| 445 | T | O | 317 | 578 | 1038 | 2 |
| 446 | I | N | 312 | 570 | 1017 | 7 |
| 446 | I | CA | 319 | 582 | 1010 | 11 |
| 446 | I | CB | 329 | 577 | 999 | 12 |
| 446 | I | CG2 | 334 | 589 | 992 | 9 |
| 446 | I | CG1 | 340 | 569 | 1006 | 5 |
| 446 | I | CD1 | 350 | 577 | 1013 | 2 |
| 446 | I | C | 307 | 588 | 1003 | 12 |
| 446 | I | O | 302 | 583 | 993 | 12 |
| 447 | E | N | 303 | 600 | 1008 | 15 |
| 447 | E | CA | 291 | 607 | 1002 | 18 |
| 447 | E | CB | 282 | 612 | 1013 | 25 |
| 447 | E | CG | 290 | 616 | 1026 | 46 |
| 447 | E | CD | 281 | 616 | 1038 | 55 |
| 447 | E | OE1 | 282 | 625 | 1046 | 59 |
| 447 | E | OE2 | 273 | 606 | 1039 | 57 |
| 447 | E | C | 296 | 618 | 993 | 19 |
| 447 | E | O | 307 | 624 | 996 | 22 |
| 448 | T | N | 289 | 621 | 983 | 19 |
| 448 | T | CA | 293 | 631 | 973 | 19 |
| 448 | T | CB | 293 | 626 | 959 | 16 |
| 448 | T | OG1 | 305 | 618 | 958 | 24 |
| 448 | T | CG2 | 295 | 638 | 949 | 14 |
| 448 | T | C | 282 | 642 | 975 | 20 |
| 448 | T | O | 270 | 639 | 972 | 22 |
| 449 | T | N | 285 | 654 | 978 | 21 |
| 449 | T | CA | 276 | 665 | 979 | 21 |
| 449 | T | CB | 274 | 668 | 994 | 24 |
| 449 | T | OG1 | 287 | 668 | 1000 | 31 |
| 449 | T | CG2 | 265 | 658 | 1001 | 26 |
| 449 | T | C | 279 | 677 | 972 | 21 |
| 449 | T | O | 291 | 679 | 967 | 23 |
| 450 | T | N | 269 | 686 | 971 | 22 |
| 450 | T | CA | 271 | 699 | 964 | 17 |
| 450 | T | CB | 259 | 702 | 955 | 15 |
| 450 | T | OG1 | 258 | 692 | 945 | 19 |
| 450 | T | CG2 | 261 | 716 | 949 | 15 |
| 450 | T | C | 272 | 709 | 975 | 17 |
| 450 | T | O | 262 | 712 | 982 | 19 |
| 451 | V | N | 284 | 716 | 976 | 14 |
| 451 | V | CA | 286 | 726 | 986 | 13 |
| 451 | V | CB | 296 | 721 | 996 | 16 |
| 451 | V | CG1 | 291 | 708 | 1004 | 15 |
| 451 | V | CG2 | 309 | 717 | 989 | 15 |
| 451 | V | C | 290 | 739 | 982 | 17 |
| 451 | V | O | 296 | 741 | 971 | 22 |
| 452 | P | N | 288 | 750 | 990 | 16 |
| 452 | P | CD | 281 | 749 | 1003 | 18 |
| 452 | P | CA | 292 | 763 | 987 | 14 |
| 452 | P | CB | 288 | 771 | 999 | 16 |
| 452 | P | CG | 278 | 763 | 1005 | 15 |
| 452 | P | C | 307 | 763 | 985 | 13 |
| 452 | P | O | 315 | 758 | 992 | 13 |
| 453 | Q | N | 312 | 770 | 974 | 14 |
| 453 | Q | CA | 326 | 771 | 971 | 17 |
| 453 | Q | CB | 328 | 778 | 958 | 20 |
| 453 | Q | CG | 329 | 794 | 959 | 19 |
| 453 | Q | CD | 327 | 801 | 946 | 17 |
| 453 | Q | OE1 | 323 | 813 | 946 | 19 |
| 453 | Q | NE2 | 330 | 794 | 935 | 15 |
| 453 | Q | C | 334 | 777 | 982 | 16 |
| 453 | Q | O | 329 | 785 | 990 | 16 |
| 454 | D | N | 347 | 775 | 982 | 15 |
| 454 | D | CA | 356 | 780 | 992 | 16 |
| 454 | D | CB | 366 | 770 | 997 | 26 |
| 454 | D | CG | 377 | 767 | 988 | 32 |
| 454 | D | OD1 | 375 | 765 | 976 | 36 |
| 454 | D | OD2 | 389 | 767 | 993 | 41 |
| 454 | D | C | 364 | 792 | 985 | 11 |
| 454 | D | O | 364 | 793 | 973 | 11 |
| 455 | A | N | 371 | 799 | 993 | 10 |
| 455 | A | CA | 379 | 811 | 988 | 8 |
| 455 | A | CB | 387 | 817 | 999 | 4 |
| 455 | A | C | 388 | 807 | 976 | 13 |
| 455 | A | O | 390 | 815 | 967 | 20 |
| 456 | V | N | 394 | 796 | 977 | 12 |
| 456 | V | CA | 403 | 792 | 966 | 11 |
| 456 | V | CB | 411 | 779 | 969 | 5 |
| 456 | V | CG1 | 417 | 773 | 957 | 3 |
| 456 | V | CG2 | 422 | 782 | 979 | 7 |
| 456 | V | C | 395 | 790 | 953 | 16 |
| 456 | V | O | 399 | 796 | 943 | 20 |
| 457 | S | N | 385 | 783 | 954 | 18 |
| 457 | S | CA | 376 | 780 | 942 | 17 |
| 457 | S | CB | 364 | 772 | 946 | 17 |
| 457 | S | OG | 355 | 771 | 935 | 11 |
| 457 | S | C | 371 | 793 | 936 | 18 |
| 457 | S | O | 372 | 795 | 924 | 24 |
| 458 | R | N | 367 | 803 | 944 | 19 |
| 458 | R | CA | 362 | 816 | 939 | 16 |
| 458 | R | CB | 357 | 824 | 951 | 13 |
| 458 | R | CG | 346 | 834 | 946 | 17 |
| 458 | R | CD | 341 | 842 | 957 | 21 |
| 458 | R | NE | 330 | 851 | 953 | 24 |
| 458 | R | CZ | 317 | 848 | 953 | 24 |
| 458 | R | NH1 | 313 | 836 | 958 | 26 |
| 458 | R | NH2 | 308 | 857 | 949 | 24 |
| 458 | R | C | 373 | 823 | 932 | 19 |
| 458 | R | O | 371 | 827 | 920 | 19 |
| 459 | S | N | 384 | 826 | 939 | 24 |
| 459 | S | CA | 395 | 833 | 932 | 28 |
| 459 | S | CB | 407 | 834 | 942 | 28 |

TABLE 3-continued

| | | | | | | |
|---|---|---|---|---|---|---|
| 459 | S | OG | 415 | 823 | 941 | 36 |
| 459 | S | C | 400 | 827 | 920 | 28 |
| 459 | S | O | 403 | 834 | 910 | 29 |
| 460 | Q | N | 400 | 814 | 920 | 23 |
| 460 | Q | CA | 405 | 806 | 908 | 22 |
| 460 | Q | CB | 407 | 792 | 911 | 24 |
| 460 | Q | CG | 421 | 787 | 907 | 36 |
| 460 | Q | CD | 428 | 779 | 918 | 41 |
| 460 | Q | OE1 | 440 | 779 | 919 | 43 |
| 460 | Q | NE2 | 420 | 771 | 925 | 47 |
| 460 | Q | C | 395 | 807 | 896 | 19 |
| 460 | Q | O | 399 | 810 | 885 | 25 |
| 461 | R | N | 382 | 805 | 899 | 15 |
| 461 | R | CA | 372 | 805 | 855 | 14 |
| 461 | R | CB | 358 | 802 | 894 | 11 |
| 461 | R | CG | 357 | 787 | 896 | 11 |
| 461 | R | CD | 342 | 784 | 901 | 18 |
| 461 | R | NE | 339 | 770 | 901 | 16 |
| 461 | R | CZ | 329 | 764 | 907 | 16 |
| 461 | R | NH1 | 321 | 772 | 913 | 19 |
| 461 | R | NH2 | 327 | 751 | 906 | 15 |
| 461 | R | C | 371 | 819 | 553 | 17 |
| 461 | R | O | 371 | 822 | 871 | 20 |
| 462 | R | N | 371 | 829 | 892 | 17 |
| 462 | R | CA | 371 | 843 | 888 | 21 |
| 462 | R | CB | 369 | 852 | 900 | 16 |
| 462 | R | CG | 371 | 867 | 898 | 16 |
| 462 | R | CD | 373 | 875 | 910 | 18 |
| 462 | R | NE | 386 | 873 | 916 | 22 |
| 462 | R | CZ | 392 | 881 | 925 | 23 |
| 462 | R | NH1 | 384 | 891 | 931 | 26 |
| 462 | R | NH2 | 404 | 879 | 929 | 23 |
| 462 | R | C | 384 | 847 | 880 | 26 |
| 462 | R | O | 383 | 856 | 871 | 27 |
| 463 | G | N | 395 | 841 | 884 | 26 |
| 463 | G | CA | 407 | 844 | 878 | 26 |
| 463 | G | C | 408 | 841 | 863 | 25 |
| 463 | G | O | 419 | 842 | 857 | 31 |
| 464 | R | N | 397 | 836 | 858 | 27 |
| 464 | R | CA | 397 | 832 | 844 | 27 |
| 464 | R | CB | 388 | 821 | 841 | 29 |
| 464 | R | CG | 391 | 808 | 848 | 31 |
| 464 | R | CD | 405 | 804 | 845 | 33 |
| 464 | R | NE | 406 | 796 | 833 | 38 |
| 464 | R | CZ | 413 | 784 | 831 | 40 |
| 464 | R | NH1 | 421 | 780 | 841 | 42 |
| 464 | R | NH2 | 412 | 778 | 820 | 38 |
| 464 | R | C | 393 | 844 | 835 | 28 |
| 464 | R | O | 391 | 843 | 823 | 25 |
| 465 | T | N | 393 | 856 | 841 | 28 |
| 465 | T | CA | 390 | 868 | 834 | 31 |
| 465 | T | CB | 375 | 871 | 836 | 28 |
| 465 | T | OG1 | 372 | 883 | 829 | 35 |
| 465 | T | CG2 | 371 | 874 | 851 | 25 |
| 465 | T | C | 398 | 879 | 840 | 34 |
| 465 | T | O | 404 | 878 | 851 | 38 |
| 466 | G | N | 398 | 891 | 833 | 35 |
| 466 | G | CA | 405 | 902 | 838 | 37 |
| 466 | G | C | 420 | 899 | 839 | 39 |
| 466 | G | O | 428 | 905 | 846 | 36 |
| 467 | R | N | 424 | 889 | 831 | 42 |
| 467 | R | CA | 438 | 886 | 830 | 45 |
| 467 | R | CB | 439 | 871 | 825 | 47 |
| 467 | R | CG | 447 | 862 | 834 | 52 |
| 467 | R | CD | 449 | 848 | 828 | 55 |
| 467 | R | NE | 438 | 839 | 832 | 55 |
| 467 | R | CZ | 438 | 826 | 830 | 55 |
| 467 | R | NH1 | 448 | 820 | 823 | 56 |
| 467 | R | NH2 | 428 | 819 | 834 | 58 |
| 467 | R | C | 445 | 895 | 820 | 46 |
| 467 | R | O | 447 | 892 | 808 | 45 |
| 468 | G | N | 449 | 907 | 825 | 44 |
| 468 | G | CA | 456 | 916 | 817 | 47 |
| 468 | G | C | 446 | 927 | 811 | 47 |
| 468 | G | O | 450 | 938 | 810 | 49 |
| 469 | R | N | 434 | 922 | 809 | 48 |
| 469 | R | CA | 424 | 931 | 803 | 48 |
| 469 | R | CB | 417 | 925 | 791 | 51 |
| 469 | R | CG | 424 | 912 | 786 | 55 |
| 469 | R | CD | 413 | 902 | 781 | 58 |
| 469 | R | NE | 401 | 902 | 789 | 66 |
| 469 | R | CZ | 398 | 894 | 799 | 70 |
| 469 | R | NH1 | 407 | 885 | 803 | 72 |
| 469 | R | NH2 | 387 | 896 | 806 | 69 |
| 469 | R | C | 413 | 933 | 814 | 49 |
| 469 | R | O | 414 | 927 | 825 | 50 |
| 470 | R | N | 403 | 941 | 811 | 47 |
| 470 | R | CA | 392 | 943 | 821 | 46 |
| 470 | R | CB | 385 | 956 | 818 | 48 |
| 470 | R | CG | 380 | 964 | 830 | 55 |
| 470 | R | CD | 370 | 956 | 838 | 59 |
| 470 | R | NE | 364 | 964 | 848 | 62 |
| 470 | R | CZ | 370 | 970 | 858 | 62 |
| 470 | R | NH1 | 384 | 968 | 859 | 62 |
| 470 | R | NH2 | 364 | 977 | 868 | 60 |
| 470 | R | C | 384 | 931 | 819 | 44 |
| 470 | R | O | 384 | 924 | 809 | 44 |
| 471 | G | N | 376 | 927 | 830 | 40 |
| 471 | G | CA | 368 | 916 | 830 | 30 |
| 471 | G | C | 356 | 917 | 839 | 26 |
| 471 | G | O | 356 | 926 | 848 | 24 |
| 472 | I | N | 346 | 908 | 837 | 25 |
| 472 | I | CA | 334 | 909 | 846 | 26 |
| 472 | I | CB | 322 | 913 | 838 | 27 |
| 472 | I | CG2 | 309 | 914 | 847 | 14 |
| 472 | I | CG1 | 324 | 926 | 830 | 28 |
| 472 | I | CD1 | 314 | 928 | 819 | 35 |
| 472 | I | C | 332 | 895 | 852 | 25 |
| 472 | I | O | 333 | 885 | 845 | 23 |
| 473 | Y | N | 329 | 895 | 865 | 23 |
| 473 | Y | CA | 327 | 883 | 872 | 18 |
| 473 | Y | CB | 336 | 882 | 884 | 14 |
| 473 | Y | CG | 334 | 869 | 893 | 13 |
| 473 | Y | CD1 | 336 | 857 | 888 | 10 |
| 473 | Y | CE1 | 334 | 845 | 896 | 9 |
| 473 | Y | CD2 | 329 | 871 | 906 | 17 |
| 473 | Y | CE2 | 326 | 859 | 914 | 14 |
| 473 | Y | CZ | 329 | 847 | 909 | 12 |
| 473 | Y | OH | 326 | 836 | 916 | 7 |
| 473 | Y | C | 312 | 883 | 878 | 16 |
| 473 | Y | O | 309 | 892 | 886 | 18 |
| 474 | R | N | 304 | 875 | 872 | 19 |
| 474 | R | CA | 290 | 874 | 876 | 21 |
| 474 | R | CB | 281 | 873 | 864 | 25 |
| 474 | R | CG | 283 | 883 | 853 | 23 |
| 474 | R | CD | 270 | 891 | 851 | 29 |
| 474 | R | NE | 272 | 902 | 841 | 28 |
| 474 | R | CZ | 276 | 900 | 828 | 33 |
| 474 | R | NH1 | 278 | 888 | 824 | 33 |
| 474 | R | NH2 | 277 | 911 | 821 | 33 |
| 474 | R | C | 288 | 862 | 886 | 18 |
| 474 | R | O | 291 | 851 | 882 | 19 |
| 475 | F | N | 283 | 865 | 898 | 16 |
| 475 | F | CA | 281 | 854 | 907 | 20 |
| 475 | F | CB | 290 | 857 | 919 | 16 |
| 475 | F | CG | 287 | 870 | 926 | 17 |
| 475 | F | CD1 | 294 | 881 | 921 | 17 |
| 475 | F | CD2 | 278 | 871 | 936 | 18 |
| 475 | F | CE1 | 291 | 894 | 927 | 21 |
| 475 | F | CE2 | 275 | 883 | 942 | 18 |
| 475 | F | CZ | 282 | 895 | 938 | 21 |
| 475 | F | C | 267 | 852 | 913 | 19 |
| 475 | F | O | 259 | 862 | 914 | 16 |
| 476 | V | N | 263 | 840 | 915 | 23 |
| 476 | V | CA | 250 | 837 | 921 | 24 |
| 476 | V | CB | 246 | 822 | 920 | 22 |
| 476 | V | CG1 | 233 | 819 | 928 | 23 |
| 476 | V | CG2 | 245 | 818 | 906 | 26 |
| 476 | V | C | 249 | 842 | 935 | 26 |
| 476 | V | O | 239 | 848 | 939 | 32 |
| 477 | T | N | 259 | 839 | 943 | 27 |
| 477 | T | CA | 260 | 843 | 957 | 25 |
| 477 | T | CB | 259 | 830 | 966 | 26 |
| 477 | T | OG1 | 271 | 823 | 966 | 31 |
| 477 | T | CG2 | 247 | 821 | 961 | 28 |
| 477 | T | C | 273 | 849 | 960 | 25 |
| 477 | T | O | 283 | 846 | 953 | 28 |
| 478 | P | N | 274 | 858 | 970 | 28 |

TABLE 3-continued

| | | | | | | |
|---|---|---|---|---|---|---|
| 478 | P | CD | 262 | 862 | 978 | 30 |
| 478 | P | CA | 286 | 865 | 974 | 32 |
| 478 | P | CB | 281 | 878 | 980 | 34 |
| 478 | P | CG | 267 | 875 | 985 | 32 |
| 478 | P | C | 295 | 858 | 985 | 34 |
| 478 | P | O | 307 | 862 | 986 | 42 |
| 479 | G | N | 290 | 850 | 993 | 32 |
| 479 | G | CA | 298 | 843 | 1003 | 37 |
| 479 | G | C | 309 | 835 | 998 | 39 |
| 479 | G | O | 313 | 835 | 986 | 39 |
| 480 | E | N | 315 | 827 | 1007 | 40 |
| 480 | E | CA | 326 | 817 | 1004 | 37 |
| 480 | E | CB | 337 | 825 | 996 | 38 |
| 480 | E | CG | 350 | 827 | 1004 | 42 |
| 480 | E | CD | 359 | 837 | 997 | 44 |
| 480 | E | OE1 | 368 | 842 | 1003 | 49 |
| 480 | E | OE2 | 357 | 839 | 985 | 48 |
| 480 | E | C | 331 | 811 | 1017 | 28 |
| 480 | E | O | 333 | 818 | 1027 | 24 |
| 481 | R | N | 334 | 798 | 1016 | 28 |
| 481 | R | CA | 338 | 791 | 1028 | 27 |
| 481 | R | CB | 335 | 776 | 1026 | 24 |
| 481 | R | CG | 320 | 773 | 1027 | 25 |
| 481 | R | CD | 318 | 758 | 1030 | 34 |
| 481 | R | NE | 321 | 750 | 1018 | 43 |
| 481 | R | CZ | 333 | 744 | 1016 | 49 |
| 481 | R | NH1 | 342 | 745 | 1025 | 53 |
| 481 | R | NH2 | 335 | 737 | 1005 | 45 |
| 481 | R | C | 353 | 793 | 1030 | 24 |
| 481 | R | O | 361 | 796 | 1020 | 24 |
| 482 | P | N | 358 | 791 | 1042 | 20 |
| 482 | P | CD | 351 | 786 | 1054 | 19 |
| 482 | P | CA | 373 | 792 | 1045 | 14 |
| 482 | P | CB | 374 | 790 | 1060 | 11 |
| 482 | P | CG | 362 | 781 | 1063 | 18 |
| 482 | P | C | 381 | 782 | 1037 | 16 |
| 482 | P | O | 376 | 772 | 1033 | 15 |
| 483 | S | N | 393 | 786 | 1034 | 18 |
| 483 | S | CA | 402 | 778 | 1026 | 22 |
| 483 | S | CB | 410 | 786 | 1016 | 26 |
| 483 | S | OG | 415 | 797 | 1023 | 33 |
| 483 | S | C | 412 | 771 | 1035 | 21 |
| 483 | S | O | 414 | 774 | 1047 | 19 |
| 484 | G | N | 419 | 761 | 1029 | 18 |
| 484 | G | CA | 430 | 754 | 1037 | 16 |
| 484 | G | C | 427 | 741 | 1043 | 9 |
| 484 | G | O | 436 | 735 | 1048 | 15 |
| 485 | M | N | 415 | 737 | 1043 | 10 |
| 485 | M | CA | 411 | 724 | 1049 | 7 |
| 485 | M | CB | 401 | 726 | 1060 | 5 |
| 485 | M | CG | 405 | 734 | 1072 | 15 |
| 485 | M | SD | 391 | 740 | 1082 | 20 |
| 485 | M | CE | 381 | 748 | 1069 | 17 |
| 485 | M | C | 405 | 714 | 1039 | 8 |
| 485 | M | O | 399 | 718 | 1029 | 12 |
| 486 | F | N | 408 | 701 | 1041 | 7 |
| 486 | F | CA | 402 | 691 | 1033 | 3 |
| 486 | F | CB | 412 | 687 | 1021 | 2 |
| 486 | F | CG | 425 | 681 | 1025 | 2 |
| 486 | F | CD1 | 436 | 688 | 1026 | 4 |
| 486 | F | CD2 | 426 | 667 | 1028 | 7 |
| 486 | F | CE1 | 449 | 683 | 1029 | 3 |
| 486 | F | CE2 | 438 | 661 | 1032 | 3 |
| 486 | F | CZ | 449 | 669 | 1032 | 4 |
| 486 | F | C | 398 | 678 | 1041 | 4 |
| 486 | F | O | 402 | 676 | 1052 | 6 |
| 487 | D | N | 388 | 671 | 1035 | 3 |
| 487 | D | CA | 383 | 659 | 1042 | 5 |
| 487 | D | CB | 369 | 656 | 1035 | 8 |
| 487 | D | CG | 361 | 647 | 1044 | 14 |
| 487 | D | OD1 | 356 | 651 | 1054 | 24 |
| 487 | D | OD2 | 359 | 635 | 1040 | 18 |
| 487 | D | C | 392 | 647 | 1042 | 8 |
| 487 | D | O | 400 | 645 | 1033 | 9 |
| 488 | S | N | 389 | 639 | 1052 | 8 |
| 488 | S | CA | 397 | 626 | 1054 | 5 |
| 488 | S | CB | 392 | 619 | 1067 | 3 |
| 488 | S | OG | 397 | 606 | 1067 | 13 |
| 488 | S | C | 395 | 617 | 1042 | 10 |
| 488 | S | O | 404 | 608 | 1040 | 14 |
| 489 | S | N | 385 | 619 | 1034 | 7 |
| 489 | S | CA | 383 | 611 | 1023 | 5 |
| 489 | S | CB | 369 | 614 | 1016 | 12 |
| 489 | S | OG | 368 | 627 | 1013 | 21 |
| 489 | S | C | 394 | 613 | 1012 | 6 |
| 489 | S | O | 397 | 604 | 1004 | 4 |
| 490 | V | N | 400 | 625 | 1013 | 6 |
| 490 | V | CA | 410 | 628 | 1003 | 6 |
| 490 | V | CB | 415 | 643 | 1004 | 3 |
| 490 | V | CG1 | 427 | 645 | 997 | 2 |
| 490 | V | CG2 | 404 | 651 | 999 | 2 |
| 490 | V | C | 422 | 619 | 1007 | 11 |
| 490 | V | O | 430 | 615 | 999 | 19 |
| 491 | L | N | 424 | 616 | 1020 | 8 |
| 491 | L | CA | 435 | 607 | 1024 | 6 |
| 491 | L | CB | 435 | 607 | 1040 | 4 |
| 491 | L | CG | 440 | 620 | 1046 | 11 |
| 491 | L | CD1 | 440 | 620 | 1061 | 4 |
| 491 | L | CD2 | 454 | 624 | 1041 | 2 |
| 491 | L | C | 432 | 593 | 1019 | 7 |
| 491 | L | O | 441 | 586 | 1015 | 10 |
| 492 | C | N | 419 | 589 | 1019 | 10 |
| 492 | C | CA | 415 | 576 | 1014 | 7 |
| 492 | C | CB | 400 | 575 | 1015 | 9 |
| 492 | C | SG | 393 | 559 | 1009 | 6 |
| 492 | C | C | 419 | 575 | 999 | 9 |
| 492 | C | O | 423 | 565 | 994 | 12 |
| 493 | E | N | 416 | 586 | 991 | 9 |
| 493 | E | CA | 420 | 586 | 977 | 9 |
| 493 | E | CB | 416 | 600 | 971 | 10 |
| 493 | E | CG | 401 | 603 | 974 | 25 |
| 493 | E | CD | 396 | 615 | 965 | 30 |
| 493 | E | OE1 | 389 | 612 | 955 | 33 |
| 493 | E | OE2 | 399 | 626 | 967 | 31 |
| 493 | E | C | 435 | 584 | 975 | 13 |
| 493 | E | O | 439 | 577 | 965 | 19 |
| 494 | C | N | 443 | 590 | 984 | 13 |
| 494 | C | CA | 457 | 589 | 983 | 8 |
| 494 | C | CB | 464 | 596 | 994 | 11 |
| 494 | C | SG | 463 | 614 | 993 | 6 |
| 494 | C | C | 462 | 574 | 984 | 9 |
| 494 | C | O | 470 | 569 | 976 | 9 |
| 495 | Y | N | 456 | 567 | 994 | 7 |
| 495 | Y | CA | 459 | 553 | 995 | 6 |
| 495 | Y | CB | 453 | 547 | 1008 | 6 |
| 495 | Y | CG | 460 | 552 | 1020 | 8 |
| 495 | Y | CD1 | 470 | 544 | 1026 | 2 |
| 495 | Y | CE1 | 477 | 548 | 1037 | 5 |
| 495 | Y | CD2 | 456 | 563 | 1027 | 8 |
| 495 | Y | CE2 | 463 | 568 | 1038 | 4 |
| 495 | Y | CZ | 473 | 560 | 1043 | 7 |
| 495 | Y | OH | 480 | 564 | 1055 | 15 |
| 495 | Y | C | 455 | 545 | 983 | 5 |
| 495 | Y | O | 461 | 536 | 978 | 11 |
| 496 | D | N | 443 | 549 | 978 | 12 |
| 496 | D | CA | 437 | 543 | 966 | 12 |
| 496 | D | CB | 423 | 551 | 963 | 15 |
| 496 | D | CG | 414 | 542 | 955 | 17 |
| 496 | D | OD1 | 416 | 541 | 943 | 21 |
| 496 | D | OD2 | 404 | 537 | 961 | 15 |
| 496 | D | C | 446 | 545 | 954 | 9 |
| 496 | D | O | 449 | 535 | 947 | 9 |
| 497 | A | N | 451 | 557 | 952 | 6 |
| 497 | A | CA | 460 | 559 | 941 | 7 |
| 497 | A | CB | 463 | 574 | 939 | 2 |
| 497 | A | C | 473 | 552 | 943 | 11 |
| 497 | A | O | 479 | 546 | 934 | 16 |
| 498 | G | N | 478 | 553 | 956 | 12 |
| 498 | G | CA | 491 | 546 | 959 | 8 |
| 498 | G | C | 490 | 532 | 955 | 10 |
| 498 | G | O | 499 | 526 | 949 | 14 |
| 499 | C | N | 478 | 526 | 957 | 10 |
| 499 | C | CA | 476 | 512 | 954 | 9 |
| 499 | C | CB | 464 | 596 | 962 | 9 |
| 499 | C | SG | 467 | 502 | 979 | 16 |
| 499 | C | C | 472 | 509 | 939 | 7 |
| 499 | C | O | 478 | 500 | 934 | 15 |
| 500 | A | N | 464 | 517 | 934 | 6 |

TABLE 3-continued

| | | | | | | |
|---|---|---|---|---|---|---|
| 500 | A | CA | 460 | 515 | 920 | 4 |
| 500 | A | CB | 446 | 522 | 918 | 2 |
| 500 | A | C | 470 | 520 | 909 | 11 |
| 500 | A | O | 471 | 514 | 899 | 14 |
| 501 | W | N | 476 | 532 | 912 | 11 |
| 501 | W | CA | 485 | 538 | 903 | 10 |
| 501 | W | CB | 481 | 552 | 901 | 10 |
| 501 | W | CG | 468 | 554 | 894 | 6 |
| 501 | W | CD2 | 465 | 552 | 880 | 7 |
| 501 | W | CE2 | 452 | 554 | 878 | 5 |
| 501 | W | CE3 | 474 | 550 | 868 | 10 |
| 501 | W | CD1 | 456 | 556 | 900 | 9 |
| 501 | W | NE1 | 446 | 557 | 890 | 14 |
| 501 | W | CZ2 | 446 | 554 | 865 | 7 |
| 501 | W | CZ3 | 468 | 549 | 856 | 5 |
| 501 | W | CH2 | 454 | 551 | 854 | 7 |
| 501 | W | C | 500 | 537 | 905 | 12 |
| 501 | W | O | 508 | 535 | 896 | 12 |
| 502 | Y | N | 504 | 540 | 918 | 11 |
| 502 | Y | CA | 518 | 540 | 920 | 10 |
| 502 | Y | CB | 520 | 553 | 928 | 5 |
| 502 | Y | CG | 513 | 565 | 922 | 3 |
| 502 | Y | CD1 | 515 | 568 | 908 | 5 |
| 502 | Y | CE1 | 508 | 578 | 902 | 6 |
| 502 | Y | CD2 | 504 | 572 | 929 | 2 |
| 502 | Y | CE2 | 496 | 583 | 923 | 2 |
| 502 | Y | CZ | 499 | 585 | 909 | 5 |
| 502 | Y | OH | 492 | 596 | 903 | 17 |
| 502 | Y | C | 526 | 529 | 927 | 12 |
| 502 | Y | O | 537 | 530 | 930 | 12 |
| 503 | E | N | 519 | 517 | 928 | 15 |
| 503 | E | CA | 525 | 506 | 934 | 22 |
| 503 | E | CB | 536 | 501 | 925 | 30 |
| 503 | E | CG | 532 | 499 | 910 | 47 |
| 503 | E | CD | 540 | 489 | 903 | 54 |
| 503 | E | OE1 | 544 | 479 | 910 | 61 |
| 503 | E | OE2 | 542 | 490 | 891 | 60 |
| 503 | E | C | 532 | 509 | 947 | 18 |
| 503 | E | O | 543 | 506 | 950 | 20 |
| 504 | L | N | 524 | 516 | 956 | 15 |
| 504 | L | CA | 528 | 520 | 969 | 13 |
| 504 | L | CB | 525 | 534 | 972 | 7 |
| 504 | L | CG | 533 | 545 | 965 | 2 |
| 504 | L | CD1 | 527 | 558 | 968 | 2 |
| 504 | L | CD2 | 547 | 545 | 969 | 6 |
| 504 | L | C | 521 | 511 | 979 | 13 |
| 504 | L | O | 509 | 509 | 978 | 23 |
| 505 | T | N | 528 | 506 | 989 | 14 |
| 505 | T | CA | 521 | 498 | 999 | 16 |
| 505 | T | CB | 531 | 490 | 1008 | 18 |
| 505 | T | OG1 | 540 | 499 | 1016 | 20 |
| 505 | T | CG2 | 540 | 481 | 1000 | 9 |
| 505 | T | C | 515 | 508 | 1008 | 16 |
| 505 | T | O | 519 | 520 | 1008 | 15 |
| 506 | P | N | 504 | 505 | 1015 | 17 |
| 506 | P | CD | 497 | 492 | 1015 | 12 |
| 506 | P | CA | 497 | 515 | 1024 | 11 |
| 506 | P | CB | 487 | 507 | 1031 | 11 |
| 506 | P | CG | 483 | 496 | 1021 | 12 |
| 506 | P | C | 507 | 521 | 1033 | 9 |
| 506 | P | O | 506 | 533 | 1037 | 15 |
| 507 | A | N | 517 | 513 | 1037 | 7 |
| 507 | A | CA | 528 | 518 | 1046 | 8 |
| 507 | A | CB | 536 | 507 | 1051 | 5 |
| 507 | A | C | 536 | 529 | 1040 | 8 |
| 507 | A | O | 539 | 539 | 1046 | 14 |
| 508 | E | N | 540 | 527 | 1028 | 11 |
| 508 | E | CA | 548 | 537 | 1020 | 4 |
| 508 | E | CB | 553 | 531 | 1007 | 10 |
| 508 | E | CG | 564 | 520 | 1009 | 24 |
| 508 | E | CD | 567 | 511 | 997 | 32 |
| 508 | E | OE1 | 578 | 505 | 996 | 42 |
| 508 | E | OE2 | 558 | 511 | 988 | 28 |
| 508 | E | C | 540 | 549 | 1018 | 6 |
| 508 | E | O | 546 | 560 | 1018 | 3 |
| 509 | T | N | 527 | 548 | 1016 | 7 |
| 509 | T | CA | 519 | 559 | 1013 | 3 |
| 509 | T | CB | 504 | 555 | 1009 | 7 |
| 509 | T | OG1 | 505 | 547 | 997 | 5 |
| 509 | T | CG2 | 495 | 567 | 1007 | 2 |
| 509 | T | C | 517 | 567 | 1026 | 5 |
| 509 | T | O | 517 | 580 | 1026 | 6 |
| 510 | S | N | 517 | 560 | 1038 | 5 |
| 510 | S | CA | 516 | 567 | 1051 | 5 |
| 510 | S | CB | 515 | 556 | 1061 | 5 |
| 510 | S | OG | 502 | 551 | 1062 | 16 |
| 510 | S | C | 528 | 576 | 1054 | 6 |
| 510 | S | O | 527 | 586 | 1059 | 8 |
| 511 | V | N | 540 | 571 | 1050 | 7 |
| 511 | V | CA | 552 | 579 | 1052 | 8 |
| 511 | V | CB | 564 | 572 | 1047 | 10 |
| 511 | V | CG1 | 576 | 581 | 1049 | 12 |
| 511 | V | CG2 | 566 | 559 | 1055 | 7 |
| 511 | V | C | 551 | 592 | 1045 | 11 |
| 511 | V | O | 553 | 603 | 1050 | 11 |
| 512 | R | N | 548 | 591 | 1032 | 9 |
| 512 | R | CA | 546 | 603 | 1024 | 9 |
| 512 | R | CB | 544 | 599 | 1009 | 7 |
| 512 | R | CG | 556 | 594 | 1002 | 11 |
| 512 | R | CD | 553 | 581 | 995 | 9 |
| 512 | R | NE | 554 | 583 | 980 | 13 |
| 512 | R | CZ | 564 | 577 | 973 | 13 |
| 512 | R | NH1 | 572 | 569 | 978 | 12 |
| 512 | R | NH2 | 564 | 579 | 960 | 16 |
| 512 | R | C | 536 | 613 | 1029 | 11 |
| 512 | R | O | 537 | 625 | 1029 | 16 |
| 513 | L | N | 524 | 607 | 1033 | 12 |
| 513 | L | CA | 513 | 616 | 1038 | 10 |
| 513 | L | CB | 500 | 608 | 1039 | 10 |
| 513 | L | CG | 494 | 603 | 1026 | 7 |
| 513 | L | CD1 | 482 | 594 | 1029 | 5 |
| 513 | L | CD2 | 490 | 615 | 1017 | 7 |
| 513 | L | C | 517 | 621 | 1051 | 7 |
| 513 | L | O | 514 | 633 | 1055 | 16 |
| 514 | R | N | 524 | 613 | 1059 | 7 |
| 514 | R | CA | 529 | 617 | 1072 | 9 |
| 514 | R | CB | 537 | 606 | 1078 | 15 |
| 514 | R | CG | 543 | 609 | 1091 | 24 |
| 514 | R | CD | 534 | 606 | 1103 | 28 |
| 514 | R | NE | 526 | 617 | 1106 | 30 |
| 514 | R | CZ | 514 | 617 | 1111 | 30 |
| 514 | R | NH1 | 507 | 605 | 1112 | 15 |
| 514 | R | NH2 | 507 | 628 | 1114 | 29 |
| 514 | R | C | 537 | 630 | 1071 | 11 |
| 514 | R | O | 536 | 639 | 1079 | 15 |
| 515 | A | N | 546 | 630 | 1061 | 12 |
| 515 | A | CA | 555 | 642 | 1059 | 9 |
| 515 | A | CB | 565 | 638 | 1048 | 3 |
| 515 | A | C | 547 | 654 | 1055 | 14 |
| 515 | A | O | 551 | 665 | 1059 | 17 |
| 516 | Y | N | 536 | 652 | 1047 | 13 |
| 516 | Y | CA | 528 | 663 | 1043 | 7 |
| 516 | Y | CB | 517 | 658 | 1033 | 8 |
| 516 | Y | CG | 508 | 669 | 1028 | 10 |
| 516 | Y | CD1 | 498 | 674 | 1036 | 11 |
| 516 | Y | CE1 | 489 | 684 | 1031 | 2 |
| 516 | Y | CD2 | 509 | 673 | 1015 | 5 |
| 516 | Y | CE2 | 501 | 683 | 1010 | 9 |
| 516 | Y | CZ | 491 | 689 | 1018 | 5 |
| 516 | Y | OH | 483 | 698 | 1013 | 6 |
| 516 | Y | C | 521 | 669 | 1055 | 8 |
| 516 | Y | O | 522 | 681 | 1058 | 8 |
| 517 | L | N | 514 | 661 | 1063 | 7 |
| 517 | L | CA | 507 | 666 | 1075 | 5 |
| 517 | L | CB | 500 | 654 | 1082 | 7 |
| 517 | L | CG | 489 | 647 | 1075 | 10 |
| 517 | L | CD1 | 482 | 637 | 1085 | 7 |
| 517 | L | CD2 | 479 | 657 | 1069 | 7 |
| 517 | L | C | 516 | 673 | 1084 | 10 |
| 517 | L | O | 514 | 684 | 1089 | 17 |
| 518 | N | N | 528 | 667 | 1087 | 12 |
| 518 | N | CA | 537 | 672 | 1097 | 16 |
| 518 | N | CB | 548 | 662 | 1100 | 24 |
| 518 | N | CG | 542 | 650 | 1108 | 26 |
| 518 | N | OD1 | 547 | 639 | 1107 | 29 |
| 518 | N | ND2 | 531 | 653 | 1115 | 23 |
| 518 | N | C | 544 | 685 | 1092 | 16 |
| 518 | N | O | 552 | 691 | 1099 | 18 |

TABLE 3-continued

| | | | | | | |
|---|---|---|---|---|---|---|
| 519 | T | N | 542 | 689 | 1079 | 15 |
| 519 | T | CA | 548 | 701 | 1074 | 11 |
| 519 | T | CB | 552 | 699 | 1059 | 9 |
| 519 | T | OG1 | 561 | 688 | 1058 | 11 |
| 519 | T | CG2 | 559 | 712 | 1054 | 8 |
| 519 | T | C | 538 | 712 | 1075 | 12 |
| 519 | T | O | 526 | 711 | 1070 | 19 |
| 520 | P | N | 542 | 724 | 1081 | 15 |
| 520 | P | CD | 555 | 725 | 1086 | 17 |
| 520 | P | CA | 533 | 736 | 1082 | 15 |
| 520 | P | CB | 540 | 744 | 1093 | 21 |
| 520 | P | CG | 553 | 735 | 1097 | 18 |
| 520 | P | C | 531 | 744 | 1070 | 14 |
| 520 | P | O | 539 | 743 | 1061 | 17 |
| 521 | G | N | 521 | 752 | 1070 | 12 |
| 521 | G | CA | 518 | 760 | 1058 | 9 |
| 521 | G | C | 511 | 754 | 1047 | 12 |
| 521 | G | O | 509 | 760 | 1036 | 16 |
| 522 | L | N | 506 | 742 | 1049 | 13 |
| 522 | L | CA | 499 | 734 | 1038 | 11 |
| 522 | L | CB | 506 | 721 | 1036 | 7 |
| 522 | L | CG | 519 | 720 | 1029 | 2 |
| 522 | L | CD1 | 525 | 706 | 1031 | 2 |
| 522 | L | CD2 | 518 | 724 | 1015 | 2 |
| 522 | L | C | 485 | 732 | 1043 | 9 |
| 522 | L | O | 482 | 734 | 1055 | 6 |
| 523 | P | N | 476 | 729 | 1034 | 11 |
| 523 | P | CD | 478 | 728 | 1019 | 3 |
| 523 | P | CA | 462 | 726 | 1037 | 8 |
| 523 | P | CB | 456 | 721 | 1024 | 12 |
| 523 | P | CG | 464 | 729 | 1014 | 2 |
| 523 | P | C | 462 | 715 | 1048 | 7 |
| 523 | P | O | 469 | 706 | 1048 | 14 |
| 524 | V | N | 452 | 716 | 1058 | 5 |
| 524 | V | CA | 452 | 707 | 1068 | 2 |
| 524 | V | CB | 451 | 714 | 1082 | 6 |
| 524 | V | CG1 | 464 | 721 | 1085 | 6 |
| 524 | V | CG2 | 439 | 723 | 1082 | 2 |
| 524 | V | C | 440 | 697 | 1067 | 2 |
| 524 | V | O | 430 | 700 | 1061 | 4 |
| 525 | C | N | 442 | 686 | 1074 | 2 |
| 525 | C | CA | 432 | 675 | 1074 | 5 |
| 525 | C | CB | 434 | 666 | 1062 | 3 |
| 525 | C | SG | 422 | 653 | 1061 | 23 |
| 525 | C | C | 434 | 668 | 1087 | 8 |
| 525 | C | O | 444 | 669 | 1094 | 15 |
| 526 | Q | N | 424 | 660 | 1091 | 11 |
| 526 | Q | CA | 425 | 652 | 1103 | 9 |
| 526 | Q | CB | 411 | 646 | 1107 | 11 |
| 526 | Q | CG | 401 | 657 | 1111 | 19 |
| 526 | Q | CD | 404 | 663 | 1124 | 21 |
| 526 | Q | OE1 | 414 | 670 | 1126 | 26 |
| 526 | Q | NE2 | 394 | 662 | 1133 | 22 |
| 526 | Q | C | 434 | 640 | 1100 | 11 |
| 526 | Q | O | 434 | 635 | 1089 | 14 |
| 527 | D | N | 442 | 637 | 1110 | 9 |
| 527 | D | CA | 452 | 626 | 1109 | 12 |
| 527 | D | CB | 463 | 627 | 1119 | 15 |
| 527 | D | CG | 474 | 617 | 1117 | 22 |
| 527 | D | OD1 | 484 | 617 | 1124 | 28 |
| 527 | D | OD2 | 472 | 608 | 1107 | 26 |
| 527 | D | C | 445 | 612 | 1111 | 15 |
| 527 | D | O | 442 | 608 | 1122 | 19 |
| 528 | H | N | 441 | 606 | 1100 | 13 |
| 528 | H | CA | 435 | 593 | 1101 | 7 |
| 528 | H | CB | 421 | 594 | 1094 | 9 |
| 528 | H | CG | 411 | 602 | 1102 | 7 |
| 528 | H | CD2 | 411 | 607 | 1114 | 5 |
| 528 | H | ND1 | 400 | 607 | 1096 | 7 |
| 528 | H | CE1 | 393 | 614 | 1105 | 5 |
| 528 | H | NE2 | 400 | 614 | 1116 | 2 |
| 528 | H | C | 443 | 583 | 1093 | 9 |
| 528 | H | O | 439 | 573 | 1088 | 13 |
| 529 | L | N | 456 | 587 | 1091 | 6 |
| 529 | L | CA | 466 | 579 | 1084 | 6 |
| 529 | L | CB | 480 | 585 | 1086 | 6 |
| 529 | L | CG | 486 | 595 | 1076 | 5 |
| 529 | L | CD1 | 475 | 603 | 1070 | 3 |
| 529 | L | CD2 | 496 | 603 | 1083 | 4 |
| 529 | L | C | 466 | 564 | 1088 | 6 |
| 529 | L | O | 466 | 556 | 1079 | 9 |
| 530 | E | N | 467 | 562 | 1101 | 9 |
| 530 | E | CA | 467 | 548 | 1106 | 15 |
| 530 | E | CB | 470 | 549 | 1121 | 24 |
| 530 | E | CG | 475 | 536 | 1127 | 41 |
| 530 | E | CD | 480 | 538 | 1141 | 50 |
| 530 | E | OE1 | 472 | 536 | 1150 | 50 |
| 530 | E | OE2 | 492 | 541 | 1143 | 58 |
| 530 | E | C | 454 | 541 | 1103 | 10 |
| 530 | E | O | 455 | 529 | 1101 | 15 |
| 531 | F | N | 443 | 548 | 1103 | 8 |
| 531 | F | CA | 430 | 541 | 1100 | 6 |
| 531 | F | CB | 419 | S51 | 1103 | 3 |
| 531 | F | CG | 406 | 546 | 1097 | 2 |
| 531 | F | CD1 | 399 | 536 | 1103 | 6 |
| 531 | F | CD2 | 401 | 552 | 1086 | 2 |
| 531 | F | CE1 | 387 | 531 | 1098 | 4 |
| 531 | F | CE2 | 389 | 547 | 1080 | 2 |
| 531 | F | CZ | 382 | 537 | 1086 | 5 |
| 531 | F | C | 430 | 536 | 1086 | 8 |
| 531 | F | O | 428 | 524 | 1083 | 3 |
| 532 | W | N | 432 | 546 | 1077 | 7 |
| 532 | W | CA | 431 | 542 | 1063 | 2 |
| 532 | W | CB | 433 | 554 | 1054 | 4 |
| 532 | W | CG | 421 | 564 | 1054 | 2 |
| 532 | W | CD2 | 408 | 561 | 1051 | 4 |
| 532 | W | CE2 | 400 | 572 | 1054 | 5 |
| 532 | W | CE3 | 401 | 549 | 1046 | 6 |
| 532 | W | CD1 | 421 | 577 | 1058 | 4 |
| 532 | W | NE1 | 409 | 582 | 1058 | 2 |
| 532 | W | CZ2 | 386 | 573 | 1052 | 5 |
| 532 | W | CZ3 | 388 | 550 | 1044 | 17 |
| 532 | W | CH2 | 380 | 561 | 1047 | 10 |
| 532 | W | C | 442 | 532 | 1060 | 2 |
| 532 | W | O | 440 | 522 | 1053 | 7 |
| 533 | E | N | 454 | 535 | 1065 | 2 |
| 533 | E | CA | 465 | 525 | 1062 | 6 |
| 533 | E | CB | 477 | 528 | 1070 | 10 |
| 533 | E | CG | 488 | 518 | 1066 | 9 |
| 533 | E | CD | 501 | 520 | 1075 | 9 |
| 533 | E | OE1 | 503 | 532 | 1079 | 20 |
| 533 | E | OE2 | 508 | 510 | 1076 | 12 |
| 533 | E | C | 460 | 511 | 1065 | 7 |
| 533 | E | O | 463 | 502 | 1057 | 12 |
| 534 | S | N | 454 | 509 | 1076 | 11 |
| 534 | S | CA | 449 | 496 | 1080 | 11 |
| 534 | S | CB | 445 | 496 | 1095 | 4 |
| 534 | S | OG | 432 | 503 | 1096 | 6 |
| 534 | S | C | 438 | 490 | 1071 | 13 |
| 534 | S | O | 438 | 478 | 1068 | 18 |
| 535 | V | N | 429 | 499 | 1066 | 14 |
| 535 | V | CA | 418 | 494 | 1057 | 8 |
| 535 | V | CB | 409 | 506 | 1053 | 6 |
| 535 | V | CG1 | 401 | 502 | 1041 | 2 |
| 535 | V | CG2 | 399 | 508 | 1065 | 2 |
| 535 | V | C | 424 | 488 | 1045 | 9 |
| 535 | V | O | 421 | 477 | 1041 | 18 |
| 536 | F | N | 433 | 496 | 1038 | 10 |
| 536 | F | CA | 439 | 492 | 1025 | 8 |
| 536 | F | CB | 446 | 504 | 1019 | 9 |
| 536 | F | CG | 436 | 513 | 1012 | 7 |
| 536 | F | CD1 | 432 | 511 | 999 | 7 |
| 536 | F | CD2 | 430 | 524 | 1019 | 3 |
| 536 | F | CE1 | 423 | 519 | 993 | 3 |
| 536 | F | CE2 | 420 | 532 | 1013 | 2 |
| 536 | F | CZ | 417 | 530 | 1000 | 2 |
| 536 | F | C | 449 | 480 | 1027 | 10 |
| 536 | F | O | 451 | 473 | 1017 | 10 |
| 537 | T | N | 454 | 479 | 1039 | 11 |
| 537 | T | CA | 463 | 468 | 1041 | 6 |
| 537 | T | CB | 470 | 469 | 1055 | 5 |
| 537 | T | OG1 | 478 | 481 | 1056 | 3 |
| 537 | T | CG2 | 478 | 457 | 1058 | 10 |
| 537 | T | C | 456 | 454 | 1040 | 8 |
| 537 | T | O | 463 | 444 | 1036 | 12 |
| 538 | G | N | 443 | 454 | 1042 | 11 |
| 538 | G | CA | 436 | 442 | 1042 | 5 |
| 538 | G | C | 430 | 439 | 1028 | 8 |

TABLE 3-continued

| | | | | | | |
|---|---|---|---|---|---|---|
| 538 | G | O | 424 | 428 | 1026 | 7 |
| 539 | L | N | 430 | 449 | 1019 | 13 |
| 539 | L | CA | 425 | 448 | 1006 | 11 |
| 539 | L | CB | 420 | 461 | 1001 | 7 |
| 539 | L | CG | 406 | 466 | 1003 | 5 |
| 539 | L | CD1 | 400 | 460 | 1016 | 4 |
| 539 | L | CD2 | 405 | 481 | 1004 | 2 |
| 539 | L | C | 435 | 442 | 997 | 12 |
| 539 | L | O | 441 | 449 | 989 | 9 |
| 540 | T | N | 437 | 428 | 998 | 10 |
| 540 | T | CA | 447 | 421 | 990 | 6 |
| 540 | T | CB | 456 | 413 | 999 | 4 |
| 540 | T | OG1 | 447 | 405 | 1008 | 8 |
| 540 | T | CG2 | 465 | 421 | 1008 | 7 |
| 540 | T | C | 441 | 412 | 979 | 8 |
| 540 | T | O | 429 | 409 | 980 | 15 |
| 541 | H | N | 449 | 408 | 970 | 7 |
| 541 | H | CA | 445 | 399 | 959 | 7 |
| 541 | H | CB | 441 | 385 | 965 | 4 |
| 541 | H | CG | 452 | 380 | 974 | 2 |
| 541 | H | CD2 | 451 | 375 | 987 | 7 |
| 541 | H | ND1 | 465 | 379 | 970 | 5 |
| 541 | H | CE1 | 472 | 374 | 981 | 10 |
| 541 | H | NE2 | 464 | 372 | 991 | 10 |
| 541 | H | C | 433 | 404 | 951 | 8 |
| 541 | H | O | 423 | 397 | 949 | 8 |
| 542 | I | N | 434 | 417 | 947 | 9 |
| 542 | I | CA | 423 | 424 | 940 | 7 |
| 542 | I | CB | 426 | 439 | 939 | 3 |
| 542 | I | CG2 | 439 | 442 | 931 | 3 |
| 542 | I | CG1 | 414 | 446 | 933 | 2 |
| 542 | I | CD1 | 415 | 461 | 933 | 2 |
| 542 | I | C | 424 | 418 | 925 | 8 |
| 542 | I | O | 433 | 411 | 922 | 9 |
| 543 | D | N | 413 | 420 | 918 | 13 |
| 543 | D | CA | 413 | 414 | 904 | 12 |
| 543 | D | CB | 398 | 412 | 900 | 21 |
| 543 | D | CG | 398 | 404 | 887 | 28 |
| 543 | D | OD1 | 394 | 392 | 888 | 37 |
| 543 | D | OD2 | 401 | 410 | 876 | 31 |
| 543 | D | C | 419 | 424 | 895 | 10 |
| 543 | D | O | 415 | 436 | 893 | 9 |
| 544 | A | N | 430 | 420 | 889 | 10 |
| 544 | A | CA | 438 | 428 | 880 | 11 |
| 544 | A | CB | 450 | 420 | 875 | 9 |
| 544 | A | C | 430 | 435 | 869 | 10 |
| 544 | A | O | 432 | 447 | 866 | 14 |
| 545 | H | N | 422 | 427 | 862 | 10 |
| 545 | H | CA | 414 | 432 | 851 | 8 |
| 545 | H | CB | 407 | 421 | 844 | 4 |
| 545 | H | CG | 399 | 426 | 832 | 12 |
| 545 | H | CD2 | 402 | 434 | 822 | 5 |
| 545 | H | ND1 | 386 | 422 | 830 | 8 |
| 545 | H | CE1 | 381 | 427 | 819 | 9 |
| 545 | H | NE2 | 390 | 435 | 814 | 12 |
| 545 | H | C | 404 | 443 | 855 | 11 |
| 545 | H | O | 402 | 453 | 849 | 16 |
| 546 | F | N | 397 | 440 | 867 | 6 |
| 546 | F | CA | 387 | 450 | 871 | 3 |
| 546 | F | CB | 380 | 444 | 883 | 5 |
| 546 | F | CG | 369 | 434 | 880 | 3 |
| 546 | F | CD1 | 363 | 434 | 868 | 5 |
| 546 | F | CD2 | 366 | 424 | 890 | 9 |
| 546 | F | CE1 | 353 | 424 | 865 | 12 |
| 546 | F | CE2 | 356 | 415 | 887 | 11 |
| 546 | F | CZ | 350 | 415 | 875 | 9 |
| 546 | F | C | 394 | 463 | 874 | 7 |
| 546 | F | O | 390 | 474 | 870 | 9 |
| 547 | L | N | 405 | 462 | 882 | 8 |
| 547 | L | CA | 412 | 474 | 886 | 7 |
| 547 | L | CB | 424 | 471 | 894 | 9 |
| 547 | L | CG | 432 | 483 | 899 | 6 |
| 547 | L | CD1 | 424 | 492 | 908 | 6 |
| 547 | L | CD2 | 445 | 478 | 906 | 5 |
| 547 | L | C | 416 | 481 | 873 | 4 |
| 547 | L | O | 417 | 494 | 873 | 8 |
| 548 | S | N | 419 | 474 | 863 | 6 |
| 548 | S | CA | 424 | 479 | 850 | 5 |
| 548 | S | CB | 428 | 467 | 841 | 6 |
| 548 | S | OG | 433 | 472 | 829 | 26 |
| 548 | S | C | 413 | 487 | 844 | 6 |
| 548 | S | O | 415 | 498 | 839 | 10 |
| 549 | Q | N | 401 | 481 | 844 | 7 |
| 549 | Q | CA | 389 | 488 | 838 | 4 |
| 549 | Q | CB | 377 | 478 | 838 | 6 |
| 549 | Q | CG | 379 | 466 | 830 | 5 |
| 549 | Q | CD | 367 | 458 | 827 | 14 |
| 549 | Q | OE1 | 363 | 449 | 835 | 16 |
| 549 | Q | NE2 | 360 | 462 | 817 | 22 |
| 549 | Q | C | 386 | 501 | 846 | 7 |
| 549 | Q | O | 384 | 511 | 840 | 8 |
| 550 | T | N | 384 | 500 | 859 | 5 |
| 550 | T | CA | 381 | 512 | 867 | 3 |
| 550 | T | CB | 380 | 509 | 882 | 2 |
| 550 | T | OG1 | 392 | 504 | 887 | 9 |
| 550 | T | CG2 | 368 | 499 | 884 | 2 |
| 550 | T | C | 392 | 523 | 866 | 5 |
| 550 | T | O | 389 | 535 | 866 | 10 |
| 551 | K | N | 404 | 519 | 865 | 7 |
| 551 | K | CA | 415 | 529 | 863 | 12 |
| 551 | K | CB | 428 | 522 | 863 | 8 |
| 551 | K | CG | 434 | 519 | 877 | 2 |
| 551 | K | CD | 445 | 509 | 877 | 6 |
| 551 | K | CE | 457 | 515 | 870 | 5 |
| 551 | K | NZ | 469 | 509 | 875 | 7 |
| 551 | K | C | 413 | 537 | 851 | 15 |
| 551 | K | O | 415 | 549 | 851 | 19 |
| 552 | Q | N | 409 | 530 | 840 | 18 |
| 552 | Q | CA | 407 | 536 | 827 | 18 |
| 552 | Q | CB | 407 | 526 | 816 | 24 |
| 552 | Q | CG | 398 | 529 | 804 | 30 |
| 552 | Q | CD | 384 | 524 | 805 | 36 |
| 552 | Q | OE1 | 381 | 515 | 813 | 32 |
| 552 | Q | NE2 | 375 | 530 | 796 | 31 |
| 552 | Q | C | 395 | 545 | 826 | 13 |
| 552 | Q | O | 395 | 555 | 820 | 17 |
| 553 | A | N | 384 | 540 | 832 | 9 |
| 553 | A | CA | 372 | 548 | 832 | 7 |
| 553 | A | CB | 361 | 540 | 840 | 3 |
| 553 | A | C | 373 | 561 | 838 | 12 |
| 553 | A | O | 365 | 570 | 836 | 22 |
| 554 | G | N | 384 | 563 | 846 | 14 |
| 554 | G | CA | 386 | 576 | 853 | 13 |
| 554 | G | C | 377 | 580 | 865 | 16 |
| 554 | G | O | 378 | 591 | 870 | 14 |
| 555 | D | N | 369 | 570 | 869 | 21 |
| 555 | D | CA | 361 | 572 | 881 | 22 |
| 555 | D | CB | 352 | 560 | 884 | 27 |
| 555 | D | CG | 361 | 547 | 884 | 30 |
| 555 | D | OD1 | 363 | 542 | 895 | 24 |
| 555 | D | OD2 | 366 | 543 | 873 | 31 |
| 555 | D | C | 369 | 576 | 893 | 24 |
| 555 | D | O | 381 | 576 | 893 | 26 |
| 556 | N | N | 362 | 579 | 904 | 24 |
| 556 | N | CA | 369 | 583 | 916 | 23 |
| 556 | N | CB | 360 | 591 | 925 | 26 |
| 556 | N | CG | 363 | 606 | 924 | 27 |
| 556 | N | OD1 | 356 | 614 | 929 | 34 |
| 556 | N | ND2 | 374 | 609 | 917 | 23 |
| 556 | N | C | 377 | 572 | 925 | 25 |
| 556 | N | O | 388 | 575 | 928 | 30 |
| 557 | F | N | 371 | 562 | 929 | 21 |
| 557 | F | CA | 378 | 552 | 938 | 19 |
| 557 | F | CB | 370 | 550 | 951 | 11 |
| 557 | F | CG | 371 | 561 | 960 | 8 |
| 557 | F | CD1 | 381 | 562 | 970 | 11 |
| 557 | F | CD2 | 362 | 572 | 959 | 5 |
| 557 | F | CE1 | 382 | 573 | 979 | 5 |
| 557 | F | CE2 | 363 | 583 | 968 | 9 |
| 557 | F | CZ | 373 | 583 | 978 | 9 |
| 557 | F | C | 381 | 539 | 930 | 17 |
| 557 | F | O | 375 | 529 | 934 | 16 |
| 558 | P | N | 389 | 539 | 920 | 14 |
| 558 | P | CD | 397 | 551 | 916 | 11 |
| 558 | P | CA | 393 | 528 | 912 | 10 |
| 558 | P | CB | 405 | 533 | 904 | 12 |
| 558 | P | CG | 409 | 546 | 910 | 13 |
| 558 | P | C | 396 | 515 | 920 | 12 |

TABLE 3-continued

| | | | | | | |
|---|---|---|---|---|---|---|
| 558 | P | O | 391 | 505 | 917 | 14 |
| 559 | Y | N | 404 | 517 | 930 | 14 |
| 559 | Y | CA | 408 | 505 | 938 | 9 |
| 559 | Y | CB | 420 | 508 | 948 | 8 |
| 559 | Y | CG | 427 | 495 | 952 | 11 |
| 559 | Y | CD1 | 423 | 488 | 963 | 7 |
| 559 | Y | CE1 | 429 | 476 | 967 | 2 |
| 559 | Y | CD2 | 437 | 490 | 944 | 5 |
| 559 | Y | CE2 | 443 | 478 | 948 | 2 |
| 559 | Y | CZ | 439 | 471 | 959 | 4 |
| 559 | Y | OH | 445 | 460 | 963 | 11 |
| 559 | Y | C | 396 | 500 | 947 | 4 |
| 559 | Y | O | 393 | 488 | 946 | 5 |
| 560 | L | N | 390 | 508 | 954 | 4 |
| 560 | L | CA | 378 | 504 | 962 | 3 |
| 560 | L | CB | 373 | 516 | 971 | 5 |
| 560 | L | CG | 382 | 522 | 981 | 8 |
| 560 | L | CD1 | 374 | 532 | 989 | 2 |
| 560 | L | CD2 | 389 | 512 | 990 | 6 |
| 560 | L | C | 367 | 499 | 954 | 2 |
| 560 | L | O | 360 | 490 | 958 | 6 |
| 561 | V | N | 365 | 505 | 942 | 2 |
| 561 | V | CA | 354 | 500 | 934 | 2 |
| 561 | V | CB | 352 | 509 | 922 | 2 |
| 561 | V | CG1 | 340 | 504 | 913 | 2 |
| 561 | V | CG2 | 348 | 523 | 927 | 2 |
| 561 | V | C | 358 | 486 | 928 | 2 |
| 561 | V | O | 350 | 477 | 928 | 11 |
| 562 | A | N | 370 | 485 | 923 | 2 |
| 562 | A | CA | 375 | 473 | 917 | 2 |
| 562 | A | CB | 388 | 474 | 911 | 7 |
| 562 | A | C | 375 | 462 | 928 | 4 |
| 562 | A | O | 373 | 450 | 925 | 7 |
| 563 | Y | N | 378 | 466 | 940 | 2 |
| 563 | Y | CA | 379 | 456 | 951 | 4 |
| 563 | Y | CB | 387 | 461 | 963 | 2 |
| 563 | Y | CG | 392 | 450 | 971 | 2 |
| 563 | Y | CD1 | 404 | 444 | 967 | 2 |
| 563 | Y | CE1 | 409 | 432 | 973 | 2 |
| 563 | Y | CD2 | 386 | 445 | 982 | 5 |
| 563 | Y | CE2 | 390 | 433 | 988 | 2 |
| 563 | Y | CZ | 402 | 427 | 984 | 3 |
| 563 | Y | OH | 406 | 416 | 990 | 5 |
| 563 | Y | C | 365 | 451 | 954 | 8 |
| 563 | Y | O | 363 | 439 | 956 | 13 |
| 564 | Q | N | 356 | 461 | 956 | 6 |
| 564 | Q | CA | 342 | 457 | 959 | 5 |
| 564 | Q | CB | 333 | 469 | 960 | 8 |
| 564 | Q | CG | 318 | 466 | 962 | 7 |
| 564 | Q | CD | 315 | 459 | 975 | 7 |
| 564 | Q | OE1 | 314 | 465 | 986 | 10 |
| 564 | Q | NE2 | 314 | 445 | 975 | 2 |
| 564 | Q | C | 337 | 447 | 948 | 7 |
| 564 | Q | O | 331 | 437 | 951 | 12 |
| 565 | A | N | 340 | 451 | 936 | 7 |
| 565 | A | CA | 336 | 443 | 924 | 5 |
| 565 | A | CB | 339 | 450 | 911 | 2 |
| 565 | A | C | 343 | 429 | 924 | 8 |
| 565 | A | O | 338 | 419 | 919 | 13 |
| 566 | T | N | 356 | 429 | 929 | 9 |
| 566 | T | CA | 363 | 417 | 929 | 6 |
| 566 | T | CB | 377 | 419 | 935 | 3 |
| 566 | T | OG1 | 385 | 428 | 926 | 4 |
| 566 | T | CG2 | 385 | 406 | 936 | 2 |
| 566 | T | C | 356 | 407 | 938 | 9 |
| 566 | T | O | 354 | 396 | 934 | 13 |
| 567 | V | N | 354 | 411 | 950 | 12 |
| 567 | V | CA | 347 | 403 | 960 | 10 |
| 567 | V | CB | 345 | 411 | 973 | 8 |
| 567 | V | CG1 | 335 | 403 | 983 | 4 |
| 567 | V | CG2 | 358 | 413 | 980 | 2 |
| 567 | V | C | 333 | 398 | 955 | 11 |
| 567 | V | O | 330 | 386 | 956 | 15 |
| 568 | C | N | 326 | 407 | 949 | 15 |
| 568 | C | CA | 313 | 403 | 944 | 14 |
| 568 | C | CB | 306 | 415 | 938 | 14 |
| 568 | C | SG | 299 | 427 | 949 | 17 |
| 568 | C | C | 314 | 392 | 933 | 15 |
| 568 | C | O | 308 | 382 | 935 | 16 |
| 569 | A | N | 322 | 395 | 923 | 14 |
| 569 | A | CA | 324 | 385 | 912 | 10 |
| 569 | A | CB | 333 | 391 | 902 | 8 |
| 569 | A | C | 328 | 372 | 917 | 9 |
| 569 | A | O | 324 | 361 | 912 | 13 |
| 570 | R | N | 337 | 371 | 927 | 11 |
| 570 | R | CA | 342 | 359 | 932 | 11 |
| 570 | R | CB | 354 | 361 | 942 | 9 |
| 570 | R | CG | 367 | 360 | 936 | 9 |
| 570 | R | CD | 378 | 368 | 943 | 12 |
| 570 | R | NE | 390 | 370 | 935 | 15 |
| 570 | R | CZ | 400 | 377 | 939 | 11 |
| 570 | R | NH1 | 401 | 383 | 951 | 12 |
| 570 | R | NH2 | 410 | 379 | 930 | 13 |
| 570 | R | C | 331 | 351 | 939 | 14 |
| 570 | R | O | 331 | 339 | 940 | 19 |
| 571 | A | N | 321 | 358 | 944 | 11 |
| 571 | A | CA | 310 | 351 | 951 | 13 |
| 571 | A | CB | 306 | 359 | 964 | 13 |
| 571 | A | C | 298 | 351 | 942 | 20 |
| 571 | A | O | 287 | 346 | 947 | 22 |
| 572 | Q | N | 299 | 355 | 930 | 20 |
| 572 | Q | CA | 288 | 355 | 921 | 22 |
| 572 | Q | CB | 283 | 340 | 918 | 28 |
| 572 | Q | CG | 292 | 333 | 908 | 41 |
| 572 | Q | CD | 297 | 320 | 913 | 54 |
| 572 | Q | OE1 | 292 | 309 | 909 | 59 |
| 572 | Q | NE2 | 307 | 320 | 922 | 57 |
| 572 | Q | C | 276 | 362 | 926 | 22 |
| 572 | Q | O | 264 | 359 | 924 | 26 |
| 573 | A | N | 279 | 373 | 933 | 19 |
| 573 | A | CA | 269 | 382 | 939 | 16 |
| 573 | A | CB | 272 | 385 | 954 | 6 |
| 573 | A | C | 269 | 394 | 931 | 18 |
| 573 | A | O | 279 | 398 | 924 | 24 |
| 574 | P | N | 258 | 401 | 930 | 15 |
| 574 | P | CD | 245 | 398 | 936 | 11 |
| 574 | P | CA | 257 | 414 | 922 | 12 |
| 574 | P | CB | 242 | 415 | 919 | 11 |
| 574 | P | CG | 236 | 409 | 931 | 11 |
| 574 | P | C | 263 | 425 | 930 | 10 |
| 574 | P | O | 265 | 425 | 942 | 12 |
| 575 | P | N | 266 | 437 | 923 | 10 |
| 575 | P | CD | 264 | 439 | 908 | 3 |
| 575 | P | CA | 271 | 448 | 930 | 7 |
| 575 | P | CB | 277 | 457 | 919 | 9 |
| 575 | P | CG | 269 | 453 | 906 | 11 |
| 575 | P | C | 260 | 456 | 938 | 5 |
| 575 | P | O | 248 | 453 | 935 | 9 |
| 576 | P | N | 264 | 465 | 947 | 6 |
| 576 | P | CD | 278 | 469 | 950 | 5 |
| 576 | P | CA | 255 | 472 | 955 | 7 |
| 576 | P | CB | 263 | 483 | 961 | 6 |
| 576 | P | CG | 277 | 478 | 961 | 3 |
| 576 | P | C | 243 | 477 | 947 | 8 |
| 576 | P | O | 232 | 478 | 952 | 11 |
| 577 | S | N | 245 | 480 | 934 | 9 |
| 577 | S | CA | 235 | 485 | 926 | 13 |
| 577 | S | CB | 231 | 500 | 929 | 11 |
| 577 | S | OG | 242 | 508 | 927 | 23 |
| 577 | S | C | 240 | 484 | 912 | 16 |
| 577 | S | O | 251 | 480 | 910 | 20 |
| 578 | W | N | 232 | 489 | 902 | 18 |
| 578 | W | CA | 237 | 488 | 888 | 17 |
| 578 | W | CB | 228 | 480 | 879 | 17 |
| 578 | W | CG | 228 | 465 | 881 | 16 |
| 578 | W | CD2 | 239 | 457 | 878 | 13 |
| 578 | W | CE2 | 236 | 444 | 883 | 15 |
| 578 | W | CE3 | 252 | 459 | 871 | 14 |
| 578 | W | CD1 | 219 | 458 | 888 | 10 |
| 578 | W | NE1 | 224 | 445 | 889 | 16 |
| 578 | W | CZ2 | 245 | 433 | 881 | 13 |
| 578 | W | CZ3 | 260 | 448 | 869 | 10 |
| 578 | W | CH2 | 257 | 435 | 874 | 7 |
| 578 | W | C | 240 | 502 | 882 | 21 |
| 578 | W | O | 237 | 505 | 871 | 24 |
| 579 | D | N | 246 | 510 | 891 | 21 |
| 579 | D | CA | 249 | 524 | 887 | 25 |
| 579 | D | CB | 252 | 533 | 899 | 35 |

TABLE 3-continued

| | | | | | | |
|---|---|---|---|---|---|---|
| 579 | D | CG | 262 | 544 | 896 | 47 |
| 579 | D | OD1 | 260 | 552 | 887 | 58 |
| 579 | D | OD2 | 272 | 545 | 904 | 51 |
| 579 | D | C | 262 | 523 | 879 | 25 |
| 579 | D | O | 270 | 514 | 881 | 25 |
| 580 | Q | N | 264 | 532 | 869 | 27 |
| 580 | Q | CA | 276 | 532 | 861 | 27 |
| 580 | Q | CB | 278 | 545 | 854 | 28 |
| 580 | Q | CG | 276 | 545 | 839 | 42 |
| 580 | Q | CD | 270 | 532 | 834 | 46 |
| 580 | Q | OE1 | 275 | 525 | 825 | 49 |
| 580 | Q | NE2 | 258 | 529 | 840 | 47 |
| 580 | Q | C | 289 | 528 | 868 | 22 |
| 580 | Q | O | 298 | 522 | 863 | 26 |
| 581 | M | N | 289 | 532 | 881 | 18 |
| 581 | M | CA | 301 | 529 | 889 | 20 |
| 581 | M | CB | 298 | 533 | 904 | 20 |
| 581 | M | CG | 305 | 525 | 914 | 21 |
| 581 | M | SD | 301 | 531 | 931 | 23 |
| 581 | M | CE | 306 | 548 | 929 | 17 |
| 581 | M | C | 304 | 514 | 889 | 21 |
| 581 | M | O | 316 | 510 | 889 | 27 |
| 582 | W | N | 294 | 506 | 888 | 19 |
| 582 | W | CA | 296 | 491 | 888 | 18 |
| 582 | W | CB | 286 | 485 | 898 | 14 |
| 582 | W | CG | 285 | 491 | 911 | 5 |
| 582 | W | CD2 | 296 | 491 | 921 | 11 |
| 582 | W | CE2 | 291 | 498 | 932 | 9 |
| 582 | W | CE3 | 308 | 484 | 922 | 8 |
| 582 | W | CD1 | 275 | 499 | 916 | 7 |
| 582 | W | NE1 | 279 | 503 | 929 | 7 |
| 582 | W | CZ2 | 299 | 500 | 943 | 7 |
| 582 | W | CZ3 | 316 | 486 | 933 | 3 |
| 582 | W | CH2 | 311 | 494 | 944 | 2 |
| 582 | W | C | 295 | 485 | 874 | 17 |
| 582 | W | O | 293 | 473 | 873 | 18 |
| 583 | K | N | 296 | 493 | 864 | 18 |
| 583 | K | CA | 295 | 488 | 850 | 17 |
| 583 | K | CB | 296 | 500 | 840 | 23 |
| 583 | K | CG | 310 | 507 | 840 | 29 |
| 583 | K | CD | 310 | 518 | 830 | 33 |
| 583 | K | CE | 324 | 522 | 827 | 43 |
| 583 | K | NZ | 325 | 531 | 815 | 44 |
| 583 | K | C | 305 | 477 | 846 | 18 |
| 583 | K | O | 303 | 470 | 836 | 20 |
| 584 | C | N | 317 | 476 | 853 | 20 |
| 584 | C | CA | 326 | 466 | 849 | 23 |
| 584 | C | CB | 340 | 467 | 856 | 24 |
| 584 | C | SG | 339 | 465 | 874 | 29 |
| 584 | C | C | 320 | 452 | 851 | 23 |
| 584 | C | O | 326 | 442 | 846 | 23 |
| 585 | L | N | 309 | 451 | 858 | 20 |
| 585 | L | CA | 303 | 438 | 860 | 17 |
| 585 | L | CB | 299 | 438 | 875 | 14 |
| 585 | L | CG | 310 | 437 | 885 | 8 |
| 585 | L | CD1 | 305 | 440 | 899 | 14 |
| 585 | L | CD2 | 317 | 424 | 885 | 10 |
| 585 | L | C | 290 | 436 | 852 | 17 |
| 585 | L | O | 286 | 425 | 851 | 19 |
| 586 | I | N | 285 | 446 | 845 | 17 |
| 586 | I | CA | 274 | 444 | 836 | 20 |
| 586 | I | CB | 272 | 456 | 827 | 22 |
| 586 | I | CG2 | 262 | 452 | 816 | 13 |
| 586 | I | CG1 | 265 | 468 | 835 | 22 |
| 586 | I | CD1 | 269 | 481 | 828 | 30 |
| 586 | I | C | 275 | 431 | 828 | 20 |
| 586 | I | O | 265 | 424 | 826 | 18 |
| 587 | R | N | 287 | 429 | 824 | 22 |
| 587 | R | CA | 290 | 417 | 816 | 28 |
| 587 | R | CB | 306 | 416 | 814 | 29 |
| 587 | R | CG | 310 | 413 | 800 | 37 |
| 587 | R | CD | 324 | 407 | 800 | 40 |
| 587 | R | NE | 333 | 412 | 810 | 46 |
| 587 | R | CZ | 342 | 406 | 816 | 44 |
| 587 | R | NH1 | 345 | 393 | 813 | 39 |
| 587 | R | NH2 | 350 | 412 | 826 | 50 |
| 587 | R | C | 285 | 404 | 822 | 28 |
| 587 | R | O | 282 | 394 | 815 | 29 |
| 588 | L | N | 285 | 403 | 835 | 24 |

TABLE 3-continued

| | | | | | | |
|---|---|---|---|---|---|---|
| 588 | L | CA | 280 | 391 | 842 | 20 |
| 588 | L | CB | 291 | 387 | 853 | 23 |
| 588 | L | CG | 305 | 392 | 851 | 27 |
| 588 | L | CD1 | 314 | 386 | 862 | 25 |
| 588 | L | CD2 | 310 | 388 | 837 | 33 |
| 588 | L | C | 267 | 393 | 849 | 19 |
| 588 | L | O | 263 | 384 | 857 | 19 |
| 589 | K | N | 260 | 404 | 846 | 21 |
| 589 | K | CA | 247 | 406 | 852 | 27 |
| 589 | K | CB | 239 | 417 | 843 | 26 |
| 589 | K | CG | 227 | 423 | 851 | 21 |
| 589 | K | CD | 225 | 437 | 846 | 27 |
| 589 | K | CE | 213 | 443 | 852 | 34 |
| 589 | K | NZ | 211 | 457 | 848 | 42 |
| 589 | K | C | 238 | 394 | 853 | 27 |
| 589 | K | O | 233 | 391 | 864 | 25 |
| 590 | P | N | 237 | 386 | 843 | 29 |
| 590 | P | CD | 243 | 388 | 829 | 33 |
| 590 | P | CA | 229 | 373 | 843 | 29 |
| 590 | P | CB | 229 | 369 | 829 | 34 |
| 590 | P | CG | 241 | 375 | 823 | 36 |
| 590 | P | C | 234 | 362 | 852 | 30 |
| 590 | P | O | 226 | 354 | 857 | 31 |
| 591 | T | N | 247 | 362 | 856 | 31 |
| 591 | T | CA | 253 | 352 | 864 | 32 |
| 591 | T | CB | 267 | 348 | 860 | 32 |
| 591 | T | OG1 | 275 | 360 | 860 | 33 |
| 591 | T | CG2 | 266 | 343 | 845 | 34 |
| 591 | T | C | 254 | 356 | 879 | 29 |
| 591 | T | O | 257 | 347 | 888 | 30 |
| 592 | L | N | 251 | 368 | 882 | 27 |
| 592 | L | CA | 252 | 373 | 896 | 20 |
| 592 | L | CB | 257 | 388 | 895 | 12 |
| 592 | L | CG | 272 | 391 | 895 | 13 |
| 592 | L | CD1 | 281 | 378 | 891 | 2 |
| 592 | L | CD2 | 275 | 402 | 884 | 7 |
| 592 | L | C | 239 | 373 | 902 | 20 |
| 592 | L | O | 229 | 378 | 897 | 20 |
| 593 | H | N | 239 | 367 | 914 | 18 |
| 593 | H | CA | 226 | 365 | 922 | 23 |
| 593 | H | CB | 219 | 353 | 918 | 31 |
| 593 | H | CG | 217 | 351 | 903 | 38 |
| 593 | H | CD2 | 208 | 355 | 895 | 42 |
| 593 | H | ND1 | 226 | 343 | 896 | 45 |
| 593 | H | CE1 | 223 | 343 | 883 | 46 |
| 593 | H | NE2 | 212 | 350 | 882 | 46 |
| 593 | H | C | 229 | 366 | 937 | 22 |
| 593 | H | O | 239 | 362 | 941 | 24 |
| 594 | G | N | 219 | 370 | 944 | 29 |
| 594 | G | CA | 220 | 370 | 959 | 17 |
| 594 | G | C | 224 | 383 | 965 | 17 |
| 594 | G | O | 227 | 393 | 959 | 20 |
| 595 | P | N | 225 | 383 | 979 | 14 |
| 595 | P | CD | 223 | 371 | 988 | 18 |
| 595 | P | CA | 229 | 395 | 986 | 16 |
| 595 | P | CB | 228 | 390 | 1001 | 15 |
| 595 | P | CG | 229 | 375 | 1000 | 13 |
| 595 | P | C | 243 | 398 | 982 | 16 |
| 595 | P | O | 251 | 390 | 979 | 17 |
| 596 | T | N | 246 | 411 | 983 | 16 |
| 596 | T | CA | 260 | 416 | 979 | 14 |
| 596 | T | CB | 259 | 429 | 972 | 9 |
| 596 | T | OG1 | 272 | 437 | 974 | 13 |
| 596 | T | CG2 | 248 | 438 | 976 | 19 |
| 596 | T | C | 268 | 417 | 992 | 14 |
| 596 | T | O | 263 | 422 | 1002 | 14 |
| 597 | P | N | 280 | 411 | 992 | 13 |
| 597 | P | CD | 287 | 404 | 981 | 9 |
| 597 | P | CA | 289 | 412 | 1004 | 12 |
| 597 | P | CB | 300 | 402 | 1001 | 9 |
| 597 | P | CG | 301 | 401 | 986 | 7 |
| 597 | P | C | 294 | 426 | 1004 | 11 |
| 597 | P | O | 304 | 429 | 998 | 12 |
| 598 | L | N | 288 | 434 | 1012 | 9 |
| 598 | L | CA | 292 | 448 | 1014 | 9 |
| 598 | L | CB | 281 | 456 | 1020 | 13 |
| 598 | L | CG | 274 | 468 | 1013 | 14 |
| 598 | L | CD1 | 271 | 479 | 1024 | 10 |
| 598 | L | CD2 | 283 | 474 | 1003 | 6 |

TABLE 3-continued

| | | | | | | |
|---|---|---|---|---|---|---|
| 598 | L | C | 305 | 450 | 1021 | 12 |
| 598 | L | O | 306 | 444 | 1032 | 20 |
| 599 | L | N | 314 | 458 | 1016 | 12 |
| 599 | L | CA | 326 | 461 | 1022 | 10 |
| 599 | L | CB | 338 | 461 | 1012 | 9 |
| 599 | L | CG | 339 | 448 | 1004 | 6 |
| 599 | L | CD1 | 352 | 448 | 995 | 2 |
| 599 | L | CD2 | 339 | 436 | 1014 | 2 |
| 599 | L | C | 326 | 476 | 1028 | 8 |
| 599 | L | O | 331 | 479 | 1039 | 11 |
| 600 | Y | N | 319 | 485 | 1021 | 12 |
| 600 | Y | CA | 318 | 498 | 1025 | 6 |
| 600 | Y | CB | 331 | 506 | 1024 | 2 |
| 600 | Y | CG | 340 | 500 | 1013 | 4 |
| 600 | Y | CD1 | 336 | 501 | 1000 | 2 |
| 600 | Y | CE1 | 344 | 495 | 990 | 3 |
| 600 | Y | CD2 | 352 | 494 | 1016 | 2 |
| 600 | Y | CE2 | 360 | 488 | 1007 | 2 |
| 600 | Y | CZ | 356 | 489 | 993 | 4 |
| 600 | Y | OH | 364 | 484 | 984 | 3 |
| 600 | Y | C | 308 | 505 | 1015 | 4 |
| 600 | Y | O | 305 | 499 | 1004 | 6 |
| 601 | R | N | 302 | 516 | 1018 | 8 |
| 601 | R | CA | 293 | 523 | 1009 | 7 |
| 601 | R | CB | 281 | 528 | 1016 | 9 |
| 601 | R | CG | 273 | 517 | 1024 | 9 |
| 601 | R | CD | 265 | 524 | 1034 | 9 |
| 601 | R | NE | 256 | 514 | 1041 | 12 |
| 601 | R | CZ | 245 | 509 | 1036 | 9 |
| 601 | R | NH1 | 241 | 512 | 1024 | 15 |
| 601 | R | NH2 | 238 | 500 | 1043 | 17 |
| 601 | R | C | 299 | 534 | 1001 | 12 |
| 601 | R | O | 304 | 544 | 1007 | 13 |
| 602 | L | N | 299 | 534 | 988 | 14 |
| 602 | L | CA | 305 | 544 | 979 | 11 |
| 602 | L | CB | 314 | 539 | 969 | 12 |
| 602 | L | CG | 324 | 528 | 974 | 4 |
| 602 | L | CD1 | 331 | 522 | 961 | 4 |
| 602 | L | CD2 | 335 | 534 | 982 | 10 |
| 602 | L | C | 293 | 551 | 972 | 16 |
| 602 | L | O | 295 | 560 | 964 | 21 |
| 603 | G | N | 281 | 546 | 975 | 17 |
| 603 | G | CA | 269 | 551 | 969 | 15 |
| 603 | G | C | 257 | 544 | 974 | 20 |
| 603 | G | O | 256 | 540 | 985 | 24 |
| 604 | A | N | 246 | 544 | 966 | 19 |
| 604 | A | CA | 234 | 538 | 970 | 18 |
| 604 | A | CB | 222 | 543 | 961 | 16 |
| 604 | A | C | 235 | 523 | 969 | 15 |
| 604 | A | O | 240 | 518 | 959 | 18 |
| 605 | V | N | 229 | 516 | 979 | 11 |
| 605 | V | CA | 230 | 502 | 979 | 12 |
| 605 | V | CB | 235 | 497 | 992 | 8 |
| 605 | V | CG1 | 234 | 482 | 993 | 15 |
| 605 | V | CG2 | 250 | 501 | 994 | 14 |
| 605 | V | C | 215 | 497 | 977 | 12 |
| 605 | V | O | 207 | 498 | 987 | 14 |
| 606 | Q | N | 212 | 492 | 966 | 19 |
| 606 | Q | CA | 198 | 488 | 963 | 23 |
| 606 | Q | CB | 194 | 492 | 949 | 24 |
| 606 | Q | CG | 192 | 507 | 947 | 31 |
| 606 | Q | CD | 190 | 511 | 933 | 40 |
| 606 | Q | OE1 | 197 | 519 | 927 | 47 |
| 606 | Q | NE2 | 179 | 505 | 927 | 47 |
| 606 | Q | C | 197 | 473 | 964 | 26 |
| 606 | Q | O | 185 | 468 | 966 | 29 |
| 607 | N | N | 208 | 466 | 964 | 23 |
| 607 | N | CA | 207 | 451 | 966 | 22 |
| 607 | N | CB | 219 | 445 | 959 | 18 |
| 607 | N | CG | 218 | 430 | 958 | 16 |
| 607 | N | OD1 | 207 | 424 | 956 | 20 |
| 607 | N | ND2 | 229 | 423 | 961 | 17 |
| 607 | N | C | 208 | 447 | 981 | 26 |
| 607 | N | O | 213 | 455 | 989 | 28 |
| 608 | E | N | 202 | 436 | 984 | 26 |
| 608 | E | CA | 202 | 430 | 997 | 28 |
| 608 | E | CB | 195 | 417 | 998 | 36 |
| 608 | E | CG | 183 | 415 | 988 | 50 |
| 608 | E | CD | 187 | 406 | 977 | 58 |
| 608 | E | OE1 | 181 | 408 | 966 | 61 |
| 608 | E | OE2 | 195 | 397 | 979 | 60 |
| 608 | E | C | 217 | 428 | 1000 | 27 |
| 608 | E | O | 225 | 425 | 991 | 29 |
| 609 | V | N | 221 | 430 | 1013 | 21 |
| 609 | V | CA | 235 | 428 | 1016 | 22 |
| 609 | V | CB | 241 | 441 | 1020 | 25 |
| 609 | V | CG1 | 238 | 452 | 1010 | 19 |
| 609 | V | CG2 | 237 | 445 | 1034 | 23 |
| 609 | V | C | 237 | 418 | 1027 | 22 |
| 609 | V | O | 228 | 415 | 1035 | 25 |
| 610 | T | N | 250 | 413 | 1027 | 22 |
| 610 | T | CA | 254 | 404 | 1038 | 20 |
| 610 | T | CB | 255 | 389 | 1032 | 24 |
| 610 | T | OG1 | 256 | 380 | 1043 | 32 |
| 610 | T | CG2 | 268 | 388 | 1024 | 23 |
| 610 | T | C | 267 | 408 | 1043 | 17 |
| 610 | T | O | 275 | 413 | 1035 | 20 |
| 611 | L | N | 270 | 407 | 1056 | 16 |
| 611 | L | CA | 282 | 412 | 1061 | 13 |
| 611 | L | CB | 279 | 422 | 1072 | 14 |
| 611 | L | CG | 268 | 432 | 1069 | 12 |
| 611 | L | CD1 | 264 | 439 | 1082 | 17 |
| 611 | L | CD2 | 272 | 442 | 1058 | 15 |
| 611 | L | C | 291 | 400 | 1067 | 11 |
| 611 | L | O | 298 | 402 | 1077 | 11 |
| 612 | T | N | 289 | 389 | 1061 | 10 |
| 612 | T | CA | 297 | 377 | 1066 | 13 |
| 612 | T | CB | 289 | 364 | 1062 | 15 |
| 612 | T | OG1 | 285 | 364 | 1049 | 18 |
| 612 | T | CG2 | 278 | 362 | 1072 | 12 |
| 612 | T | C | 311 | 376 | 1060 | 12 |
| 612 | T | O | 319 | 369 | 1065 | 20 |
| 613 | H | N | 313 | 384 | 1049 | 14 |
| 613 | H | CA | 326 | 383 | 1042 | 8 |
| 613 | R | CB | 326 | 391 | 1029 | 3 |
| 613 | R | CG | 337 | 387 | 1020 | 4 |
| 613 | H | CD2 | 337 | 378 | 1009 | 5 |
| 613 | H | ND1 | 349 | 392 | 1021 | 8 |
| 613 | H | CE1 | 357 | 386 | 1012 | 5 |
| 613 | H | NE2 | 349 | 378 | 1004 | 2 |
| 613 | H | C | 337 | 388 | 1051 | 8 |
| 613 | R | O | 337 | 398 | 1057 | 14 |
| 614 | P | N | 348 | 379 | 1051 | 10 |
| 614 | P | CD | 348 | 366 | 1045 | 10 |
| 614 | P | CA | 360 | 382 | 1059 | 10 |
| 614 | P | CB | 370 | 371 | 1054 | 11 |
| 614 | P | CG | 361 | 360 | 1051 | 7 |
| 614 | P | C | 365 | 396 | 1058 | 13 |
| 614 | P | O | 370 | 402 | 1067 | 14 |
| 615 | I | N | 365 | 402 | 1046 | 11 |
| 615 | I | CA | 369 | 415 | 1043 | 11 |
| 615 | I | CB | 370 | 419 | 1028 | 9 |
| 615 | I | CG2 | 373 | 433 | 1026 | 9 |
| 615 | I | CG1 | 380 | 410 | 1021 | 5 |
| 615 | I | CD1 | 394 | 411 | 1027 | 11 |
| 615 | I | C | 361 | 425 | 1050 | 15 |
| 615 | I | O | 366 | 435 | 1056 | 16 |
| 616 | T | N | 347 | 423 | 1050 | 12 |
| 616 | T | CA | 338 | 432 | 1057 | 10 |
| 616 | T | CB | 323 | 427 | 1055 | 13 |
| 616 | T | OG1 | 321 | 426 | 1041 | 12 |
| 616 | T | CG2 | 314 | 437 | 1061 | 10 |
| 616 | T | C | 341 | 432 | 1071 | 6 |
| 616 | T | O | 341 | 442 | 1078 | 7 |
| 617 | K | N | 343 | 420 | 1077 | 11 |
| 617 | K | CA | 346 | 418 | 1091 | 13 |
| 617 | K | CB | 347 | 403 | 1094 | 18 |
| 617 | K | CG | 334 | 396 | 1092 | 19 |
| 617 | K | CD | 335 | 381 | 1094 | 28 |
| 617 | K | CE | 326 | 375 | 1105 | 32 |
| 617 | K | NZ | 316 | 365 | 1100 | 40 |
| 617 | K | C | 359 | 425 | 1095 | 9 |
| 617 | K | O | 360 | 431 | 1105 | 12 |
| 618 | Y | N | 369 | 424 | 1086 | 7 |
| 618 | Y | CA | 382 | 430 | 1088 | 6 |
| 618 | Y | CB | 392 | 426 | 1078 | 5 |
| 618 | Y | CG | 405 | 434 | 1078 | 7 |
| 618 | Y | CD1 | 415 | 431 | 1088 | 8 |

TABLE 3-continued

| | | | | | | |
|---|---|---|---|---|---|---|
| 618 | Y | CE1 | 426 | 439 | 1088 | 8 |
| 618 | Y | CD2 | 407 | 445 | 1070 | 6 |
| 618 | Y | CE2 | 418 | 453 | 1070 | 4 |
| 618 | Y | CZ | 428 | 450 | 1080 | 7 |
| 618 | Y | OH | 439 | 457 | 1080 | 13 |
| 618 | Y | C | 381 | 446 | 1088 | 10 |
| 618 | Y | O | 386 | 452 | 1097 | 12 |
| 619 | I | N | 374 | 451 | 1078 | 10 |
| 619 | I | CA | 372 | 465 | 1077 | 10 |
| 619 | I | CB | 366 | 469 | 1064 | 8 |
| 619 | I | CG2 | 362 | 484 | 1064 | 9 |
| 619 | I | CG1 | 375 | 466 | 1052 | 12 |
| 619 | I | CD1 | 369 | 470 | 1038 | 8 |
| 619 | I | C | 364 | 470 | 1089 | 11 |
| 619 | I | O | 366 | 482 | 1093 | 15 |
| 620 | M | N | 355 | 462 | 1094 | 11 |
| 620 | M | CA | 347 | 466 | 1105 | 13 |
| 620 | M | CB | 336 | 455 | 1108 | 11 |
| 620 | M | CG | 324 | 457 | 1099 | 16 |
| 620 | M | SD | 310 | 448 | 1105 | 27 |
| 620 | M | CE | 310 | 434 | 1095 | 25 |
| 620 | M | C | 356 | 467 | 1117 | 11 |
| 620 | M | O | 355 | 476 | 1125 | 14 |
| 621 | A | N | 366 | 457 | 1119 | 11 |
| 621 | A | CA | 375 | 458 | 1130 | 7 |
| 621 | A | CB | 384 | 446 | 1129 | 8 |
| 621 | A | C | 383 | 471 | 1129 | 8 |
| 621 | A | O | 386 | 477 | 1140 | 11 |
| 622 | C | N | 387 | 475 | 1117 | 11 |
| 622 | C | CA | 395 | 487 | 1116 | 13 |
| 622 | C | CB | 399 | 489 | 1101 | 13 |
| 622 | C | SG | 408 | 476 | 1094 | 15 |
| 622 | C | C | 387 | 499 | 1120 | 16 |
| 622 | C | O | 393 | 510 | 1123 | 19 |
| 623 | M | N | 374 | 498 | 1121 | 15 |
| 623 | M | CA | 365 | 508 | 1125 | 11 |
| 623 | M | CB | 350 | 505 | 1123 | 17 |
| 623 | M | CG | 346 | 505 | 1108 | 14 |
| 623 | M | SD | 354 | 518 | 1099 | 16 |
| 623 | M | CE | 344 | 532 | 1102 | 10 |
| 623 | M | C | 366 | 512 | 1140 | 9 |
| 623 | M | O | 361 | 522 | 1145 | 13 |
| 624 | S | N | 373 | 505 | 1148 | 12 |
| 624 | S | CA | 376 | 507 | 1162 | 15 |
| 624 | S | CB | 377 | 494 | 1170 | 14 |
| 624 | S | OG | 367 | 485 | 1165 | 18 |
| 624 | S | C | 390 | 514 | 1164 | 17 |
| 624 | S | O | 395 | 516 | 1175 | 18 |
| 625 | A | N | 395 | 518 | 1152 | 17 |
| 625 | A | CA | 408 | 525 | 1150 | 17 |
| 625 | A | CB | 408 | 532 | 1137 | 19 |
| 625 | A | C | 410 | 535 | 1162 | 21 |
| 625 | A | O | 418 | 533 | 1171 | 19 |
| 626 | D | N | 403 | 546 | 1160 | 22 |
| 626 | D | CA | 404 | 558 | 1169 | 22 |
| 626 | D | CB | 415 | 555 | 1179 | 27 |
| 626 | D | CG | 410 | 559 | 1193 | 36 |
| 626 | D | OD1 | 411 | 571 | 1197 | 37 |
| 626 | D | OD2 | 406 | 550 | 1202 | 43 |
| 626 | D | C | 408 | 570 | 1160 | 21 |
| 626 | D | O | 420 | 573 | 1158 | 19 |
| 627 | L | N | 397 | 576 | 1156 | 18 |
| 627 | L | CA | 398 | 587 | 1147 | 17 |
| 627 | L | CB | 389 | 585 | 1135 | 14 |
| 627 | L | CG | 383 | 571 | 1135 | 17 |
| 627 | L | CD1 | 368 | 572 | 1131 | 17 |
| 627 | L | CD2 | 389 | 562 | 1125 | 8 |
| 627 | L | C | 395 | 600 | 1153 | 17 |
| 627 | L | O | 387 | 601 | 1163 | 21 |
| 628 | E | N | 401 | 610 | 1147 | 21 |
| 628 | E | CA | 399 | 624 | 1149 | 16 |
| 628 | E | CB | 411 | 631 | 1143 | 20 |
| 628 | E | CG | 422 | 634 | 1153 | 33 |
| 628 | E | CD | 420 | 647 | 1161 | 40 |
| 628 | E | OE1 | 408 | 649 | 1165 | 43 |
| 628 | E | OE2 | 429 | 655 | 1162 | 42 |
| 628 | E | C | 386 | 629 | 1144 | 14 |
| 628 | E | O | 383 | 626 | 1132 | 14 |
| 629 | V | N | 379 | 636 | 1152 | 12 |
| 629 | V | CA | 366 | 642 | 1148 | 13 |
| 629 | V | CB | 355 | 634 | 1154 | 15 |
| 629 | V | CG1 | 348 | 641 | 1166 | 16 |
| 629 | V | CG2 | 343 | 631 | 1145 | 15 |
| 629 | V | C | 365 | 657 | 1153 | 15 |
| 629 | V | O | 366 | 659 | 1165 | 20 |
| 630 | V | N | 363 | 665 | 1143 | 19 |
| 630 | V | CA | 362 | 680 | 1146 | 22 |
| 630 | V | CB | 360 | 687 | 1133 | 23 |
| 630 | V | CG1 | 345 | 689 | 1129 | 25 |
| 630 | V | CG2 | 366 | 701 | 1133 | 23 |
| 630 | V | C | 350 | 683 | 1155 | 25 |
| 630 | V | O | 338 | 678 | 1152 | 25 |
| 631 | T | N | 347 | 693 | 1167 | 29 |
| 631 | T | CA | 333 | 694 | 1173 | 33 |
| 631 | T | CB | 332 | 689 | 1188 | 32 |
| 631 | T | OG1 | 341 | 696 | 1196 | 39 |
| 631 | T | CG2 | 334 | 673 | 1189 | 30 |
| 631 | T | C | 330 | 709 | 1174 | 38 |
| 631 | T | O | 323 | 713 | 1184 | 25 |
| 631 | T | OT | 335 | 716 | 1165 | 39 |
| 800 | P | P | 525 | 825 | 884 | 41 |
| 800 | P | O1 | 511 | 821 | 884 | 46 |
| 800 | P | O2 | 529 | 830 | 871 | 49 |
| 800 | P | O3 | 527 | 835 | 894 | 43 |
| 800 | P | O4 | 533 | 813 | 886 | 42 |
| 1800 | P | P | −131 | 687 | 1320 | 21 |
| 1800 | P | O1 | −140 | 691 | 1331 | 28 |
| 1800 | P | O2 | −136 | 694 | 1307 | 23 |
| 1800 | P | O3 | −117 | 692 | 1322 | 16 |
| 1800 | P | O4 | −131 | 673 | 1318 | 22 |
| 750 | X | OH2 | 378 | 387 | 1090 | 15 |
| 751 | X | OH2 | 534 | 575 | 1096 | 27 |
| 752 | X | OH2 | 591 | 578 | 1003 | 23 |
| 753 | X | OH2 | 541 | 446 | 1178 | 66 |
| 754 | X | OH2 | 348 | 422 | 1126 | 13 |
| 755 | X | OH2 | 302 | 408 | 1033 | 15 |
| 756 | X | OH2 | 285 | 706 | 1232 | 13 |
| 757 | X | OH2 | 526 | 741 | 1233 | 28 |
| 758 | X | OH2 | 255 | 584 | 1090 | 19 |
| 759 | X | OH2 | 227 | 550 | 1151 | 23 |
| 760 | X | OH2 | 572 | 606 | 1069 | 22 |
| 761 | X | OH2 | 488 | 817 | 907 | 23 |
| 762 | X | OH2 | 499 | 770 | 880 | 31 |
| 763 | X | OH2 | 509 | 794 | 901 | 33 |
| 764 | X | OH2 | 666 | 843 | 934 | 31 |
| 765 | X | OH2 | 731 | 741 | 845 | 20 |
| 766 | X | OH2 | 727 | 675 | 929 | 37 |
| 767 | X | OH2 | 612 | 575 | 850 | 21 |
| 768 | X | OH2 | 618 | 611 | 776 | 30 |
| 769 | X | OH2 | 657 | 694 | 1083 | 52 |
| 770 | X | OH2 | 486 | 690 | 1062 | 15 |
| 771 | X | OH2 | 300 | 911 | 1074 | 15 |
| 772 | X | OH2 | 343 | 968 | 1168 | 15 |
| 773 | X | OH2 | 404 | 663 | 1359 | 15 |
| 774 | X | OH2 | 325 | 839 | 1338 | 15 |
| 775 | X | OH2 | 496 | 656 | 1231 | 15 |
| 776 | X | OH2 | 545 | 805 | 1265 | 15 |
| 777 | X | OH2 | 622 | 594 | 795 | 15 |
| 778 | X | OH2 | 232 | 873 | 936 | 15 |
| 779 | X | OH2 | 148 | 826 | 882 | 15 |
| 780 | X | OH2 | 543 | 807 | 1062 | 49 |
| 781 | X | OH2 | 256 | 900 | 1224 | 36 |
| 782 | X | OH2 | 367 | 818 | 1378 | 33 |
| 783 | X | OH2 | 390 | 898 | 1346 | 31 |
| 784 | X | OH2 | 179 | 757 | 1354 | 25 |
| 785 | X | OH2 | 225 | 771 | 1324 | 12 |
| 786 | X | OH2 | 279 | 812 | 1083 | 37 |
| 787 | X | OH2 | 258 | 734 | 1181 | 28 |
| 788 | X | OH2 | 449 | 891 | 1310 | 10 |
| 789 | X | OH2 | 488 | 841 | 1130 | 23 |
| 790 | X | OH2 | 485 | 738 | 1286 | 19 |
| 791 | X | OH2 | 466 | 820 | 1162 | 30 |
| 792 | X | OH2 | 525 | 703 | 1173 | 62 |
| 794 | X | OH2 | 525 | 799 | 1187 | 27 |
| 795 | X | OH2 | 425 | 918 | 1350 | 10 |
| 796 | X | OH2 | 440 | 880 | 1362 | 35 |
| 797 | X | OH2 | 402 | 916 | 1373 | 22 |
| 798 | X | OH2 | 479 | 997 | 1301 | 48 |

TABLE 3-continued

| | | | | | | |
|---|---|---|---|---|---|---|
| 799 | X | OH2 | 516 | 815 | 1418 | 47 |
| 801 | X | OH2 | 293 | 900 | 1183 | 16 |
| 802 | X | OH2 | 327 | 836 | 1311 | 18 |
| 803 | X | OH2 | 435 | 1018 | 1378 | 9 |
| 804 | X | OH2 | 199 | 863 | 1669 | 35 |
| 805 | X | OH2 | 358 | 715 | 1404 | 25 |
| 806 | X | OH2 | 287 | 564 | 1275 | 52 |
| 807 | X | OH2 | 280 | 787 | 1383 | 17 |
| 808 | X | OH2 | 276 | 735 | 1358 | 12 |
| 809 | X | OH2 | 210 | 794 | 1321 | 12 |
| 810 | X | OH2 | 192 | 765 | 1333 | 19 |
| 811 | X | OH2 | 200 | 753 | 1383 | 30 |
| 812 | X | OH2 | 209 | 831 | 1323 | 22 |
| 813 | X | OH2 | 247 | 892 | 1350 | 50 |
| 815 | X | OH2 | 323 | 906 | 1332 | 43 |
| 818 | X | OH2 | 458 | 1093 | 1362 | 34 |
| 819 | X | OH2 | 231 | 1014 | 1247 | 38 |
| 820 | X | OH2 | −244 | 826 | 1314 | 47 |
| 821 | X | OH2 | 332 | 743 | 1150 | 19 |
| 822 | X | OH2 | 477 | 864 | 1322 | 28 |
| 823 | X | OH2 | 639 | 783 | 1345 | 50 |
| 824 | X | OH2 | 437 | 949 | 1241 | 21 |
| 825 | X | OH2 | 419 | 918 | 1161 | 6 |
| 826 | X | OH2 | 363 | 832 | 1035 | 21 |
| 827 | X | OH2 | 397 | 885 | 1099 | 7 |
| 830 | X | OH2 | 400 | 950 | 1133 | 6 |
| 831 | X | OH2 | 520 | 897 | 1183 | 15 |
| 832 | X | OH2 | 483 | 795 | 1091 | 25 |
| 833 | X | OH2 | 318 | 876 | 1033 | 61 |
| 834 | X | OH2 | 361 | 498 | 1363 | 52 |
| 835 | X | OH2 | 517 | 708 | 1107 | 33 |
| 836 | X | OH2 | 651 | 787 | 1034 | 30 |
| 837 | X | OH2 | 479 | 825 | 1364 | 29 |
| 839 | X | OH2 | 570 | 702 | 1486 | 48 |
| 841 | X | OH2 | 454 | 787 | 1526 | 47 |
| 842 | X | OH2 | 349 | 602 | 1453 | 56 |
| 844 | X | OH2 | 192 | 715 | 1275 | 64 |
| 845 | X | OH2 | 346 | 631 | 1323 | 25 |
| 846 | X | OH2 | 407 | 590 | 1322 | 34 |
| 847 | X | OH2 | 641 | 821 | 1331 | 35 |
| 848 | X | OH2 | 444 | 605 | 1260 | 32 |
| 850 | X | OH2 | 236 | 611 | 1172 | 28 |
| 852 | X | OH2 | 524 | 796 | 1304 | 33 |
| 853 | X | OH2 | 544 | 923 | 1133 | 2 |
| 854 | X | OH2 | 573 | 925 | 1138 | 6 |
| 856 | X | OH2 | 494 | 798 | 1053 | 29 |
| 858 | X | OH2 | 739 | 899 | 881 | 50 |
| 859 | X | OH2 | 715 | 760 | 858 | 12 |
| 860 | X | OH2 | 684 | 674 | 856 | 23 |
| 861 | X | OH2 | 670 | 655 | 938 | 20 |
| 862 | X | OH2 | 504 | 636 | 837 | 2 |
| 863 | X | OH2 | 396 | 618 | 772 | 58 |
| 864 | X | OH2 | 492 | 657 | 889 | 14 |
| 865 | X | OH2 | 435 | 655 | 817 | 42 |
| 866 | X | OH2 | 554 | 711 | 762 | 19 |
| 867 | X | OH2 | 632 | 821 | 697 | 58 |
| 868 | X | OH2 | 606 | 716 | 758 | 24 |
| 869 | X | OH2 | 548 | 602 | 781 | 9 |
| 870 | X | OH2 | 222 | 583 | 932 | 43 |
| 871 | X | OH2 | 374 | 571 | 643 | 36 |
| 872 | X | OH2 | 477 | 411 | 971 | 27 |
| 874 | X | OH2 | 621 | 644 | 806 | 16 |
| 875 | X | OH2 | 529 | 780 | 1009 | 10 |
| 876 | X | OH2 | 443 | 774 | 1008 | 13 |
| 877 | X | OH2 | 429 | 750 | 1001 | 15 |
| 878 | X | OH2 | 395 | 766 | 867 | 15 |
| 879 | X | OH2 | 391 | 754 | 923 | 40 |
| 880 | X | OH2 | 344 | 649 | 942 | 24 |
| 881 | X | OH2 | 485 | 704 | 988 | 20 |
| 882 | X | OH2 | 635 | 651 | 1025 | 14 |
| 883 | X | OH2 | 642 | 635 | 1149 | 57 |
| 884 | X | OH2 | 702 | 673 | 1007 | 18 |
| 885 | X | OH2 | 484 | 755 | 1071 | 4 |
| 886 | X | OH2 | 516 | 855 | 1033 | 39 |
| 887 | X | OH2 | 359 | 959 | 786 | 51 |
| 888 | X | OH2 | 407 | 858 | 908 | 14 |
| 889 | X | OH2 | 464 | 859 | 929 | 34 |
| 890 | X | OH2 | 271 | 947 | 842 | 24 |
| 891 | X | OH2 | 204 | 884 | 863 | 42 |
| 892 | X | OH2 | 246 | 883 | 956 | 25 |
| 893 | X | OH2 | 22 | 870 | 990 | 25 |
| 894 | X | OH2 | 175 | 764 | 873 | 38 |
| 895 | X | OH2 | 300 | 591 | 968 | 28 |
| 896 | X | OH2 | 327 | 726 | 886 | 27 |
| 897 | X | OH2 | 462 | 758 | 867 | 35 |
| 898 | X | OH2 | 269 | 552 | 1142 | 38 |
| 899 | X | OH2 | 278 | 484 | 1132 | 40 |
| 900 | X | OH2 | 314 | 479 | 1140 | 23 |
| 901 | X | OH2 | 404 | 587 | 940 | 22 |
| 902 | X | OH2 | 518 | 487 | 1038 | 9 |
| 903 | X | OH2 | 412 | 712 | 1111 | 24 |
| 905 | X | OH2 | 440 | 602 | 1159 | 21 |
| 906 | X | OH2 | 457 | 575 | 1124 | 13 |
| 907 | X | OH2 | 455 | 504 | 1200 | 25 |
| 908 | X | OH2 | 424 | 507 | 1125 | 19 |
| 909 | X | OH2 | 428 | 455 | 1127 | 26 |
| 910 | X | OH2 | 478 | 457 | 993 | 47 |
| 912 | X | OH2 | 418 | 723 | 955 | 20 |
| 913 | X | OH2 | 484 | 585 | 867 | 42 |
| 914 | X | OH2 | 487 | 593 | 779 | 38 |
| 915 | X | OH2 | 396 | 559 | 879 | 19 |
| 916 | X | OH2 | 320 | 344 | 1033 | 28 |
| 918 | X | OH2 | 269 | 516 | 953 | 18 |
| 919 | X | OH2 | 237 | 332 | 923 | 22 |
| 920 | X | OH2 | 286 | 509 | 978 | 2 |
| 921 | X | OH2 | 237 | 550 | 865 | 46 |
| 922 | X | OH2 | 190 | 585 | 1014 | 27 |
| 923 | X | OH2 | 250 | 564 | 941 | 27 |
| 924 | X | OH2 | 200 | 435 | 1033 | 19 |
| 925 | X | OH2 | 176 | 492 | 984 | 28 |
| 926 | X | OH2 | 292 | 394 | 1105 | 18 |
| 927 | X | OH2 | 389 | 406 | 1119 | 33 |
| 928 | X | OH2 | 415 | 387 | 1060 | 34 |
| 929 | X | OH2 | 362 | 418 | 1288 | 56 |
| 930 | X | OH2 | 304 | 403 | 1130 | 30 |
| 931 | X | OH2 | 373 | 921 | 1064 | 37 |
| 932 | X | OH2 | 315 | 961 | 1226 | 44 |
| 933 | X | OH2 | 276 | 889 | 1339 | 32 |
| 935 | X | OH2 | 381 | 741 | 1420 | 26 |
| 936 | X | OH2 | 218 | 935 | 997 | 57 |
| 937 | X | OH2 | 464 | 936 | 1264 | 27 |
| 938 | X | OH2 | 422 | 740 | 1109 | 20 |
| 939 | X | OH2 | 391 | 816 | 1052 | 30 |
| 941 | X | OH2 | 418 | 985 | 1230 | 66 |
| 942 | X | OH2 | 464 | 916 | 1221 | 19 |
| 943 | X | OH2 | 531 | 642 | 1146 | 56 |
| 944 | X | OH2 | 64 | 635 | 1143 | 32 |
| 946 | X | OH2 | 709 | 720 | 1119 | 39 |
| 947 | X | OH2 | 213 | 682 | 1210 | 50 |
| 948 | X | OH2 | 248 | 540 | 1195 | 15 |
| 949 | X | OH2 | 291 | 523 | 1187 | 42 |
| 950 | X | OH2 | 318 | 572 | 1140 | 19 |
| 951 | X | OH2 | 306 | 466 | 1278 | 27 |
| 952 | X | OH2 | 575 | 889 | 1104 | 27 |
| 953 | X | OH2 | 502 | 768 | 1010 | 17 |
| 954 | X | OH2 | 483 | 796 | 930 | 21 |
| 955 | X | OH2 | 758 | 764 | 922 | 34 |
| 956 | X | OH2 | 487 | 635 | 807 | 12 |
| 957 | X | OH2 | 551 | 567 | 790 | 28 |
| 958 | X | OH2 | 584 | 637 | 867 | 11 |
| 959 | X | OH2 | 612 | 632 | 679 | 27 |
| 960 | X | OH2 | 641 | 542 | 810 | 55 |
| 961 | X | OH2 | 781 | 536 | 1107 | 44 |
| 962 | X | OH2 | 479 | 671 | 908 | 23 |
| 963 | X | OH2 | 488 | 598 | 807 | 30 |
| 964 | X | OH2 | 371 | 879 | 1060 | 38 |
| 965 | X | OH2 | 199 | 815 | 938 | 15 |
| 966 | X | OH2 | 343 | 635 | 1080 | 33 |
| 967 | X | OH2 | 235 | 471 | 1070 | 31 |
| 968 | X | OH2 | 294 | 513 | 1055 | 9 |
| 969 | X | OH2 | 381 | 647 | 1082 | 10 |
| 970 | X | OH2 | 486 | 528 | 990 | 2 |
| 971 | X | OH2 | 499 | 500 | 916 | 6 |
| 972 | X | OH2 | 515 | 559 | 1108 | 40 |
| 973 | X | OH2 | 445 | 535 | 1167 | 19 |
| 914 | X | OH2 | 478 | 586 | 1123 | 15 |
| 975 | X | OH2 | 506 | 485 | 1063 | 16 |
| 976 | X | OH2 | 460 | 436 | 953 | 24 |

TABLE 3-continued

| | | | | | | |
|---|---|---|---|---|---|---|
| 977 | X | OH2 | 367 | 370 | 890 | 34 |
| 978 | X | OH2 | 345 | 504 | 856 | 26 |
| 979 | X | OH2 | 454 | 658 | 765 | 39 |
| 980 | X | OH2 | 302 | 490 | 981 | 14 |
| 981 | X | OH2 | 161 | 487 | 964 | 28 |
| 982 | X | OH2 | 311 | 441 | 822 | 17 |
| 983 | X | OH2 | 336 | 450 | 812 | 21 |
| 984 | X | OH2 | 254 | 350 | 960 | 26 |
| 985 | X | OH2 | 257 | 557 | 1050 | 43 |
| 986 | X | OH2 | 213 | 492 | 1024 | 20 |
| 1801 | X | OH2 | 52 | 841 | 1023 | 15 |
| 1802 | X | OH2 | 150 | 770 | 812 | 43 |
| 1803 | X | OH2 | 82 | 858 | 997 | 20 |
| 1804 | X | OH2 | 166 | 881 | 1019 | 27 |
| 1805 | X | OH2 | 136 | 980 | 918 | 37 |
| 1806 | X | OH2 | 1 | 883 | 968 | 31 |
| 1809 | X | OH2 | 17 | 614 | 1092 | 30 |
| 1810 | X | OH2 | 93 | 684 | 1061 | 50 |
| 1812 | X | OH2 | −195 | 755 | 1064 | 57 |
| 1813 | X | OH2 | −5 | 621 | 1087 | 42 |
| 1814 | X | OH2 | 49 | 514 | 1061 | 29 |
| 1815 | X | OH2 | −65 | 634 | 1132 | 17 |
| 1816 | X | OH2 | −29 | 619 | 1029 | 22 |
| 1817 | X | OH2 | −216 | 539 | 1068 | 47 |
| 1818 | X | OH2 | 147 | 569 | 1101 | 23 |
| 1820 | X | OH2 | −272 | 596 | 1026 | 18 |
| 1822 | X | OH2 | 119 | 576 | 888 | 17 |
| 1823 | X | OH2 | −93 | 483 | 1115 | 60 |
| 1824 | X | OH2 | −310 | 331 | 1151 | 44 |
| 1825 | X | OH2 | −249 | 603 | 1177 | 36 |
| 1826 | X | OH2 | −114 | 642 | 1199 | 19 |
| 1827 | X | OH2 | −127 | 661 | 1144 | 31 |
| 1829 | X | OH2 | −108 | 655 | 1332 | 38 |
| 1830 | X | OH2 | −87 | 743 | 1272 | 21 |
| 1832 | X | OH2 | −184 | 683 | 1373 | 21 |
| 1833 | X | OH2 | −100 | 580 | 1349 | 17 |
| 1834 | X | OH2 | −27 | 550 | 1324 | 14 |
| 1835 | X | OH2 | 117 | 558 | 1362 | 34 |
| 1836 | X | OH2 | −21 | 565 | 1297 | 10 |
| 1837 | X | OH2 | −23 | 530 | 1368 | 2 |
| 1838 | X | OH2 | −74 | 796 | 1473 | 31 |
| 1839 | X | OH2 | −94 | 645 | 1396 | 34 |
| 1840 | X | OH2 | −114 | 575 | 1601 | 44 |
| 1841 | X | OH2 | −102 | 491 | 1344 | 9 |
| 1844 | X | OH2 | −135 | 469 | 1312 | 44 |
| 1845 | X | OH2 | −168 | 468 | 1274 | 23 |
| 1846 | X | OH2 | −39 | 592 | 1222 | 4 |
| 1847 | X | OH2 | 9 | 661 | 1207 | 40 |
| 1848 | X | OH2 | 20 | 682 | 1290 | 25 |
| 1849 | X | OH2 | 19 | 626 | 1262 | 15 |
| 1850 | X | OH2 | −51 | 696 | 1269 | 22 |
| 1851 | X | OH2 | 72 | 686 | 1219 | 47 |
| 1852 | X | OH2 | −8 | 556 | 1341 | 23 |
| 1853 | X | OH2 | −331 | 554 | 1014 | 45 |
| 1854 | X | OH2 | −185 | 628 | 965 | 40 |
| 1855 | X | OH2 | −57 | 690 | 1310 | 26 |
| 1856 | X | OH2 | −73 | 698 | 1345 | 50 |
| 1857 | X | OH2 | −138 | 735 | 1219 | 39 |
| 1858 | X | OH2 | −8 | 725 | 1161 | 35 |
| 1859 | X | OH2 | −45 | 763 | 1302 | 23 |
| 1860 | X | OH2 | −68 | 740 | 1228 | 34 |
| 1861 | X | OH2 | 159 | 796 | 1225 | 46 |
| 1862 | X | OH2 | −197 | 941 | 1240 | 48 |
| 1863 | X | OH2 | 120 | 852 | 1268 | 33 |
| 1864 | X | OH2 | 132 | 874 | 1337 | 31 |
| 1866 | X | OH2 | 155 | 910 | 1392 | 17 |
| 1867 | X | OH2 | 102 | 761 | 1228 | 36 |
| 1868 | X | OH2 | 15 | 742 | 1143 | 46 |
| 1869 | X | OH2 | 72 | 894 | 1408 | 11 |
| 1870 | X | OH2 | 306 | 683 | 1443 | 58 |
| 1873 | X | OH2 | 115 | 604 | 1270 | 44 |
| 1874 | X | OH2 | 93 | 675 | 1315 | 17 |
| 1875 | X | OH2 | 102 | 623 | 1349 | 11 |
| 1876 | X | OH2 | 193 | 669 | 1222 | 49 |
| 1877 | X | OH2 | 250 | 551 | 1115 | 25 |
| 1881 | X | OH2 | 305 | 951 | 1296 | 38 |
| 1882 | X | OH2 | 200 | 792 | 1633 | 38 |
| 1883 | X | OH2 | 72 | 665 | 1232 | 54 |
| 1884 | X | OH2 | 89 | 568 | 1228 | 16 |
| 1885 | X | OH2 | 144 | 528 | 1053 | 47 |
| 1886 | X | OH2 | 64 | 584 | 1127 | 21 |
| 1888 | X | OH2 | 120 | 718 | 1160 | 55 |
| 1889 | X | OH2 | −41 | 730 | 1445 | 61 |
| 1890 | X | OH2 | −45 | 724 | 1370 | 31 |
| 1891 | X | OH2 | −7 | 731 | 1448 | 16 |
| 1892 | X | OH2 | −60 | 849 | 1421 | 37 |
| 1893 | X | OH2 | 121 | 915 | 1412 | 57 |
| 1894 | X | OH2 | 100 | 544 | 1383 | 23 |
| 1895 | X | OH2 | 7 | 495 | 1339 | 22 |
| 1896 | X | OH2 | 34 | 433 | 1224 | 6 |
| 1897 | X | OH2 | 70 | 374 | 1224 | 19 |
| 1898 | X | OH2 | −25 | 301 | 1351 | 55 |
| 1899 | X | OH2 | −77 | 361 | 1091 | 41 |
| 1900 | X | OH2 | −13 | 460 | 1103 | 30 |
| 1901 | X | OH2 | −153 | 462 | 1191 | 17 |
| 1902 | X | OH2 | 71 | 507 | 1269 | 29 |
| 1903 | X | OH2 | 83 | 424 | 1382 | 22 |
| 1904 | X | OH2 | 237 | 513 | 1254 | 21 |
| 1905 | X | OH2 | 222 | 501 | 1232 | 11 |
| 1906 | X | OH2 | 220 | 572 | 1143 | 33 |
| 1908 | X | OH2 | 161 | 543 | 1253 | 54 |
| 1909 | X | OH2 | 249 | 392 | 1072 | 31 |
| 1910 | X | OH2 | 110 | 387 | 1085 | 52 |
| 1911 | X | OH2 | 60 | 830 | 941 | 28 |
| 1912 | X | OH2 | 49 | 774 | 892 | 25 |
| 1913 | X | OH2 | 125 | 790 | 799 | 34 |
| 1914 | X | OH2 | 37 | 618 | 1106 | 14 |
| 1915 | X | OH2 | −113 | 714 | 1072 | 33 |
| 1916 | X | OH2 | −66 | 807 | 1042 | 36 |
| 1918 | X | OH2 | −32 | 712 | 856 | 31 |
| 1919 | X | OH2 | 134 | 494 | 1046 | 15 |
| 1920 | X | OH2 | −127 | 535 | 1143 | 41 |
| 1921 | X | OH2 | −122 | 638 | 1147 | 23 |
| 1922 | X | OH2 | −114 | 733 | 1234 | 17 |
| 1923 | X | OH2 | −292 | 630 | 1318 | 26 |
| 1924 | X | OH2 | −209 | 481 | 1361 | 42 |
| 1925 | X | OH2 | −123 | 442 | 1339 | 54 |
| 1926 | X | OH2 | −8 | 627 | 1329 | 28 |
| 1927 | X | OH2 | −57 | 640 | 1336 | 39 |
| 1928 | X | OH2 | 52 | 602 | 1383 | 32 |
| 1929 | X | OH2 | −108 | 571 | 1450 | 30 |
| 1930 | X | OH2 | −124 | 480 | 1334 | 21 |
| 1931 | X | OH2 | 32 | 410 | 1299 | 33 |
| 1932 | X | OH2 | −247 | 468 | 1281 | 38 |
| 1933 | X | OH2 | −37 | 669 | 1196 | 22 |
| 1934 | X | OH2 | 29 | 666 | 1176 | 11 |
| 1935 | X | OH2 | −18 | 655 | 1203 | 20 |
| 1936 | X | OH2 | −69 | 761 | 1186 | 19 |
| 1937 | X | OH2 | 78 | 807 | 1474 | 35 |
| 1939 | X | OH2 | 109 | 588 | 1310 | 58 |
| 1941 | X | OH2 | 19 | 657 | 1476 | 10 |
| 1942 | X | OH2 | 67 | 682 | 1194 | 28 |
| 1943 | X | OH2 | 215 | 497 | 1152 | 13 |
| 1944 | X | OH2 | 217 | 540 | 1046 | 34 |
| 1945 | X | OH2 | 65 | 641 | 1164 | 29 |
| 1946 | X | OH2 | 61 | 613 | 1196 | 13 |
| 1947 | X | OH2 | 166 | 639 | 1094 | 63 |
| 1948 | X | OH2 | 93 | 571 | 1111 | 19 |
| 1949 | X | OH2 | 0 | 645 | 1252 | 30 |
| 1950 | X | OH2 | 29 | 379 | 1168 | 33 |
| 1951 | X | OH2 | −56 | 574 | 1140 | 12 |
| 1952 | X | OH2 | −157 | 723 | 1195 | 57 |
| 1953 | X | OH2 | 24 | 484 | 1092 | 24 |
| 1954 | X | OH2 | 32 | 414 | 1070 | 50 |
| 1955 | X | OH2 | 231 | 423 | 1382 | 56 |
| 1956 | X | OH2 | 210 | 330 | 1308 | 54 |
| 1957 | X | OH2 | 72 | 505 | 1372 | 25 |
| 1958 | X | OH2 | 98 | 437 | 1086 | 23 |
| 1959 | X | OH2 | 111 | 744 | 820 | 26 |
| 1960 | X | OH2 | −36 | 786 | 1105 | 14 |
| 1961 | X | OH2 | −17 | 884 | 1173 | 57 |
| 1962 | X | OH2 | −76 | 395 | 1325 | 28 |
| 1963 | X | OH2 | −137 | 489 | 1404 | 23 |
| 1964 | X | OH2 | 54 | 485 | 1087 | 11 |
| 1965 | X | OH2 | 63 | 472 | 1065 | 19 |
| 1966 | X | OH2 | 143 | 860 | 1166 | 21 |
| END | | | | | | |

We claim:

1. A crystalline composition comprising an HCV NS3/NS4A polypeptide complex which polypeptide comprises an amino acid sequence selected from the group consisting of SEQ ID NO: 1, SEQ ID NO: 2 and SEQ ID NO: 3, and
wherein said crystalline composition effectively diffracts x-rays for the determination of the atomic coordinates of the protein to a resolution of at least about 2.5 Ångströms.

2. The composition of claim 1, wherein the HCV NS3/NS4A polypeptide complex comprises SEQ ID NO: 1.

3. The composition of claim 1, wherein the HCV NS3/NS4A polypeptide complex comprises SEQ ID NO: 2.

4. The composition of claim 1, wherein the HCV NS3/NS4A polypeptide complex comprises SEQ ID NO: 3.

5. A method of preparing a crystal of a purified HCV NS3/NS4A polypeptide which comprises an amino acid sequence selected from the group consisting of SEQ ID NO: 1, SEQ ID NO: 2 and SEQ ID NO: 3, comprising the steps of:

(a) stabilizing a NS3/NS4A protein preparation in a solution containing a protein stabilizing agent;

(b) subjecting the NS3/NS4A protein preparation to anion exchange column chromatography; and (c) allowing crystals to form in a precipitant containing a protein stabilizing agent, a salt and polyethylene glycol under conditions in which crystallization occurs.

6. The method of claim 5, wherein the crystal is allowed to form using a microbatch method.

7. The method of claim 5, wherein the crystal is allowed to form using vapor diffusion.

8. The method of claim 5, wherein the protein stabilizing agent is glycerol.

9. The method of claim 8, wherein the glycerol is provided at a concentration of 10% (volume/volume).

10. The method of claim 5, wherein the polyethylene glycol has a molecular weight of 5000–7000 daltons.

* * * * *

SEQUENCE LISTING

<160> NUMBER OF SEQ ID NOS: 5

<210> SEQ ID NO 1
<211> LENGTH: 665
<212> TYPE: PRT
<213> ORGANISM: Hepatitis C virus
<220> FEATURE:
<221> NAME/KEY: HCV HIS-NS4A21-32-GSGS-NS3(3-631)
<222> LOCATION: (1)..(665)
<223> OTHER INFORMATION:
<220> FEATURE:
<221> NAME/KEY: HCVNS3_3-631
<222> LOCATION: (38)..(665)
<223> OTHER INFORMATION:

<400> SEQUENCE: 1

Met Gly Ser Ser His His His His His Ser Ser Gly Leu Val Pro
1               5                   10                  15

Arg Gly Ser His Met Gly Ser Val Val Ile Val Gly Arg Ile Ile Leu
                20                  25                  30

Ser Gly Ser Gly Ser Ile Thr Ala Tyr Ser Gln Gln Thr Arg Gly Leu
            35                  40                  45

Leu Gly Cys Ile Ile Thr Ser Leu Thr Gly Arg Asp Lys Asn Gln Val
    50                  55                  60

Glu Gly Glu Val Gln Val Val Ser Thr Ala Thr Gln Ser Phe Leu Ala
65                  70                  75                  80

Thr Cys Val Asn Gly Val Cys Trp Thr Val Tyr His Gly Ala Gly Ser
                85                  90                  95

Lys Thr Leu Ala Gly Pro Lys Gly Pro Ile Thr Gln Met Tyr Thr Asn
            100                 105                 110

Val Asp Gln Asp Leu Val Gly Trp Gln Ala Pro Pro Gly Ala Arg Ser
        115                 120                 125

Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
145                 150                 155                 160

Leu Leu Ser Pro Arg Pro Val Ser Tyr Leu Lys Gly Ser Ser Gly Gly
                165                 170                 175

Pro Leu Leu Cys Pro Ser Gly His Ala Val Gly Ile Phe Arg Ala Ala
            180                 185                 190

Val Cys Thr Arg Gly Val Ala Lys Ala Val Asp Phe Val Pro Val Glu
        195                 200                 205

Ser Met Glu Thr Thr Met Arg Ser Pro Val Phe Thr Asp Asn Ser Ser
    210                 215                 220

Pro Pro Ala Val Pro Gln Ser Phe Gln Val Ala His Leu His Ala Pro
225                 230                 235                 240

Thr Gly Ser Gly Lys Ser Thr Lys Val Pro Ala Ala Tyr Ala Ala Gln
                245                 250                 255

Gly Tyr Lys Val Leu Val Leu Asn Pro Ser Val Ala Ala Thr Leu Gly
            260                 265                 270

Phe Gly Ala Tyr Met Ser Lys Ala His Gly Ile Asp Pro Asn Ile Arg
        275                 280                 285

Thr Gly Val Arg Thr Ile Thr Thr Gly Ala Pro Val Thr Tyr Ser Thr
    290                 295                 300

Tyr Gly Lys Phe Leu Ala Asp Gly Gly Cys Ser Gly Gly Ala Tyr Asp
305                 310                 315                 320

```
Ile Ile Ile Cys Asp Glu Cys His Ser Thr Asp Ser Thr Thr Ile Leu
            325                 330                 335

Gly Ile Gly Thr Val Leu Asp Gln Ala Glu Thr Ala Gly Ala Arg Leu
            340                 345                 350

Val Val Leu Ala Thr Ala Thr Pro Pro Gly Ser Val Thr Val Pro His
            355                 360                 365

Pro Asn Ile Glu Glu Val Ala Leu Ser Asn Thr Gly Glu Ile Pro Phe
            370                 375                 380

Tyr Gly Lys Ala Ile Pro Ile Glu Ala Ile Arg Gly Gly Arg His Leu
385                 390                 395                 400

Ile Phe Cys His Ser Lys Lys Lys Cys Asp Glu Leu Ala Ala Lys Leu
                405                 410                 415

Ser Gly Leu Gly Ile Asn Ala Val Ala Tyr Tyr Arg Gly Leu Asp Val
                420                 425                 430

Ser Val Ile Pro Thr Ile Gly Asp Val Val Val Ala Thr Asp Ala
                435                 440                 445

Leu Met Thr Gly Tyr Thr Gly Asp Phe Asp Ser Val Ile Asp Cys Asn
            450                 455                 460

Thr Cys Val Thr Gln Thr Val Asp Phe Ser Leu Asp Pro Thr Phe Thr
465                 470                 475                 480

Ile Glu Thr Thr Thr Val Pro Gln Asp Ala Val Ser Arg Ser Gln Arg
                485                 490                 495

Arg Gly Arg Thr Gly Arg Gly Arg Gly Ile Tyr Arg Phe Val Thr
                500                 505                 510

Pro Gly Glu Arg Pro Ser Gly Met Phe Asp Ser Ser Val Leu Cys Glu
            515                 520                 525

Cys Tyr Asp Ala Gly Cys Ala Trp Tyr Glu Leu Thr Pro Ala Glu Thr
            530                 535                 540

Ser Val Arg Leu Arg Ala Tyr Leu Asn Thr Pro Gly Leu Pro Val Cys
545                 550                 555                 560

Gln Asp His Leu Glu Phe Trp Glu Ser Val Phe Thr Gly Leu Thr His
                565                 570                 575

Ile Asp Ala His Phe Leu Ser Gln Thr Lys Gln Ala Gly Asp Asn Phe
            580                 585                 590

Pro Tyr Leu Val Ala Tyr Gln Ala Thr Val Cys Ala Arg Ala Gln Ala
            595                 600                 605

Pro Pro Pro Ser Trp Asp Gln Met Trp Lys Cys Leu Ile Arg Leu Lys
            610                 615                 620

Pro Thr Leu His Gly Pro Thr Pro Leu Leu Tyr Arg Leu Gly Ala Val
625                 630                 635                 640

Gln Asn Glu Val Thr Leu Thr His Pro Ile Thr Lys Tyr Ile Met Ala
                645                 650                 655

Cys Met Ser Ala Asp Leu Glu Val Val
            660                 665

<210> SEQ ID NO 2
<211> LENGTH: 665
<212> TYPE: PRT
<213> ORGANISM: Hepatitis C virus

<400> SEQUENCE: 2

Met Gly Ser Ser His His His His His His Ser Ser Gly Leu Val Pro
1               5                   10                  15

Arg Gly Ser His Met Gly Ser Val Val Ile Val Gly Arg Ile Ile Leu
```

-continued

```
                    20                  25                  30
Ser Gly Ser Gly Ser Ile Thr Ala Tyr Ser Gln Gln Thr Arg Gly Leu
             35                  40                  45
Leu Gly Cys Ile Ile Thr Ser Leu Thr Gly Arg Asp Lys Asn Gln Val
 50                  55                  60
Glu Gly Glu Val Gln Val Val Ser Thr Ala Thr Gln Ser Phe Leu Ala
 65                  70                  75                  80
Thr Cys Val Asn Gly Val Cys Trp Thr Val Tyr His Gly Ala Gly Ser
                 85                  90                  95
Lys Thr Leu Ala Gly Pro Lys Gly Pro Ile Thr Gln Met Tyr Thr Asn
                100                 105                 110
Val Asp Gln Asp Leu Val Gly Trp Gln Ala Pro Pro Gly Ala Arg Ser
            115                 120                 125
Leu Thr Pro Cys Thr Cys Gly Ser Ser Asp Leu Tyr Leu Val Thr Arg
        130                 135                 140
His Ala Asp Val Ile Pro Val Arg Arg Arg Gly Asp Ser Arg Gly Ser
145                 150                 155                 160
Leu Leu Ser Pro Arg Pro Val Ser Tyr Leu Lys Gly Ser Ala Gly Gly
                165                 170                 175
Pro Leu Leu Cys Pro Ser Gly His Ala Val Gly Ile Phe Arg Ala Ala
            180                 185                 190
Val Cys Thr Arg Gly Val Ala Lys Ala Val Asp Phe Val Pro Val Glu
        195                 200                 205
Ser Met Glu Thr Thr Met Arg Ser Pro Val Phe Thr Asp Asn Ser Ser
    210                 215                 220
Pro Pro Ala Val Pro Gln Ser Phe Gln Val Ala His Leu His Ala Pro
225                 230                 235                 240
Thr Gly Ser Gly Lys Ser Thr Lys Val Pro Ala Ala Tyr Ala Ala Gln
                245                 250                 255
Gly Tyr Lys Val Leu Val Leu Asn Pro Ser Val Ala Ala Thr Leu Gly
            260                 265                 270
Phe Gly Ala Tyr Met Ser Lys Ala His Gly Ile Asp Pro Asn Ile Arg
        275                 280                 285
Thr Gly Val Arg Thr Ile Thr Thr Gly Ala Pro Val Thr Tyr Ser Thr
    290                 295                 300
Tyr Gly Lys Phe Leu Ala Asp Gly Gly Cys Ser Gly Gly Ala Tyr Asp
305                 310                 315                 320
Ile Ile Ile Cys Asp Glu Cys His Ser Thr Asp Ser Thr Thr Ile Leu
                325                 330                 335
Gly Ile Gly Thr Val Leu Asp Gln Ala Glu Thr Ala Gly Ala Arg Leu
            340                 345                 350
Val Val Leu Ala Thr Ala Thr Pro Pro Gly Ser Val Thr Val Pro His
        355                 360                 365
Pro Asn Ile Glu Glu Val Ala Leu Ser Asn Thr Gly Glu Ile Pro Phe
    370                 375                 380
Tyr Gly Lys Ala Ile Pro Ile Glu Ala Ile Arg Gly Gly Arg His Leu
385                 390                 395                 400
Ile Phe Cys His Ser Lys Lys Cys Asp Glu Leu Ala Ala Lys Leu
                405                 410                 415
Ser Gly Leu Gly Ile Asn Ala Val Ala Tyr Tyr Arg Gly Leu Asp Val
            420                 425                 430
Ser Val Ile Pro Thr Ile Gly Asp Val Val Val Val Ala Thr Asp Ala
        435                 440                 445
```

```
Leu Met Thr Gly Tyr Thr Gly Asp Phe Asp Ser Val Ile Asp Cys Asn
    450                 455                 460
Thr Cys Val Thr Gln Thr Val Asp Phe Ser Leu Asp Pro Thr Phe Thr
465                 470                 475                 480
Ile Glu Thr Thr Thr Val Pro Gln Asp Ala Val Ser Arg Ser Gln Arg
                485                 490                 495
Arg Gly Arg Thr Gly Arg Gly Arg Gly Ile Tyr Arg Phe Val Thr
                500                 505                 510
Pro Gly Glu Arg Pro Ser Gly Met Phe Asp Ser Ser Val Leu Cys Glu
            515                 520                 525
Cys Tyr Asp Ala Gly Cys Ala Trp Tyr Glu Leu Thr Pro Ala Glu Thr
        530                 535                 540
Ser Val Arg Leu Arg Ala Tyr Leu Asn Thr Pro Gly Leu Pro Val Cys
545                 550                 555                 560
Gln Asp His Leu Glu Phe Trp Glu Ser Val Phe Thr Gly Leu Thr His
                565                 570                 575
Ile Asp Ala His Phe Leu Ser Gln Thr Lys Gln Ala Gly Asp Asn Phe
                580                 585                 590
Pro Tyr Leu Val Ala Tyr Gln Ala Thr Val Cys Ala Arg Ala Gln Ala
            595                 600                 605
Pro Pro Pro Ser Trp Asp Gln Met Trp Lys Cys Leu Ile Arg Leu Lys
        610                 615                 620
Pro Thr Leu His Gly Pro Thr Pro Leu Leu Tyr Arg Leu Gly Ala Val
625                 630                 635                 640
Gln Asn Glu Val Thr Leu Thr His Pro Ile Thr Lys Tyr Ile Met Ala
                645                 650                 655
Cys Met Ser Ala Asp Leu Glu Val Val
            660                 665

<210> SEQ ID NO 3
<211> LENGTH: 665
<212> TYPE: PRT
<213> ORGANISM: Hepatitis C virus

<400> SEQUENCE: 3

Met Gly Ser Ser His His His His His His Ser Ser Gly Leu Val Pro
1               5                   10                  15
Arg Gly Ser His Met Gly Ser Val Ile Val Gly Arg Ile Ile Leu
            20                  25                  30
Ser Gly Ser Gly Ser Ile Thr Ala Tyr Ser Gln Gln Thr Arg Gly Leu
        35                  40                  45
Leu Gly Cys Ile Ile Thr Ser Leu Thr Gly Arg Asp Lys Asn Gln Val
    50                  55                  60
Glu Gly Glu Val Gln Val Val Ser Thr Ala Thr Gln Ser Phe Leu Ala
65                  70                  75                  80
Thr Cys Val Asn Gly Val Cys Trp Thr Val Tyr His Gly Ala Gly Ser
                85                  90                  95
Lys Thr Leu Ala Gly Pro Lys Gly Pro Ile Thr Gln Met Tyr Thr Asn
            100                 105                 110
Val Asp Gln Asp Leu Val Gly Trp Gln Ala Pro Pro Gly Ala Arg Ser
        115                 120                 125
Leu Thr Pro Cys Thr Cys Gly Ser Ser Asp Leu Tyr Leu Val Thr Arg
    130                 135                 140

His Ala Asp Val Ile Pro Val Arg Arg Arg Gly Asp Ser Arg Gly Ser
```

```
                                      -continued
145                 150                 155                 160
Leu Leu Ser Pro Arg Pro Val Ser Tyr Leu Lys Gly Ser Ala Gly Gly
                165                 170                 175
Pro Leu Leu Cys Pro Ser Gly His Ala Val Gly Ile Phe Arg Ala Ala
            180                 185                 190
Val Cys Thr Arg Gly Val Ala Lys Ala Val Asp Phe Val Pro Val Glu
        195                 200                 205
Ser Met Glu Thr Thr Met Arg Ser Pro Val Phe Thr Asp Asn Ser Ser
    210                 215                 220
Pro Pro Ala Val Pro Gln Ser Phe Gln Val Ala His Leu His Ala Pro
225                 230                 235                 240
Thr Gly Ser Gly Lys Ser Thr Lys Val Pro Ala Ala Tyr Ala Ala Gln
                245                 250                 255
Gly Tyr Lys Val Leu Val Leu Asn Pro Ser Val Ala Ala Thr Leu Gly
            260                 265                 270
Phe Gly Ala Tyr Met Ser Lys Ala His Gly Ile Asp Pro Asn Ile Arg
        275                 280                 285
Thr Gly Val Arg Thr Ile Thr Thr Gly Ala Pro Val Thr Tyr Ser Thr
    290                 295                 300
Tyr Gly Lys Phe Leu Ala Asp Gly Gly Cys Ser Gly Gly Ala Tyr Asp
305                 310                 315                 320
Ile Ile Ile Cys Asp Glu Cys His Ser Thr Asp Ser Thr Thr Ile Leu
                325                 330                 335
Gly Ile Gly Thr Val Leu Asp Gln Ala Glu Thr Ala Gly Ala Arg Leu
            340                 345                 350
Val Val Leu Ala Thr Ala Thr Pro Pro Gly Ser Val Thr Val Pro His
        355                 360                 365
Pro Asn Ile Glu Glu Val Ala Leu Ser Asn Thr Gly Glu Ile Pro Phe
    370                 375                 380
Tyr Gly Lys Ala Ile Pro Ile Glu Ala Ile Arg Gly Gly Arg His Leu
385                 390                 395                 400
Ile Phe Cys His Ser Lys Lys Cys Asp Glu Leu Ala Ala Lys Leu
                405                 410                 415
Ser Gly Leu Gly Ile Asn Ala Val Ala Tyr Tyr Arg Gly Leu Asp Val
            420                 425                 430
Ser Val Ile Pro Thr Ile Gly Asp Val Val Val Ala Thr Asp Ala
        435                 440                 445
Leu Met Thr Gly Tyr Thr Gly Asp Phe Asp Ser Val Ile Asp Cys Asn
    450                 455                 460
Thr Cys Val Thr Gln Thr Val Asp Phe Ser Leu Asp Pro Thr Phe Thr
465                 470                 475                 480
Ile Glu Thr Thr Thr Val Pro Gln Asp Ala Val Ser Arg Ser Gln Arg
                485                 490                 495
Arg Gly Arg Thr Gly Arg Gly Arg Gly Ile Tyr Arg Phe Val Thr
            500                 505                 510
Pro Gly Glu Arg Pro Ser Gly Met Phe Asp Ser Ser Val Leu Cys Glu
        515                 520                 525
Cys Tyr Asp Ala Gly Cys Ala Trp Tyr Glu Leu Thr Pro Ala Glu Thr
    530                 535                 540
Ser Val Arg Leu Arg Ala Tyr Leu Asn Thr Pro Gly Leu Pro Val Cys
545                 550                 555                 560
Gln Asp His Leu Glu Phe Trp Glu Ser Val Phe Thr Gly Leu Thr His
                565                 570                 575
```

```
Ile Asp Ala His Phe Leu Ser Gln Thr Lys Gln Ala Gly Asp Asn Phe
            580                 585                 590

Pro Tyr Leu Val Ala Tyr Gln Ala Thr Val Cys Ala Arg Ala Gln Ala
        595                 600                 605

Pro Pro Pro Ser Trp Asp Gln Met Trp Lys Cys Leu Ile Arg Leu Lys
        610                 615                 620

Pro Thr Leu His Gly Pro Thr Pro Leu Leu Tyr Arg Leu Gly Ala Val
625                 630                 635                 640

Gln Asn Glu Val Thr Leu Thr His Pro Ile Thr Lys Tyr Ile Met Ala
                645                 650                 655

Cys Met Ser Ala Asp Leu Glu Val Val
            660                 665

<210> SEQ ID NO 4
<211> LENGTH: 31
<212> TYPE: DNA
<213> ORGANISM: Artificial Sequence
<220> FEATURE:
<223> OTHER INFORMATION: Primer for mutagenesis

<400> SEQUENCE: 4
ggaaactact atggcgtctc cggtcttcac g                              31

<210> SEQ ID NO 5
<211> LENGTH: 31
<212> TYPE: DNA
<213> ORGANISM: Artificial Sequence
<220> FEATURE:
<223> OTHER INFORMATION: Primer for mutagenesis

<400> SEQUENCE: 5
cgtgaagacc ggagacgcca tagtagtttc c                              31
```